(12) United States Patent
Gonzalez et al.

(10) Patent No.: US 10,994,017 B2
(45) Date of Patent: May 4, 2021

(54) NERVE LABELING COMPOSITIONS AND USES THEREOF

(71) Applicant: Avelas Biosciences, Inc., La Jolla, CA (US)

(72) Inventors: Jesus Gonzalez, Carlsbad, CA (US); Junjie Liu, San Diego, CA (US); Marcel Miampamba, San Diego, CA (US)

(73) Assignee: Avelas Biosciences, Inc., La Jolla, CA (US)

( * ) Notice: Subject to any disclaimer, the term of this patent is extended or adjusted under 35 U.S.C. 154(b) by 31 days.

(21) Appl. No.: 16/466,259

(22) PCT Filed: Dec. 1, 2017

(86) PCT No.: PCT/US2017/064329
§ 371 (c)(1),
(2) Date: Jun. 3, 2019

(87) PCT Pub. No.: WO2018/102762
PCT Pub. Date: Jun. 7, 2018

(65) Prior Publication Data
US 2020/0061200 A1     Feb. 27, 2020

Related U.S. Application Data

(60) Provisional application No. 62/429,617, filed on Dec. 2, 2016, provisional application No. 62/429,615, filed on Dec. 2, 2016.

(51) Int. Cl.
*A61K 47/64* (2017.01)
*A61K 49/00* (2006.01)

(52) U.S. Cl.
CPC .......... *A61K 47/64* (2017.08); *A61K 49/0032* (2013.01); *A61K 49/0043* (2013.01); *A61K 49/0056* (2013.01)

(58) Field of Classification Search
None
See application file for complete search history.

(56) References Cited

U.S. PATENT DOCUMENTS

| | | | |
|---|---|---|---|
| 4,496,542 A | 1/1985 | Skiles et al. | |
| 4,659,839 A | 4/1987 | Nicolotti et al. | |
| 6,391,280 B1 | 5/2002 | Hiatt et al. | |
| 6,602,980 B1 | 8/2003 | Eyre | |
| 7,452,964 B2 | 11/2008 | Pasqualini et al. | |
| 7,781,565 B2 | 8/2010 | Pasqualini et al. | |
| 8,642,561 B2 | 2/2014 | Jiang et al. | |
| 8,685,372 B2 | 4/2014 | Tsien et al. | |
| 9,072,773 B2 | 7/2015 | Gonzalez et al. | |
| 9,353,154 B2 | 5/2016 | Gonzalez et al. | |
| 2004/0253243 A1 | 12/2004 | Epstein et al. | |
| 2006/0094672 A1 | 5/2006 | Pasqualini et al. | |
| 2006/0228420 A1 | 10/2006 | Martin | |
| 2007/0072251 A1 | 3/2007 | Kairemo et al. | |
| 2007/0243554 A1 | 10/2007 | Jagota et al. | |
| 2011/0097392 A1 | 4/2011 | Wang et al. | |
| 2012/0288447 A1 | 11/2012 | Lee et al. | |
| 2013/0149373 A1* | 6/2013 | Kumar-Singh | A61K 38/00 424/450 |
| 2013/0202537 A1* | 8/2013 | Gonzalez | G09F 13/22 424/9.6 |
| 2013/0202583 A1* | 8/2013 | Jiang | G01N 33/6893 424/94.62 |
| 2014/0228292 A1* | 8/2014 | Nordkild | A61K 47/644 514/10.1 |
| 2014/0294727 A1 | 10/2014 | Narasimhaswamy et al. | |
| 2016/0166714 A1 | 6/2016 | Bradbury et al. | |

FOREIGN PATENT DOCUMENTS

| | | |
|---|---|---|
| EP | 2611822 A2 | 7/2013 |
| KR | 20110053119 A | 5/2011 |
| WO | WO-2006096487 A2 | 9/2006 |
| WO | WO-2006105392 A2 | 10/2006 |
| WO | WO-2010121023 A2 | 10/2010 |
| WO | WO-2012031250 A2 | 3/2012 |
| WO | WO-2018102762 A1 | 6/2018 |

OTHER PUBLICATIONS

Arcidiacono et al. Cy5 labeled antimicrobial peptides for enhanced detection of *Escherichia coli* 0157:H7. Biosens Bioelectron. 23(11):1721-1727 (2008).
Barany et al. Solid-phase peptide synthesis. In: The Peptides: Analysis, Synthesis, Biology vol. 2: Special Methods in Peptide Synthesis Part A. New York: Academic Press.pp. 3-284 (1979).
Bennet et al. Neurotransmitter, hormone or drug receptor binding methods. In: Neurotransmitter Receptor Binding. 2nd ed. Yamamura, H. ed. New York: Raven Press 61-89 (1985).
Chemical Book, FMOC-LYS(5/6-FAM)-OH, Jan. 1, 2008, Retrieved from the Internet: URL:http://www.chemicalbook.com/ProductChemicalPropertiesCB5335804_EN.htm, retrieved on Feb. 20, 2014.
Jin et al. Transduction of human catalase mediated by an HIV-1 TAT protein basic domain and arginine-rich peptides into mammalian cells. Free Radic boil Med 31(11):1509-1519 (2001).
Kaltenbronn et al. In: Proceedings 11th American Peptide Symposium. Netherlands: ESCOM Publishers; 1990: 969-970.
Kobbert et al. Current concepts in neuroanatomical tracing. Progress in Neurobiology 62:327-351 (2000).
Lyon et al. Self-hydrolyzing maleimides improve the stability and pharmacological properties of antibody-drug conjugates. Nat. Biotechnol. 32(10):1059-1062 (2014).

(Continued)

*Primary Examiner* — Adam Weidner
(74) *Attorney, Agent, or Firm* — Goodwin Procter LLP

(57) ABSTRACT

Described herein are methods and compositions for nerve delivery molecules that carry imaging cargo or therapeutic cargo to the neurons or nerves.

2 Claims, 5 Drawing Sheets
Specification includes a Sequence Listing.

(56) References Cited

OTHER PUBLICATIONS

Marangos et al. In vivo visualization of the cochlear nerve and nuclei with fluorescent axonal tracers. Hearing Research.162:48-52 (2001).
Merrifield et al. Solid Phase Peptide Synthesis I. J Am Chem Soc 85:2149-2154 (1963).
Mikawa et al. Novel peptide ligands for integrin alpha 4 beta 1 overexpressed in cancer cells. Mol Cancer Ther 3(10):1329-1334 (2004).
O'Malley et al. Fluorescent Retrograde Axonal Tracing of the Facial Nerve. The Laryngoscope 116:1792-1797 (2006).
Pan et al. Lipid membrane editing with peptide cargo linkers in cells and synthetic nanostructures. The FASEB Journal 24(8):2928-2937 (2010).
PCT/US2010/031231 International Preliminary Report on Patentability dated Oct. 27, 2011.
PCT/US2010/031231 International Search Report dated Jan. 3, 2011.
PCT/US2011/050411 International Preliminary Report on Patentability dated Mar. 5, 2013.
PCT/US2011/050411 International Search Report and Written Opinion dated Oct. 31, 2012.
PCT/US2017/064329 International Search Report and Written Opinion dated Mar. 30, 2018.
Richmond et al. Efficacy of seven retrograde tracers, compared in multiple-labelling studies of feline motoneurones. Journal of Neuroscience Methods53:35-46 (1994).
Schmerr et al. A diagnostic test for scrapie-infected sheep using a capillary electrophoresis immunoassay with fluorescentlabeled peptides. Electrophoresis 19:409-414 (1998).
Spatola et al. Chemistry and Biochemistry of Amino Acids, Peptides and Proteins. B. Weinstein, ed. New York: Marcel Dekker.7:267-357 (1983).
Tanabe et al. Fibroblast growth factor-inducible-14 is induced in axotomized neurons and promotes neurite outgrowth. J Neurosci 23(29):9675-9686 (2003).
U.S. Appl. No. 13/819,312 Office Action dated Dec. 3, 2014.
U.S. Appl. No. 13/819,312 Office Action dated Jun. 4, 2014.
U.S. Appl. No. 14/736,194 Office Action dated Jan. 20, 2016.
Albrecht et al. Monospecific bivalent scFv-SH: Effects of linker length and location of an engineered cysteine on production, antigen binding activity and free SH accessibility. J Immunol Methods 310(1-2):100-116 (2006).
Li et al. Engineering and optimization of an allosteric biosensor protein for peroxisome proliferator-activated receptor ligands. Biosens Bioelectron 29(1):132-139 (2011).
Zhang et al. Analysis of the relationship between end-to-end distance and activity of single-chain antibody against colorectal carcinoma. Theor Biol Med Model 9:38 (2012).

\* cited by examiner

NERVE LABELING COMPOSITIONS AND USES THEREOF

CROSS-REFERENCE

This application claims the benefit of U.S. Provisional Application No. 62/429,615, filed Dec. 2, 2016, and U.S. Provisional Application No. 62/429,617, filed Dec. 2, 2016, the disclosures of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Dec. 1, 2017, is named 39088-718_601_SL.txt and is 5,523 bytes in size.

SUMMARY OF THE INVENTION

Disclosed herein, in certain embodiments, are nerve delivery molecules. Further disclosed herein, in certain embodiments, are pharmaceutical compositions comprising nerve delivery molecules for targeted delivery of a cargo (e.g., an imaging cargo or a therapeutic cargo) to a nerve site of interest. Also disclosed herein, in certain embodiments, are methods of making the nerve delivery molecules, methods of imaging, and methods of delivery of such molecules.

Disclosed herein, in certain embodiments, are nerve delivery molecules, comprising a peptide sequence according to Formula (I): $[(X_A—X_B—X_C)-L_1]_n-L_2-C$, wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ is absent or is a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is a cargo; and n is an integer between 1 and 5; and wherein $L_1$ is bound to at any position on $X_A—X_B—X_C$, $L_2$ is bound to $L_1$, and C is bound to $L_2$.

Disclosed herein, in certain embodiments, are nerve delivery molecules, comprising a peptide sequence according to Formula (Ia): $[(X_A—X_B—X_C)-L_1]_n-L_2-C$, wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ is absent or is a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is a cargo; and n is an integer between 1 and 5; and wherein $L_1$ is bound to at any position on $X_A—X_B—X_C$, $L_2$ is bound to $L_1$, and C is bound to $L_2$.

Disclosed herein, in certain embodiments, are nerve delivery molecules, comprising a peptide sequence according to Formula (II):

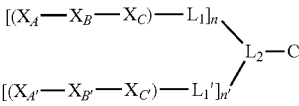

wherein $X_A$ and $X_{A'}$ are each independently selected from: Asp, Arg, Glu, Thr, His, Lys, Phe, or Ser; $X_B$ and $X_{B'}$ are each independently selected from: His, Lys, Thr, Glu, Ser, Asp, Phe, or Arg; $X_C$ and $X_{C'}$ are each independently selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is a cargo; and n and n' are each independently an integer between 1 and 5; and wherein $L_1$ is bound to at any position on $X_A—X_B—X_C$, $L_{1'}$ is bound to at any position on $X_{A'}—X_{B'}—X_{C'}$, $L_2$ is bound to $L_1$ and $L_{1'}$, and C is bound to $L_2$.

Disclosed herein, in certain embodiments, are nerve delivery molecules, comprising a peptide sequence according to Formula (IIa):

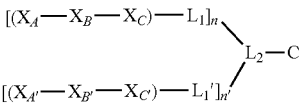

wherein $X_A$ and $X_{A'}$ are each independently selected from: D-Asp, D-Arg, D-Glu, D-Thr, D-His, D-Lys, D-Phe, or D-Ser; $X_B$ and $X_{B'}$ are each independently selected from: D-His, D-Lys, D-Thr, D-Glu, D-Ser, D-Asp, D-Phe, or D-Arg; $X_C$ and $X_{C'}$ are each independently selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is a cargo; and n and n' are each independently an integer between 1 and 5; and wherein $L_1$ is bound to at any position on $X_A—X_B—X_C$, $L_{1'}$ is bound to at any position on $X_{A'}—X_{B'}—X_{C'}$, $L_2$ is bound to $L_1$ and $L_{1'}$, and C is bound to $L_2$.

Disclosed herein, in certain embodiments, is a nerve delivery molecule, comprising a peptide sequence according to Formula (III):

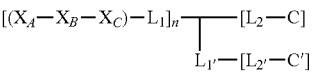

wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently a cargo; and n is an integer between 1 and 5; and wherein $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$.

Disclosed herein, in certain embodiments, are nerve delivery molecules, comprising a peptide sequence according to Formula (IIIa):

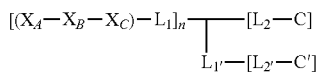

wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently a cargo; and n is an integer between 1 and 5; and wherein $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$.

Disclosed herein, in certain embodiments, are nerve delivery molecules according to NDM-36, NDM-37, NDM-38, NDM-39, NDM-40, NDM-41, NDM-42, NDM-43, NDM-44, NDM-45, NDM-46, NDM-47, NDM-48, NDM-49, NDM-50, NDM-51, NDM-52, NDM-53, NDM-54, NDM-55, NDM-56, NDM-57, NDM-58, NDM-59, NDM-60, NDM-61, NDM-62, NDM-63, NDM-64, NDM-65, NDM-66, NDM-67, NDM-68, NDM-69, NDM-70, NDM-71, NDM-72, NDM-73, NDM-74, NDM-75, NDM-76, NDM-77, NDM-78, NDM-79, NDM-80, NDM-81, NDM-82, NDM-83, NDM-84, NDM-85, NDM-86, NDM-87, NDM-88, NDM-89, NDM-90, NDM-91, NDM-92, NDM-93, NDM-94, NDM-95, NDM-96, NDM-97, NDM-98, NDM-99, T-NDM-1, T-NDM-2, T-NDM-3, T-NDM-4, T-NDM-5, T-NDM-6, T-NDM-7, T-NDM-8, T-NDM-9, T-NDM-10, T-NDM-11, T-NDM-12, T-NDM-13, T-NDM-14, T-NDM-15, T-NDM-16, T-NDM-17, T-NDM-18, T-NDM-19, T-NDM-20, T-NDM-21, T-NDM-22, T-NDM-23, T-NDM-24, T-NDM-25, T-NDM-26, T-NDM-27, T-NDM-28, T-NDM-29, T-NDM-30, T-NDM-31, T-NDM-32, T-NDM-33, T-NDM-34, T-NDM-35, T-NDM-36, T-NDM-37, T-NDM-38, T-NDM-39, T-NDM-40, T-NDM-41, T-NDM-42, T-NDM-43, T-NDM-44, T-NDM-45, T-NDM-46, T-NDM-47, T-NDM-48, T-NDM-49, T-NDM-50, T-NDM-51, T-NDM-52, T-NDM-53 or T-NDM-54.

Disclosed herein, in certain embodiments, is a nerve delivery molecule according to NDM-38.

Disclosed herein, in certain embodiments, is a nerve delivery molecule according to NDM-40.

Disclosed herein, in certain embodiments, is a nerve delivery molecule according to NDM-70.

Disclosed herein, in certain embodiments, is a nerve delivery molecule according to NDM-85.

Disclosed herein, in certain embodiments, are methods of delivering an imaging cargo to a target neuron, nerve, or tissue or external structure associated therewith, comprising contacting the target neuron, nerve, or tissue or external structure associated therewith with a nerve delivery molecule described above.

Disclosed herein, in certain embodiments, are methods of delivering a therapeutic cargo to a target neuron, nerve, or tissue or external structure associated therewith, comprising contacting the target neuron, nerve, or tissue or external structure associated therewith with a nerve delivery molecule described above.

Disclosed herein, in certain embodiments, are methods of visualizing a target neuron, nerve, or tissue or external structure associated therewith in a subject in need thereof, comprising: (i) administering to the subject a nerve delivery molecule described above that localizes to the target neuron, nerve, or tissue or external structure associated therewith in the subject; and (ii) visualizing the imaging cargo.

Disclosed herein, in certain embodiments, are methods of imaging a target neuron, nerve, or tissue or external structure associated therewith, comprising imaging a target neuron, nerve, or tissue or external structure associated therewith contacted with a nerve delivery molecule described above, wherein the cargo is an imaging agent.

Disclosed herein, in certain embodiments, are methods of delivering a therapeutic cargo to a target neuron, nerve, or tissue or external structure associated therewith of interest in a subject in need thereof, comprising: administering to the subject a nerve delivery molecule described above that localizes to the target neuron, nerve, or tissue or external structure associated therewith' in the subject.

Disclosed herein, in certain embodiments, are pharmaceutical compositions comprising: a nerve delivery molecule described above; and a pharmaceutically acceptable carrier or excipient.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows the fluorescence image of cervical or thoracic nerves in a mouse. FIG. 2B shows the reflected light image of same surgical field in the same mouse.

FIG. 3A shows the fluorescence image of cervical and thoracic nerves in a mouse. FIG. 3B shows the reflected light image of same surgical field in the same mouse. Nerves are more clearly visualized utilizing NDM-38.

FIG. 4A shows the fluorescence image of splanchich nerve in a mouse. FIG. 4B shows the reflected light image of same surgical field in the same mouse. Nerves are more clearly visualized utilizing NDM-38.

FIG. 5A shows the fluorescence image of renal nerve in a mouse. FIG. 5B shows the reflected light image of same surgical field in the same mouse.

DETAILED DESCRIPTION OF THE INVENTION

Figure 1:
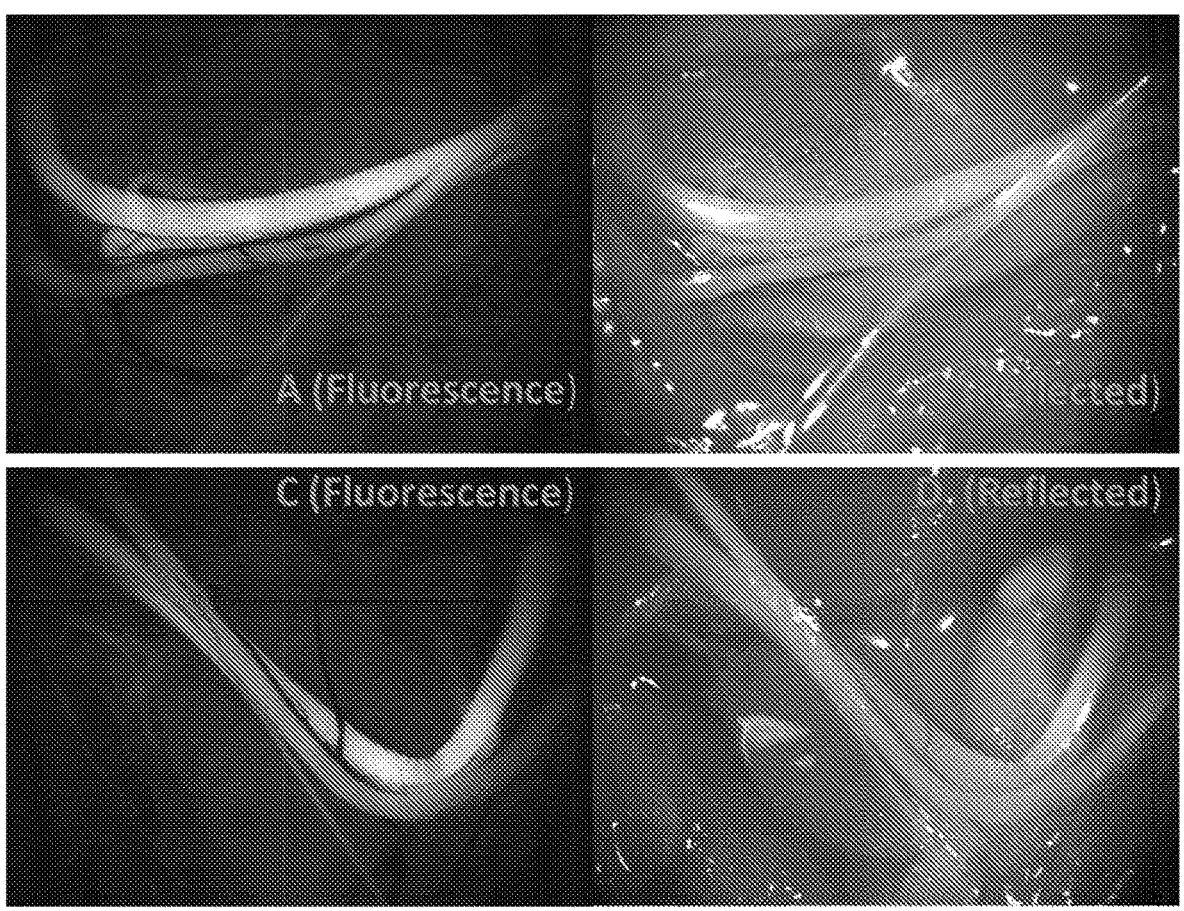
FIG. 1 exemplifies very high fluorescence contrast (nerve/background) of mouse sciatic nerve using NDM-40. Nerve structures are visible in fluorescence images that are not seen in reflected light images. Panels A and C illustrate the fluorescence images of two different sciatic nerves in a mouse. Panels B and D illustrate the reflected light images of the same two different sciatic nerves in a mouse.
Figure 2A:
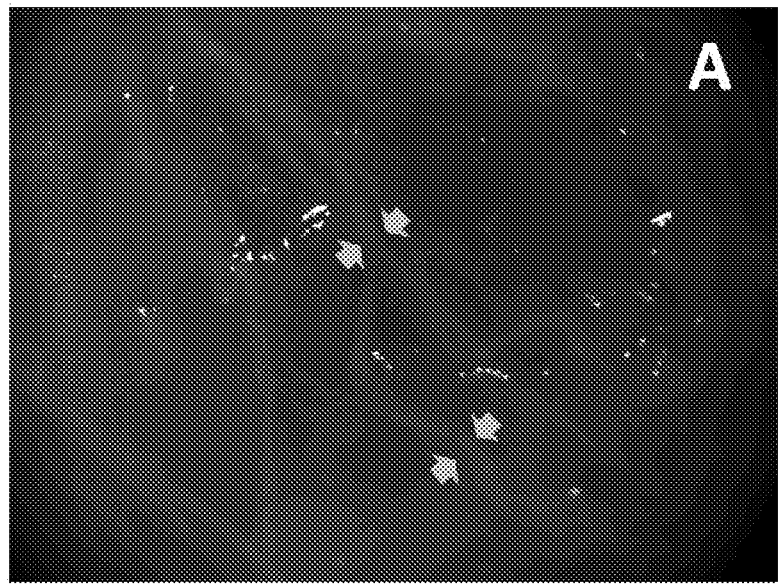
FIG. 2A-FIG. 2B exemplify very high fluorescence contrast (nerve/background) of mouse dorsal subcutaneous cervical or thoracic nerves in mice administered NDM-38. Nerves, indicated by arrows, have significantly enhanced contrast and visualization using fluorescence imaging due to NDM-38 compared to reflected light images.
Figure 2B:
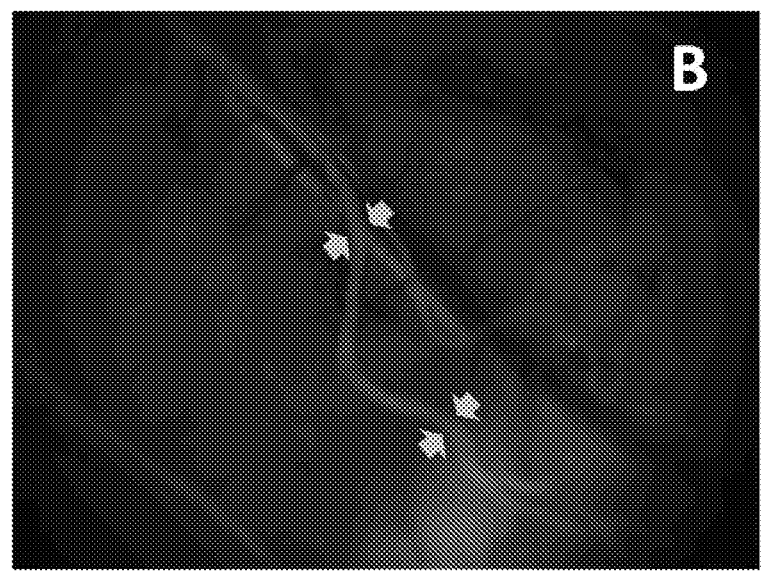
Figure 3A:
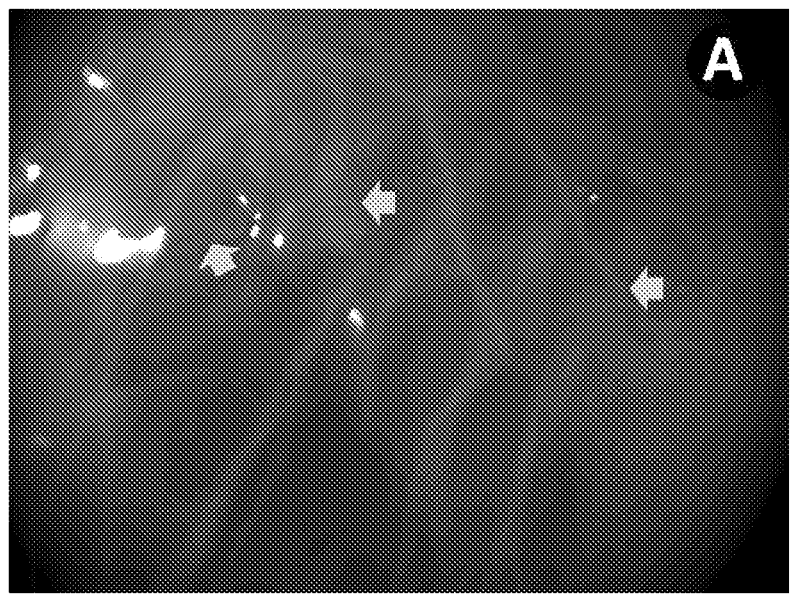
FIG. 3A-FIG. 3B exemplify very high fluorescence contrast (nerve/background) of mouse dorsal subcutaneous cervical and thoracic nerves in mice administered NDM-38. Nerves, indicated by arrows, have significantly enhanced contrast and visualization using fluorescence imaging due to NDM-38 compared to reflected light images.
Figure 3B:
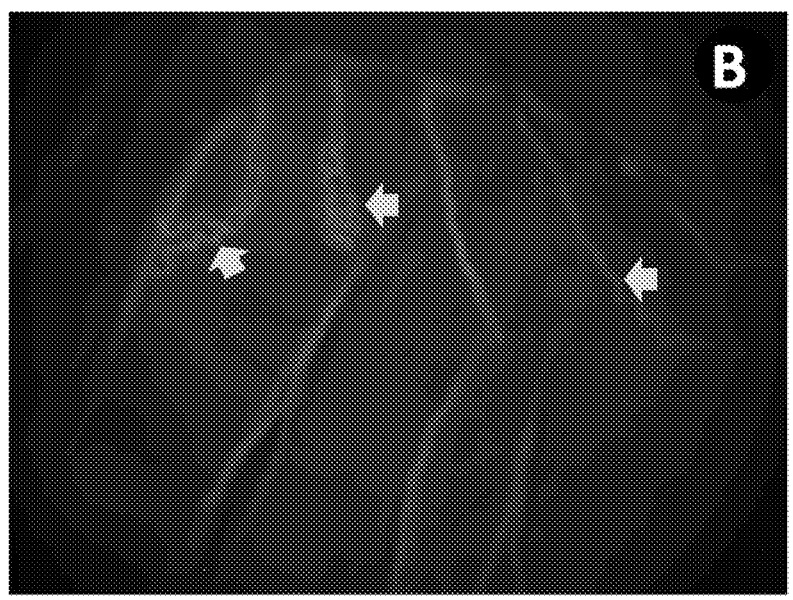
Figure 4A:
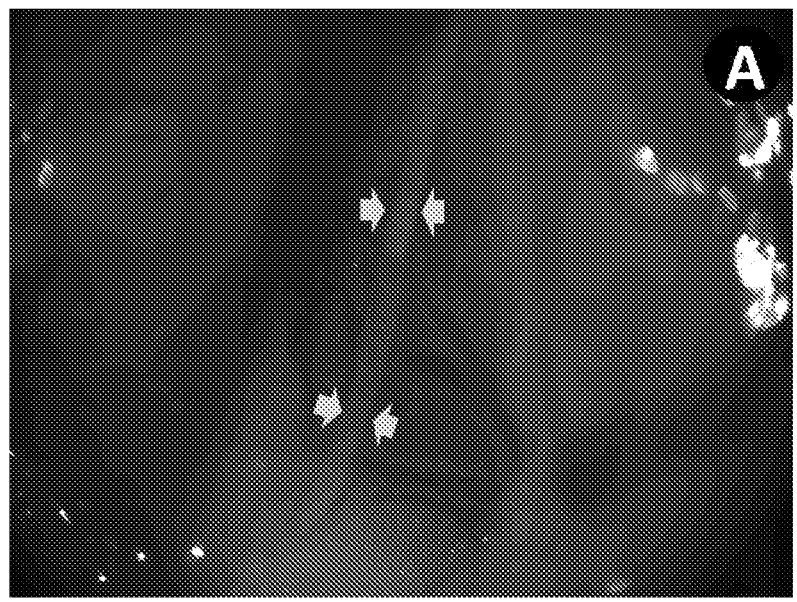
FIG. 4A-FIG. 4B exemplify very high fluorescence contrast (nerve/background) of splanchic nerve using NDM-38. Nerves, indicated by arrows, have significantly enhanced contrast and visualization using fluorescence imaging due to NDM-38 compared to reflected light images.
Figure 4B:
Figure 5A:
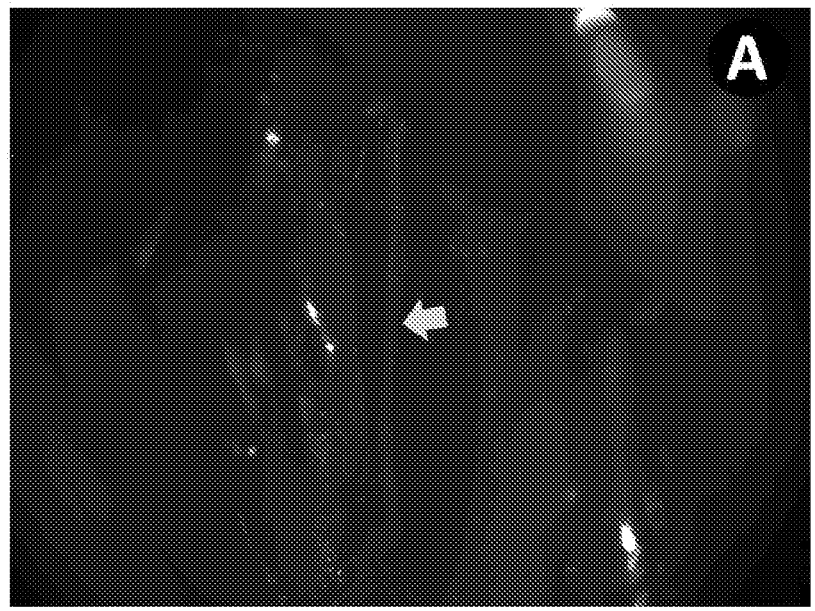
FIG. 5A-FIG. 5B exemplify very high fluorescence contrast (nerve/background) of mouse renal nerve using NDM-38. Nerves, indicated by arrows, have significantly enhanced contrast and visualization using fluorescence imaging due to NDM-38 compared to reflected light images.
Figure 5B:
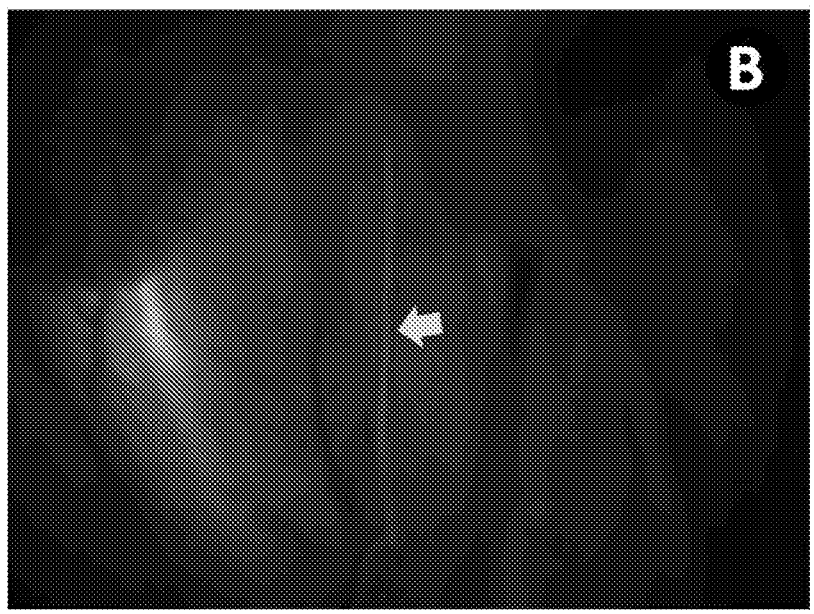

Nerve delivery molecules (NDMs) allow the targeted delivery of imaging agent cargos and/or therapeutic agent cargos to neuron or nerves. In some embodiments, nerve delivery molecules comprise at least one cargo moiety (C) and one or more linkers that connect the cargo to a peptide sequence comprising a $X_A$—$X_B$—$X_C$ motif. In some instances, nerve delivery molecules are subjected to rapid pharmacokinetic clearance with short plasma half-life, broad distribution, and slow wash out from multiple non-target tissues with non-specific uptake. Thus, there is a need for a nerve delivery molecule with improved biostability and enhanced plasma life, and accumulation in target tissue relative to non-target tissue. For imaging cargos, there is a need for increased contrast in target tissue relative to background tissue.

Certain Terminology

As used herein, the following terms have the meanings ascribed to them unless specified otherwise.

As used herein, the term "delivery molecule" refers to any agent (e.g., peptide, protein, nucleic acid polymer, aptamer, or small molecule) that associates with (e.g., binds to) a target of interest. The target of interest may be a tissue, a cell, a cellular structure (e.g., an organelle), a protein, a peptide, a polysaccharide, or a nucleic acid polymer. In some embodiments, the delivery molecule is any agent that associates with (e.g., binds to) one or more neurons, nerves, or tissues or structures associated therewith.

The terms "polypeptide," "peptide" and "protein" are used interchangeably herein to refer to a polymer of amino acid residues. The terms apply to naturally occurring amino acid polymers as well as amino acid polymers in which one or more amino acid residues is a non-naturally occurring amino acid (e.g., an amino acid analog). The terms encompass amino acid chains of any length, including full length proteins (i.e., antigens), wherein the amino acid residues are linked by covalent peptide bonds.

Where an amino acid sequence is provided herein, L-, D-, or beta amino acid versions of the sequence are also contemplated as well as retro, inversion, and retro-inversion isoforms. Peptides also include amino acid polymers in which one or more amino acid residues is an artificial chemical analogue of a corresponding naturally occurring amino acid, as well as to naturally occurring amino acid polymers. In addition, the term applies to amino acids joined by a peptide linkage or by other modified linkages (e.g., where the peptide bond is replaced by an α-ester, a β-ester, a thioamide, phosphonamide, carbamate, hydroxylate, and the like (see, e.g., Spatola, (1983) *Chem. Biochem. Amino Acids and Proteins* 7: 267-357), where the amide is replaced with a saturated amine (see, e.g., Skiles et al., U.S. Pat. No. 4,496,542, which is incorporated herein by reference, and Kaltenbronn et al., (1990) Pp. 969-970 in Proc. 11th American Peptide Symposium, ESCOM Science Publishers, The Netherlands, and the like)).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acids are grouped as hydrophobic amino acids, polar amino acids, non-polar amino acids, and charged amino acids. Hydrophobic amino acids include small hydrophobic amino acids and large hydrophobic amino acids. Small hydrophobic amino acid can be glycine, alanine, proline, and analogs thereof. Large hydrophobic amino acids can be valine, leucine, isoleucine, phenylalanine, methionine, tryptophan, and analogs thereof. Polar amino acids can be serine, threonine, asparagine, glutamine, cysteine, tyrosine, and analogs thereof. Non-polar amino acids can be glycine, alanine, valine, leucine, isoleucine, methionine, phenylalanine, tryptophan, proline, and analogs thereof. Charged amino acids can be lysine, arginine, histidine, aspartate, glutamate, and analogs thereof. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids are either D amino acids or L amino acids.

In some instances, one or more of the amino acid residues in the Formulas I, II and III described herein is modified to a polar amino acid. As discussed above, exemplary polar amino acids include serine, threonine, asparagine, glutamine, cysteine, tyrosine, and analogs thereof.

In other instances, one or more of the amino acid residues in the Formulas I, II and III described herein is modified to a non-polar amino acid. Exemplary non-polar amino acids include glycine, alanine, valine, leucine, isoleucine, methionine, phenylalanine, tryptophan, proline, and analogs thereof.

In some cases, one or more of the amino acid residues in the Formulas I, II and III described herein is modified a hydrophobic amino acids. Exemplary hydrophobic amino acids include small hydrophobic amino acid such as glycine, alanine, proline, and analogs thereof, and large hydrophobic amino acids such as valine, leucine, isoleucine, phenylalanine, methionine, tryptophan, and analogs thereof.

In other cases, one or more of the amino acid residues in the Formulas I, II and III described herein is modified to a charged amino acid. Exemplary charged amino acids include lysine, arginine, histidine, aspartate, glutamate, and analogs thereof.

In some embodiments, one of skill will recognize that one or more of the amino acid residues in the Formulas I, II and III described herein may be conservatively modified. Conservative substitution tables providing functionally similar amino acids are well known in the art. For examples, the following table illustrates exemplary conservative substitutions.

| Original Residue | Conserved Substitutions |
| --- | --- |
| Ala | Ser, Gly, Thr, Cys, Val |
| Arg | Lys, Gln, His, Asn, Glu |
| Asn | Gln, His, Asp, Lys, Ser, Thr, Arg, Glu |
| Asp | Glu, Asn, Gln, Ser |
| Cys | Ser, Ala |
| Gln | Asn, Arg, Glu, His, Lys Met, Asp, Ser |
| Glu | Asp, Gln, Lys, Arg, Asn, His, Ser |
| Gly | Pro, Ala, Ser |
| His | Asn, Gln, Arg, Tyr, Glu |
| Ile | Leu, Val, Met, Phe |
| Leu | Ile, Val, Met, Phe |

In some cases, such conservatively modified variants are in addition to and do not exclude polymorphic variants, interspecies homologs, and alleles of the invention.

The term PEG means polyethylene glycol polymer. In some embodiments, the PEG is a polydisperse. In some embodiments, the PEG is a discreet unit.

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

The term "pharmaceutically acceptable" as used herein, refers to a material that does not abrogate the biological activity or properties of the agents described herein, and is relatively nontoxic (i.e., the toxicity of the material significantly outweighs the benefit of the material). In some instances, a pharmaceutically acceptable material may be administered to an individual without causing or minimally causing undesirable biological effects or significantly interacting in a deleterious manner with any of the components of the composition in which it is contained.

The term "surgery" as used herein, refers to any method used to manipulate, change, or cause an effect by a physical intervention. These methods include, but are not limited to open surgery, endoscopic surgery, laparoscopic surgery, minimally invasive surgery, robotic surgery, any procedures that may affect any neuron or nerve, such as placement of retractors during spinal surgery, electrically conducting cardiac tissue or nerve ablation, epidural injection, intrathecal injections, neuron or nerve blocks, implantation of devices such as neuron or nerve stimulators and implantation of pumps. The term "guided surgery" as used herein, refers to any surgical procedure where the surgeon employs an imaging cargo to guide the surgery.

Nerve Delivery Molecules (NDMs)

Disclosed herein, in certain embodiments, are nerve delivery molecules comprising a $X_A$—$X_B$—$X_C$ motif conjugated to a cargo (e.g., an imaging cargo or a therapeutic cargo) either directly or indirectly via a linker.

Nerve Delivery Molecules of Formula (I)

In some embodiments, a nerve delivery molecule described herein comprises a peptide sequence according to Formula (I):

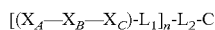

$[(X_A—X_B—X_C)\text{-}L_1]_n\text{-}L_2\text{-}C$ wherein, $X_A$ is selected from: Asp, Arg, Glu, Thr, His, Lys, Phe, or Ser;

$X_B$ is selected from: His, Lys, Thr, Glu, Ser, Asp, Phe, or Arg;

$X_C$ is selected from: Asp, Arg, Glu, Thr, His, Lys, Phe, or Ser;

$L_1$ is absent or is a linker comprising:
 i) 1-10 Ala residues (SEQ ID NO: 1);
 ii) 3-10 Gly residues (SEQ ID NO: 2);
 iii) a polymer comprising 1-10 ethylene glycol units; or
 iv) an aliphatic chain comprising a chain length of 1-10 carbon atoms;

$L_2$ is a linker comprising:
 i) an amino acid selected from: Lys, Glu, Cys, or Asp;
 ii) a polymer comprising 1-10 ethylene glycol units; or
 iii) an aliphatic chain comprising a chain length of 1-10 carbon atoms;

C is a cargo; and n is an integer between 1 and 5; and wherein $L_1$ is bound to at any position on $X_A$—$X_B$—$X_C$, $L_2$ is bound to $L_1$, and C is bound to $L_2$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, the nerve delivery molecule of Formula (I) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ comprises an L-amino acid. In some embodiments, $L_1$ comprises a D-amino acid. In some embodiments, $L_1$ comprises 10 amino acids. In some embodiments, $L_1$ comprises 9 amino acids. In some embodiments, $L_1$ comprises 8 amino acids. In some embodiments, $L_1$ comprises 7 amino acids. In some embodiments, $L_1$ comprises 6 amino acids. In some embodiments, $L_1$ comprises 5 amino acids. In some embodiments, $L_1$ comprises 4 amino acids. In some embodiments, $L_1$ comprises 3 amino acids. In some embodiments, $L_1$ comprises 2 amino acids. In some embodiments, $L_1$ comprises 1 amino acid. In some embodiments, $L_1$ comprises a series of 10 Ala residues (SEQ ID NO: 3). In some embodiments, $L_1$ comprises a series of 9 Ala residues (SEQ ID NO: 4). In some embodiments, $L_1$ comprises a series of 8 Ala residues (SEQ ID NO: 5). In some embodiments, $L_1$ comprises a series of 7 Ala residues (SEQ ID NO: 6). In some embodiments, $L_1$ comprises a series of 6 Ala residues (SEQ ID NO: 7). In some embodiments, $L_1$ comprises a series of 5 Ala residues (SEQ ID NO: 8). In some embodiments, $L_1$ comprises a series of 4 Ala residues (SEQ ID NO: 9). In some embodiments, $L_1$ comprises a series of 3 Ala residues. In some embodiments, $L_1$ comprises a series of 2 Ala residues. In some embodiments, $L_1$ comprises a series of 1 Ala residue. In some embodiments, $L_1$ comprises a series of 10 Gly residues (SEQ ID NO: 10). In some embodiments, $L_1$ comprises a series of 9 Gly residues (SEQ ID NO: 21). In some embodiments, $L_1$ comprises a series of 8 Gly residues (SEQ ID NO: 22). In some embodiments, $L_1$ comprises a series of 7 Gly residues (SEQ ID NO: 23). In some embodiments, $L_1$ comprises a series of 6 Gly residues (SEQ ID NO: 24). In some embodiments, $L_1$ comprises a series of 5 Gly residues (SEQ ID NO: 11). In some embodiments, $L_1$ comprises a series of 4 Gly residues (SEQ ID NO: 12). In some embodiments, $L_1$ comprises a series of 3 Gly residues.

In some embodiments, $L_1$ comprises a polymer comprising 10 ethylene glycol units. In some embodiments, $L_1$ comprises a polymer comprising 9 ethylene glycol units. In some embodiments, $L_1$ comprises a polymer comprising 8 ethylene glycol units. In some embodiments, $L_1$ comprises a polymer comprising 7 ethylene glycol units. In some embodiments, $L_1$ comprises a polymer comprising 6 ethylene glycol units. In some embodiments, $L_1$ comprises a polymer comprising 5 ethylene glycol units. In some embodiments, $L_1$ comprises a polymer comprising 4 ethylene glycol units. In some embodiments, $L_1$ comprises a polymer comprising 3 ethylene glycol units. In some embodiments, $L_1$ comprises a polymer comprising 2 ethylene glycol units. In some embodiments, $L_1$ comprises a polymer comprising 1 ethylene glycol unit.

In some embodiments, $L_1$ comprises an aliphatic chain comprising a chain length of 10 carbon atoms. In some embodiments, $L_1$ comprises an aliphatic chain comprising a chain length of 9 carbon atoms. In some embodiments, $L_1$ comprises an aliphatic chain comprising a chain length of 8 carbon atoms. In some embodiments, $L_1$ comprises an aliphatic chain comprising a chain length of 7 carbon atoms. In some embodiments, $L_1$ comprises an aliphatic chain comprising a chain length of 6 carbon atoms. In some embodiments, $L_1$ comprises an aliphatic chain comprising a chain length of 5 carbon atoms. In some embodiments, $L_1$ comprises an aliphatic chain comprising a chain length of 4 carbon atoms. In some embodiments, $L_1$ comprises an aliphatic chain comprising a chain length of 3 carbon atoms. In some embodiments, $L_1$ comprises an aliphatic chain comprising a chain length of 2 carbon atoms. In some embodiments, $L_1$ comprises an aliphatic chain comprising a chain length of 1 carbon atom.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_2$ comprises a polymer comprising 10 ethylene glycol units. In some embodiments, $L_2$ comprises a polymer comprising 9 ethylene glycol units. In some embodiments, $L_2$ comprises a polymer comprising 8 ethylene glycol units. In some embodiments, $L_2$ comprises a polymer comprising 7 ethylene glycol units. In some embodiments, $L_2$ comprises a polymer comprising 6 ethylene glycol units. In some embodiments, $L_2$ comprises a polymer comprising 5 ethylene glycol units. In some embodiments, $L_2$ comprises a polymer comprising 4 ethylene glycol units. In some embodiments, $L_2$ comprises a polymer comprising 3 ethylene glycol units. In some embodiments, $L_2$ comprises a polymer comprising 2 ethylene glycol units. In some embodiments, $L_2$ comprises a polymer comprising 1 ethylene glycol unit.

In some embodiments, $L_2$ comprises an aliphatic chain comprising a chain length of 10 carbon atoms. In some embodiments, $L_2$ comprises an aliphatic chain comprising a chain length of 9 carbon atoms. In some embodiments, $L_2$ comprises an aliphatic chain comprising a chain length of 8 carbon atoms. In some embodiments, $L_2$ comprises an aliphatic chain comprising a chain length of 7 carbon atoms. In some embodiments, $L_2$ comprises an aliphatic chain comprising a chain length of 6 carbon atoms. In some embodiments, $L_2$ comprises an aliphatic chain comprising a chain length of 5 carbon atoms. In some embodiments, $L_2$ comprises an aliphatic chain comprising a chain length of 4 carbon atoms. In some embodiments, $L_2$ comprises an aliphatic chain comprising a chain length of 3 carbon atoms. In some embodiments, $L_2$ comprises an aliphatic chain comprising a chain length of 2 carbon atoms. In some embodiments, $L_2$ comprises an aliphatic chain comprising a chain length of 1 carbon atom.

In some embodiments, $L_1$ comprises a series of 3 Ala residues and $L_2$ comprises an amino acid selected from Lys or Cys. In some embodiments, $L_1$ comprises a series of 2 Ala residues and $L_2$ comprises an amino acid selected from Lys or Cys. In some embodiments, $L_1$ comprises a series of 3 Gly residues and $L_2$ comprises an amino acid selected from Lys or Cys. In some embodiments, $L_1$ comprises a series of 3 Ala residues and $L_2$ comprises an amino acid selected from D-Lys or D-Cys. In some embodiments, $L_1$ comprises a series of 2 Ala residues and $L_2$ comprises an amino acid selected from D-Lys or D-Cys. In some embodiments, $L_1$ comprises a series of 3 Gly residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

In some embodiments, the cargo C is an imaging cargo. In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4, 7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the cargo C is a therapeutic cargo. In some embodiments, the therapeutic cargo comprises comprises a chemotherapeutic agent, a cytotoxin, a steroid, an immunotherapeutic agent, a targeted therapy agent, or an anti-inflammatory agent. In some embodiments, the therapeutic agent comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is a cargo that promotes regeneration of neuron or nerve tissue. In some embodiments, the therapeutic cargo is a growth factor.

In some embodiments, the therapeutic cargo is a local anesthetic.

In some embodiments, the therapeutic cargo is an antiepileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

Nerve Delivery Molecules of Formula (Ia)

In some embodiments, a nerve delivery molecule described herein comprises a peptide sequence according to the Formula (Ia):

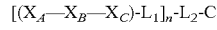

wherein, $X_A$ is selected from: D-Asp, D-Arg, D-Glu, D-Thr, D-His, D-Lys, D-Phe, or D-Ser;

$X_B$ is selected from: D-His, D-Lys, D-Thr, D-Glu, D-Ser, D-Asp, D-Phe, or D-Arg;

$X_C$ is selected from: D-Asp, D-Arg, D-Glu, D-Thr, D-His, D-Lys, D-Phe, or D-Ser;

$L_1$ is absent or is a linker comprising:
  i) 1-10 D-Ala residues;
  ii) a polymer comprising 1-10 ethylene glycol units; or
  iii) an aliphatic chain comprising a chain length of 1-10 carbon atoms;

$L_2$ is a linker comprising:
  i) an amino acid selected from: Lys, Glu, Cys, or Asp;
  ii) a polymer comprising 1-10 ethylene glycol units; or
  iii) an aliphatic chain comprising a chain length of 1-10 carbon atoms;

C is a cargo; and n is an integer between 1 and 5; and wherein $L_1$ is bound to at any position on $X_A$—$X_B$—$X_C$, $L_2$ is bound to $L_1$, and C is bound to $L_2$.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

As described supra, $L_1$ comprises 1-10 amino acids. In some embodiments, $L_1$ comprises 10 amino acids. In some embodiments, $L_1$ comprises 9 amino acids. In some embodiments, $L_1$ comprises 8 amino acids. In some embodiments, $L_1$ comprises 7 amino acids. In some embodiments, $L_1$ comprises 6 amino acids. In some embodiments, $L_1$ comprises 5 amino acids. In some embodiments, $L_1$ comprises 4 amino acids. In some embodiments, $L_1$ comprises 3 amino acids. In some embodiments, $L_1$ comprises 2 amino acids. In some embodiments, $L_1$ comprises 1 amino acid. In some embodiments, $L_1$ comprises a series of 10 D-Ala residues. In some embodiments, $L_1$ comprises a series of 9 D-Ala residues. In some embodiments, $L_1$ comprises a series of 8 D-Ala residues. In some embodiments, $L_1$ comprises a series of 7 D-Ala residues. In some embodiments, $L_1$ comprises a series of 6 D-Ala residues. In some embodiments, $L_1$ comprises a series of 5 D-Ala residues. In some embodiments, $L_1$ comprises a series of 4 D-Ala residues. In some embodiments, $L_1$ comprises a series of 3 D-Ala residues. In some embodiments, $L_1$ comprises a series of 2 D-Ala residues. In some embodiments, $L_1$ comprises a series of 1 D-Ala residue.

In some embodiments, $L_1$ comprises a polymer comprising 10 ethylene glycol units. In some embodiments, $L_1$ comprises a polymer comprising 9 ethylene glycol units. In some embodiments, $L_1$ comprises a polymer comprising 8 ethylene glycol units. In some embodiments, $L_1$ comprises a polymer comprising 7 ethylene glycol units. In some embodiments, $L_1$ comprises a polymer comprising 6 ethylene glycol units. In some embodiments, $L_1$ comprises a polymer comprising 5 ethylene glycol units. In some embodiments, $L_1$ comprises a polymer comprising 4 ethylene glycol units. In some embodiments, $L_1$ comprises a polymer comprising 3 ethylene glycol units. In some embodiments, $L_1$ comprises a polymer comprising 2 ethylene glycol units. In some embodiments, $L_1$ comprises a polymer comprising 1 ethylene glycol unit.

In some embodiments, $L_1$ comprises an aliphatic chain comprising a chain length of 10 carbon atoms. In some embodiments, $L_1$ comprises an aliphatic chain comprising a chain length of 9 carbon atoms. In some embodiments, $L_1$ comprises an aliphatic chain comprising a chain length of 8 carbon atoms. In some embodiments, $L_1$ comprises an aliphatic chain comprising a chain length of 7 carbon atoms. In some embodiments, $L_1$ comprises an aliphatic chain comprising a chain length of 6 carbon atoms. In some embodiments, $L_1$ comprises an aliphatic chain comprising a chain length of 5 carbon atoms. In some embodiments, $L_1$ comprises an aliphatic chain comprising a chain length of 4 carbon atoms. In some embodiments, $L_1$ comprises an aliphatic chain comprising a chain length of 3 carbon atoms. In some embodiments, $L_1$ comprises an aliphatic chain comprising a chain length of 2 carbon atoms. In some embodiments, $L_1$ comprises an aliphatic chain comprising a chain length of 1 carbon atom.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_2$ comprises a polymer comprising 10 ethylene glycol units. In some embodiments, $L_2$ comprises a polymer comprising 9 ethylene glycol units. In some embodiments, $L_2$ comprises a polymer comprising 8 ethylene glycol units. In some embodiments, $L_2$ comprises a polymer comprising 7 ethylene glycol units. In some embodiments, $L_2$ comprises a polymer comprising 6 ethylene glycol units. In some embodiments, $L_2$ comprises a polymer comprising 5 ethylene glycol units. In some embodiments, $L_2$ comprises a polymer comprising 4 ethylene glycol units. In some embodiments, $L_2$ comprises a polymer comprising 3 ethylene glycol units. In some embodiments, $L_2$ comprises a polymer comprising 2 ethylene glycol units. In some embodiments, $L_2$ comprises a polymer comprising 1 ethylene glycol unit.

In some embodiments, $L_2$ comprises an aliphatic chain comprising a chain length of 10 carbon atoms. In some embodiments, $L_2$ comprises an aliphatic chain comprising a chain length of 9 carbon atoms. In some embodiments, $L_2$ comprises an aliphatic chain comprising a chain length of 8 carbon atoms. In some embodiments, $L_2$ comprises an aliphatic chain comprising a chain length of 7 carbon atoms. In some embodiments, $L_2$ comprises an aliphatic chain comprising a chain length of 6 carbon atoms. In some embodiments, $L_2$ comprises an aliphatic chain comprising a chain length of 5 carbon atoms. In some embodiments, $L_2$ comprises an aliphatic chain comprising a chain length of 4 carbon atoms. In some embodiments, $L_2$ comprises an aliphatic chain comprising a chain length of 3 carbon atoms. In some embodiments, $L_2$ comprises an aliphatic chain comprising a chain length of 2 carbon atoms. In some embodiments, $L_2$ comprises an aliphatic chain comprising a chain length of 1 carbon atom.

In some embodiments, $L_1$ comprises a series of 3 D-Ala residues and $L_2$ comprises an amino acid selected from Lys or Cys. In some embodiments, $L_1$ comprises a series of 2 D-Ala residues and $L_2$ comprises an amino acid selected from Lys or Cys. In some embodiments, $L_1$ comprises a series of 3 D-Ala residues and $L_2$ comprises an amino acid selected from D-Lys or D-Cys. In some embodiments, $L_1$ comprises a series of 2 D-Ala residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

In some embodiments, the cargo C is an imaging cargo. In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complex, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the cargo C is a therapeutic cargo. In some embodiments, the therapeutic cargo comprises comprises a chemotherapeutic agent, a cytotoxin, a steroid, an immunotherapeutic agent, a targeted therapy agent, or an anti-inflammatory agent. In some embodiments, the therapeutic agent comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is a cargo that promotes regeneration of neuron or nerve tissue. In some embodiments, the therapeutic cargo is a growth factor.

In some embodiments, the therapeutic cargo is a local anesthetic.

In some embodiments, the therapeutic cargo is an antiepileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

Nerve Delivery Molecules of Formula (II)

In some embodiments, a nerve delivery molecule described herein comprises a peptide sequence according to the Formula (II):

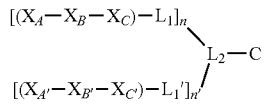

wherein, $X_A$ and $X_{A'}$ are each independently selected from: Asp, Arg, Glu, Thr, His, Lys, Phe, or Ser;

$X_B$ and $X_{B'}$ are each independently selected from: His, Lys, Thr, Glu, Ser, Asp, Phe, or Arg;

$X_C$ and $X_{C'}$ are each independently selected from: Asp, Arg, Glu, Thr, His, Lys, Phe, or Ser;

$L_1$ and $L_{1'}$ are each independently absent or are each independently a linker comprising: i) 1-10 Ala residues (SEQ ID NO: 1);

ii) 3-10 Gly residues (SEQ ID NO: 2);

iii) a polymer comprising 1-10 ethylene glycol units; or iv) an aliphatic chain comprising a chain length of 1-10 carbon atoms;

$L_2$ is a linker comprising:

i) an amino acid selected from: Lys, Glu, Cys, or Asp;

ii) a polymer comprising 1-10 ethylene glycol units; or iii) an aliphatic chain comprising a chain length of 1-10 carbon atoms;

C is a cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_{A'}$ is selected from: Arg, His, or Lys. In some embodiments, $X_{A'}$ is selected from: Asp, Glu, Thr or Ser. In some embodiments, $X_{A'}$ is selected from: Asp or Glu. In some embodiments, $X_{A'}$ is selected from: Thr or Ser. In some embodiments, $X_{A'}$ is selected from: Glu or Thr. In some embodiments, $X_{A'}$ is Glu. In some embodiments, $X_{A'}$ is Thr. In some embodiments, $X_{A'}$ is Asp. In some embodiments, $X_{A'}$ is Arg. In some embodiments, $X_{A'}$ is His. In some embodiments, $X_{A'}$ is Lys. In some embodiments, $X_{A'}$ is Ser. In some embodiments, $X_{A'}$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_{B'}$ is selected from: His, Lys, Glu or Arg. In some embodiments, $X_{B'}$ is selected from: Thr, Glu, Ser or Asp. In some embodiments, $X_{B'}$ is selected from: His, Thr, Ser or Asp. In some embodiments, $X_{B'}$ is His. In some embodiments, $X_{B'}$ is Lys. In some embodiments, $X_{B'}$ is Thr. In some embodiments, $X_{B'}$ is Glu. In some embodiments, $X_{B'}$ is Ser. In some embodiments, $X_{B'}$ is Asp. In some embodiments, $X_{B'}$ is Arg. In some embodiments, $X_{B'}$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_{C'}$ is selected from: Arg, His or Lys. In some embodiments, $X_{C'}$ is selected from: Asp, Glu, Thr or Ser. In some embodiments, $X_{C'}$ is selected from: Asp or Glu. In some embodiments, $X_{C'}$ is selected from: Thr or Ser. In some embodiments, $X_{C'}$ is selected from: Glu or Thr. In some embodiments, $X_{C'}$ is Glu. In some embodiments, $X_{C'}$ is Thr. In some embodiments, $X_{C'}$ is Asp. In some embodiments, $X_{C'}$ is Arg. In some embodiments, $X_{C'}$ is His. In some embodiments, $X_{C'}$ is Lys. In some embodiments, $X_{C'}$ is Ser. In some embodiments, $X_{C'}$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, $X_{A'}$—$X_{B'}$—$X_{C'}$ is EHT or THE. In some instances, $X_{A'}$—$X_{B'}$—$X_{C'}$ is EHT. In other instances, $X_{A'}$—$X_{B'}$—$X_{C'}$ is THE.

In some embodiments, the nerve delivery molecule of Formula (II) comprises a naturally occurring amino acid or a non-naturally occurring amino acid. In some embodiments, $X_A$, $X_B$, $X_C$, $X_{A'}$, $X_{B'}$, and $X_{C'}$ each independently comprises a D-amino acid. In some embodiments, the amino acid residues of $X_A$, $X_B$ and $X_C$ are D-amino acids. In some embodiments, the amino acid residues of $X_{A'}$, $X_{B'}$ and $X_{C'}$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 10 amino acids. In some embodiments, $L_1$ and $L_{1'}$ each independently comprises 9 amino acids. In some embodiments, $L_1$ and $L_{1'}$ each independently comprises 8 amino acids. In some embodiments, $L_1$ and $L_{1'}$ each independently comprises 7 amino acids. In some embodiments, $L_1$ and $L_{1'}$ each independently comprises 6 amino acids. In some embodiments, $L_1$ and $L_{1'}$ each independently comprises 5 amino acids. In some embodiments, $L_1$ and $L_{1'}$ each independently comprises 4 amino acids. In some embodiments, $L_1$ and $L_{1'}$ each independently comprises 3 amino acids. In some embodiments, $L_1$ and $L_{1'}$ each independently comprises 2 amino acids. In some embodiments, $L_1$ and $L_{1'}$ each independently comprises 1 amino acid. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_1$ and $L_{1'}$ each independently comprises a polymer comprising 10 ethylene glycol units. In some embodiments, $L_1$ and $L_{1'}$ each independently comprises a polymer comprising 9 ethylene glycol units. In some embodiments, $L_1$ and $L_{1'}$ each independently comprises a polymer comprising 8 ethylene glycol units. In some embodiments, $L_1$ and $L_{1'}$ each independently comprises a polymer comprising 7 ethylene glycol units. In some embodiments, $L_1$ and $L_{1'}$ each independently comprises a polymer comprising 6 ethylene glycol units. In some embodiments, $L_1$ and $L_{1'}$ each independently comprises a polymer comprising 5 ethylene glycol units. In some embodiments, $L_1$ and $L_{1'}$ each independently comprises a polymer comprising 4 ethylene glycol units. In some embodiments, $L_1$ and $L_{1'}$ each independently comprises a polymer comprising 3 ethylene glycol units. In some embodiments, $L_1$ and $L_{1'}$ each independently comprises a polymer comprising 2 ethylene glycol units. In some embodiments, $L_1$ and $L_{1'}$ each independently comprises a polymer comprising 1 ethylene glycol unit.

In some embodiments, $L_1$ and $L_{1'}$ each independently comprises an aliphatic chain comprising a chain length of 10 carbon atoms. In some embodiments, $L_1$ and $L_{1'}$ each independently comprises an aliphatic chain comprising a chain length of 9 carbon atoms. In some embodiments, $L_1$ and $L_{1'}$ each independently comprises an aliphatic chain comprising a chain length of 8 carbon atoms. In some embodiments, $L_1$ and $L_{1'}$ each independently comprises an aliphatic chain comprising a chain length of 7 carbon atoms. In some embodiments, $L_1$ and $L_{1'}$ each independently comprises an aliphatic chain comprising a chain length of 6 carbon atoms. In some embodiments, $L_1$ and $L_{1'}$ each independently comprises an aliphatic chain comprising a chain length of 5 carbon atoms. In some embodiments, $L_1$ and $L_{1'}$ each independently comprises an aliphatic chain comprising a chain length of 4 carbon atoms. In some embodiments, $L_1$ and $L_{1'}$ each independently comprises an aliphatic chain comprising a chain length of 3 carbon atoms. In some embodiments, $L_1$ and $L_{1'}$ each independently comprises an aliphatic chain comprising a chain length of 2 carbon atoms. In some embodiments, $L_1$ and $L_{1'}$ each independently comprises an aliphatic chain comprising a chain length of 1 carbon atom.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_2$ comprises a polymer comprising 10 ethylene glycol units. In some embodiments, $L_2$ comprises a polymer comprising 9 ethylene glycol units. In some embodiments, $L_2$ comprises a polymer comprising 8 ethylene glycol units. In some embodiments, $L_2$ comprises a polymer comprising 7 ethylene glycol units. In some embodiments, $L_2$ comprises a polymer comprising 6 ethylene glycol units. In some embodiments, $L_2$ comprises a polymer comprising 5 ethylene glycol units. In some embodiments, $L_2$ comprises a polymer comprising 4 ethylene glycol units. In some embodiments, $L_2$ comprises a polymer comprising 3 ethylene glycol units. In some embodiments, $L_2$ comprises a polymer comprising 2 ethylene glycol units. In some embodiments, $L_2$ comprises a polymer comprising 1 ethylene glycol unit.

In some embodiments, $L_2$ comprises an aliphatic chain comprising a chain length of 10 carbon atoms. In some embodiments, $L_2$ comprises an aliphatic chain comprising a chain length of 9 carbon atoms. In some embodiments, $L_2$ comprises an aliphatic chain comprising a chain length of 8 carbon atoms. In some embodiments, $L_2$ comprises an aliphatic chain comprising a chain length of 7 carbon atoms. In some embodiments, $L_2$ comprises an aliphatic chain comprising a chain length of 6 carbon atoms. In some embodiments, $L_2$ comprises an aliphatic chain comprising a chain length of 5 carbon atoms. In some embodiments, $L_2$ comprises an aliphatic chain comprising a chain length of 4 carbon atoms. In some embodiments, $L_2$ comprises an aliphatic chain comprising a chain length of 3 carbon atoms. In some embodiments, $L_2$ comprises an aliphatic chain comprising a chain length of 2 carbon atoms. In some embodiments, $L_2$ comprises an aliphatic chain comprising a chain length of 1 carbon atom.

In some embodiments, $L_1$ and $L_{1'}$ each independently comprises a series of 3 Ala residues and $L_2$ comprises an amino acid selected from Lys or Cys. In some embodiments, $L_1$ and $L_{1'}$ each independently comprises a series of 2 Ala residues and $L_2$ comprises an amino acid selected from Lys or Cys. In some embodiments, $L_1$ and $L_{1'}$ each independently comprises a series of 3 Gly residues and $L_2$ comprises an amino acid selected from Lys or Cys. In some embodiments, $L_1$ and $L_{1'}$ each independently comprises a series of 3 Ala residues and $L_2$ comprises an amino acid selected from D-Lys or D-Cys. In some embodiments, $L_1$ and $L_{1'}$ each independently comprises a series of 2 Ala residues and $L_2$ comprises an amino acid selected from D-Lys or D-Cys. In some embodiments, $L_1$ and $L_{1'}$ each independently comprises a series of 3 Gly residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A''}$. In some embodiments, $L_{1'}$ is bound to $X_{B''}$. In some embodiments, $L_{1'}$ is bound to $X_{C''}$.

In some embodiments, the cargo C is an imaging cargo. In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the cargo C is a therapeutic cargo. In some embodiments, the therapeutic cargo comprises comprises a chemotherapeutic agent, a cytotoxin, a steroid, an immunotherapeutic agent, a targeted therapy agent, or an anti-inflammatory agent. In some embodiments, the therapeutic agent comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is a cargo that promotes regeneration of neuron or nerve tissue. In some embodiments, the therapeutic cargo is a growth factor.

In some embodiments, the therapeutic cargo is a local anesthetic.

In some embodiments, the therapeutic cargo is an antiepileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

Nerve Delivery Molecules of Formula (IIa)

In some embodiments, the nerve delivery molecule comprises a peptide sequence according to the Formula (IIa):

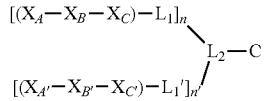

wherein,

X$_A$ and X$_{A'}$ are each independently selected from: D-Asp, D-Arg, D-Glu, D-Thr, D-His, D-Lys, D-Phe, or D-Ser;

X$_B$ and X$_{B'}$ are each independently selected from: D-His, D-Lys, D-Thr, D-Glu, D-Ser, D-Asp, D-Phe, or D-Arg;

X$_C$ and X$_{C'}$ are each independently selected from: D-Asp, D-Arg, D-Glu, D-Thr, D-His, D-Lys, D-Phe, or D-Ser;

L$_1$ and L$_{1'}$ are each independently absent or are each independently a linker comprising:
  i) 1-10 D-Ala residues;
  ii) a polymer comprising 1-10 ethylene glycol units; or
  iii) an aliphatic chain comprising a chain length of 1-10 carbon atoms;

L$_2$ is a linker comprising:
  i) an amino acid selected from: Lys, Glu, Cys, or Asp;
  ii) a polymer comprising 1-10 ethylene glycol units; or
  iii) an aliphatic chain comprising a chain length of 1-10 carbon atoms;

C is a cargo; and n and n' are each independently an integer between 1 and 5; and wherein L$_1$ is bound to at any position on X$_A$—X$_B$—X$_C$, L$_{1'}$ is bound to at any position on X$_{A'}$—X$_{B'}$—X$_{C'}$, L$_2$ is bound to L$_1$ and L$_{1'}$, and C is bound to L$_2$.

In some embodiments, X$_A$ is selected from: D-Arg, D-His or D-Lys. In some embodiments, X$_A$ is selected from: D-Asp, D-Glu, D-Thr or D-Ser. In some embodiments, X$_A$ is selected from: D-Asp or D-Glu. In some embodiments, X$_A$ is selected from: D-Thr or D-Ser. In some embodiments, X$_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_{A'}$ is selected from: D-Arg, D-His, or D-Lys. In some embodiments, $X_{A'}$ is selected from: D-Asp, D-Glu, D-Thr or D-Ser. In some embodiments, $X_{A'}$ is selected from: D-Asp or D-Glu. In some embodiments, $X_{A'}$ is selected from: D-Thr or D-Ser. In some embodiments, $X_{A'}$ is selected from: D-Glu or D-Thr. In some embodiments, $X_{A'}$ is D-Glu. In some embodiments, $X_{A'}$ is D-Thr. In some embodiments, $X_{A'}$ is D-Asp. In some embodiments, $X_{A'}$ is D-Arg. In some embodiments, $X_{A'}$ is D-His. In some embodiments, $X_{A'}$ is D-Lys. In some embodiments, $X_{A'}$ is D-Ser. In some embodiments, $X_{A'}$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_{B'}$ is selected from: D-His, D-Lys, D-Glu or D-Arg. In some embodiments, $X_{B'}$ is selected from: D-Thr, D-Glu, D-Ser or D-Asp. In some embodiments, $X_{B'}$ is selected from: D-His, D-Thr, D-Ser or D-Asp. In some embodiments, $X_{B'}$ is D-His. In some embodiments, $X_{B'}$ is D-Lys. In some embodiments, $X_{B'}$ is D-Thr. In some embodiments, $X_{B'}$ is D-Glu. In some embodiments, $X_{B'}$ is D-Ser. In some embodiments, $X_{B'}$ is D-Asp. In some embodiments, $X_{B'}$ is D-Arg. In some embodiments, $X_{B'}$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_{C'}$ is selected from: D-Arg, D-His or D-Lys. In some embodiments, $X_{C'}$ is selected from: D-Asp, D-Glu, D-Thr or D-Ser. In some embodiments, $X_{C'}$ is selected from: D-Asp or D-Glu. In some embodiments, $X_{C'}$ is selected from: D-Thr or D-Ser. In some embodiments, $X_{C'}$ is selected from: D-Glu or D-Thr. In some embodiments, $X_{C'}$ is D-Glu. In some embodiments, $X_{C'}$ is D-Thr. In some embodiments, $X_{C'}$ is D-Asp. In some embodiments, $X_{C'}$ is D-Arg. In some embodiments, $X_{C'}$ is D-His. In some embodiments, $X_{C'}$ is D-Lys. In some embodiments, $X_{C'}$ is D-Ser. In some embodiments, $X_{C'}$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $X_{A'}$—$X_{B'}$—$X_{C'}$ is EHT or THE, in which the amino acid residues are D-amino acid residues. In some instances, $X_{A'}$—$X_{B'}$—$X_{C'}$ is EHT, in which the amino acid residues are D-amino acid residues. In other instances, $X_{A'}$—$X_{B'}$—$X_{C'}$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 10 amino acids. In some embodiments, $L_1$ and $L_{1'}$ each independently comprises 9 amino acids. In some embodiments, $L_1$ and $L_{1'}$ each independently comprises 8 amino acids. In some embodiments, $L_1$ and $L_{1'}$ each independently comprises 7 amino acids. In some embodiments, $L_1$ and $L_{1'}$ each independently comprises 6 amino acids. In some embodiments, $L_1$ and $L_{1'}$ each independently comprises 5 amino acids. In some embodiments, $L_1$ and $L_{1'}$ each independently comprises 4 amino acids. In some embodiments, $L_1$ and $L_{1'}$ each independently comprises 3 amino acids. In some embodiments, $L_1$ and $L_{1'}$ each independently comprises 2 amino acids. In some embodiments, $L_1$ and $L_{1'}$ each independently comprises 1 amino acid. In some embodiments, $L_1$ and $L_{1'}$ each independently comprises a series of D-10 Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_1$ and $L_{1'}$ each independently comprises a polymer comprising 10 ethylene glycol units. In some embodiments, $L_1$ and $L_{1'}$ each independently comprises a polymer comprising 9 ethylene glycol units. In some embodiments, $L_1$ and $L_{1'}$ each independently comprises a polymer comprising 8 ethylene glycol units. In some embodiments, $L_1$ and $L_{1'}$ each independently comprises a polymer comprising 7 ethylene glycol units. In some embodiments, $L_1$ and $L_{1'}$ each independently comprises a polymer comprising 6 ethylene glycol units. In some embodiments, $L_1$ and $L_{1'}$ each independently comprises a polymer comprising 5 ethylene glycol units. In some embodiments, $L_1$ and $L_{1'}$ each independently comprises a polymer comprising 4 ethylene glycol units. In some embodiments, $L_1$ and $L_{1'}$ each independently comprises a polymer comprising 3 ethylene glycol units. In some embodiments, $L_1$ and $L_{1'}$ each independently comprises a polymer comprising 2 ethylene glycol units. In some embodiments, $L_1$ and $L_{1'}$ each independently comprises a polymer comprising 1 ethylene glycol unit.

In some embodiments, $L_1$ and $L_{1'}$ each independently comprises an aliphatic chain comprising a chain length of 10 carbon atoms. In some embodiments, $L_1$ and $L_{1'}$ each independently comprises an aliphatic chain comprising a chain length of 9 carbon atoms. In some embodiments, $L_1$ and $L_{1'}$ each independently comprises an aliphatic chain comprising a chain length of 8 carbon atoms. In some embodiments, $L_1$ and $L_{1'}$ each independently comprises an aliphatic chain comprising a chain length of 7 carbon atoms. In some embodiments, $L_1$ and $L_{1'}$ each independently comprises an aliphatic chain comprising a chain length of 6 carbon atoms. In some embodiments, $L_1$ and $L_{1'}$ each independently comprises an aliphatic chain comprising a chain length of 5 carbon atoms. In some embodiments, $L_1$ and $L_{1'}$ each independently comprises an aliphatic chain comprising a chain length of 4 carbon atoms. In some embodiments, $L_1$ and $L_{1'}$ each independently comprises an aliphatic chain comprising a chain length of 3 carbon atoms. In some embodiments, $L_1$ and $L_{1'}$ each independently comprises an aliphatic chain comprising a chain length of 2 carbon atoms. In some embodiments, $L_1$ and $L_{1'}$ each independently comprises an aliphatic chain comprising a chain length of 1 carbon atom.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_2$ comprises a polymer comprising 10 ethylene glycol units. In some embodiments, $L_2$ comprises a polymer comprising 9 ethylene glycol units. In some embodiments, $L_2$ comprises a polymer comprising 8 ethylene glycol units. In some embodiments, $L_2$ comprises a polymer comprising 7 ethylene glycol units. In some embodiments, $L_2$ comprises a polymer comprising 6 ethylene glycol units. In some embodiments, $L_2$ comprises a polymer comprising 5 ethylene glycol units. In some embodiments, $L_2$ comprises a polymer comprising 4 ethylene glycol units. In some embodiments, $L_2$ comprises a polymer comprising 3 ethylene glycol units. In some embodiments, $L_2$ comprises a polymer comprising 2 ethylene glycol units. In some embodiments, $L_2$ comprises a polymer comprising 1 ethylene glycol unit.

In some embodiments, $L_2$ comprises an aliphatic chain comprising a chain length of 10 carbon atoms. In some embodiments, $L_2$ comprises an aliphatic chain comprising a chain length of 9 carbon atoms. In some embodiments, $L_2$ comprises an aliphatic chain comprising a chain length of 8 carbon atoms. In some embodiments, $L_2$ comprises an aliphatic chain comprising a chain length of 7 carbon atoms. In some embodiments, $L_2$ comprises an aliphatic chain comprising a chain length of 6 carbon atoms. In some embodiments, $L_2$ comprises an aliphatic chain comprising a chain length of 5 carbon atoms. In some embodiments, $L_2$ comprises an aliphatic chain comprising a chain length of 4 carbon atoms. In some embodiments, $L_2$ comprises an aliphatic chain comprising a chain length of 3 carbon atoms. In some embodiments, $L_2$ comprises an aliphatic chain comprising a chain length of 2 carbon atoms. In some embodiments, $L_2$ comprises an aliphatic chain comprising a chain length of 1 carbon atom.

In some embodiments, $L_1$ and $L_{1'}$ each independently comprises a series of 3 D-Ala residues and $L_2$ comprises an amino acid selected from Lys or Cys. In some embodiments, $L_1$ and $L_{1'}$ each independently comprises a series of 2 D-Ala residues and $L_2$ comprises an amino acid selected from Lys or Cys. In some embodiments, $L_1$ and $L_{1'}$ each independently comprises a series of 3 D-Ala residues and $L_2$ comprises an amino acid selected from D-Lys or D-Cys. In some embodiments, $L_1$ and $L_{1'}$ each independently comprises a series of 2 D-Ala residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A'}$. In some embodiments, $L_{1'}$ is bound to $X_{B'}$. In some embodiments, $L_{1'}$ is bound to $X_{C'}$.

In some embodiments, the cargo C is an imaging cargo. In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N''-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the cargo C is a therapeutic cargo. In some embodiments, the therapeutic cargo comprises comprises a chemotherapeutic agent, a cytotoxin, a steroid, an immunotherapeutic agent, a targeted therapy agent, or an anti-inflammatory agent. In some embodiments, the therapeutic agent comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is a cargo that promotes regeneration of neuron or nerve tissue. In some embodiments, the therapeutic cargo is a growth factor.

In some embodiments, the therapeutic cargo is a local anesthetic.

In some embodiments, the therapeutic cargo is an anti-epileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

Nerve Delivery Molecules of Formula (III)

In some embodiments, a nerve delivery molecule described herein comprises a peptide sequence according to the Formula (III):

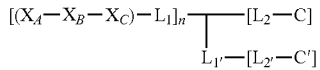

wherein, $X_A$ is selected from: Asp, Arg, Glu, Thr, His, Lys, Phe, or Ser;

$X_B$ is selected from: His, Lys, Thr, Glu, Ser, Asp, Phe, or Arg;

$X_C$ is selected from: Asp, Arg, Glu, Thr, His, Lys, Phe, or Ser;

$L_1$ and $L_{1'}$ are each independently absent or are each independently a linker comprising:

i) 1-10 Ala residues (SEQ ID NO: 1);
ii) 3-10 Gly residues (SEQ ID NO: 2);
iii) a polymer comprising 1-10 ethylene glycol units; or
iv) an aliphatic chain comprising a chain length of 1-10 carbon atoms;

$L_2$ and $L_{2'}$ are each independently a linker comprising:

i) an amino acid selected from: Lys, Glu, Cys, or Asp;
ii) a polymer comprising 1-10 ethylene glycol units; or
iii) an aliphatic chain comprising a chain length of 1-10 carbon atoms;

C and C' are each independently a cargo; and n is an integer between 1 and 5; and wherein, $L_1$ is bound to at any position on $X_A$—$X_B$—$X_C$;
$L_2$ is bound to $L_1$;
C is bound to $L_2$;
$L_{1'}$ is bound to $L_2$ or is bound to $L_1$;
$L_{2'}$ is bound to $L_{1'}$; and
C' is bound to $L_{2'}$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, the nerve delivery molecule of Formula (III) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 10 amino acids. In some embodiments, $L_1$ and $L_{1'}$ each independently comprises 9 amino acids. In some embodiments, $L_1$ and $L_{1'}$ each independently comprises 8 amino acids. In some embodiments, $L_1$ and $L_{1'}$ each independently comprises 7 amino acids. In some embodiments, $L_1$ and $L_{1'}$ each independently comprises 6 amino acids. In some embodiments, $L_1$ and $L_{1'}$ each independently comprises 5 amino acids. In some embodiments, $L_1$ and $L_{1'}$ each independently comprises 4 amino acids. In some embodiments, $L_1$ and $L_{1'}$ each independently comprises 3 amino acids. In some embodiments, $L_1$ and $L_{1'}$ each independently comprises 2 amino acids. In some embodiments, $L_1$ and $L_{1'}$ each independently comprises 1 amino acid. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_1$ and $L_{1'}$ each independently comprises a polymer comprising 10 ethylene glycol units. In some embodiments, $L_1$ and $L_{1'}$ each independently comprises a polymer comprising 9 ethylene glycol units. In some embodiments, $L_1$ and $L_{1'}$ each independently comprises a polymer comprising 8 ethylene glycol units. In some embodiments, $L_1$ and $L_{1'}$ each independently comprises a polymer comprising 7 ethylene glycol units. In some embodiments, $L_1$ and $L_{1'}$ each independently comprises a polymer comprising 6 ethylene glycol units. In some embodiments, $L_1$ and $L_{1'}$ each independently comprises a polymer comprising 5 ethylene glycol units. In some embodiments, $L_1$ and $L_{1'}$ each independently comprises a polymer comprising 4 ethylene glycol units. In some embodiments, $L_1$ and $L_{1'}$ each independently comprises a polymer comprising 3 ethylene glycol units. In some embodiments, $L_1$ and $L_{1'}$ each independently comprises a polymer comprising 2 ethylene glycol units. In some embodiments, $L_1$ and $L_{1'}$ each independently comprises a polymer comprising 1 ethylene glycol unit.

In some embodiments, $L_1$ and $L_{1'}$ each independently comprises an aliphatic chain comprising a chain length of 10 carbon atoms. In some embodiments, $L_1$ and $L_{1'}$ each independently comprises an aliphatic chain comprising a chain length of 9 carbon atoms. In some embodiments, $L_1$ and $L_{1'}$ each independently comprises an aliphatic chain comprising a chain length of 8 carbon atoms. In some embodiments, $L_1$ and $L_{1'}$ each independently comprises an aliphatic chain comprising a chain length of 7 carbon atoms. In some embodiments, $L_1$ and $L_{1'}$ each independently comprises an aliphatic chain comprising a chain length of 6 carbon atoms. In some embodiments, $L_1$ and $L_{1'}$ each independently comprises an aliphatic chain comprising a chain length of 5 carbon atoms. In some embodiments, $L_1$ and $L_{1'}$ each independently comprises an aliphatic chain comprising a chain length of 4 carbon atoms. In some embodiments, $L_1$ and $L_{1'}$ each independently comprises an aliphatic chain comprising a chain length of 3 carbon atoms. In some embodiments, $L_1$ and $L_{1'}$ each independently comprises an aliphatic chain comprising a chain length of 2 carbon atoms. In some embodiments, $L_1$ and $L_{1'}$ each independently comprises an aliphatic chain comprising a chain length of 1 carbon atom.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_2$ and $L_{2'}$ each independently comprises a polymer comprising 10 ethylene glycol units. In some embodiments, $L_2$ and $L_{2'}$ each independently comprises a polymer comprising 9 ethylene glycol units. In some embodiments, $L_2$ and $L_{2'}$ each independently comprises a polymer comprising 8 ethylene glycol units. In some embodiments, $L_2$ and $L_{2'}$ each independently comprises a polymer comprising 7 ethylene glycol units. In some embodiments, $L_2$ and $L_{2'}$ each independently comprises a polymer comprising 6 ethylene glycol units. In some embodiments, $L_2$ and $L_{2'}$ each independently comprises a polymer comprising 5 ethylene glycol units. In some embodiments, $L_2$ and $L_{2'}$ each independently comprises a polymer comprising 4 ethylene glycol units. In some embodiments, $L_2$ and $L_{2'}$ each independently comprises a polymer comprising 3 ethylene glycol units. In some embodiments, $L_2$ and $L_{2'}$ each independently comprises a polymer comprising 2 ethylene glycol units. In some embodiments, $L_2$ and $L_{2'}$ each independently comprises a polymer comprising 1 ethylene glycol unit.

In some embodiments, $L_2$ and $L_{2'}$ each independently comprises an aliphatic chain comprising a chain length of 10 carbon atoms. In some embodiments, $L_2$ and $L_{2'}$ each independently comprises an aliphatic chain comprising a chain length of 9 carbon atoms. In some embodiments, $L_2$ and $L_{2'}$ each independently comprises an aliphatic chain comprising a chain length of 8 carbon atoms. In some embodiments, $L_2$ and $L_{2'}$ each independently comprises an aliphatic chain comprising a chain length of 7 carbon atoms. In some embodiments, $L_2$ and $L_{2'}$ each independently comprises an aliphatic chain comprising a chain length of 6 carbon atoms. In some embodiments, $L_2$ and $L_{2'}$ each independently comprises an aliphatic chain comprising a chain length of 5 carbon atoms. In some embodiments, $L_2$ and L$_{2'}$ each independently comprises an aliphatic chain comprising a chain length of 4 carbon atoms. In some embodiments, L$_2$ and L$_{2'}$ each independently comprises an aliphatic chain comprising a chain length of 3 carbon atoms. In some embodiments, L$_2$ and L$_{2'}$ each independently comprises an aliphatic chain comprising a chain length of 2 carbon atoms. In some embodiments, L$_2$ and L$_{2'}$ each independently comprises an aliphatic chain comprising a chain length of 1 carbon atom.

In some embodiments, L$_1$ and L$_{1'}$ each independently comprises a series of 3 Ala residues and L$_2$ and L$_{2'}$ each independently comprises an amino acid selected from Lys or Cys. In some embodiments, L$_1$ and L$_{1'}$ each independently comprises a series of 2 Ala residues and L$_2$ and L$_{2'}$ each independently comprises an amino acid selected from Lys or Cys. In some embodiments, L$_1$ and L$_{1'}$ each independently comprises a series of 3 Gly residues and L$_2$ and L$_{2'}$ each independently comprises an amino acid selected from Lys or Cys. In some embodiments, L$_1$ and L$_{1'}$ each independently comprises a series of 3 Ala residues and L$_2$ and L$_{2'}$ each independently comprises an amino acid selected from D-Lys or D-Cys. In some embodiments, L$_1$ and L$_{1'}$ each independently comprises a series of 2 Ala residues and L$_2$ and L$_{2'}$ each independently comprises an amino acid selected from D-Lys or D-Cys. In some embodiments, L$_1$ and L$_{1'}$ each independently comprises a series of 3 Gly residues and L$_2$ and L$_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, L$_1$ is bound to X$_A$. In some embodiments, L$_1$ is bound to X$_B$. In some embodiments, L$_1$ is bound to X$_C$. In some embodiments, L$_{1'}$ is bound to L$_2$. In some embodiments, L$_{1'}$ is bound to L$_1$.

In some embodiments, the cargo C is an imaging cargo. In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the nerve delivery molecule of Formula (III) comprises two or more imaging cargos. In some cases, the imaging cargos are fluorescent. In some cases, a first fluorescent imaging cargo undergoes energy transfer to second or multiple fluorescent cargos that functionally extends the fluorescence emission to longer wavelengths. In some of these cases the emission is separated from the excitation light which facilitates detection of the emitted light. In some of these cases the extended, longer wavelength emission will have reduced tissue attenuation and deeper tissue detection properties. In some cases, the first fluorescent cargo is a xanthene. In some cases, the first fluorescent cargo is a fluorescein. In some cases, the first fluorescent cargo is a fluorinated fluorescein. In some cases, the second or multiple fluorescent cargo is an indocarbocyanine dye. In some cases, the emission is extended into the near infra-red wavelengths.

In some embodiments, the cargo C is a therapeutic cargo. In some embodiments, the therapeutic cargo comprises comprises a chemotherapeutic agent, a cytotoxin, a steroid, an immunotherapeutic agent, a targeted therapy agent, or an anti-inflammatory agent. In some embodiments, the therapeutic agent comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is a cargo that promotes regeneration of neuron or nerve tissue. In some embodiments, the therapeutic cargo is a growth factor.

In some embodiments, the therapeutic cargo is a local anesthetic.

In some embodiments, the therapeutic cargo is an anti-epileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

Nerve Delivery Molecules of Formula (IIa)

In some embodiments, the nerve delivery molecule comprises a peptide sequence according to the Formula (IIIa):

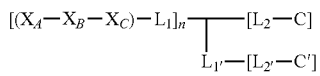

wherein, $X_A$ is selected from: D-Asp, D-Arg, D-Glu, D-Thr, D-His, D-Lys, D-Phe, or D-Ser;

$X_B$ is selected from: D-His, D-Lys, D-Thr, D-Glu, D-Ser, D-Asp, D-Phe, or D-Arg;

$X_C$ is selected from: D-Asp, D-Arg, D-Glu, D-Thr, D-His, D-Lys, D-Phe, or D-Ser;

L and $L_{1'}$ are each independently absent or are each independently a linker comprising:
  i) 1-10 D-Ala residues;
  ii) a polymer comprising 1-10 ethylene glycol units; or
  iii) an aliphatic chain comprising a chain length of 1-10 carbon atoms;

$L_2$ and $L_{2'}$ are each independently a linker comprising:
  i) an amino acid selected from: Lys, Glu, Cys, or Asp;
  ii) a polymer comprising 1-10 ethylene glycol units; or
  iii) an aliphatic chain comprising a chain length of 1-10 carbon atoms;

C and C' are each independently a cargo; and n is an integer between 1 and 5; and wherein, $L_1$ is bound to at any position on $X_A$—$X_B$—$X_C$;
$L_2$ is bound to $L_1$;
C is bound to $L_2$;
$L_{1'}$ is bound to $L_2$ or is bound to $L_1$;
$L_{2'}$ is bound to $L_{1'}$; and
C' is bound to $L_{2'}$.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 10 amino acids. In some embodiments, $L_1$ and $L_{1'}$ each independently comprises 9 amino acids. In some embodiments, $L_1$ and $L_{1'}$ each independently comprises 8 amino acids. In some embodiments, $L_1$ and $L_{1'}$ each independently comprises 7 amino acids. In some embodiments, $L_1$ and $L_{1'}$ each independently comprises 6 amino acids. In some embodiments, $L_1$ and $L_{1'}$ each independently comprises 5 amino acids. In some embodiments, $L_1$ and $L_{1'}$ each independently comprises 4 amino acids. In some embodiments, $L_1$ and $L_{1'}$ each independently comprises 3 amino acids. In some embodiments, $L_1$ and $L_{1'}$ each independently comprises 2 amino acids. In some embodiments, $L_1$ and $L_{1'}$ each independently comprises 1 amino acid. In some embodiments, $L_1$ and $L_{1'}$ each independently comprises a series of 10 D-Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_1$ and $L_{1'}$ each independently comprises a polymer comprising 10 ethylene glycol units. In some embodiments, $L_1$ and $L_{1'}$ each independently comprises a polymer comprising 9 ethylene glycol units. In some embodiments, $L_1$ and $L_{1'}$ each independently comprises a polymer comprising 8 ethylene glycol units. In some embodiments, $L_1$ and $L_{1'}$ each independently comprises a polymer comprising 7 ethylene glycol units. In some embodiments, $L_1$ and $L_{1'}$ each independently comprises a polymer comprising 6 ethylene glycol units. In some embodiments, $L_1$ and $L_{1'}$ each independently comprises a polymer comprising 5 ethylene glycol units. In some embodiments, $L_1$ and $L_{1'}$ each independently comprises a polymer comprising 4 ethylene glycol units. In some embodiments, $L_1$ and $L_{1'}$ each independently comprises a polymer comprising 3 ethylene glycol units. In some embodiments, $L_1$ and $L_{1'}$ each independently comprises a polymer comprising 2 ethylene glycol units. In some embodiments, $L_1$ and $L_{1'}$ each independently comprises a polymer comprising 1 ethylene glycol unit.

In some embodiments, $L_1$ and $L_{1'}$ each independently comprises an aliphatic chain comprising a chain length of 10 carbon atoms. In some embodiments, $L_1$ and $L_{1'}$ each independently comprises an aliphatic chain comprising a chain length of 9 carbon atoms. In some embodiments, $L_1$ and $L_{1'}$ each independently comprises an aliphatic chain comprising a chain length of 8 carbon atoms. In some embodiments, $L_1$ and $L_{1'}$ each independently comprises an aliphatic chain comprising a chain length of 7 carbon atoms. In some embodiments, $L_1$ and $L_{1'}$ each independently comprises an aliphatic chain comprising a chain length of 6 carbon atoms. In some embodiments, $L_1$ and $L_{1'}$ each independently comprises an aliphatic chain comprising a chain length of 5 carbon atoms. In some embodiments, $L_1$ and $L_{1'}$ each independently comprises an aliphatic chain comprising a chain length of 4 carbon atoms. In some embodiments, $L_1$ and $L_{1'}$ each independently comprises an aliphatic chain comprising a chain length of 3 carbon atoms. In some embodiments, $L_1$ and $L_{1'}$ each independently comprises an aliphatic chain comprising a chain length of 2 carbon atoms. In some embodiments, $L_1$ and $L_{1'}$ each independently comprises an aliphatic chain comprising a chain length of 1 carbon atom.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_2$ and $L_{2'}$ each independently comprises a polymer comprising 10 ethylene glycol units. In some embodiments, $L_2$ and $L_{2'}$ each independently comprises a polymer comprising 9 ethylene glycol units. In some embodiments, $L_2$ and $L_{2'}$ each independently comprises a polymer comprising 8 ethylene glycol units. In some embodiments, $L_2$ and $L_{2'}$ each independently comprises a polymer comprising 7 ethylene glycol units. In some embodiments, $L_2$ and $L_{2'}$ each independently comprises a polymer comprising 6 ethylene glycol units. In some embodiments, $L_2$ and $L_{2'}$ each independently comprises a polymer comprising 5 ethylene glycol units. In some embodiments, $L_2$ and $L_{2'}$ each independently comprises a polymer comprising 4 ethylene glycol units. In some embodiments, $L_2$ and $L_{2'}$ each independently comprises a polymer comprising 3 ethylene glycol units. In some embodiments, $L_2$ and $L_{2'}$ each independently comprises a polymer comprising 2 ethylene glycol units. In some embodiments, $L_2$ and $L_{2'}$ each independently comprises a polymer comprising 1 ethylene glycol unit.

In some embodiments, $L_2$ and $L_{2'}$ each independently comprises an aliphatic chain comprising a chain length of 10 carbon atoms. In some embodiments, $L_2$ and $L_{2'}$ each independently comprises an aliphatic chain comprising a chain length of 9 carbon atoms. In some embodiments, $L_2$ and $L_{2'}$ each independently comprises an aliphatic chain comprising a chain length of 8 carbon atoms. In some embodiments, $L_2$ and $L_{2'}$ each independently comprises an aliphatic chain comprising a chain length of 7 carbon atoms. In some embodiments, $L_2$ and $L_{2'}$ each independently comprises an aliphatic chain comprising a chain length of 6 carbon atoms. In some embodiments, $L_2$ and $L_{2'}$ each independently comprises an aliphatic chain comprising a chain length of 5 carbon atoms. In some embodiments, $L_2$ and $L_{2'}$ each independently comprises an aliphatic chain comprising a chain length of 4 carbon atoms. In some embodiments, $L_2$ and $L_{2'}$ each independently comprises an aliphatic chain comprising a chain length of 3 carbon atoms. In some embodiments, $L_2$ and $L_{2'}$ each independently comprises an aliphatic chain comprising a chain length of 2 carbon atoms. In some embodiments, $L_2$ and $L_{2'}$ each independently comprises an aliphatic chain comprising a chain length of 1 carbon atom.

In some embodiments, $L_1$ and $L_{1'}$ each independently comprises a series of 3 D-Ala residues and $L_2$ and $L_{2'}$ each independently comprises an amino acid selected from Lys or Cys. In some embodiments, $L_1$ and $L_{1'}$ each independently comprises a series of 2 D-Ala residues and $L_2$ and $L_{2'}$ each independently comprises an amino acid selected from Lys or Cys. In some embodiments, $L_1$ and $L_{1'}$ each independently comprises a series of 3 D-Ala residues and $L_2$ and $L_{2'}$ each independently comprises an amino acid selected from D-Lys or D-Cys. In some embodiments, $L_1$ and $L_{1'}$ each independently comprises a series of 2 D-Ala residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_{1'}$ is bound to $L_2$. In some embodiments, $L_{1'}$ is bound to $L_1$.

In some embodiments, the cargo C is an imaging cargo. In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the nerve delivery molecule of Formula (IIIa) comprises two or more imaging cargos. In some cases, the imaging cargos are fluorescent. In some cases, a first fluorescent imaging cargo undergoes energy transfer to second or multiple fluorescent cargos that functionally extends the fluorescence emission to longer wavelengths. In some of these cases the emission is separated from the excitation light which facilitates detection of the emitted light. In some of these cases the extended, longer wavelength emission will have reduced tissue attenuation and deeper tissue detection properties. In some cases, the first fluorescent cargo is a xanthene. In some cases, the first fluorescent cargo is a fluorescein. In some cases, the first fluorescent cargo is a fluorinated fluorescein. In some cases, the second or multiple fluorescent cargo is an indocarbocyanine dye. In some cases, the emission is extended into the near infra-red wavelengths.

In some embodiments, the cargo C is a therapeutic cargo. In some embodiments, the therapeutic cargo comprises comprises a chemotherapeutic agent, a cytotoxin, a steroid, an immunotherapeutic agent, a targeted therapy agent, or an anti-inflammatory agent. In some embodiments, the therapeutic agent comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is a cargo that promotes regeneration of neuron or nerve tissue. In some embodiments, the therapeutic cargo is a growth factor.

In some embodiments, the therapeutic cargo is a local anesthetic.

In some embodiments, the therapeutic cargo is an anti-epileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

In some embodiments, the nerve delivery molecule comprises a peptide sequence sharing 80% homology with a peptide sequence disclosed herein. In some embodiments, the nerve delivery molecule comprises a peptide sequence sharing 85% homology with a peptide sequence disclosed herein. In some embodiments, the nerve delivery molecule comprises a peptide sequence sharing 90% homology with a peptide sequence disclosed herein. In some embodiments, the nerve delivery molecule comprises a peptide sequence sharing 95% homology with a peptide sequence disclosed herein. In some embodiments, the nerve delivery molecule comprises a peptide sequence sharing 99% homology with a peptide sequence disclosed herein.

The peptides of the present invention are synthesized by any suitable method. For example, targeting peptides and aptamers of the present invention can be chemically synthesized by solid phase peptide synthesis.

Linkers ($L_1$, $L_{1'}$, $L_2$, and $L_{2'}$)

In some embodiments, a cargo (e.g., an imaging cargo or a therapeutic cargo) is directly attached to the nerve delivery molecule, e.g. at the end of a peptide sequence. Alternatively, in some embodiments, a cargo (e.g., an imaging cargo or a therapeutic cargo) is indirectly attached to a nerve delivery molecule disclosed herein (e.g., via a linker). In some embodiments, the linker is flexible. In some embodiments, the linker is rigid.

In some embodiments, the linker comprises a linear structure. In some embodiments, the linker comprises a non-linear structure. In some embodiments, the linker comprises a branched structure. In some embodiments, the linker comprises a cyclic structure.

Linkers include, but are not limited to, straight or branched-chain carbon linkers, heterocyclic carbon linkers, peptide linkers, and polyether linkers. For example, poly (ethylene glycol) (PEG) linkers are available from Quanta Biodesign, Powell, Ohio. These linkers optionally have amide linkages, sulfhydryl linkages, or heterofunctional linkages. poly(ethylene glycol) (PEG) linkers are hydrophilic and have high solubility in both organic and aqueous solutions along with lack of toxicity, low immunogenicity and well defined chain lengths and molecular weights make PEG moieties relevant to pharmaceutical applications.

In some embodiments, disclosed herein, are nerve delivery molecules comprising a linker (e.g., $L_1$, $L_{1'}$, $L_2$ and/or $L_{2'}$) wherein the linker is a polymer comprising 1-10 ethylene glycol units. In some embodiments, a linker described herein (e.g., $L_1$, $L_{1'}$, $L_2$ and/or $L_{2'}$) comprises a polymer comprising 10 ethylene glycol units. In some embodiments, a linker described herein (e.g., $L_1$, $L_{1'}$, $L_2$ and/or $L_{2'}$) comprises a polymer comprising 9 ethylene glycol units. In some embodiments, a linker described herein (e.g., $L_1$, $L_{1'}$, $L_2$ and/or $L_{2'}$) comprises a polymer comprising 8 ethylene glycol units. In some embodiments, a linker described herein (e.g., $L_1$, $L_{1'}$, $L_2$ and/or $L_{2'}$) comprises a polymer comprising 7 ethylene glycol units. In some embodiments, a linker described herein (e.g., $L_1$, $L_{1'}$, $L_2$ and/or $L_{2'}$) comprises a polymer comprising 6 ethylene glycol units. In some embodiments, a linker described herein (e.g., $L_1$, $L_{1'}$, $L_2$ and/or $L_{2'}$) comprises a polymer comprising 5 ethylene glycol units. In some embodiments, a linker described herein (e.g., $L_1$, $L_{1'}$, $L_2$ and/or $L_{2'}$) comprises a polymer comprising 4 ethylene glycol units. In some embodiments, a linker described herein (e.g., $L_1$, $L_{1'}$, $L_2$ and/or $L_{2'}$) comprises a polymer comprising 3 ethylene glycol units. In some embodiments, a linker described herein (e.g., $L_1$, $L_{1'}$, $L_2$ and/or $L_{2'}$) comprises a polymer comprising 2 ethylene glycol units. In some embodiments, a linker described herein (e.g., $L_1$, $L_{1'}$, $L_2$ and/or $L_{2'}$) comprises a polymer comprising 1 ethylene glycol unit.

In some embodiments, the linker is an alkyl linker, comprising, for example, 1 to 10 carbon atoms. Typical alkyl groups include, but are not limited to, methyl, ethyl, propyl, isopropyl, butyl, isobutyl, tertiary butyl, pentyl, hexyl, ethenyl, propenyl, butenyl, and the like. In some embodiments, aliphatic linkers are hydrophilic linkers. In some embodiments, disclosed herein, are nerve delivery molecules comprising a linker (e.g., $L_1$, $L_{1'}$, $L_2$ and/or $L_{2'}$) wherein the linker is an aliphatic chain comprising a chain length of 1-10 carbon atoms. In some embodiments, a linker described herein (e.g., $L_1$, $L_{1'}$, $L_2$ and/or $L_{2'}$) comprises an aliphatic chain comprising a chain length of 10 carbon atoms. In some embodiments, a linker described herein (e.g., $L_1$, $L_{1'}$, $L_2$ and/or $L_{2'}$) comprises an aliphatic chain comprising a chain length of 9 carbon atoms. In some embodiments, a linker described herein (e.g., $L_1$, $L_{1'}$, $L_2$ and/or $L_{2'}$) comprises an aliphatic chain comprising a chain length of 8 carbon atoms. In some embodiments, a linker described herein (e.g., $L_1$, $L_{1'}$, $L_2$ and/or $L_{2'}$) comprises an aliphatic chain comprising a chain length of 7 carbon atoms. In some embodiments, a linker described herein (e.g., $L_1$, $L_{1'}$, $L_2$ and/or $L_{2'}$) comprises an aliphatic chain comprising a chain length of 6 carbon atoms. In some embodiments, a linker described herein (e.g., $L_1$, $L_{1'}$, $L_2$ and/or $L_{2'}$) comprises an aliphatic chain comprising a chain length of 5 carbon atoms. In some embodiments, a linker described herein (e.g., $L_1$, $L_{1'}$, $L_2$ and/or $L_{2'}$) comprises an aliphatic chain comprising a chain length of 4 carbon atoms. In some embodiments, a linker described herein (e.g., $L_1$, $L_{1'}$, $L_2$ and/or $L_{2'}$) comprises an aliphatic chain comprising a chain length of 3 carbon atoms. In some embodiments, a linker described herein (e.g., $L_1$, $L_{1'}$, $L_2$ and/or $L_{2'}$) comprises an aliphatic chain comprising a chain length of 2 carbon atoms. In some embodiments, a linker described herein (e.g., $L_1$, $L_{1'}$, $L_2$ and/or $L_{2'}$) comprises an aliphatic chain comprising a chain length of 1 carbon atom.

In some embodiments, the linker is substituted. The term "optionally substituted" or "substituted" means that the referenced group may be substituted with one or more additional group(s). Exemplary substitution groups comprise, for example, $C_1$-$C_6$alkyl, $C_3$-$C_8$cycloalkyl, aryl, heteroaryl, $C_2$-$C_6$heteroalicyclic, hydroxy, $C_1$-$C_6$alkoxy, aryloxy, $C_1$-$C_6$alkylthio, arylthio, $C_1$-$C_6$alkylsulfoxide, arylsulfoxide, $C_1$-$C_6$alkylsulfone, arylsulfone, cyano, halo, $C_2$-$C_8$acyl, $C_2$-$C_5$acyloxy, nitro, $C_1$-$C_6$haloalkyl, $C_1$-$C_6$fluoroalkyl, and amino, including $C_1$-$C_6$alkylamino, and derivatives thereof.

In some embodiments, a linker disclosed herein comprises a zero-linker. In some instances, a zero-linker comprises a covalent bond. In some embodiments, the covalent bond comprises an ether bond, thioether bond, amine bond, amide bond, oxime bond, hydrazone, carbon-carbon bond, carbon-nitrogen bond, carbon-oxygen bond, or carbon-sulfur bond.

In some embodiments, a linker described herein further comprises a bifunctional linker. In some instances, a bifunctional linker has one functional group reactive with a group on a first molecule (e.g., a nerve delivery molecule), and a second functional group reactive on a second molecule (e.g., an imaging cargo or a therapeutic cargo). In some cases, the bifunctional linker is a homobifunctional linker or a heterobifunctional linker. Alternatively, in some embodiments, derivatization is performed to provide functional groups. Thus, for example, procedures for the generation of free sulfhydryl groups on peptides are also known (See U.S. Pat. No. 4,659,839). A linker may alternatively comprise a heterobifunctional crosslinker comprising two or more different reactive groups that form a heterocyclic ring that can interact with a nerve delivery molecule. For example, a heterobifunctional crosslinker such as cysteine may comprise an amine reactive group and a thiol-reactive group can interact with an aldehyde on a derivatized nerve delivery molecule. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups.

Exemplary homobifunctional linkers include, but are not limited to, Lomant's reagent dithiobis (succinimidylpropionate) DSP, 3'3'-dithiobis(sulfosuccinimidyl proprionate (DTSSP), disuccinimidyl suberate (DSS), bis(sulfosuccinimidyl)suberate (BS), disuccinimidyl tartrate (DST), disulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), or N,N'-hexamethylene-bis(iodoacetamide).

Exemplary heterobifunctional linker include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-α-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (sMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacetyl)aminobenzoate (sIAB), sulfosuccinimidyl(4-iodoacetyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino)hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl)butyric acid hydrazide (MPBH), 4-(N-maleimidomethyl)cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(ρ-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'-azido-2'-nitrophenylamino)hexanoate (sANPAH), sulfosuccinimidyl-6-(4'-azido-2'-nitrophenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'-dithiopropionate (sAND), N-succinimidyl-4(4-azidophenyl)1,3'-dithiopropionate (sADP), N-sulfosuccinimidyl(4-azidophenyl)-1,3'-dithiopropionate (sulfo-sADP), sulfosuccinimidyl 4-(ρ-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as 1-(ρ-Azidosalicylamido)-4-(iodoacetamido)butane (AsIB), N-[4-(ρ-azidosalicylamido)butyl]-3'-(2'-pyridyldithio)propionamide (APDP), benzophenone-4-iodoacetamide, benzophenone-4-maleimide carbonyl-reactive and photoreactive cross-linkers such as ρ-azidobenzoyl hydrazide (ABH), carboxylate-reactive and photoreactive cross-linkers such as 4-(ρ-azidosalicylamido) butylamine (AsBA), and arginine-reactive and photoreactive cross-linkers such as ρ-azidophenyl glyoxal (APG).

In some instances, the linker described herein (e.g., $L_1$, $L_{1'}$, $L_2$ and/or $L_{2'}$) further comprises a reactive functional group. In some embodiments, the reactive functional group conjugates the linker described herein (e.g., $L_1$, $L_{1'}$, $L_2$ and/or $L_{2'}$) to the cargo described herein (e.g., C and/or C'). In some cases, the reactive functional group comprises a nucleophilic group that is reactive to an electrophilic group. Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide.

In some embodiments, the linker described herein (e.g., $L_1$, $L_{1'}$, $L_2$ and/or $L_{2'}$) comprises a maleimide group, an alkyl halide group, or an iodoacetamide group.

In some embodiments, the linker described herein (e.g., $L_1$, $L_{1'}$, $L_2$ and/or $L_{2'}$) comprises a maleimide group. In some instances, the maleimide group is also referred to as a maleimide spacer. In some instances, the maleimide group further encompasses a caproic acid, forming maleimidocaproyl (mc). In some cases, the linker comprises maleimidocaproyl (mc). In some cases, the linker is maleimidocaproyl (mc). In other instances, the maleimide group comprises a maleimidomethyl group, such as succinimidyl-4-(N-maleimidomethyl)cyclohexane-1-carboxylate (sMCC) or sulfosuccinimidyl-4-(N-maleimidomethyl)cyclohexane-1-carboxylate (sulfo-sMCC) described above.

In some embodiments, the maleimide group is a self-stabilizing maleimide. In some instances, the self-stabilizing maleimide utilizes diaminopropionic acid (DPR) to incorporate a basic amino group adjacent to the maleimide to provide intramolecular catalysis of tiosuccinimide ring hydrolysis, thereby eliminating maleimide from undergoing an elimination reaction through a retro-Michael reaction. In some instances, the self-stabilizing maleimide is a maleimide group described in Lyon, et al., "Self-hydrolyzing maleimides improve the stability and pharmacological properties of antibody-drug conjugates," *Nat. Biotechnol.* 32(10): 1059-1062 (2014). In some instances, the linker comprises a self-stabilizing maleimide. In some instances, the linker is a self-stabilizing maleimide.

In some embodiments, a peptide linker consisting of one or more amino acids is used to join the nerve delivery molecule and the imaging cargo or therapeutic cargo. In some instances, the peptide linker has no specific biological activity other than to join the molecules or to preserve some minimum distance or other spatial relationship between them. However, the constituent amino acids of the linker may be selected to influence some property of the molecule such as the folding, net charge, or hydrophobicity. In some embodiments the peptide linker is relatively short, typically less than about 10 amino acids, preferably less than about 8 amino acids and more preferably less than 5 amino acids.

Cargo (C and C')

In certain embodiments, a nerve delivery molecule disclosed herein comprises a cargo (e.g., C or C'). In some embodiments, the cargo (e.g., C and/or C') is an imaging cargo. All imaging agents are encompassed within the term "imaging cargo". Specific examples of imaging agents given herein, are illustrative and are not meant to limit the imaging agents for use as imaging cargos with the nerve delivery molecules disclosed herein.

In some embodiments, the nerve delivery molecule comprises a peptide sequence that is directly bound to an imaging cargo. In some embodiments, the nerve delivery molecule comprises a peptide sequence that is indirectly (e.g., via a linker) bound to an imaging cargo. In some embodiments, the nerve delivery molecule comprises two or more peptide sequences that are directly or indirectly bound to an imaging cargo.

In some embodiments, the imaging cargo is a dye. In some embodiments, the imaging cargo is a fluorescent moiety. In some embodiments, the fluorescent moiety is selected from: a fluorescent protein, a fluorescent peptide, a fluorescent dye, a fluorescent material or a combination thereof.

All fluorescent moieties are encompassed within the term "fluorescent moiety." Specific examples of fluorescent moieties given herein are illustrative and are not meant to limit the fluorescent moieties for use with the nerve delivery molecules disclosed herein.

Examples of fluorescent dyes include, but are not limited to, xanthenes (e.g., rhodamines, rhodols and fluoresceins, and their derivatives); bimanes; coumarins and their derivatives (e.g., umbelliferone and aminomethyl coumarins); aromatic amines (e.g., dansyl; squarate dyes); benzofurans; fluorescent cyanines; indocarbocyanines; carbazoles; dicyanomethylene pyranes; polymethine; oxabenzanthrane; xanthene; pyrylium; carbostyl; perylene; acridone; quinacridone; rubrene; anthracene; coronene; phenanthrecene; pyrene; butadiene; stilbene; porphyrin; pthalocyanine; lanthanide metal chelate complexes; rare-earth metal chelate complexes; and derivatives of such dyes.

Examples of fluorescein dyes include, but are not limited to, 2',7'-difluorofluorescein, 2',7'-difluoro-carboxyfluorescein, 5-carboxyfluorescein, fluorescein-5-isothiocyanate, fluorescein-6-isothiocyanate and 6-carboxyfluorescein.

In some embodiments, the imaging cargo is a fluorescein dye. In some embodiments, the imaging cargo is a 2',7'-difluorofluorescein. In some embodiments, the imaging cargo is a 5-carboxyfluorescein. In some embodiments, the imaging cargo is a 5-carboxyfluorescein. In some embodiments, the imaging cargo is a 6-carboxyfluorescein.

Examples of rhodamine dyes include, but are not limited to, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride (sold under the tradename of TEXAS RED®).

In some embodiments, the imaging cargo is a xanthenes dye.

In some embodiments, the imaging cargo is an indocarbocyanin dye. Examples of indocarbocyanine dyes include, but are not limited to, Cy3, Cy3B, Cy3.5, Cy5, Cy5.5, Cy7, DyLight650, IRDYE680, DyLight750, Alexa Fluor 647, Alexa Fluor 750, IR800CW, ICG. In some embodiments, the imaging cargo is Cy5. In some instances, the imaging cargo is Cy7. In some instances, the imaging cargo is IR800CW. In some instances, the imaging agent is ICG.

Examples of fluorescent peptides include GFP (Green Fluorescent Protein) or derivatives of GFP (e.g., EBFP, EBFP2, Azurite, mKalama1, ECFP, Cerulean, CyPet, YFP, Citrine, Venus, YPet).

In some embodiments, the fluorescent moiety is a peptide. In some embodiments, the fluorescent moiety is Green Fluorescent Protein (GFP). In some embodiments, the fluorescent moiety is a derivative of GFP (e.g., EBFP, EBFP2, Azurite, mKalama1, ECFP, Cerulean, CyPet, YFP, Citrine, Venus, YPet).

Fluorescent labels are detected by any suitable method. For example, a fluorescent label may be detected by exciting the fluorochrome with the appropriate wavelength of light and detecting the resulting fluorescence, e.g., by microscopy, visual inspection, via photographic film, by the use of electronic detectors such as charge coupled devices (CCDs), photomultipliers, etc.

In some embodiments, the imaging cargo is labeled with a positron-emitting isotope (e.g., $^{18}$F) for positron emission tomography (PET). In some embodiments, the imaging cargo is labeled with a gamma-ray isotope (e.g., $^{99m}$Tc) for single photon emission computed tomography (SPECT). In some embodiments, the imaging cargo is labeled with a paramagnetic molecule or nanoparticle (e.g., $Gd^{3+}$ chelate or coated magnetite nanoparticle) for magnetic resonance imaging (MRI).

In some embodiments, the imaging cargo is labeled with: a radionuclide chelate, an iron oxide particle, a super paramagnetic iron oxide particle, an ultra small paramagnetic particle, a manganese chelate or gallium containing agent.

Examples of radionuclide chelates include, but are not limited to diethylene triamine pentaacetic acid (DTPA); 1,4,7,10-tetraazacyclododecane-1,4,7,10-tetraacetic acid (DOTA); 6-Hydrazinopyridine-3-carboxylic acid (HYNIC); and 1,4,7-triazacyclononane-N,N',N"-triacetic acid (NOTA).

In some embodiments, the imaging cargo is a near-infrared fluorophore for near-infra red (near-IR) imaging, a luciferase (firefly, bacterial, or coelenterate) or other luminescent molecule for bioluminescence imaging, or a perfluorocarbon-filled vesicle for ultrasound.

In some embodiments, the imaging cargo is a nuclear probe. In some embodiments, the imaging cargo is a SPECT or PET radionuclide probe. In some embodiments, the radionuclide probe is selected from: a technetium chelate, a copper chelate, a radioactive fluorine, a radioactive iodine, an indiuim chelate.

Examples of Tc chelates include, but are not limited to HYNIC, DTPA, and DOTA.

In some embodiments, the imaging cargo is a radionuclide, for example $^{99m}$Tc, $^{64}$Cu, $^{18}$F, $^{124}$I, $^{111}$In, or a combination hereof.

In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{64}$Cu radioactive isotopes of Lu, and others.

In some embodiments, the imaging cargo is conjugated to high molecular weight molecule, such as water soluble polymers including, but not limited to, dextran, polyethylene glycol (PEG), serum albumin, or poly(amidoamine) dendrimer.

In some embodiments, the cargo C and/or C' comprises a therapeutic cargo. In some cases, the cargo C and/or C' is a therapeutic cargo.

In some embodiments, the nerve delivery molecule comprises a peptide sequence that is directly bound to a therapeutic cargo. In some embodiments, the nerve delivery molecule comprises a peptide sequence that is indirectly (e.g., via a linker) bound to a therapeutic cargo. In some embodiments, the nerve delivery molecule comprises two or more peptide sequences that are directly or indirectly bound to a therapeutic cargo.

In some embodiments, therapeutic agents that act on a neuron or nerve (or a component thereof) are encompassed within the term "therapeutic cargo." Illustrative examples of therapeutic agent given herein, are not meant to limit the therapeutic cargo for use with the nerve delivery molecules disclosed herein.

In some embodiments, the therapeutic cargo is selected from a therapeutic agent that induces cell death (apoptotic or necrotic), inhibits cell death (apoptotic or necrotic), inhibits the transmission of a neuron or nerve signal (e.g., an electrochemical impulse), inhibits the release of a neurotransmitter, agonizes the activity of a GABA receptor, partially or fully inhibits the repolarization of a neuron, disrupts the conduction of an ion channel, or a combination thereof.

In some embodiments, the therapeutic cargo is an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid; a cytotoxic agent; an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is an agent that promotes regeneration of neuron or nerve tissue. In some embodiments, the therapeutic cargo is a growth factor. In some embodiments, the therapeutic cargo is a neurotrophic factor.

In some embodiments, the therapeutic cargo is a local anesthetic.

In some embodiments, the therapeutic cargo is an anti-epileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

Further Modifications

In some embodiments, the nerve delivery molecules of the present invention are optionally conjugated to high molecular weight molecules that increase the multivalency and avidity of labeling. In some embodiments, the high molecular weight molecules are water-soluble polymers. Examples of suitable water-soluble polymers include, but are not limited to, peptides, saccharides, poly(vinyls), poly(ethers), poly(amines), poly(carboxylic acids) and the like. In some embodiments, the water-soluble polymer is dextran, polyethylene glycol (PEG), polyoxyalkylene, polysialic acid, starch, or hydroxyethyl starch. Any suitable method is used to conjugate peptides to water-soluble polymers.

In some instances, the cargo described herein (e.g., C and/or C') is further derivatized with a reactive functional group. In some embodiments, the reactive functional group conjugates the cargo described herein (e.g., C and/or C') to the linker described herein (e.g., $L_1$, $L_{1'}$, $L_2$ and/or $L_{2'}$). In some cases, the reactive functional group comprises a nucleophilic group that is reactive to an electrophilic group. Exemplary electrophilic groups include carbonyl groups-such as aldehyde, ketone, carboxylic acid, ester, amide, enone, acyl halide or acid anhydride. In some embodiments, the reactive functional group is aldehyde. Exemplary nucleophilic groups include hydrazide, oxime, amino, hydrazine, thiosemicarbazone, hydrazine carboxylate, and arylhydrazide. In some embodiments, the reactive functional group is a maleimide group, an alkyl halide group, or an iodoacetamide group. In some embodiments, the reactive functional group is a maleimide group.

Exemplary Nerve Delivery Molecules

In some embodiments, disclosed herein, is a nerve delivery molecule according to NDM-36, NDM-37, NDM-38, NDM-39, NDM-40, NDM-41, NDM-42, NDM-43, NDM-44, NDM-45, NDM-46, NDM-47, NDM-48, NDM-49, NDM-50, NDM-51, NDM-52, NDM-53, NDM-54, NDM-55, NDM-56, NDM-57, NDM-58, NDM-59, NDM-60, NDM-61, NDM-62, NDM-63, NDM-64, NDM-65, NDM-66, NDM-67, NDM-68, NDM-69, NDM-70, NDM-71, NDM-72, NDM-73, NDM-74, NDM-75, NDM-76, NDM-77, NDM-78, NDM-79, NDM-80, NDM-81, NDM-82, NDM-83, NDM-84, NDM-85, NDM-86, NDM-87, NDM-88, NDM-89, NDM-90, NDM-91, NDM-92, NDM-93, NDM-94, NDM-95, NDM-96, NDM-97, NDM-98, or NDM-99.

Disclosed herein, in certain embodiments, are nerve delivery molecules according to NDM-36.

Disclosed herein, in certain embodiments, are nerve delivery molecules according to NDM-37.

Disclosed herein, in certain embodiments, are nerve delivery molecules according to NDM-38.

Disclosed herein, in certain embodiments, are nerve delivery molecules according to NDM-39.

Disclosed herein, in certain embodiments, are nerve delivery molecules according to NDM-40.

Disclosed herein, in certain embodiments, are nerve delivery molecules according to NDM-41.

Disclosed herein, in certain embodiments, are nerve delivery molecules according to NDM-42.

Disclosed herein, in certain embodiments, are nerve delivery molecules according to NDM-43.

Disclosed herein, in certain embodiments, are nerve delivery molecules according to NDM-44.

Disclosed herein, in certain embodiments, are nerve delivery molecules according to NDM-45.

Disclosed herein, in certain embodiments, are nerve delivery molecules according to NDM-46.

Disclosed herein, in certain embodiments, are nerve delivery molecules according to NDM-47.

Disclosed herein, in certain embodiments, are nerve delivery molecules according to NDM-48.

Disclosed herein, in certain embodiments, are nerve delivery molecules according to NDM-49.

Disclosed herein, in certain embodiments, are nerve delivery molecules according to NDM-50.

Disclosed herein, in certain embodiments, are nerve delivery molecules according to NDM-51.

Disclosed herein, in certain embodiments, are nerve delivery molecules according to NDM-52.

Disclosed herein, in certain embodiments, are nerve delivery molecules according to NDM-53.

Disclosed herein, in certain embodiments, are nerve delivery molecules according to NDM-54.

Disclosed herein, in certain embodiments, are nerve delivery molecules according to NDM-55.

Disclosed herein, in certain embodiments, are nerve delivery molecules according to NDM-56.

Disclosed herein, in certain embodiments, are nerve delivery molecules according to NDM-57.

Disclosed herein, in certain embodiments, are nerve delivery molecules according to NDM-58.
Disclosed herein, in certain embodiments, are nerve delivery molecules according to NDM-59.
Disclosed herein, in certain embodiments, are nerve delivery molecules according to NDM-60.
Disclosed herein, in certain embodiments, are nerve delivery molecules according to NDM-61.
Disclosed herein, in certain embodiments, are nerve delivery molecules according to NDM-62.
Disclosed herein, in certain embodiments, are nerve delivery molecules according to NDM-63.
Disclosed herein, in certain embodiments, are nerve delivery molecules according to NDM-64.
Disclosed herein, in certain embodiments, are nerve delivery molecules according to NDM-65.
Disclosed herein, in certain embodiments, are nerve delivery molecules according to NDM-66.
Disclosed herein, in certain embodiments, are nerve delivery molecules according to NDM-67.
Disclosed herein, in certain embodiments, are nerve delivery molecules according to NDM-68.
Disclosed herein, in certain embodiments, are nerve delivery molecules according to NDM-69.
Disclosed herein, in certain embodiments, are nerve delivery molecules according to NDM-70.
Disclosed herein, in certain embodiments, are nerve delivery molecules according to NDM-71.
Disclosed herein, in certain embodiments, are nerve delivery molecules according to NDM-72.
Disclosed herein, in certain embodiments, are nerve delivery molecules according to NDM-73.
Disclosed herein, in certain embodiments, are nerve delivery molecules according to NDM-74.
Disclosed herein, in certain embodiments, are nerve delivery molecules according to NDM-75.
Disclosed herein, in certain embodiments, are nerve delivery molecules according to NDM-76.
Disclosed herein, in certain embodiments, are nerve delivery molecules according to NDM-77.
Disclosed herein, in certain embodiments, are nerve delivery molecules according to NDM-78.
Disclosed herein, in certain embodiments, are nerve delivery molecules according to NDM-79.
Disclosed herein, in certain embodiments, are nerve delivery molecules according to NDM-80.
Disclosed herein, in certain embodiments, are nerve delivery molecules according to NDM-81.
Disclosed herein, in certain embodiments, are nerve delivery molecules according to NDM-82.
Disclosed herein, in certain embodiments, are nerve delivery molecules according to NDM-83.
Disclosed herein, in certain embodiments, are nerve delivery molecules according to NDM-84.
Disclosed herein, in certain embodiments, are nerve delivery molecules according to NDM-85.
Disclosed herein, in certain embodiments, are nerve delivery molecules according to NDM-86.
Disclosed herein, in certain embodiments, are nerve delivery molecules according to NDM-87.
Disclosed herein, in certain embodiments, are nerve delivery molecules according to NDM-88.
Disclosed herein, in certain embodiments, are nerve delivery molecules according to NDM-89.
Disclosed herein, in certain embodiments, are nerve delivery molecules according to NDM-90.
Disclosed herein, in certain embodiments, are nerve delivery molecules according to NDM-91.
Disclosed herein, in certain embodiments, are nerve delivery molecules according to NDM-92.
Disclosed herein, in certain embodiments, are nerve delivery molecules according to NDM-93.
Disclosed herein, in certain embodiments, are nerve delivery molecules according to NDM-94.
Disclosed herein, in certain embodiments, are nerve delivery molecules according to NDM-95.
Disclosed herein, in certain embodiments, are nerve delivery molecules according to NDM-96.
Disclosed herein, in certain embodiments, are nerve delivery molecules according to NDM-97.
Disclosed herein, in certain embodiments, are nerve delivery molecules according to NDM-98.
Disclosed herein, in certain embodiments, are nerve delivery molecules according to NDM-99.

In some embodiments, the nerve delivery molecule has a structure selected from: NDM-36, NDM-37, NDM-38, NDM-39, NDM-40, NDM-41, NDM-42, NDM-43, NDM-44, NDM-45, NDM-46, NDM-47, NDM-48, NDM-49, NDM-50, NDM-51, NDM-52, NDM-53, NDM-54, NDM-55, NDM-56, NDM-57, NDM-58, NDM-59, NDM-60, NDM-61, NDM-62, NDM-63, NDM-64, NDM-65, NDM-66, NDM-67, NDM-68, NDM-69, NDM-70, NDM-71, NDM-72, NDM-73, NDM-74, NDM-75, NDM-76, NDM-77, NDM-78, NDM-79, NDM-80, NDM-81, NDM-82, NDM-83, NDM-84, NDM-85, NDM-86, NDM-87, NDM-88, NDM-89, NDM-90, NDM-91, NDM-92, NDM-93, NDM-94, NDM-95, NDM-96, NDM-97, NDM-98, and NDM-99.

Structures NDM-36 to NDM-99

NDM-36

Ac-[D-Cys(Cy5)]-(D-Ala)-(D-Ala)-(D-Ala)-(D-Thr)-(D-His)-(D-Glu)-NH$_2$

Structures NDM-36 to NDM-99
NDM-37
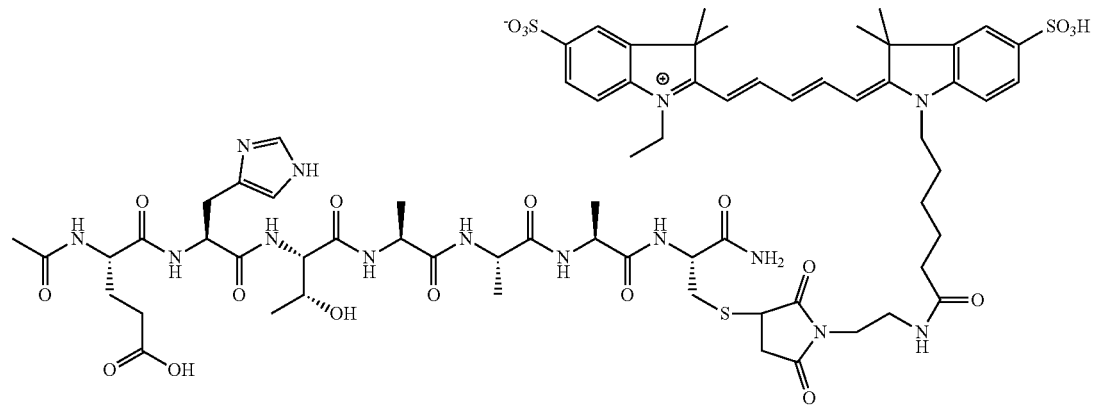
Ac-Glu-His-Thr-Ala-Ala-Ala-Cys(Cy5)-NH$_2$ (SEQ ID NO: 13)
NDM-38
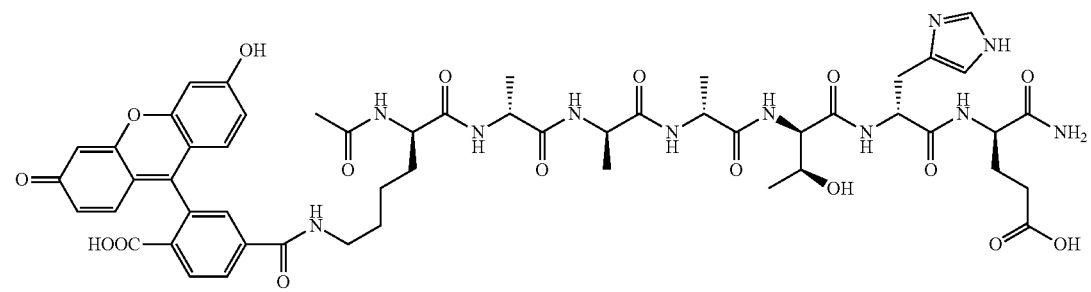
Ac-[D-Lys(6FAM)]-(D-Ala)-(D-Ala)-(D-Ala)-(D-Thr)-(D-His)-(D-Glu)-NH$_2$
NDM-39
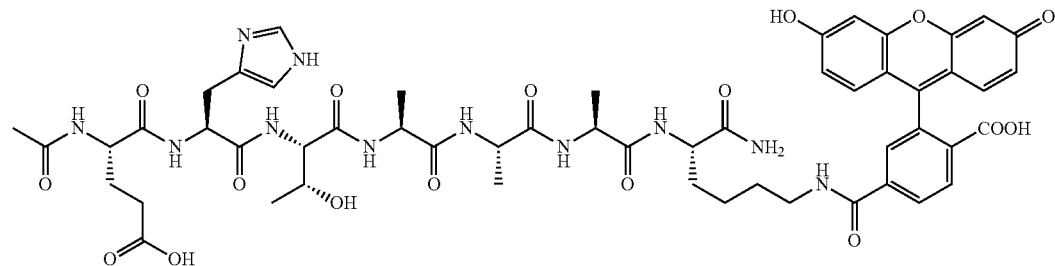 [SMILES: CC(=O)N[C@@H](CCC(=O)O)C(=O)N[C@@H](Cc1c[nH]cn1)C(=O)N[C@H](C(=O)N[C@@H](C)C(=O)N[C@@H](C)C(=O)N[C@@H](C)C(=O)N[C@@H](CCCCNC(=O)c1ccc(C(=O)O)c(-c2c3ccc(=O)cc-3oc3cc(O)ccc23)c1)C(N)=O)[C@@H](C)O]
Ac-Glu-His-Thr-Ala-Ala-Ala-Lys(6FAM)-NH$_2$ (SEQ ID NO: 14)
NDM-40
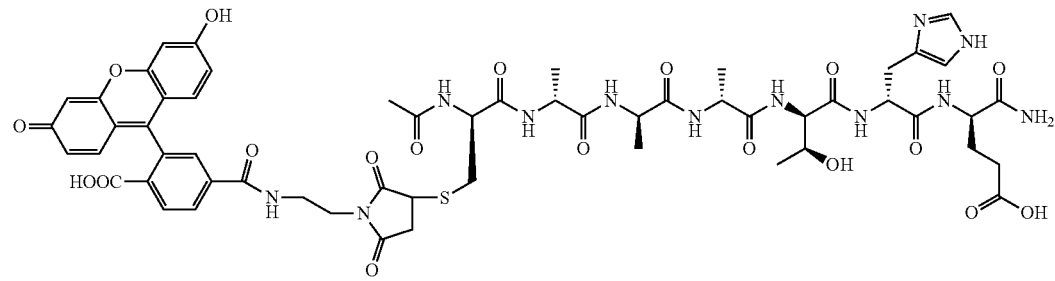 [SMILES: CC(=O)N[C@H](CSC1CC(=O)N(CCNC(=O)c2ccc(C(=O)O)c(-c3c4ccc(=O)cc-4oc4cc(O)ccc34)c2)C1=O)C(=O)N[C@H](C)C(=O)N[C@H](C)C(=O)N[C@H](C)C(=O)N[C@@H](C(=O)N[C@H](Cc1c[nH]cn1)C(=O)N[C@H](CCC(=O)O)C(N)=O)[C@H](C)O]
Ac-[D-Cys(6FAM)]-(D-Ala)-(D-Ala)-(D-Ala)-(D-Thr)-(D-His)-(D-Glu)-NH$_2$ Structures NDM-36 to NDM-99
NDM-41
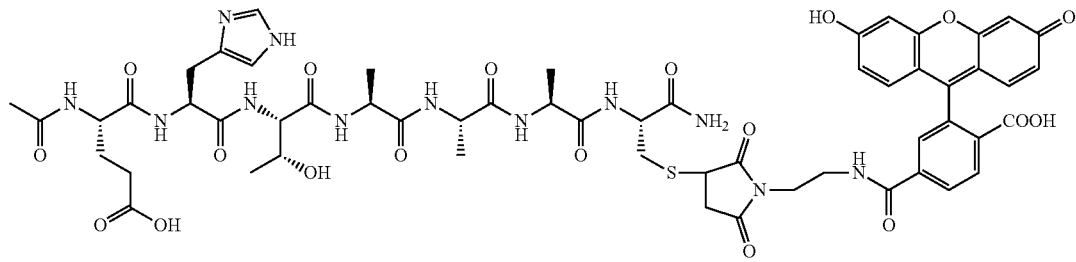 [SMILES: CC(=O)N[C@@H](CCC(=O)O)C(=O)N[C@@H](Cc1c[nH]cn1)C(=O)N[C@H](C(=O)N[C@@H](C)C(=O)N[C@@H](C)C(=O)N[C@@H](C)C(=O)N[C@@H](CSC1CC(=O)N(CCNC(=O)c2ccc(C(=O)O)c(-c3c4ccc(=O)cc-4oc4cc(O)ccc34)c2)C1=O)C(N)=O)[C@@H](C)O]
Ac-Glu-His-Thr-Ala-Ala-Ala-Cys(6FAM)-NH$_2$ (SEQ ID NO: 15)
NDM-42
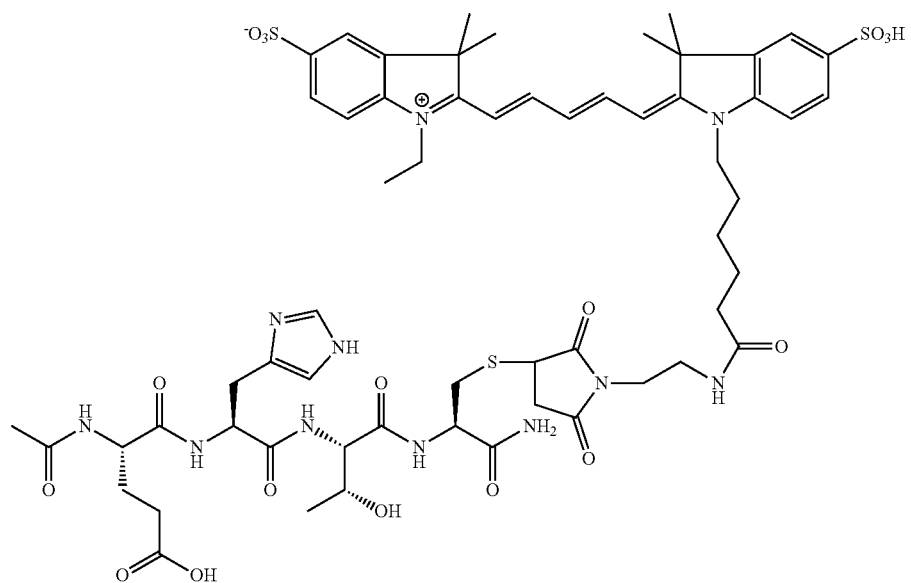
Ac-Glu-His-Thr-Cys(Cy5)-NH$_2$ (SEQ ID NO: 16)
NDM-43
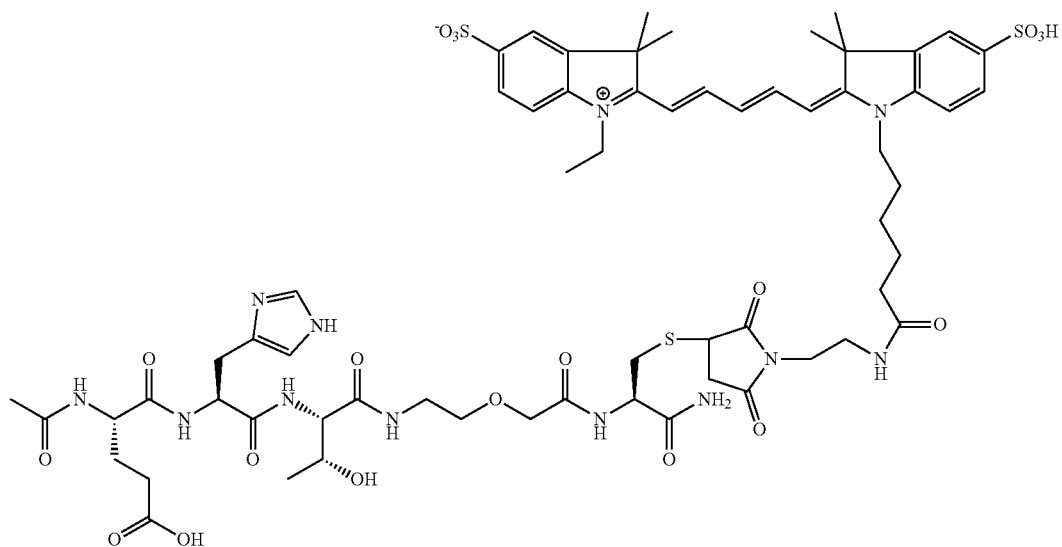
Ac-Glu-His-Thr-o-Cys(Cy5)-NH$_2$ -continued
Structures NDM-36 to NDM-99
NDM-44
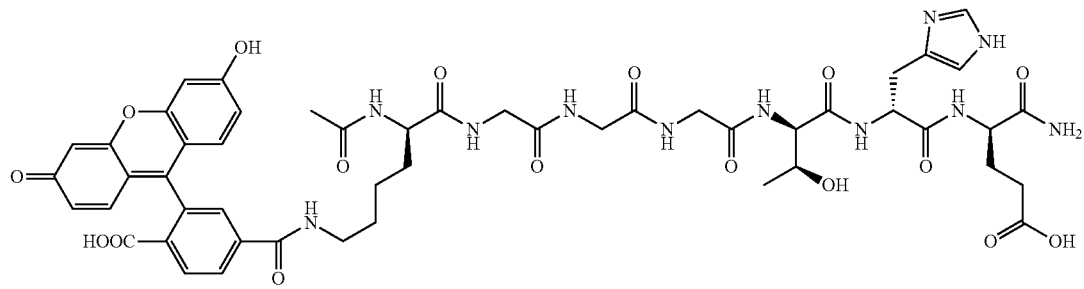 [SMILES: CC(=O)N[C@H](CCCCNC(=O)c1ccc(C(=O)O)c(-c2c3ccc(=O)cc-3oc3cc(O)ccc23)c1)C(=O)NCC(=O)NCC(=O)NCC(=O)N[C@@H](C(=O)N[C@H](Cc1c[nH]cn1)C(=O)N[C@H](CCC(=O)O)C(N)=O)[C@H](C)O]
Ac-[D-Lys(6FAM)]-Gly-Gly-Gly-(D-Thr)-(D-His)-(D-Glu)-NH$_2$
NDM-45
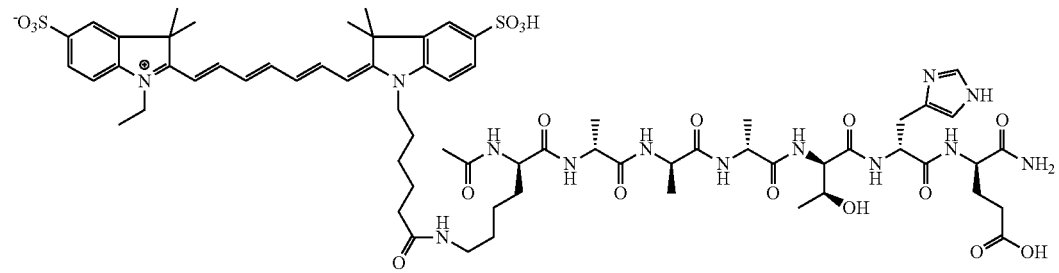
Ac-[D-Lys(Cy7)]-(D-Ala)-(D-Ala)-(D-Ala)-(D-Thr)-(D-His)-(D-Glu)-NH$_2$
NDM-46
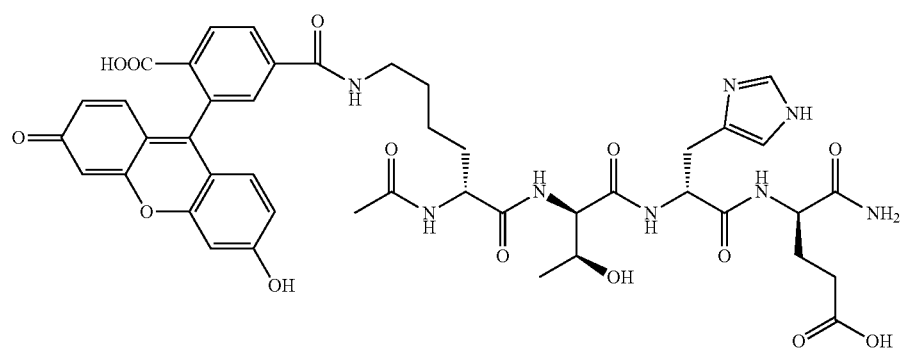 [SMILES: CC(=O)N[C@H](CCCCNC(=O)c1ccc(C(=O)O)c(-c2c3ccc(=O)cc-3oc3cc(O)ccc23)c1)C(=O)N[C@@H](C(=O)N[C@H](Cc1c[nH]cn1)C(=O)N[C@H](CCC(=O)O)C(N)=O)[C@H](C)O]
Ac-[D-Lys(6FAM)]-(D-Thr)-(D-His)-(D-Glu)-NH$_2$
NDM-47
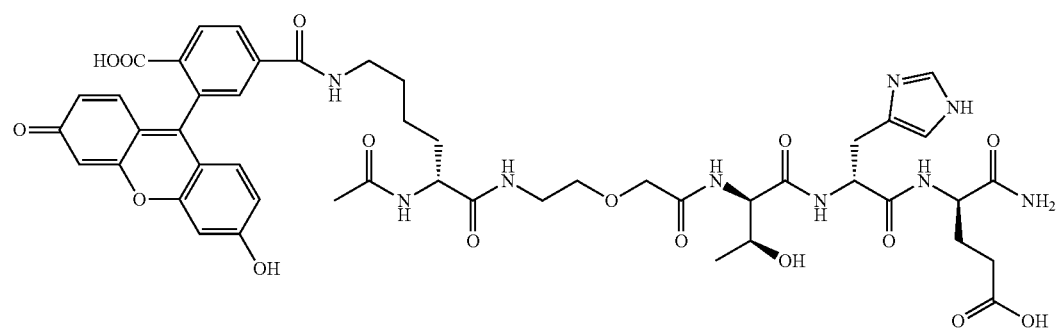 [SMILES: CC(=O)N[C@H](CCCCNC(=O)c1ccc(C(=O)O)c(-c2c3ccc(=O)cc-3oc3cc(O)ccc23)c1)C(=O)NCCOCC(=O)N[C@@H](C(=O)N[C@H](Cc1c[nH]cn1)C(=O)N[C@H](CCC(=O)O)C(N)=O)[C@H](C)O]
Ac-[D-Lys(6FAM)]-o-(D-Thr)-(D-His)-(D-Glu)-NH$_2$ -continued
Structures NDM-36 to NDM-99
NDM-48
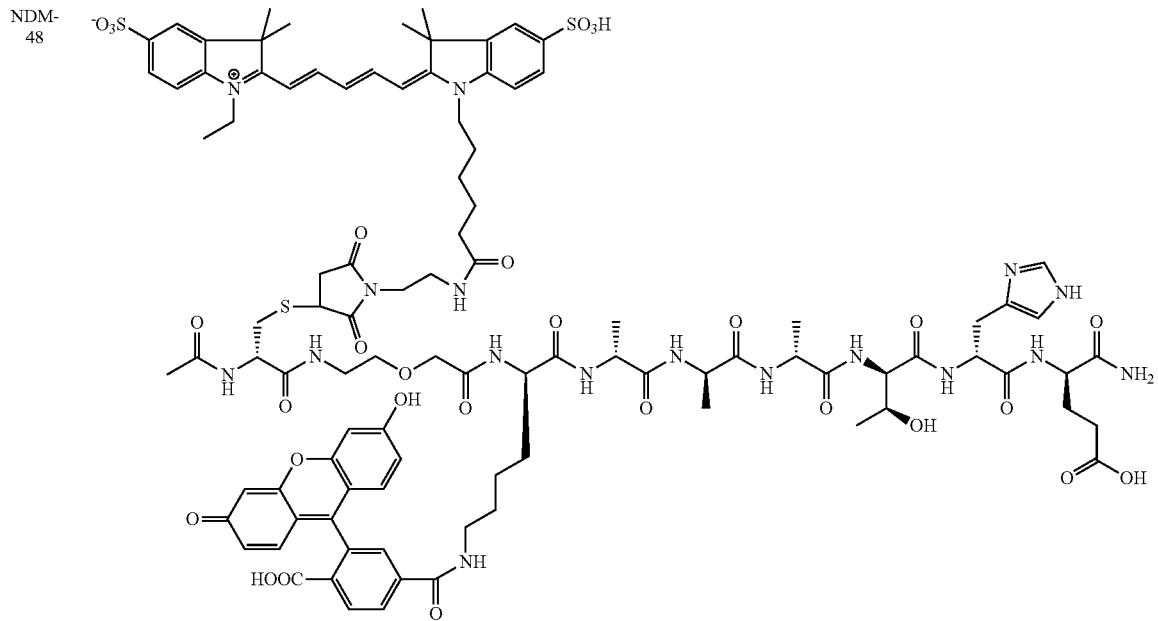
Ac-[D-Cys(Cy5)]-o-[D-Lys(6FAM)]-(D-Ala)-(D-Ala)-(D-Ala)-(D-Thr)-(D-His)-(D-Glu)-NH$_2$
NDM-49
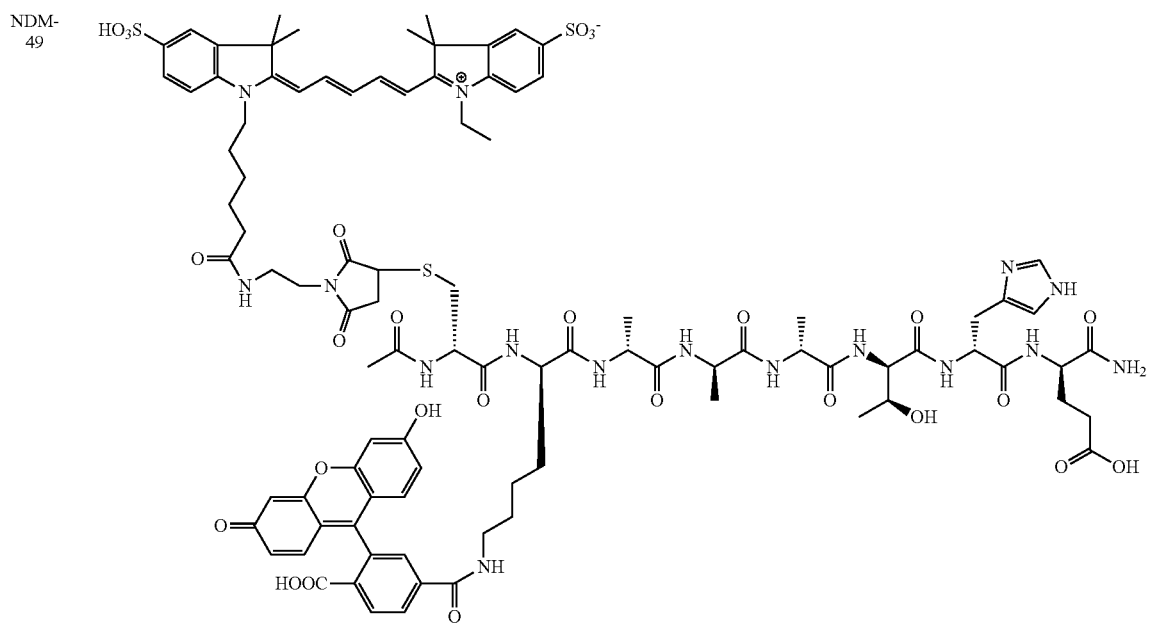
Ac-[D-Cys(Cy5)]-[D-Lys(6FAM)]-(D-Ala)-(D-Ala)-(D-Ala)-(D-Thr)-(D-His)-(D-Glu)-NH$_2$ -continued
Structures NDM-36 to NDM-99
NDM-50
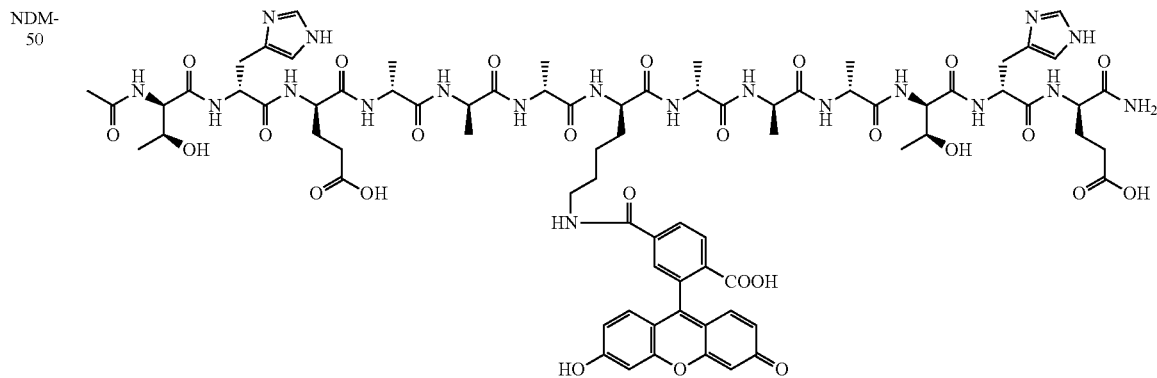
Ac-(D-Thr)-(D-His)-(D-Glu)-(D-Ala)-(D-Ala)-(D-Ala)-[D-Lys(6FAM)]-(D-Ala)-(D-Ala)-(D-Ala)-(D-Thr)-(D-His)-(D-Glu)-NH$_2$
NDM-51
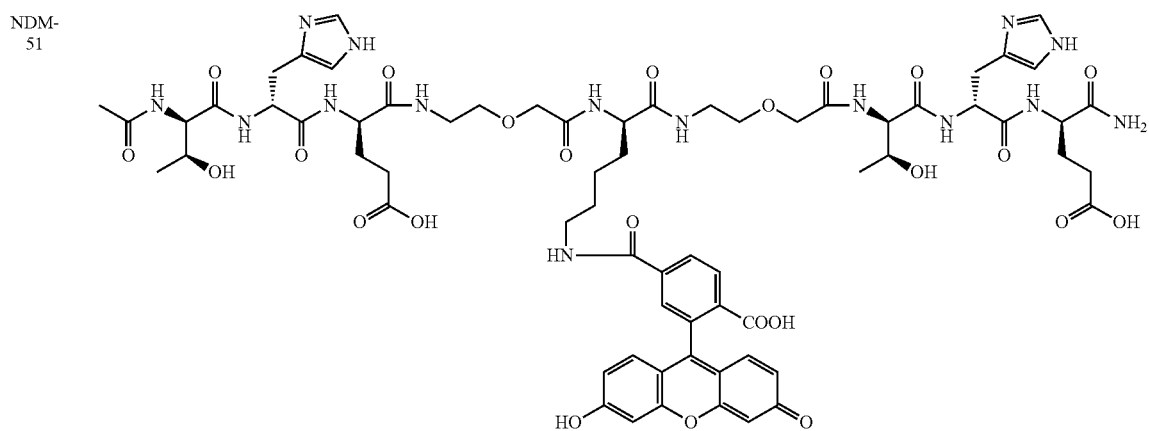
Ac-(D-Thr)-(D-His)-(D-Glu)-o-[D-Lys(6FAM)]-o-(D-Thr)-(D-His)-(D-Glu)-NH$_2$
NDM-52
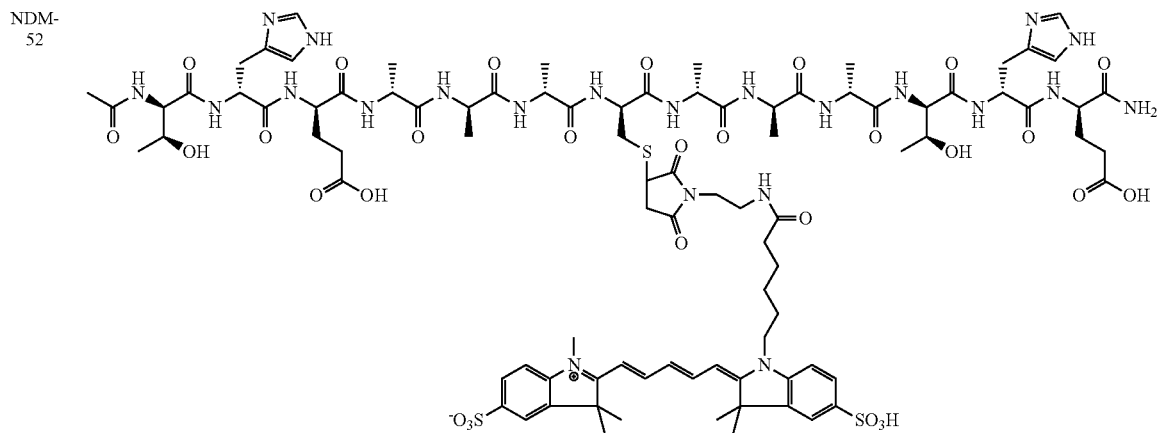
Ac-(D-Thr)-(D-His)-(D-Glu)-(D-Ala)-(D-Ala)-(D-Ala)-[D-Cys(Cy5)]-(D-Ala)-(D-Ala)-(D-Ala)-(D-Thr)-(D-His)-(D-Glu)-NH$_2$ Structures NDM-36 to NDM-99
NDM-53
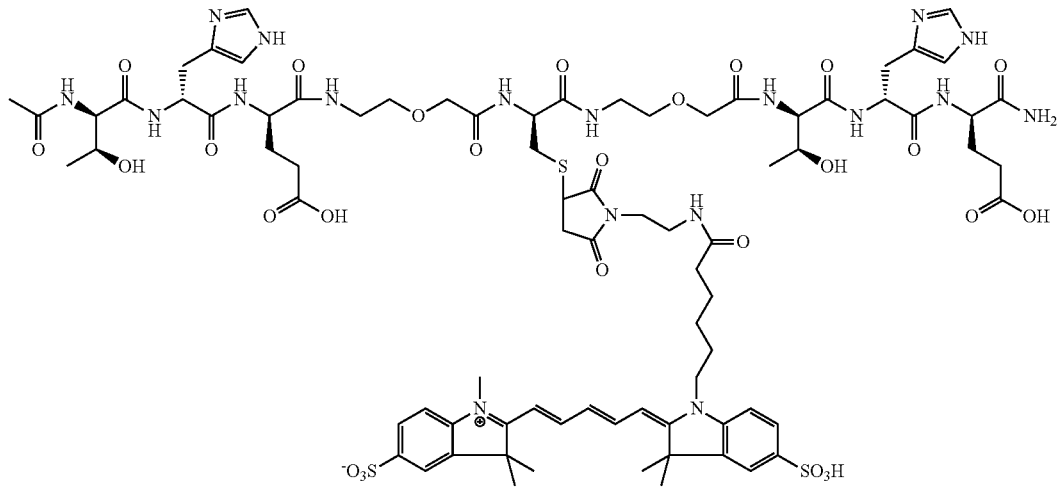
Ac-(D-Thr)-(D-His)-(D-Glu)-o-[D-Cys(Cy5)]-o-(D-Thr)-(D-His)-(D-Glu)-NH$_2$
NDM-54
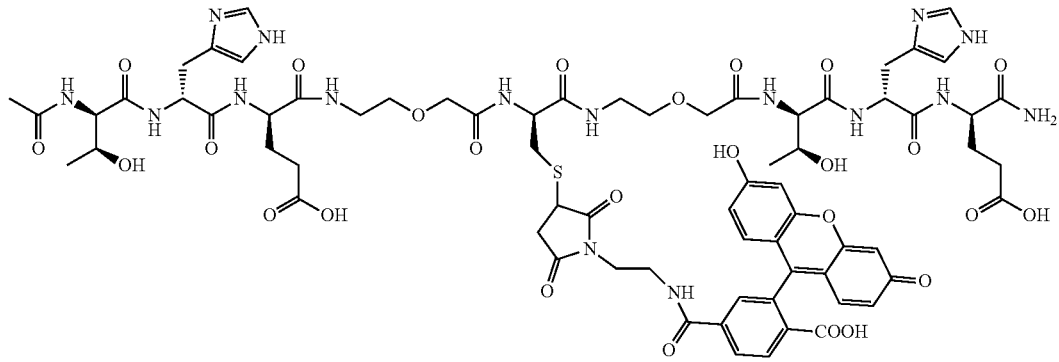 [SMILES: CC(=O)N[C@@H](C(=O)N[C@H](Cc1c[nH]cn1)C(=O)N[C@H](CCC(=O)O)C(=O)NCCOCC(=O)N[C@H](CSC1CC(=O)N(CCNC(=O)c2ccc(C(=O)O)c(-c3c4ccc(=O)cc-4oc4cc(O)ccc34)c2)C1=O)C(=O)NCCOCC(=O)N[C@@H](C(=O)N[C@H](Cc1c[nH]cn1)C(=O)N[C@H](CCC(=O)O)C(N)=O)[C@H](C)O)[C@H](C)O]
Ac-(D-Thr)-(D-His)-(D-Glu)-o-[D-Cys(6FAM)]-o-(D-Thr)-(D-His)-(D-Glu)-NH$_2$
NDM-55
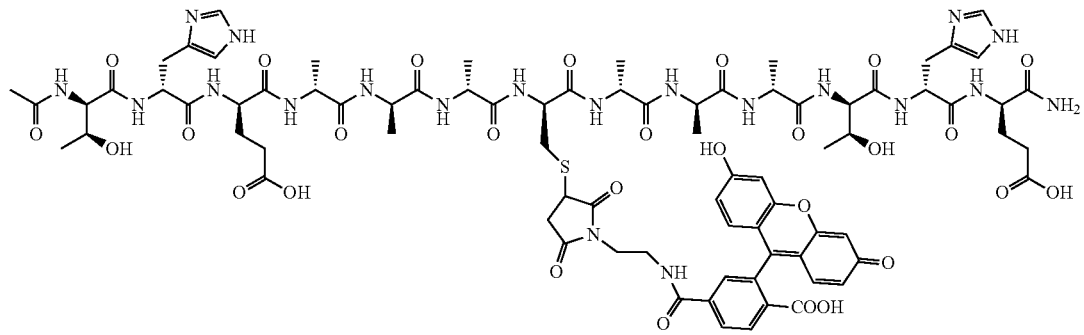 [SMILES: CC(=O)N[C@@H](C(=O)N[C@H](Cc1c[nH]cn1)C(=O)N[C@H](CCC(=O)O)C(=O)N[C@H](C)C(=O)N[C@H](C)C(=O)N[C@H](C)C(=O)N[C@H](CSC1CC(=O)N(CCNC(=O)c2ccc(C(=O)O)c(-c3c4ccc(=O)cc-4oc4cc(O)ccc34)c2)C1=O)C(=O)N[C@H](C)C(=O)N[C@H](C)C(=O)N[C@H](C)C(=O)N[C@@H](C(=O)N[C@H](Cc1c[nH]cn1)C(=O)N[C@H](CCC(=O)O)C(N)=O)[C@H](C)O)[C@H](C)O]
Ac-(D-Thr)-(D-His)-(D-Glu)-(D-Ala)-(D-Ala)-(D-Ala)-[D-Cys(6FAM)]-(D-Ala)-(D-Ala)-(D-Ala)-(D-Thr)-(D-His)-(D-Glu)-NH$_2$ Structures NDM-36 to NDM-99
NDM-56
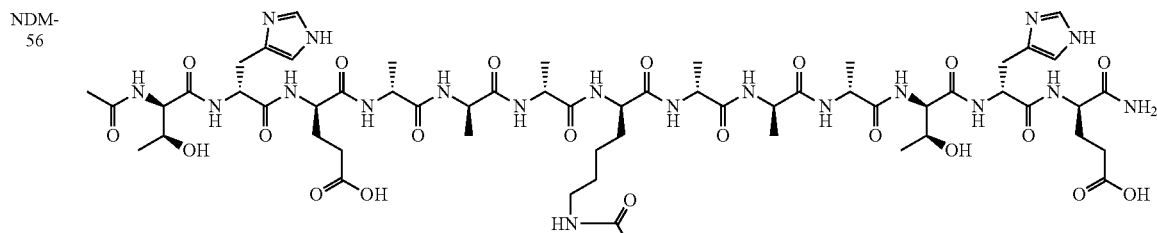
Ac-(D-Thr)-(D-His)-(D-Glu)-(D-Ala)-(D-Ala)-(D-Ala)-[D-Lys(Cy7)]-(D-Ala)-(D-Ala)-(D-Ala)-(D-Thr)-(D-His)-(D-Glu)-NH₂
NDM-57
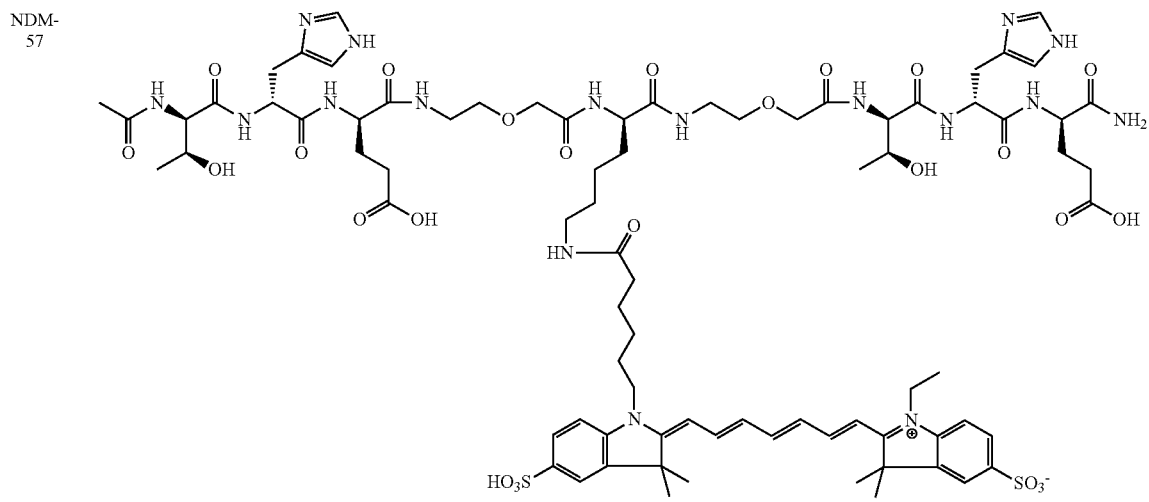
Ac-(D-Thr)-(D-His)-(D-Glu)-o-[D-Lys(Cy7)]-o-(D-Thr)-(D-His)-(D-Glu)-NH₂
NDM-58
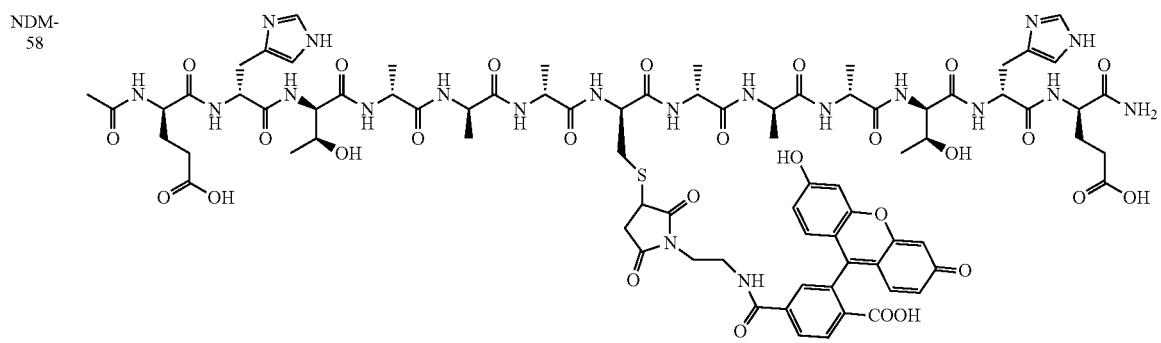
Ac-(D-Glu)-(D-His)-(D-Thr)-(D-Ala)-(D-Ala)-(D-Ala)-[D-Lys(6FAM)]-(D-Ala)-(D-Ala)-(D-Ala)-(D-Thr)-(D-His)-(D-Glu)-NH₂

| Structures NDM-36 to NDM-99 |
|---|
| NDM-59 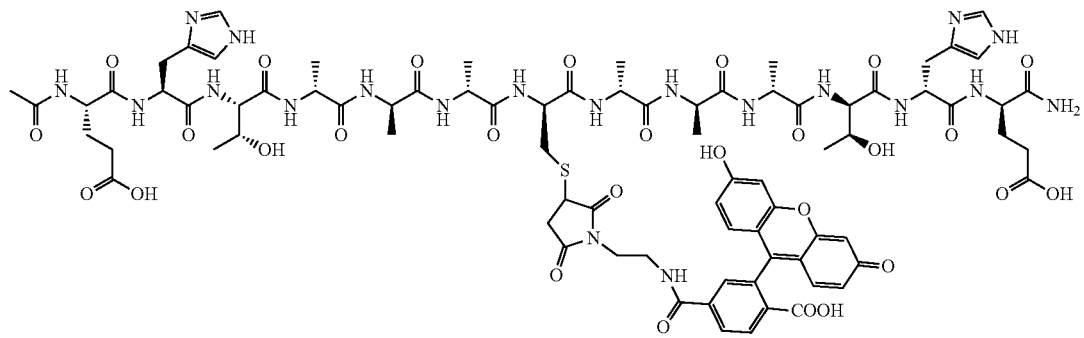 [SMILES: CC(=O)N[C@@H](CCC(=O)O)C(=O)N[C@@H](Cc1c[nH]cn1)C(=O)N[C@H](C(=O)N[C@H](C)C(=O)N[C@H](C)C(=O)N[C@H](C)C(=O)N[C@H](CSC1CC(=O)N(CCNC(=O)c2ccc(C(=O)O)c(-c3c4ccc(=O)cc-4oc4cc(O)ccc34)c2)C1=O)C(=O)N[C@H](C)C(=O)N[C@H](C)C(=O)N[C@H](C)C(=O)N[C@@H](C(=O)N[C@H](Cc1c[nH]cn1)C(=O)N[C@H](CCC(=O)O)C(N)=O)[C@H](C)O)[C@@H](C)O]<br>Ac-Glu-His-Thr-(D-Ala)-(D-Ala)-(D-Ala)-[D-Lys(6FAM)]-(D-Ala)-(D-Ala)-(D-Ala)-(D-Thr)-(D-His)-(D-Glu)-NH$_2$ |
| NDM-60 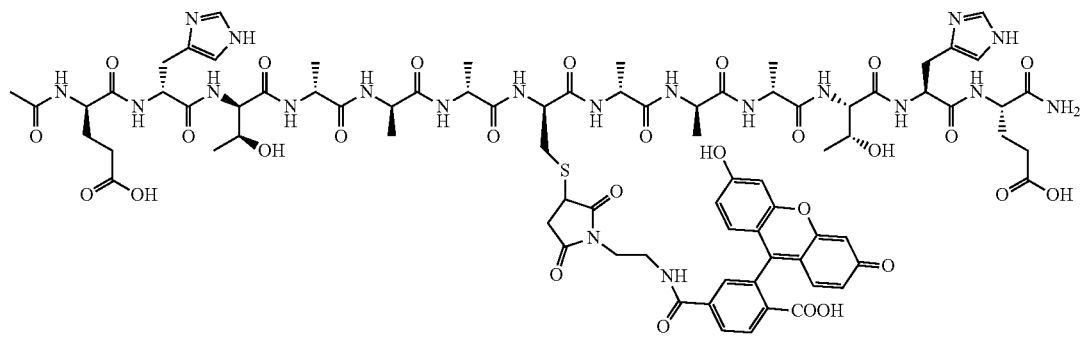 [SMILES: CC(=O)N[C@H](CCC(=O)O)C(=O)N[C@H](Cc1c[nH]cn1)C(=O)N[C@@H](C(=O)N[C@H](C)C(=O)N[C@H](C)C(=O)N[C@H](C)C(=O)N[C@H](CSC1CC(=O)N(CCNC(=O)c2ccc(C(=O)O)c(-c3c4ccc(=O)cc-4oc4cc(O)ccc34)c2)C1=O)C(=O)N[C@H](C)C(=O)N[C@H](C)C(=O)N[C@H](C)C(=O)N[C@H](C(=O)N[C@@H](Cc1c[nH]cn1)C(=O)N[C@@H](CCC(=O)O)C(N)=O)[C@@H](C)O)[C@H](C)O]<br>Ac-(D-Glu)-(D-His)-(D-Thr)-(D-Ala)-(D-Ala)-(D-Ala)-[D-Lys(6FAM)]-(D-Ala)-(D-Ala)-(D-Ala)-Thr-His-Glu-NH$_2$ |
| NDM-61 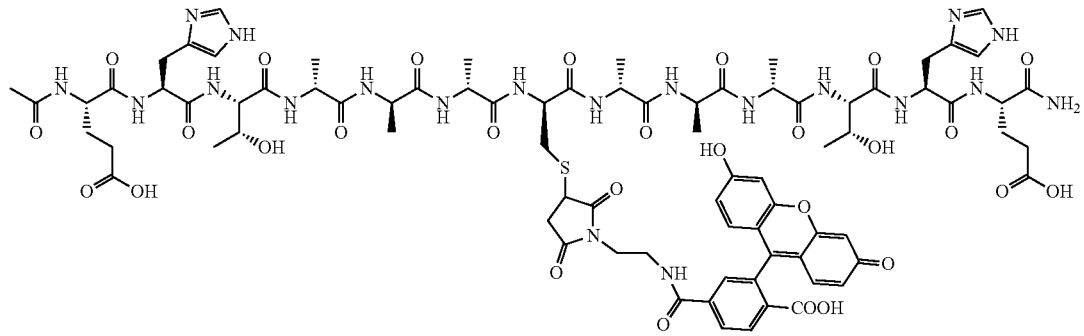 [SMILES: CC(=O)N[C@@H](CCC(=O)O)C(=O)N[C@@H](Cc1c[nH]cn1)C(=O)N[C@H](C(=O)N[C@H](C)C(=O)N[C@H](C)C(=O)N[C@H](C)C(=O)N[C@H](CSC1CC(=O)N(CCNC(=O)c2ccc(C(=O)O)c(-c3c4ccc(=O)cc-4oc4cc(O)ccc34)c2)C1=O)C(=O)N[C@H](C)C(=O)N[C@H](C)C(=O)N[C@H](C)C(=O)N[C@H](C(=O)N[C@@H](Cc1c[nH]cn1)C(=O)N[C@@H](CCC(=O)O)C(N)=O)[C@@H](C)O)[C@@H](C)O]<br>Ac-Glu-His-Thr-(D-Ala)-(D-Ala)-(D-Ala)-[D-Lys(6FAM)]-(D-Ala)-(D-Ala)-(D-Ala)-Thr-His-Glu-NH$_2$ |
| NDM-62 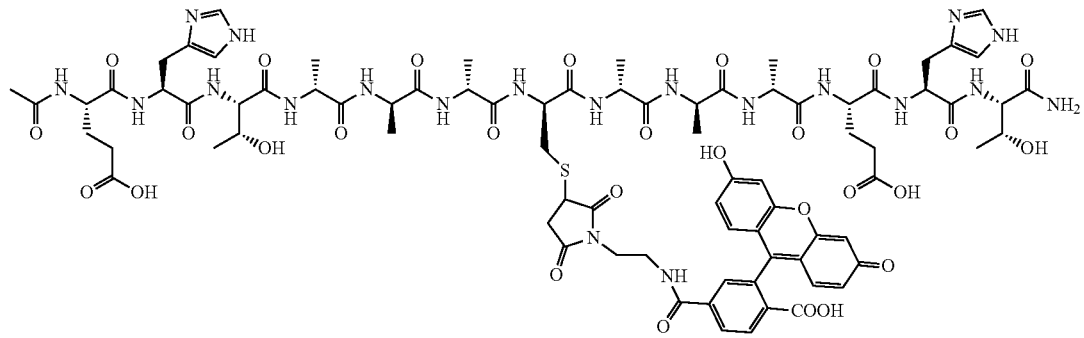 [SMILES: CC(=O)N[C@@H](CCC(=O)O)C(=O)N[C@@H](Cc1c[nH]cn1)C(=O)N[C@H](C(=O)N[C@H](C)C(=O)N[C@H](C)C(=O)N[C@H](C)C(=O)N[C@H](CSC1CC(=O)N(CCNC(=O)c2ccc(C(=O)O)c(-c3c4ccc(=O)cc-4oc4cc(O)ccc34)c2)C1=O)C(=O)N[C@H](C)C(=O)N[C@H](C)C(=O)N[C@H](C)C(=O)N[C@@H](CCC(=O)O)C(=O)N[C@@H](Cc1c[nH]cn1)C(=O)N[C@H](C(N)=O)[C@@H](C)O)[C@@H](C)O]<br>Ac-Glu-His-Thr-(D-Ala)-(D-Ala)-(D-Ala)-[D-Lys(6FAM)]-(D-Ala)-(D-Ala)-(D-Ala)-Glu-His-Thr-NH$_2$ |

Structures NDM-36 to NDM-99
NDM-63
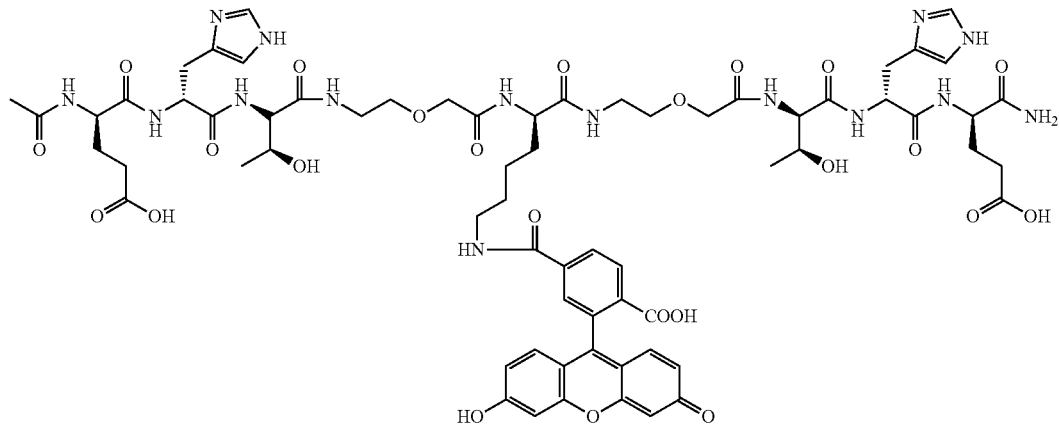
Ac-(D-Glu)-(D-His)-(D-Thr)-o-[D-Cys(6FAM)]-o-(D-Thr)-(D-His)-(D-Glu)-NH$_2$
NDM-64
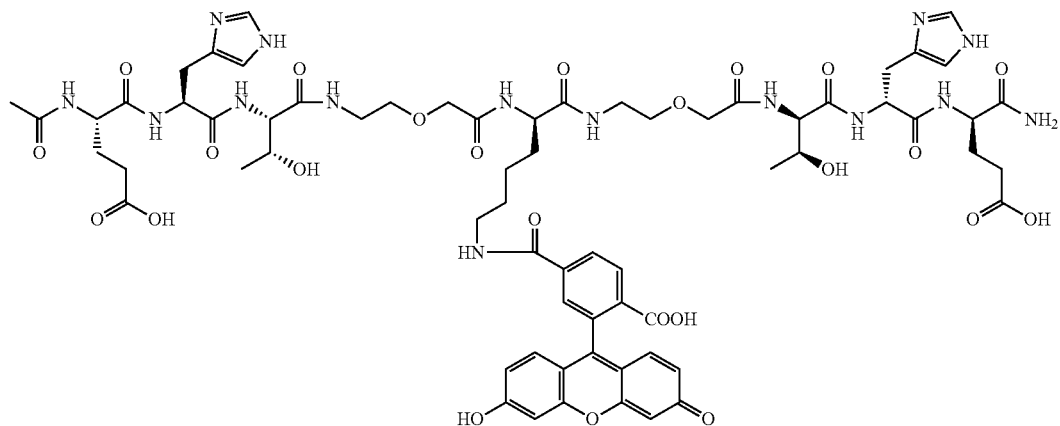 [SMILES: CC(=O)N[C@@H](CCC(=O)O)C(=O)N[C@@H](Cc1c[nH]cn1)C(=O)N[C@H](C(=O)NCCOCC(=O)N[C@H](CCCCNC(=O)c1ccc(C(=O)O)c(-c2c3ccc(=O)cc-3oc3cc(O)ccc23)c1)C(=O)NCCOCC(=O)N[C@@H](C(=O)N[C@H](Cc1c[nH]cn1)C(=O)N[C@H](CCC(=O)O)C(N)=O)[C@H](C)O)[C@@H](C)O]
Ac-Glu-His-Thr-o-[D-Cys(6FAM)]-o-(D-Thr)-(D-His)-(D-Glu)-NH$_2$
NDM-65
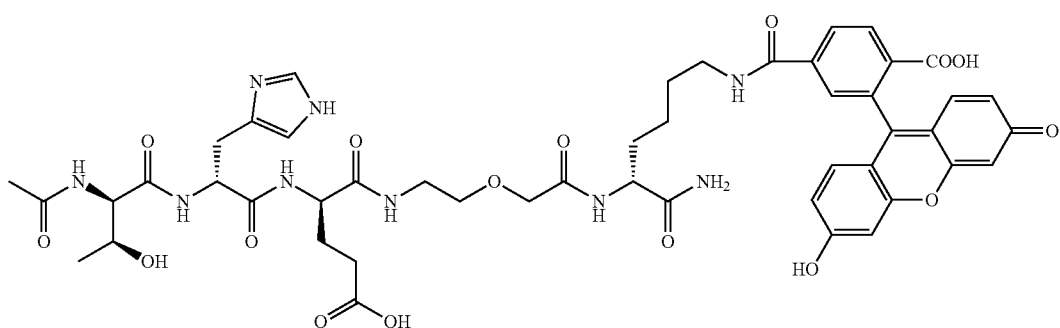 [SMILES: CC(=O)N[C@@H](C(=O)N[C@H](Cc1c[nH]cn1)C(=O)N[C@H](CCC(=O)O)C(=O)NCCOCC(=O)N[C@H](CCCCNC(=O)c1ccc(C(=O)O)c(-c2c3ccc(=O)cc-3oc3cc(O)ccc23)c1)C(N)=O)[C@H](C)O]
Ac-(D-Thr)-(D-His)-(D-Glu)-o-[D-Lys(6FAM)]-NH$_2$
NDM-66
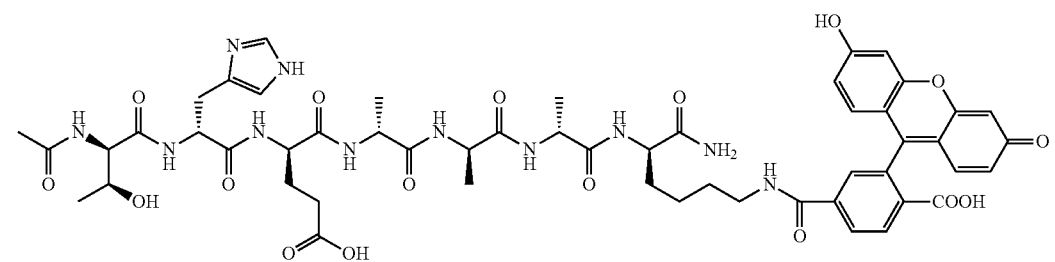 [SMILES: CC(=O)N[C@@H](C(=O)N[C@H](Cc1c[nH]cn1)C(=O)N[C@H](CCC(=O)O)C(=O)N[C@H](C)C(=O)N[C@H](C)C(=O)N[C@H](C)C(=O)N[C@H](CCCCNC(=O)c1ccc(C(=O)O)c(-c2c3ccc(=O)cc-3oc3cc(O)ccc23)c1)C(N)=O)[C@H](C)O]
Ac-(D-Thr)-(D-His)-(D-Glu)-(D-Ala)-(D-Ala)-(D-Ala)-[D-Lys(6FAM)]-NH$_2$ -continued
Structures NDM-36 to NDM-99
NDM-67
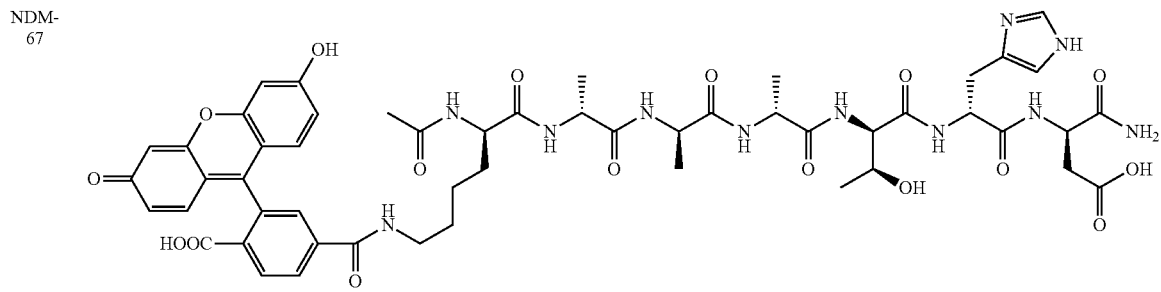
Ac-[D-Lys(6FAM)]-(D-Ala)-(D-Ala)-(D-Ala)-(D-Thr)-(D-His)-(D-Asp)-NH$_2$
NDM-68
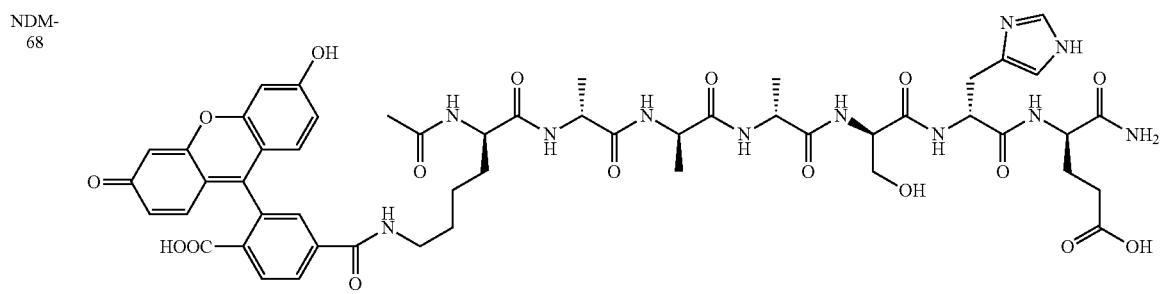
Ac-[D-Lys(6FAM)]-(D-Ala)-(D-Ala)-(D-Ala)-(D-Ser)-(D-His)-(D-Glu)-NH$_2$
NDM-69
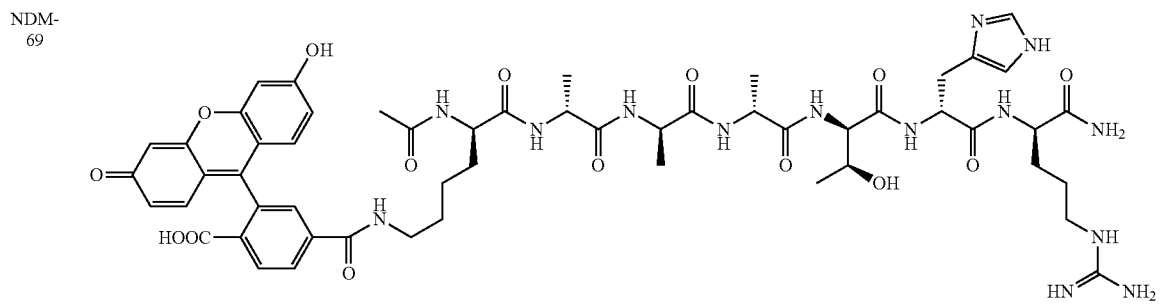
Ac-[D-Lys(6FAM)]-(D-Ala)-(D-Ala)-(D-Ala)-(D-Thr)-(D-His)-(D-Arg)-NH$_2$
NDM-70
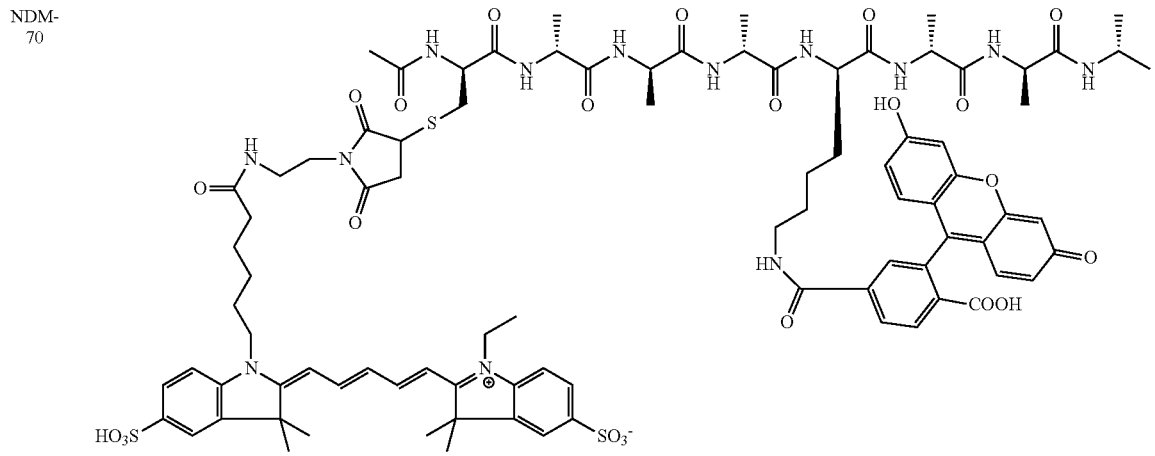

-continued
Structures NDM-36 to NDM-99
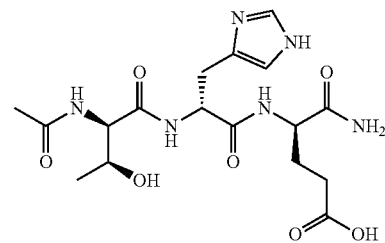
Ac-[D-Cys(Cy5)]-(D-Ala)-(D-Ala)-(D-Ala)-[D-Lys(6FAM)]-(D-Ala)-(D-Ala)-(D-Ala)-(D-Thr)-(D-His)-(D-Glu)-NH₂
NDM-71
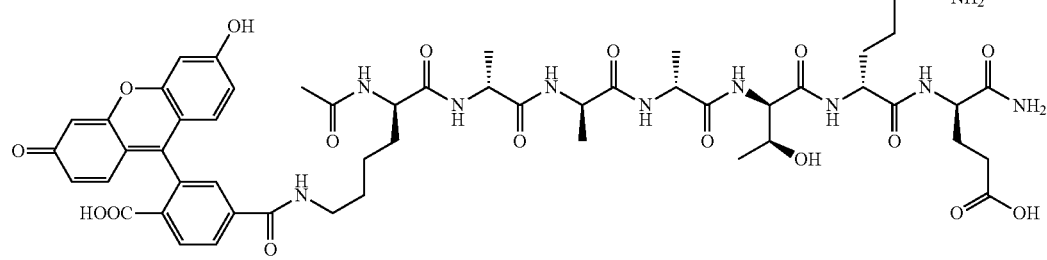
Ac-[D-Lys(6FAM)]-(D-Ala)-(D-Ala)-(D-Ala)-(D-Thr)-(D-Lys)-(D-Glu)-NH₂
NDM-72
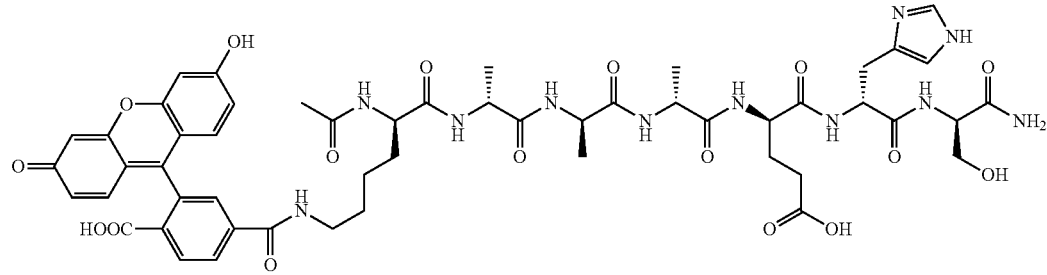 [SMILES: CC(=O)N[C@H](CCCCNC(=O)c1ccc(C(=O)O)c(-c2c3ccc(=O)cc-3oc3cc(O)ccc23)c1)C(=O)N[C@H](C)C(=O)N[C@H](C)C(=O)N[C@H](C)C(=O)N[C@H](CCC(=O)O)C(=O)N[C@H](Cc1c[nH]cn1)C(=O)N[C@H](CO)C(N)=O]
Ac-[D-Lys(6FAM)]-(D-Ala)-(D-Ala)-(D-Ala)-(D-Glu)-(D-His)-(D-Ser)-NH₂
NDM-73
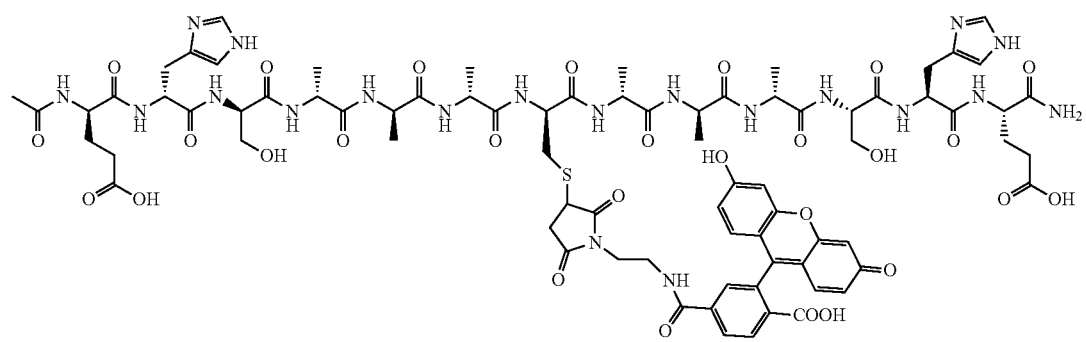 [SMILES: CC(=O)N[C@H](CCC(=O)O)C(=O)N[C@H](Cc1c[nH]cn1)C(=O)N[C@H](CO)C(=O)N[C@H](C)C(=O)N[C@H](C)C(=O)N[C@H](C)C(=O)N[C@H](CSC1CC(=O)N(CCNC(=O)c2ccc(C(=O)O)c(-c3c4ccc(=O)cc-4oc4cc(O)ccc34)c2)C1=O)C(=O)N[C@H](C)C(=O)N[C@H](C)C(=O)N[C@H](C)C(=O)N[C@@H](CO)C(=O)N[C@@H](Cc1c[nH]cn1)C(=O)N[C@@H](CCC(=O)O)C(N)=O]
Ac-(D-Glu)-(D-His)-(D-Ser)-(D-Ala)-(D-Ala)-(D-Ala)-[D-Lys(6FAM)]-(D-Ala)-(D-Ala)-(D-Ala)-Ser-His-Glu-NH₂

Structures NDM-36 to NDM-99
NDM-74
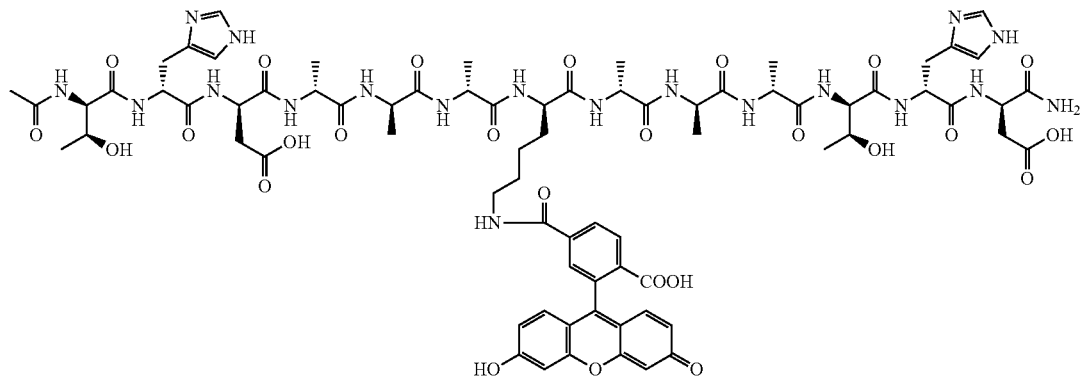 [SMILES: CC(=O)N[C@@H](C(=O)N[C@H](Cc1c[nH]cn1)C(=O)N[C@H](CC(=O)O)C(=O)N[C@H](C)C(=O)N[C@H](C)C(=O)N[C@H](C)C(=O)N[C@H](CCCCNC(=O)c1ccc(C(=O)O)c(-c2c3ccc(=O)cc-3oc3cc(O)ccc23)c1)C(=O)N[C@H](C)C(=O)N[C@H](C)C(=O)N[C@H](C)C(=O)N[C@@H](C(=O)N[C@H](Cc1c[nH]cn1)C(=O)N[C@H](CC(=O)O)C(N)=O)[C@H](C)O)[C@H](C)O]
Ac-(D-Thr)-(D-His)-(D-Asp)-(D-Ala)-(D-Ala)-(D-Ala)-[D-Lys(6FAM)]-(D-Ala)-(D-Ala)-(D-Ala)-(D-Thr)-(D-His)-(D-Asp)-NH₂
NDM-75
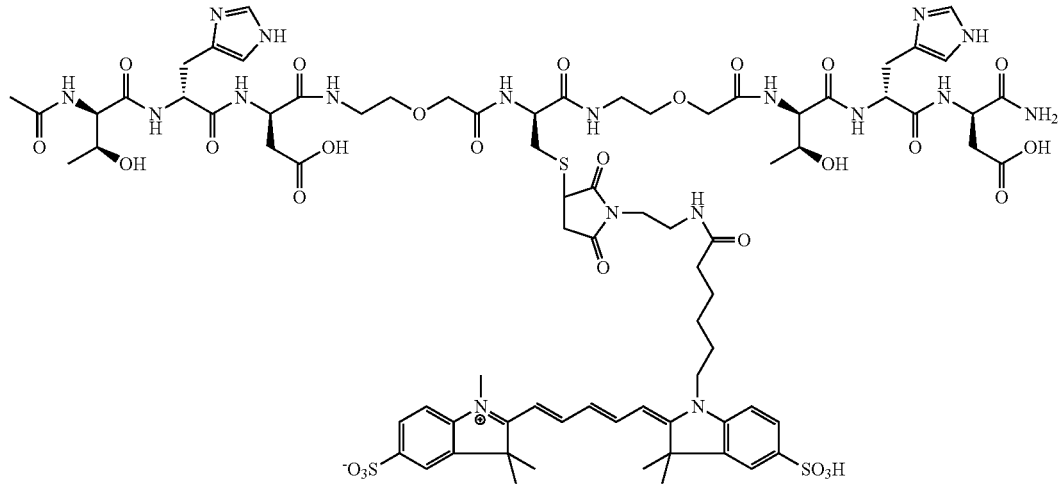
Ac-(D-Thr)-(D-His)-(D-Asp)-o-[D-Cys(Cy5)]-o-(D-Thr)-(D-His)-(D-Asp)-NH₂
NDM-76
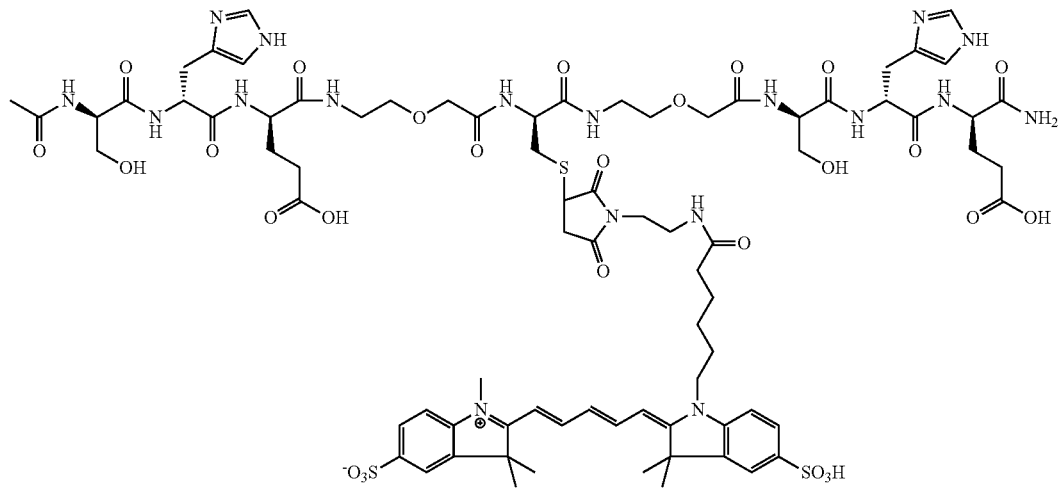
Ac-(D-Ser)-(D-His)-(D-Glu)-o-[D-Cys(Cy5)]-o-(D-Ser)-(D-His)-(D-Glu)-NH₂

Structures NDM-36 to NDM-99
NDM-77
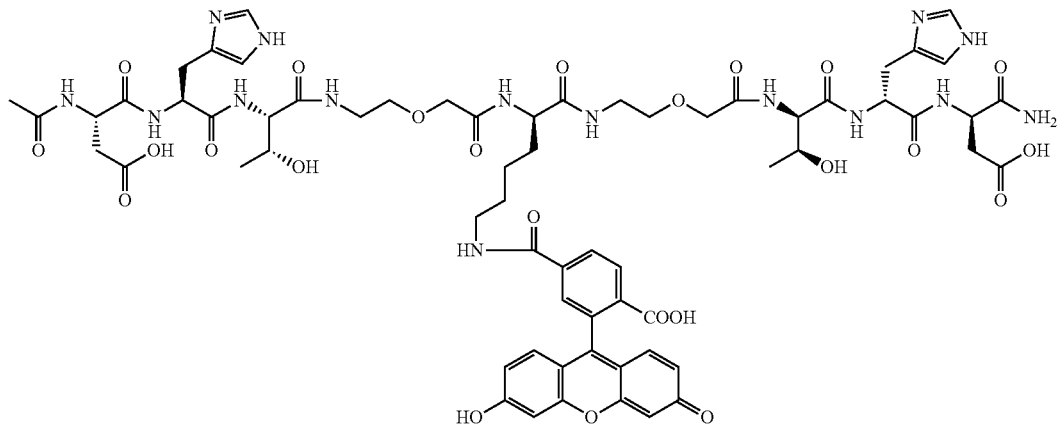 [SMILES: CC(=O)N[C@@H](CC(=O)O)C(=O)N[C@@H](Cc1c[nH]cn1)C(=O)N[C@H](C(=O)NCCOCC(=O)N[C@H](CCCCNC(=O)c1ccc(C(=O)O)c(-c2c3ccc(=O)cc-3oc3cc(O)ccc23)c1)C(=O)NCCOCC(=O)N[C@@H](C(=O)N[C@H](Cc1c[nH]cn1)C(=O)N[C@H](CC(=O)O)C(N)=O)[C@H](C)O)[C@@H](C)O]
Ac-Asp-His-Thr-o-[D-Cys(6FAM)]-o-(D-Thr)-(D-His)-(D-Asp)-NH₂
NDM-78
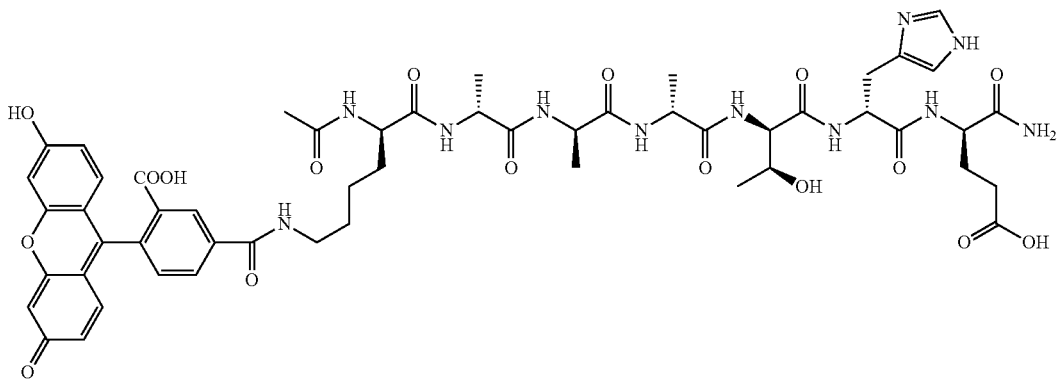 [SMILES: CC(=O)N[C@H](CCCCNC(=O)c1ccc(-c2c3ccc(=O)cc-3oc3cc(O)ccc23)c(C(=O)O)c1)C(=O)N[C@H](C)C(=O)N[C@H](C)C(=O)N[C@H](C)C(=O)N[C@@H](C(=O)N[C@H](Cc1c[nH]cn1)C(=O)N[C@H](CCC(=O)O)C(N)=O)[C@H](C)O]
Ac-[D-Lys(5FAM)]-(D-Ala)-(D-Ala)-(D-Ala)-(D-Thr)-(D-His)-(D-Glu)-NH₂
NDM-79
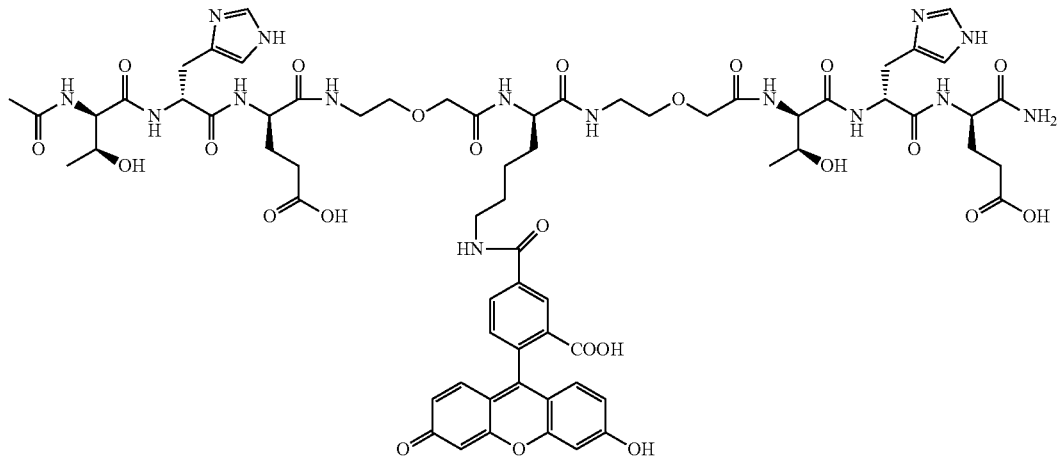 [SMILES: CC(=O)N[C@@H](C(=O)N[C@H](Cc1c[nH]cn1)C(=O)N[C@H](CCC(=O)O)C(=O)NCCOCC(=O)N[C@H](CCCCNC(=O)c1ccc(-c2c3ccc(=O)cc-3oc3cc(O)ccc23)c(C(=O)O)c1)C(=O)NCCOCC(=O)N[C@@H](C(=O)N[C@H](Cc1c[nH]cn1)C(=O)N[C@H](CCC(=O)O)C(N)=O)[C@H](C)O)[C@H](C)O]
Ac-(D-Thr)-(D-His)-(D-Glu)-o-[D-Lys(5FAM)]-o-(D-Thr)-(D-His)-(D-Glu)-NH₂

Structures NDM-36 to NDM-99
NDM-80
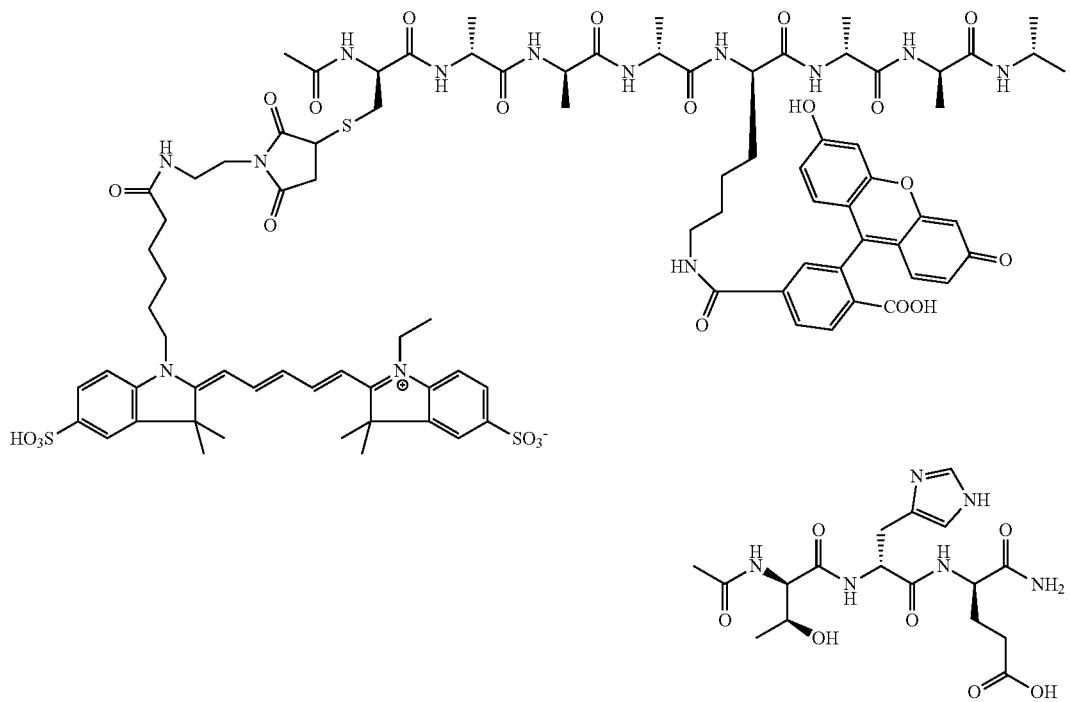
Ac-[D-Cys(Cy5)]-(D-Ala)-(D-Ala)-(D-Ala)-[D-Lys(5FAM)]-(D-Ala)-(D-Ala)-(D-Ala)-(D-Thr)-(D-His)-(D-Glu)-NH$_2$
NDM-81
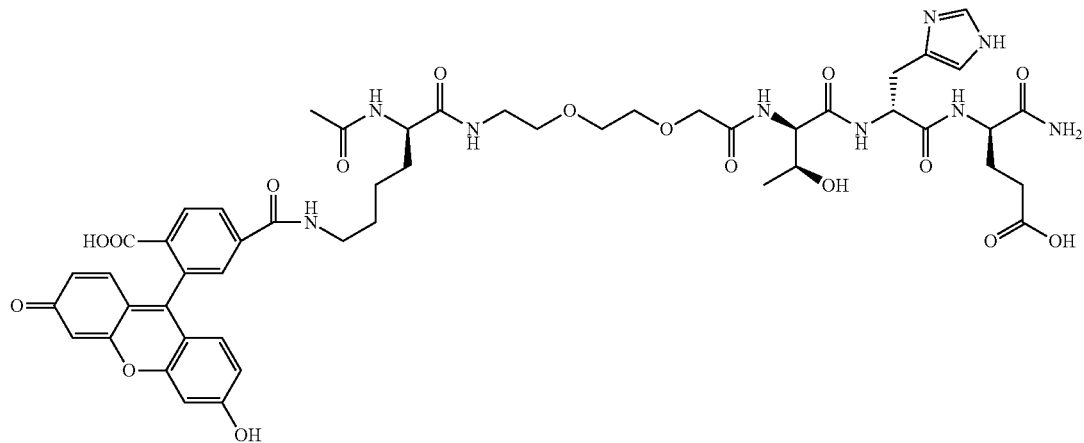 [SMILES: CC(=O)N[C@H](CCCCNC(=O)c1ccc(C(=O)O)c(-c2c3ccc(=O)cc-3oc3cc(O)ccc23)c1)C(=O)NCCOCCOCC(=O)N[C@@H](C(=O)N[C@H](Cc1c[nH]cn1)C(=O)N[C@H](CCC(=O)O)C(N)=O)[C@H](C)O]
Ac-[D-Lys(6FAM)]-PEG2-(D-Thr)-(D-His)-(D-Glu)-NH$_2$
NDM-82
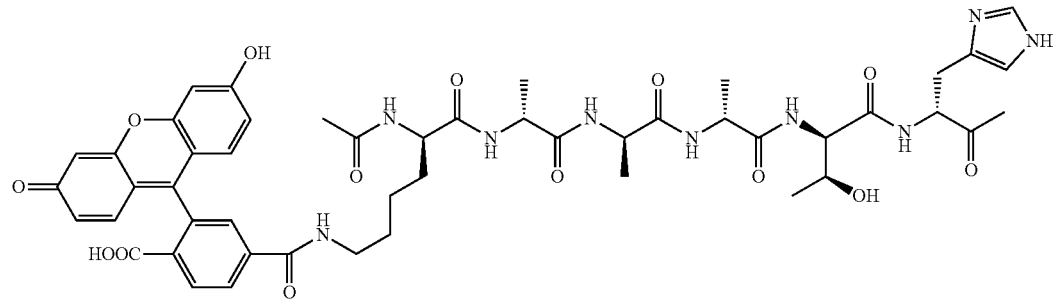

-continued
Structures NDM-36 to NDM-99
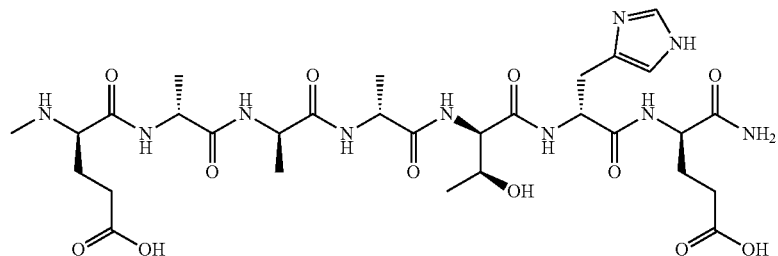
Ac-[D-Lys(6FAM)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-NH₂
NDM-83
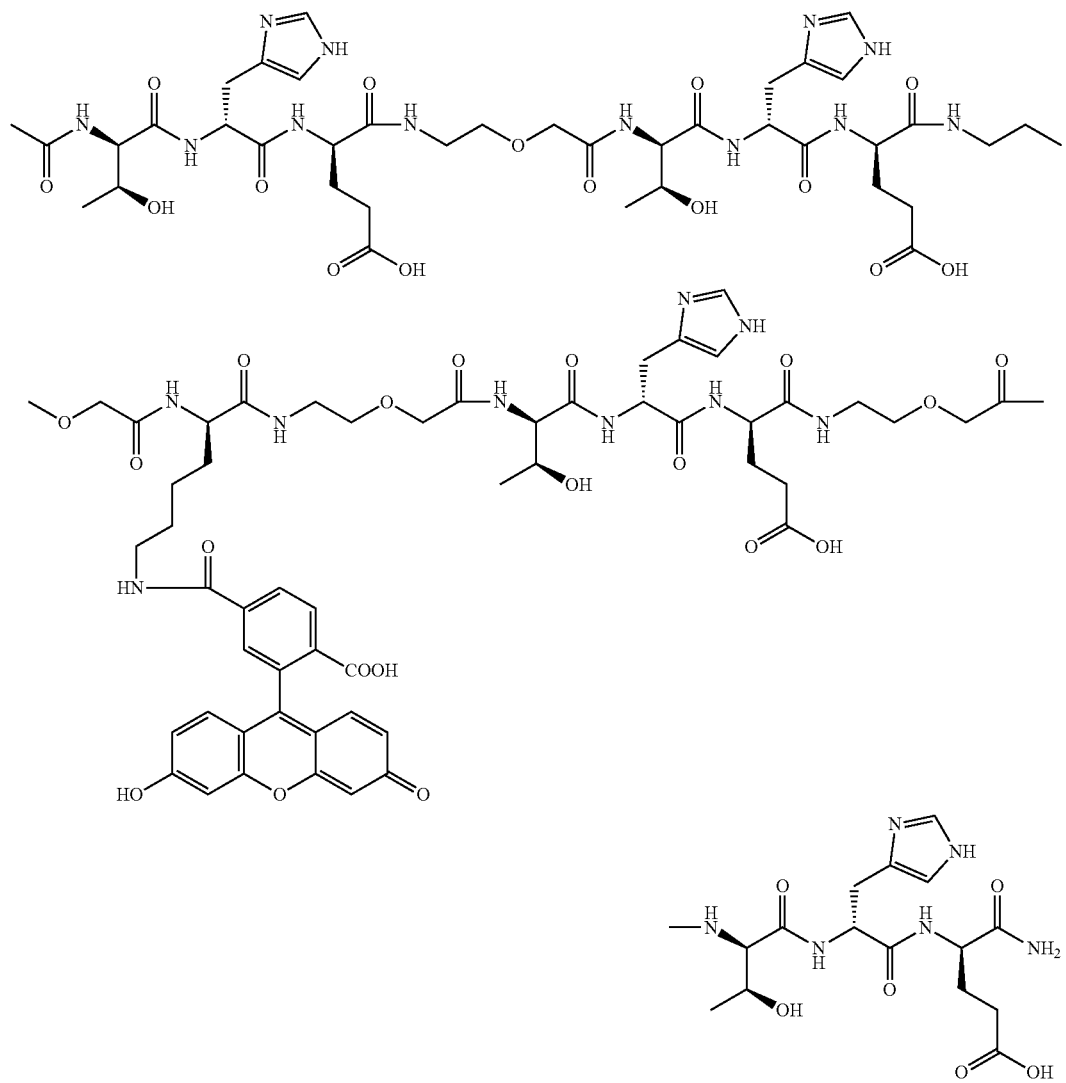
Ac-(D-Thr)-(D-His)-(D-Glu)-o-(D-Thr)-(D-His)-(D-Glu)-o-[D-Lys(6FAM)]-o-(D-Thr)-(D-His)-(D-Glu)-o-(D-Thr)-(D-His)-(D-Glu)-NH₂

Structures NDM-36 to NDM-99
NDM-84
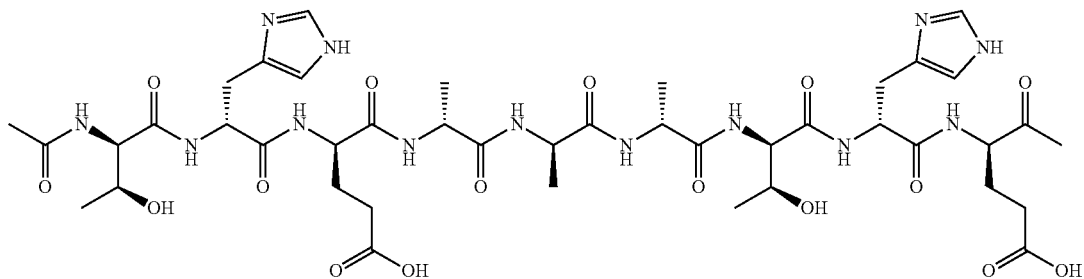
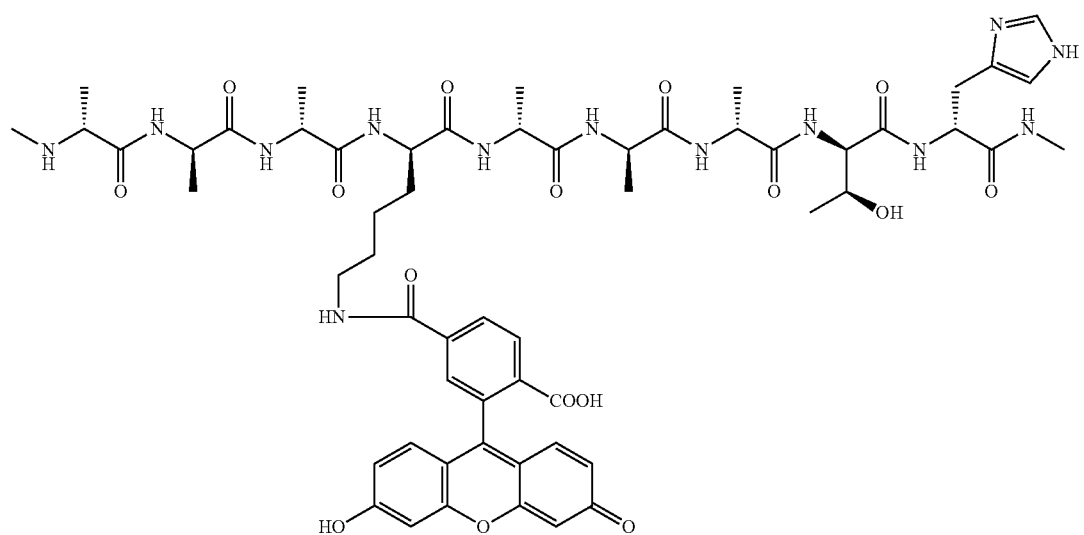
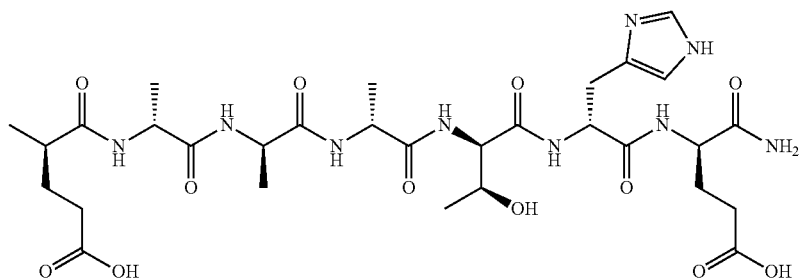
Ac-(D-Thr)-(D-His)-(D-Glu)-(D-Ala)-(D-Ala)-(D-Ala)-(D-Thr)-(D-His)-(D-Glu)-(D-Ala)-(D-Ala)-(D-Ala)-[D-Lys(6FAM)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-NH$_2$

Structures NDM-36 to NDM-99
NDM-85
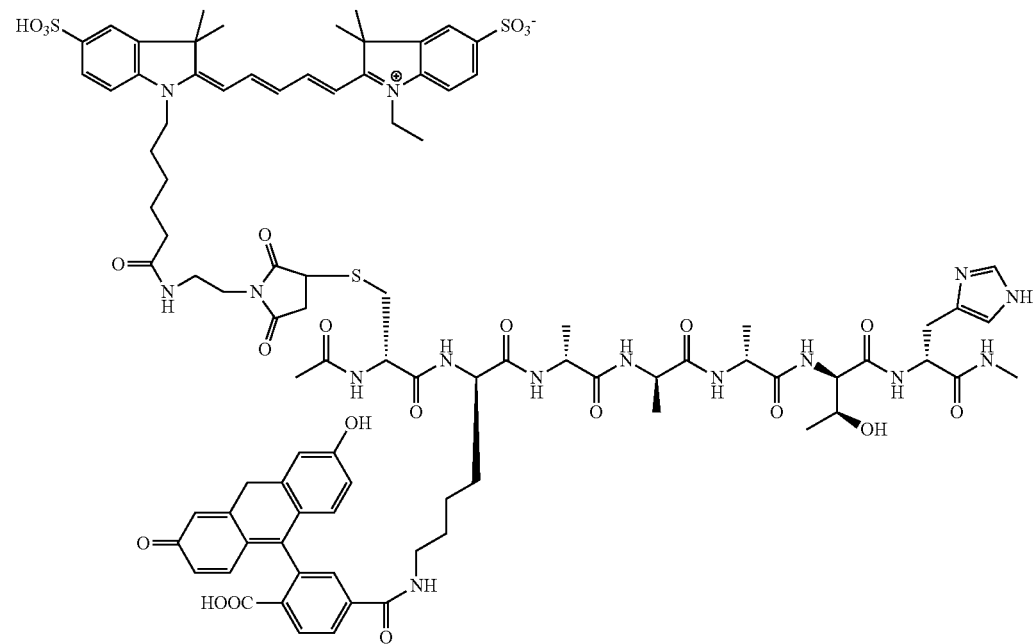
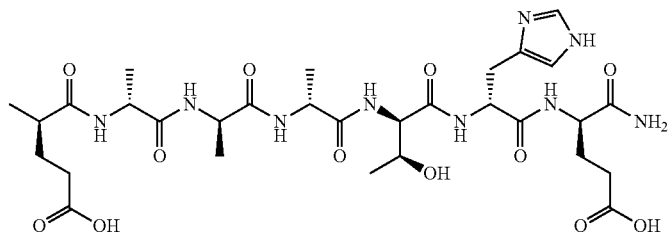
Ac-[D-Cys(Cy5)]-[D-Lys(6FAM)]-(D-Ala)-(D-Ala)-(D-Ala)-(D-Thr)-(D-His)-(D-Glu)-(D-Ala)-
(D-Ala)-(D-Ala)-(D-Thr)-(D-His)-(D-Glu)-NH$_2$
NDM-86
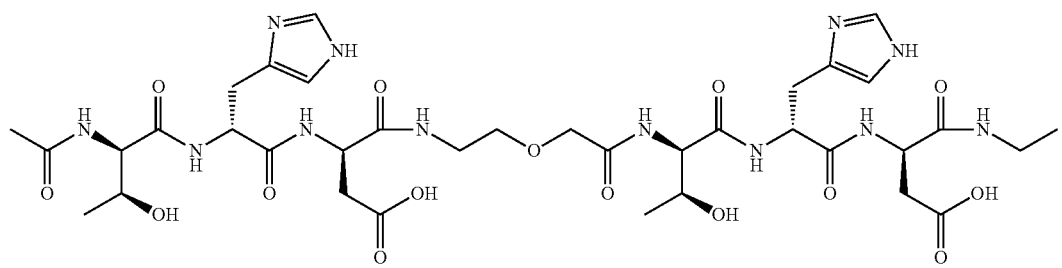

Structures NDM-36 to NDM-99
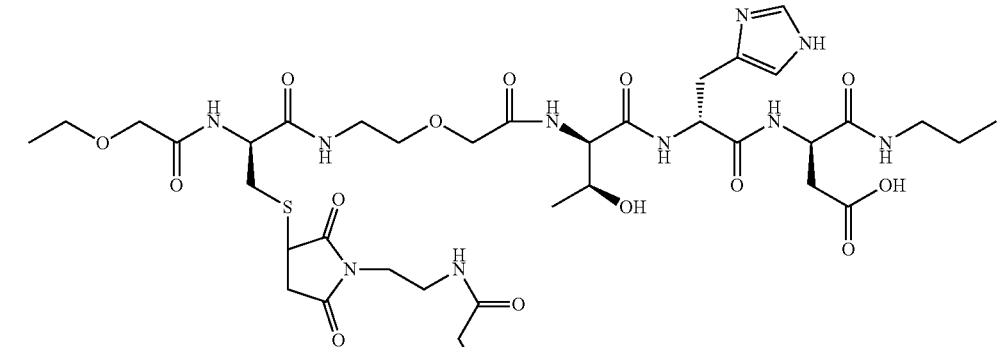
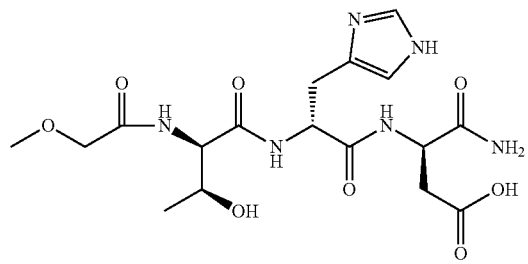
Ac-(D-Thr)-(D-His)-(D-Asp)-o-(D-Thr)-(D-His)-(D-Asp)-o-[D-Cys(Cy5)]-o-(D-Thr)-(D-His)-(D-Asp)-o-(D-Thr)-(D-His)-(D-Asp)-NH$_2$
NDM-87
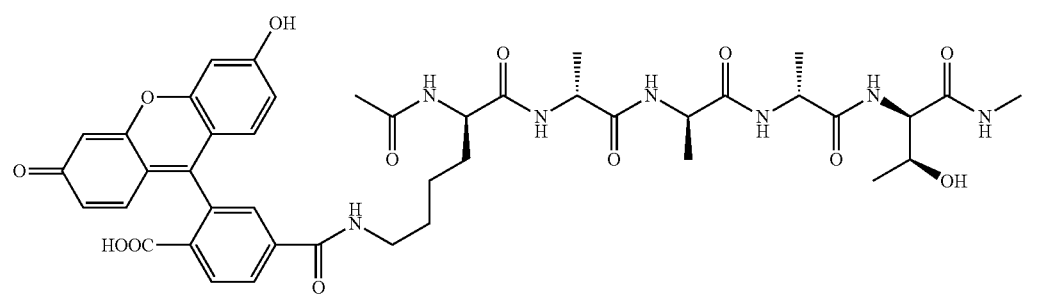
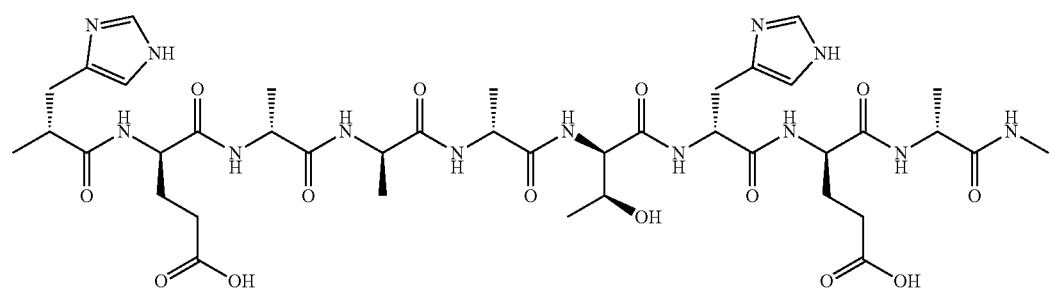

Structures NDM-36 to NDM-99
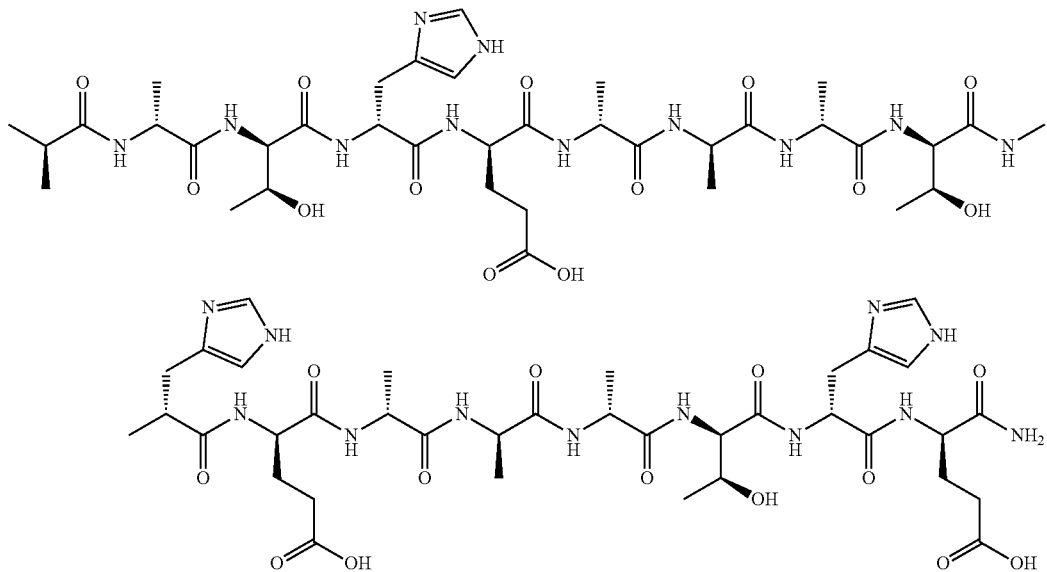
Ac-[D-Lys(6FAM)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-NH$_2$
NDM-88
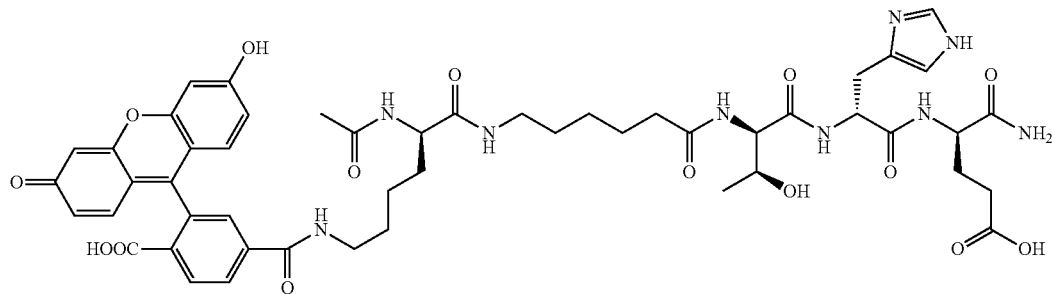 [SMILES: CC(=O)N[C@H](CCCCNC(=O)c1ccc(C(=O)O)c(-c2c3ccc(=O)cc-3oc3cc(O)ccc23)c1)C(=O)NCCCCCC(=O)N[C@@H](C(=O)N[C@H](Cc1c[nH]cn1)C(=O)N[C@H](CCC(=O)O)C(N)=O)[C@H](C)O]
Ac-[D-Lys(6FAM)]-x-(D-Thr)-(D-His)-(D-Glu)-NH$_2$
NDM-89
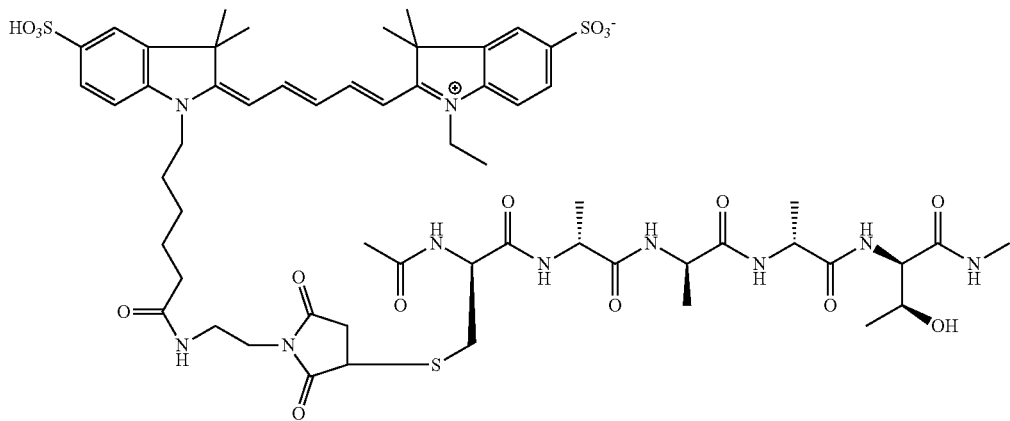

-continued
Structures NDM-36 to NDM-99
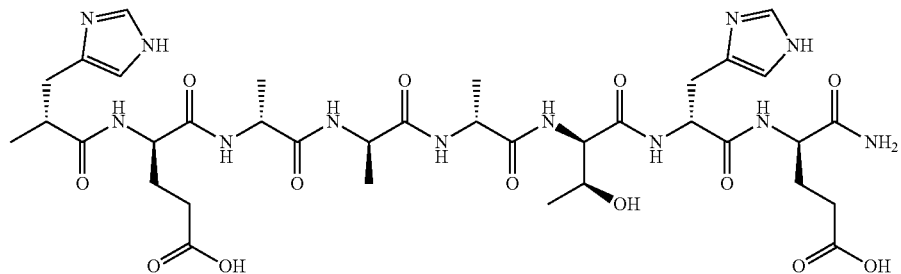
Ac-[D-Cys(Cy5)]-(D-Ala)-(D-Ala)-(D-Ala)-(D-Thr)-(D-His)-(D-Glu)-(D-Ala)-(D-Ala)-(D-Ala)-
(D-Thr)-(D-His)-(D-Glu)-NH$_2$
NDM-90
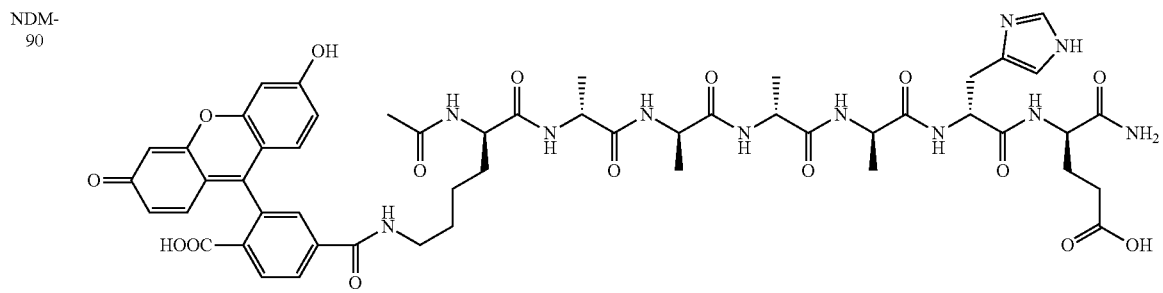
Ac-[D-Lys(6FAM)]-(D-Ala)-(D-Ala)-(D-Ala)-(D-Ala)-(D-His)-(D-Glu)-NH$_2$
NDM-91
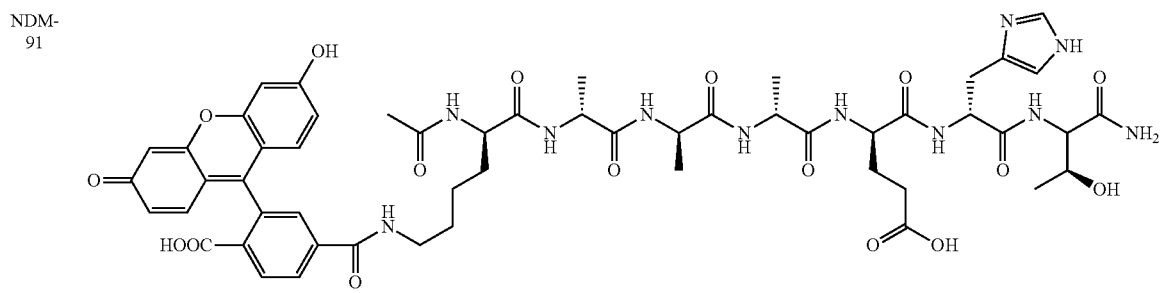
Ac-[D-Lys(6FAM)]-(D-Ala)-(D-Ala)-(D-Ala)-(D-Glu)-(D-His)-(D-Thr)-NH$_2$
NDM-92
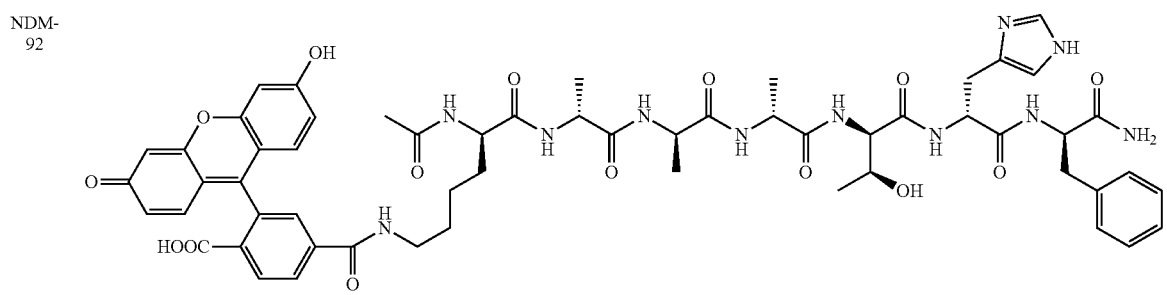
Ac-[D-Lys(6FAM)]-(D-Ala)-(D-Ala)-(D-Ala)-(D-Thr)-(D-His)-(D-Phe)-NH$_2$

Structures NDM-36 to NDM-99
NDM-93
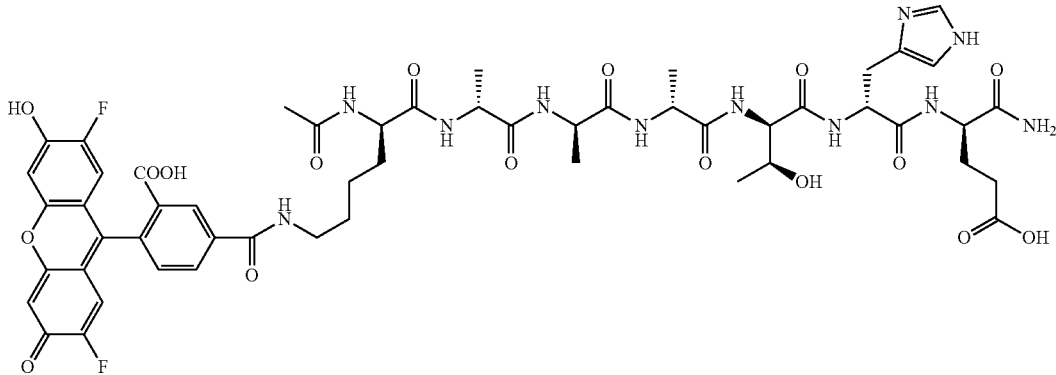 [SMILES: CC(=O)N[C@H](CCCCNC(=O)c1ccc(-c2c3cc(F)c(=O)cc-3oc3cc(O)c(F)cc23)c(C(=O)O)c1)C(=O)N[C@H](C)C(=O)N[C@H](C)C(=O)N[C@H](C)C(=O)N[C@@H](C(=O)N[C@H](Cc1c[nH]cn1)C(=O)N[C@H](CCC(=O)O)C(N)=O)[C@H](C)O]
Ac-[D-Lys(2F-5-FAM)]-(D-Ala)-(D-Ala)-(D-Ala)-(D-Thr)-(D-His)-(D-Glu)-NH$_2$
NDM-94
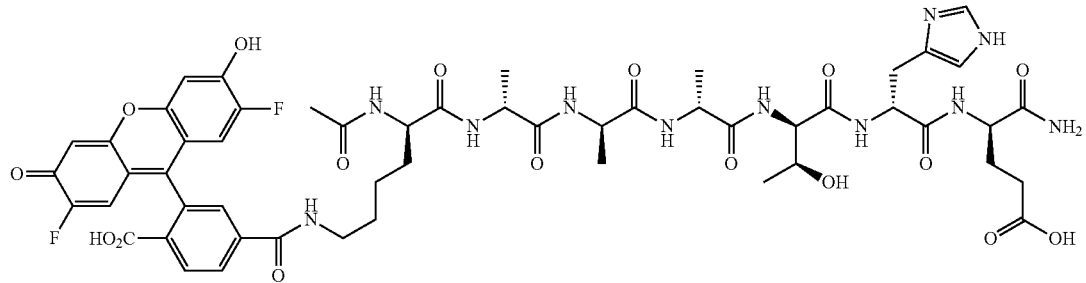 [SMILES: CC(=O)N[C@H](CCCCNC(=O)c1ccc(C(=O)O)c(-c2c3cc(F)c(=O)cc-3oc3cc(O)c(F)cc23)c1)C(=O)N[C@H](C)C(=O)N[C@H](C)C(=O)N[C@H](C)C(=O)N[C@@H](C(=O)N[C@H](Cc1c[nH]cn1)C(=O)N[C@H](CCC(=O)O)C(N)=O)[C@H](C)O]
Ac-[D-Lys(2F-6-FAM)]-(D-Ala)-(D-Ala)-(D-Ala)-(D-Thr)-(D-His)-(D-Glu)-NH$_2$
NDM-95
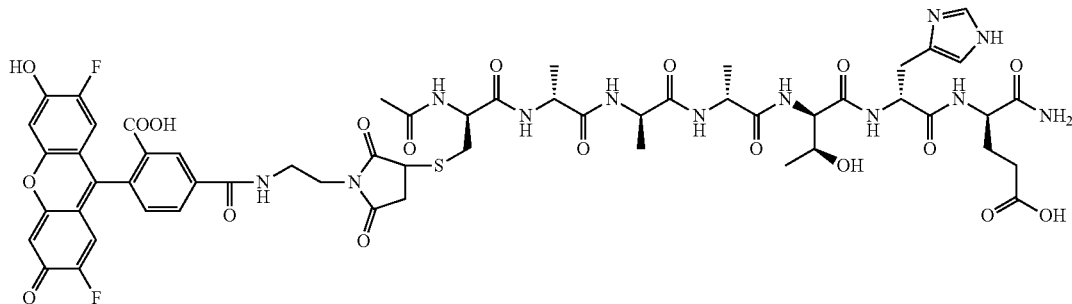 [SMILES: CC(=O)N[C@H](CSC1CC(=O)N(CCNC(=O)c2ccc(-c3c4cc(F)c(=O)cc-4oc4cc(O)c(F)cc34)c(C(=O)O)c2)C1=O)C(=O)N[C@H](C)C(=O)N[C@H](C)C(=O)N[C@H](C)C(=O)N[C@@H](C(=O)N[C@H](Cc1c[nH]cn1)C(=O)N[C@H](CCC(=O)O)C(N)=O)[C@H](C)O]
Ac-[D-Cys(2F-5-FAM)]-(D-Ala)-(D-Ala)-(D-Ala)-(D-Thr)-(D-His)-(D-Glu)-NH$_2$
NDM-96
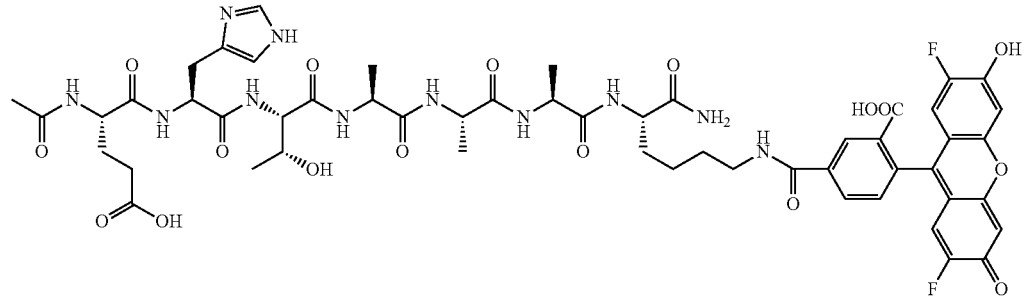 [SMILES: CC(=O)N[C@@H](CCC(=O)O)C(=O)N[C@@H](Cc1c[nH]cn1)C(=O)N[C@H](C(=O)N[C@@H](C)C(=O)N[C@@H](C)C(=O)N[C@@H](C)C(=O)N[C@@H](CCCCNC(=O)c1ccc(-c2c3cc(F)c(=O)cc-3oc3cc(O)c(F)cc23)c(C(=O)O)c1)C(N)=O)[C@@H](C)O]
Ac-Glu-His-Thr-Ala-Ala-Ala-Lys(2F-5-FAM)-NH$_2$ (SEQ ID NO: 20)

Structures NDM-36 to NDM-99
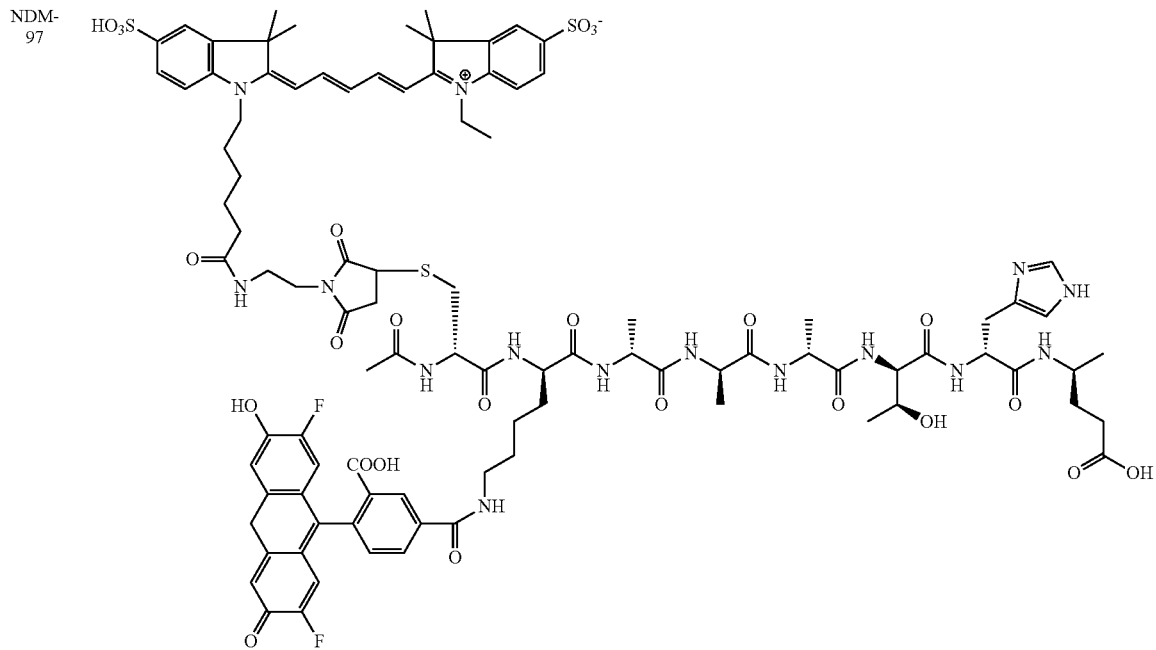
NDM-97
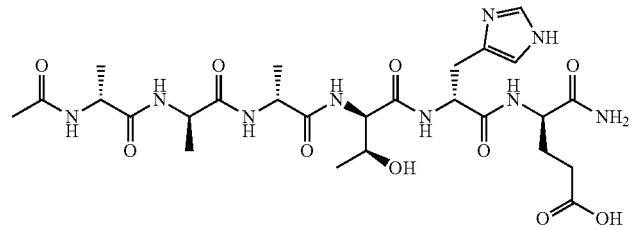
Ac-[D-Cys(Cy5)]-[D-Lys(2F-5-FAM)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-NH₂
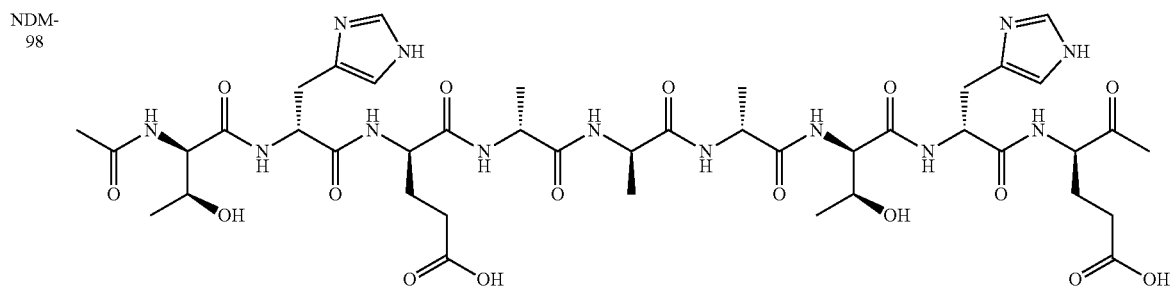
NDM-98

Structures NDM-36 to NDM-99
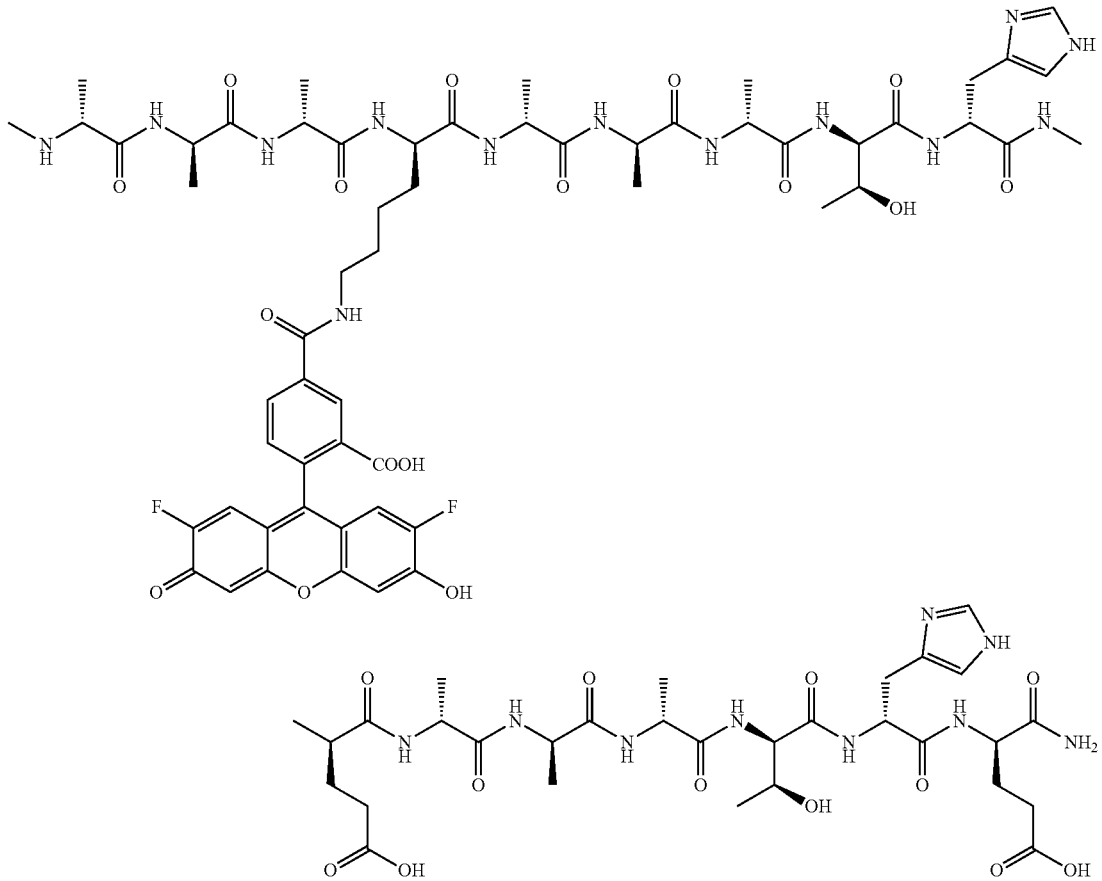
Ac-(D-Thr)-(D-His)-(D-Glu)-(D-Ala)-(D-Ala)-(D-Ala)-(D-Thr)-(D-His)-(D-Glu)-(D-Ala)-(D-Ala)-(D-Ala)-[D-Lys(2F-5-FAM)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-NH$_2$
NDM-99
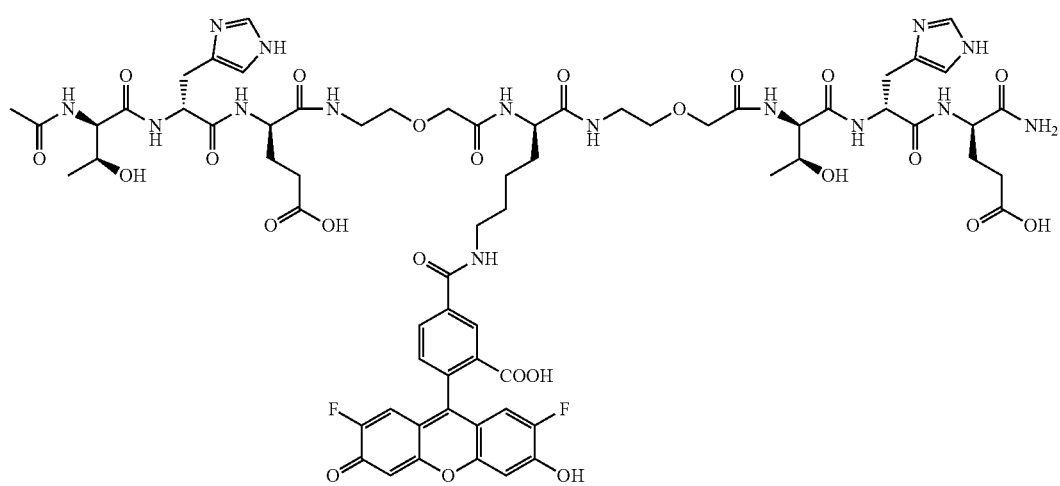 [SMILES: CC(=O)N[C@@H](C(=O)N[C@H](Cc1c[nH]cn1)C(=O)N[C@H](CCC(=O)O)C(=O)NCCOCC(=O)N[C@H](CCCCNC(=O)c1ccc(-c2c3cc(F)c(=O)cc-3oc3cc(O)c(F)cc23)c(C(=O)O)c1)C(=O)NCCOCC(=O)N[C@@H](C(=O)N[C@H](Cc1c[nH]cn1)C(=O)N[C@H](CCC(=O)O)C(N)=O)[C@H](C)O)[C@H](C)O]
Ac-(D-Thr)-(D-His)-(D-Glu)-o-[D-Lys(2F-5-FAM)]-o-(D-Thr)-(D-His)-(D-Glu)-NH$_2$
In some embodiments, disclosed herein, is a nerve delivery molecule according to a T-NDM of Table 1.

| Therapeutic Cargo | Sequences |
|---|---|
| T-NDM-1 | Ac-[D-Cys(TC)]-(D-Ala)-(D-Ala)-(D-Ala)-(D-Thr)-(D-His)-(D-Glu)-$NH_2$ |
| T-NDM-2 | Ac-Glu-His-Thr-Ala-Ala-Ala-Cys(TC)-$NH_2$ (SEQ ID NO: 17) |
| T-NDM-3 | Ac-[D-Lys(TC)]-(D-Ala)-(D-Ala)-(D-Ala)-(D-Thr)-(D-His)-(D-Glu)-$NH_2$ |
| T-NDM-4 | Ac-Glu-His-Thr-Ala-Ala-Ala-Lys(TC)-$NH_2$ (SEQ ID NO: 18) |
| T-NDM-5 | Ac-[D-Cys(TC)]-(D-Ala)-(D-Ala)-(D-Ala)-(D-Thr)-(D-His)-(D-Glu)-$NH_2$ |
| T-NDM-6 | Ac-Glu-His-Thr-Ala-Ala-Ala-Cys(TC)-$NH_2$ (SEQ ID NO: 17) |
| T-NDM-7 | Ac-Glu-His-Thr-Cys(TC)-$NH_2$ (SEQ ID NO: 19) |
| T-NDM-8 | Ac-Glu-His-Thr-o-Cys(TC)-$NH_2$ |
| T-NDM-9 | Ac-[D-Lys(TC)]-Gly-Gly-Gly-(D-Thr)-(D-His)-(D-Glu)-$NH_2$ |
| T-NDM-10 | Ac-[D-Lys(TC)]-Gly-(D-Thr)-(D-His)-(D-Glu)-$NH_2$ |
| T-NDM-11 | Ac-[D-Lys(TC)]-(D-Thr)-(D-His)-(D-Glu)-$NH_2$ |
| T-NDM-12 | Ac-[D-Lys(TC)]-o-(D-Thr)-(D-His)-(D-Glu)-$NH_2$ |
| T-NDM-13 | Ac-[D-Cys(TC1)]-o-[D-Lys(TC2)]-(D-Ala)-(D-Ala)-(D-Ala)-(D-Thr)-(D-His)-(D-Glu)-$NH_2$ |
| T-NDM-14 | Ac-[D-Cys(TC1)]-[D-Lys(TC2)]-(D-Ala)-(D-Ala)-(D-Ala)-(D-Thr)-(D-His)-(D-Glu)-$NH_2$ |
| T-NDM-15 | Ac-(D-Thr)-(D-His)-(D-Glu)-(D-Ala)-(D-Ala)-(D-Ala)-[D-Lys(TC)]-(D-Ala)-(D-Ala)-(D-Ala)-(D-Thr)-(D-His)-(D-Glu)-$NH_2$ |
| T-NDM-16 | Ac-(D-Thr)-(D-His)-(D-Glu)-o-[D-Lys(TC)]-o-(D-Thr)-(D-His)-(D-Glu)-$NH_2$ |
| T-NDM-17 | Ac-(D-Thr)-(D-His)-(D-Glu)-(D-Ala)-(D-Ala)-(D-Ala)-[D-Cys(TC)]-(D-Ala)-(D-Ala)-(D-Ala)-(D-Thr)-(D-His)-(D-Glu)-$NH_2$ |
| T-NDM-18 | Ac-(D-Thr)-(D-His)-(D-Glu)-O-[D-Cys(TC)]-o-(D-Thr)-(D-His)-(D-Glu)-$NH_2$ |
| T-NDM-19 | Ac-(D-Thr)-(D-His)-(D-Glu)-o[D-Cys(TC)]-o-(D-Thr)-(D-His)-(D-Glu)-$NH_2$ |
| T-NDM-20 | Ac-(D-Thr)-(D-His)-(D-Glu)-(D-Ala)-(D-Ala)-(D-Ala)-[D-Cys(TC)]-(D-Ala)-(D-Ala)-(D-Ala)-(D-Thr)-(D-His)-(D-Glu)-$NH_2$ |
| T-NDM-21 | Ac-(D-Thr)-(D-His)-(D-Glu)-(D-Ala)-(D-Ala)-(D-Ala)-[D-Lys(TC)]-(D-Ala)-(D-Ala)-(D-Ala)-(D-Thr)-(D-His)-(D-Glu)-$NH_2$ |
| T-NDM-22 | Ac-(D-Thr)-(D-His)-(D-Glu)-o-[D-Lys(TC)]-o-(D-Thr)-(D-His)-(D-Glu)-$NH_2$ |
| T-NDM-23 | Ac-(D-Glu)-(D-His)-(D-Thr)-(D-Ala)-(D-Ala)-(D-Ala)-[D-Lys(TC)]-(D-Ala)-(D-Ala)-(D-Ala)-(D-Thr)-(D-His)-(D-Glu)-$NH_2$ |
| T-NDM-24 | Ac-Glu-His-Thr-(D-Ala)-(D-Ala)-(D-Ala)-[D-Lys(TC)]-(D-Ala)-(D-Ala)-(D-Ala)-(D-Thr)-(D-His)-(D-Glu)-$NH_2$ |
| T-NDM-25 | Ac-(D-Glu)-(D-His)-(D-Thr)-(D-Ala)-(D-Ala)-(D-Ala)-[D-Lys(TC)]-(D-Ala)-(D-Ala)-(D-Ala)-Thr-His-Glu-$NH_2$ |
| T-NDM-26 | Ac-Glu-His-Thr-(D-Ala)-(D-Ala)-(D-Ala)-[D-Lys(TC)]-(D-Ala)-(D-Ala)-(D-Ala)-Thr-His-Glu-$NH_2$ |
| T-NDM-27 | Ac-Glu-His-Thr-(D-Ala)-(D-Ala)-(D-Ala)-[D-Lys(TC)]-(D-Ala)-(D-Ala)-(D-Ala)-Glu-His-Thr-$NH_2$ |
| T-NDM-28 | Ac-(D-Glu)-(D-His)-(D-Thr)-o-[D-Cys(TC)]-o-(D-Thr)-(D-His)-(D-Glu)-$NH_2$ |
| T-NDM-29 | Ac-Glu-His-Thr-o-[D-Cys(TC)]-o-(D-Thr)-(D-His)-(D-Glu)-$NH_2$ |
| T-NDM-30 | Ac-(D-Thr)-(D-His)-(D-Glu)-o-[D-Lys(TC)]-$NH_2$ |
| T-NDM-31 | Ac-(D-Thr)-(D-His)-(D-Glu)-(D-Ala)-(D-Ala)-(D-Ala)-[D-Lys(TC)]-$NH_2$ |
| T-NDM-32 | Ac-[D-Lys(TC)]-(D-Ala)-(D-Ala)-(D-Ala)-(D-Thr)-(D-His)-(D-Asp)-$NH_2$ |
| T-NDM-33 | Ac-[D-Lys(TC)]-(D-Ala)-(D-Ala)-(D-Ala)-(D-Ser)-(D-His)-(D-Glu)-$NH_2$ |
| T-NDM-34 | Ac-[D-Lys(TC)]-(D-Ala)-(D-Ala)-(D-Ala)-(D-Thr)-(D-His)-(D-Arg)-$NH_2$ |

-continued

| Therapeutic Cargo | Sequences |
|---|---|
| T-NDM-35 | Ac-[D-Cys(TC1)]-(D-Ala)-(D-Ala)-(D-Ala)-[D-Lys(TC2)]-(D-Ala)-(D-Ala)-(D-Ala)-(D-Thr)-(D-His)-(D-Glu)-$NH_2$ |
| T-NDM-36 | Ac-[D-Lys(TC)]-(D-Ala)-(D-Ala)-(D-Ala)-(D-Thr)-(D-Lys)-(D-Glu)-$NH_2$ |
| T-NDM-37 | Ac-[D-Lys(TC)]-(D-Ala)-(D-Ala)-(D-Ala)-(D-Glu)-(D-His)-(D-Ser)-$NH_2$ |
| T-NDM-38 | Ac-(D-Glu)-(D-His)-(D-Ser)-(D-Ala)-(D-Ala)-(D-Ala)-[D-Lys(TC)]-(D-Ala)-(D-Ala)-(D-Ala)-Ser-His-Glu-$NH_2$ |
| T-NDM-39 | Ac-(D-Thr)-(D-His)-(D-Asp)-(D-Ala)-(D-Ala)-(D-Ala)-[D-Lys(TC)]-(D-Ala)-(D-Ala)-(D-Ala)-(D-Thr)-(D-His)-(D-Asp)-$NH_2$ |
| T-NDM-40 | Ac-(D-Thr)-(D-His)-(D-Asp)-o-[D-Cys(TC)]-o-(D-Thr)-(D-His)-(D-Asp)-$NH_2$ |
| T-NDM-41 | Ac-(D-Ser)-(D-His)-(D-Glu)-o-[D-Cys(TC)]-o-(D-Ser)-(D-His)-(D-Glu)-$NH_2$ |
| T-NDM-42 | Ac-Asp-His-Thr-o-[D-Cys(TC)]-o-(D-Thr)-(D-His)-(D-Asp)-$NH_2$ |
| T-NDM-43 | Ac-[D-Lys(TC)]-(D-Ala)-(D-Ala)-(D-Ala)-(D-Thr)-(D-His)-(D-Glu)-$NH_2$ |
| T-NDM-44 | Ac-(D-Thr)-(D-His)-(D-Glu)-o-[D-Lys(TC)]-o-(D-Thr)-(D-His)-(D-Glu)-$NH_2$ |
| T-NDM-45 | Ac-[D-Cys(TC1)]-(D-Ala)-(D-Ala)-(D-Ala)-[D-Lys(TC2)]-(D-Ala)-(D-Ala)-(D-Ala)-(D-Thr)-(D-His)-(D-Glu)-$NH_2$ |
| T-NDM-46 | Ac-[D-Lys(TC)]-PEG2-(D-Thr)-(D-His)-(D-Glu)-$NH_2$ |
| T-NDM-47 | Ac-[D-Lys(TC)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-$NH_2$ |
| T-NDM-48 | Ac-(D-Thr)-(D-His)-(D-Glu)-o-(D-Thr)-(D-His)-(D-Glu)-o-[D-Lys(TC)]-o-(D-Thr)-(D-His)-(D-Glu)-o-(D-Thr)-(D-His)-(D-Glu)-$NH_2$ |
| T-NDM-49 | Ac-(D-Thr)-(D-His)-(D-Glu)-(D-Ala)-(D-Ala)-(D-Ala)-(D-Thr)-(D-His)-(D-Glu)-(D-Ala)-(D-Ala)-(D-Ala)-[D-Lys(TC)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-$NH_2$ |
| T-NDM-50 | Ac-[D-Cys(TC1)]-[D-Lys(TC2)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-$NH_2$ |
| T-NDM-51 | Ac-(D-Thr)-(D-His)-(D-Asp)-o-(D-Thr)-(D-His)-(D-Asp)-o-[D-Cys(TC)]-o-(D-Thr)-(D-His)-(D-Asp)-o-(D-Thr)-(D-His)-(D-Asp)-$NH_2$ |
| T-NDM-52 | Ac-[D-Lys(TC)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-$NH_2$ |
| T-NDM-53 | Ac-[D-Lys(TC)]-Lx-(D-Thr)-(D-His)-(D-Glu)-$NH_2$ |
| T-NDM-54 | Ac-[D-Cys(TC)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-$NH_2$ |

TC refers to therapeutic cargo.
TC1 and TC2 refer to therapeutic cargo 1 and therapeutic cargo 2, respectively.
o: 5-amino-3-oxopentanoyl; x: 6-aminohexanoyl.

Targets

Disclosed herein, in certain embodiments, are nerve delivery molecules that associate with (e.g., specifically bind to) a target neuron, nerve, or tissue (e.g., the sinoatrial node and the atrioventricular node) or structure associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination.

In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors).

In some embodiments, the target is electrically excitable tissue including nerves and muscle. In some embodiments, the target is the conducting fibers of electrically excitable tissues. In some embodiments, the target is cardiac excitable tissue.

Determining whether a nerve delivery molecule is capable of associating with (e.g., binding to) a neuron or nerve or component thereof is accomplished by any suitable method. In some embodiments, the method of determining whether a nerve delivery molecule is capable of associating with (e.g., binding to) a neuron or nerve or component thereof involves contacting a nerve delivery molecule (e.g., peptide) disclosed herein with a test agent for a period of time sufficient to allow the nerve delivery molecule and test agent to form a binding complex. The binding complex is detected using any suitable method. Suitable binding assays can be performed in vitro or in vivo and include, but are not limited to, phage display, two-hybrid screens, co-precipitation, cross-linking, and expression cloning. Other binding assays involve the use of mass spectrometry or NMR techniques to identify nerve delivery molecules bound to the target of interest. The nerve delivery molecule utilized in such assays can be naturally expressed, cloned or synthesized.

Methods of Use

In certain embodiments, the nerve delivery molecules, disclosed herein, allow the targeted delivery of imaging cargos and/or therapeutic cargos to a target neuron, nerve, or tissue or external structure associated therewith. In some embodiments, disclosed herein include the use of a nerve delivery molecule for delivering an imaging cargo and/or a therapeutic cargo (e.g., C and/or C') to a target neuron, nerve, or tissue or external structure associated therewith. In some instances, also described herein include the use of a nerve delivery molecule for visualizing a target neuron, nerve, or tissue or external structure associated therewith in a subject in need thereof. In some cases, further described herein include the use of a nerve delivery molecule for imaging a target neuron, nerve, or tissue or external structure associated therewith. In some instances, a neuron or nerve tissue or external structure associated therewith is a neuromuscular junction, the sinoatrial node, the atrioventricular node, or a combination thereof.

Methods of Delivering Imaging Cargos

Disclosed herein, in certain embodiments, are methods of delivering an imaging cargo to a target neuron, nerve, or tissue or external structure associated therewith, comprising contacting the target neuron, nerve, or tissue or external structure associated therewith with a nerve delivery molecule comprising a peptide sequence according to Formula (I):

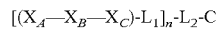

wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ is absent or is a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n is an integer between 1 and 5; and wherein $L_1$ is bound to at any position on $X_A$—$X_B$—$X_C$, $L_2$ is bound to $L_1$, and C is bound to $L_2$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, the nerve delivery molecule of Formula (I) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ comprises an L-amino acid. In some embodiments, $L_1$ comprises a D-amino acid. In some embodiments, $L_1$ comprises 1-10 amino acids. In some embodiments, $L_1$ comprises 2 amino acids. In some embodiments, $L_1$ comprises 3 amino acids. In some embodiments, $L_1$ comprises a series of 10 Ala residues (SEQ ID NO: 3). In some embodiments, $L_1$ comprises a series of 9 Ala residues (SEQ ID NO: 4). In some embodiments, $L_1$ comprises a series of 8 Ala residues (SEQ ID NO: 5). In some embodiments, $L_1$ comprises a series of 7 Ala residues (SEQ ID NO: 6). In some embodiments, $L_1$ comprises a series of 6 Ala residues (SEQ ID NO: 7). In some embodiments, $L_1$ comprises a series of 5 Ala residues (SEQ ID NO: 8). In some embodiments, $L_1$ comprises a series of 4 Ala residues (SEQ ID NO: 9). In some embodiments, $L_1$ comprises a series of 3 Ala residues. In some embodiments, $L_1$ comprises a series of 2 Ala residues. In some embodiments, $L_1$ comprises a series of 1 Ala residue. In some embodiments, $L_1$ comprises a series of 10 Gly residues (SEQ ID NO: 10). In some embodiments, $L_1$ comprises a series of 9 Gly residues (SEQ ID NO: 21). In some embodiments, $L_1$ comprises a series of 8 Gly residues (SEQ ID NO: 22). In some embodiments, $L_1$ comprises a series of 7 Gly residues (SEQ ID NO: 23). In some embodiments, $L_1$ comprises a series of 6 Gly residues (SEQ ID NO: 24). In some embodiments, $L_1$ comprises a series of 5 Gly residues (SEQ ID NO: 11). In some embodiments, $L_1$ comprises a series of 4 Gly residues (SEQ ID NO: 12). In some embodiments, $L_1$ comprises a series of 3 Gly residues.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ comprises a series of 3 Ala residues and $L_2$ comprises an amino acid selected from Lys or Cys. In some embodiments, $L_1$ comprises a series of 2 Ala residues and $L_2$ comprises an amino acid selected from Lys or Cys. In some embodiments, $L_1$ comprises a series of 3 Gly residues and $L_2$ comprises an amino acid selected from Lys or Cys. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp. In some embodiments, $L_1$ comprises a series of 3 Ala residues and $L_2$ comprises an amino acid selected from D-Lys or D-Cys. In some embodiments, $L_1$ comprises a series of 2 Ala residues and $L_2$ comprises an amino acid selected from D-Lys or D-Cys. In some embodiments, $L_1$ comprises a series of 3 Gly residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complex, a rare-earth metal chelate complex, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in certain embodiments, are methods of delivering an imaging cargo to a target neuron, nerve, or tissue or external structure associated therewith, comprising contacting the target neuron, nerve, or tissue or external structure associated therewith with a nerve delivery molecule comprising a peptide sequence according to Formula (Ia):

$$[(X_A—X_B—X_C)-L_1]_n-L_2-C$$

wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ is absent or is a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n is an integer between 1 and 5; and wherein $L_1$ is bound to at any position on $X_A—X_B—X_C$, $L_2$ is bound to $L_1$, and C is bound to $L_2$.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A—X_B—X_C$ is EHT or THE, in which the amino acid residues are D-amino acid residues. In some instances, $X_A—X_B—X_C$ is EHT, in which the amino acid residues are D-amino acid residues. In other instances, $X_A—X_B—X_C$ is THE, in which the amino acid residues are D-amino acid residues.

In some embodiments, $L_1$ comprises 1-10 amino acids. In some embodiments, $L_1$ comprises 2 amino acids. In some embodiments, $L_1$ comprises 3 amino acids. In some embodiments, $L_1$ comprises a series of 10 D-Ala residues. In some embodiments, $L_1$ comprises a series of 9 D-Ala residues. In some embodiments, $L_1$ comprises a series of 8 D-Ala residues. In some embodiments, $L_1$ comprises a series of 7 D-Ala residues. In some embodiments, $L_1$ comprises a series of 6 D-Ala residues. In some embodiments, $L_1$ comprises a series of 5 D-Ala residues. In some embodiments, $L_1$ comprises a series of 4 D-Ala residues. In some embodiments, $L_1$ comprises a series of 3 D-Ala residues. In some embodiments, $L_1$ comprises a series of 2 D-Ala residues. In some embodiments, $L_1$ comprises a series of 1 D-Ala residue.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ comprises a series of 3 D-Ala residues and $L_2$ comprises an amino acid selected from Lys or Cys. In some embodiments, $L_1$ comprises a series of 2 D-Ala residues and $L_2$ comprises an amino acid selected from Lys or Cys. In some embodiments, $L_1$ comprises a series of 3 D-Ala residues and $L_2$ comprises an amino acid selected from D-Lys or D-Cys. In some embodiments, $L_1$ comprises a series of 2 D-Ala residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

Disclosed herein, in certain embodiments, are methods of delivering an imaging cargo to a target neuron, nerve, or tissue or external structure associated therewith, comprising contacting the target neuron, nerve, or tissue or external structure associated therewith with a nerve delivery molecule comprising a peptide sequence according to Formula (II):

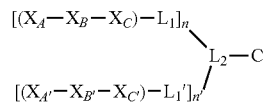

wherein $X_A$ and $X_{A'}$ are each independently selected from: Asp, Arg, Glu, Thr, His, Lys, Phe, or Ser; $X_B$ and $X_{B'}$ are each independently selected from: His, Lys, Thr, Glu, Ser, Asp, Phe, or Arg; $X_C$ and $X_{C'}$ are each independently selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_{A'}$ is selected from: Arg, His, or Lys. In some embodiments, $X_{A'}$ is selected from: Asp, Glu, Thr or Ser. In some embodiments, $X_{A'}$ is selected from: Asp or Glu. In some embodiments, $X_{A'}$ is selected from: Thr or Ser. In some embodiments, $X_{A'}$ is selected from: Glu or Thr. In some embodiments, $X_{A'}$ is Glu. In some embodiments, $X_{A'}$ is Thr. In some embodiments, $X_{A'}$ is Asp. In some embodiments, $X_{A'}$ is Arg. In some embodiments, $X_{A'}$ is His. In some embodiments, $X_{A'}$ is Lys. In some embodiments, $X_{A'}$ is Ser. In some embodiments, $X_{A'}$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_{B'}$ is selected from: His, Lys, Glu or Arg. In some embodiments, $X_{B'}$ is selected from: Thr, Glu, Ser or Asp. In some embodiments, $X_{B'}$ is selected from: His, Thr, Ser or Asp. In some embodiments, $X_{B'}$ is His. In some embodiments, $X_{B'}$ is Lys. In some embodiments, $X_{B'}$ is Thr. In some embodiments, $X_{B'}$ is Glu. In some embodiments, $X_{B'}$ is Ser. In some embodiments, $X_{B'}$ is Asp. In some embodiments, $X_{B'}$ is Arg. In some embodiments, $X_{B'}$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_{C'}$ is selected from: Arg, His or Lys. In some embodiments, $X_{C'}$ is selected from: Asp, Glu, Thr or Ser. In some embodiments, $X_{C'}$ is selected from: Asp or Glu. In some embodiments, $X_{C'}$ is selected from: Thr or Ser. In some embodiments, $X_{C'}$ is selected from: Glu or Thr. In some embodiments, $X_{C'}$ is Glu. In some embodiments, $X_{C'}$ is Thr. In some embodiments, $X_{C'}$ is Asp. In some embodiments, $X_{C'}$ is Arg. In some embodiments, $X_{C'}$ is His. In some embodiments, $X_{C'}$ is Lys. In some embodiments, $X_{C'}$ is Ser. In some embodiments, $X_{C'}$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, $X_{A'}$—$X_{B'}$—$X_{C'}$ is EHT or THE. In some instances, $X_{A'}$—$X_{B'}$—$X_{C'}$ is EHT. In other instances, $X_{A'}$—$X_{B'}$—$X_{C'}$ is THE.

In some embodiments, the nerve delivery molecule of Formula (II) comprises a naturally occurring amino acid or a non-naturally occurring amino acid. In some embodiments, $X_A$, $X_B$, $X_C$, $X_{A'}$, $X_{B'}$, and $X_{C'}$ each independently comprises a D-amino acid. In some embodiments, the amino acid residues of $X_A$, $X_B$ and $X_C$ are D-amino acids. In some embodiments, the amino acid residues of $X_{A'}$, $X_{B'}$, and $X_{C'}$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 1-10 amino acids. In some embodiments, $L_1$ comprises 2 amino acids. In some embodiments, $L_1$ comprises 3 amino acids. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ and $L_{1'}$ each independently comprises a series of 3 Ala residues and $L_2$ comprises an amino acid selected from Lys or Cys. In some embodiments, $L_1$ and $L_{1'}$ each independently comprises a series of 2 Ala residues and $L_2$ comprises an amino acid selected from Lys or Cys. In some embodiments, $L_1$ and $L_{1'}$ each independently comprises a series of 3 Gly residues and $L_2$ comprises an amino acid selected from Lys or Cys. In some embodiments, $L_1$ and $L_{1'}$ each independently comprises a series of 3 Ala residues and $L_2$ comprises an amino acid selected from D-Lys or D-Cys. In some embodiments, $L_1$ and $L_{1'}$ each independently comprises a series of 2 Ala residues and $L_2$ comprises an amino acid selected from D-Lys or D-Cys. In some embodiments, $L_1$ and $L_{1'}$ each independently comprises a series of 3 Gly residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A'}$. In some embodiments, $L_{1'}$ is bound to $X_{B'}$. In some embodiments, $L_{1'}$ is bound to $X_{C'}$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}Tc$, $^{64}Cu$, $^{18}F$, $^{124}I$, $^{111}In$, or a combination thereof. In some embodiments, the imaging cargo is $^{211}At$, $^{131}I$, $^{125}I$, $^{90}Y$, $^{186}Re$, $^{188}Re$, $^{153}Sm$, $^{212}Bi$, $^{32}P$, $^{11}C$, $^{201}Tl$, $^{57}Ga$, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in certain embodiments, are methods of delivering an imaging cargo to a target, neuron, nerve, or tissue or external structure associated therewith comprising contacting the target neuron, nerve, or tissue or external structure associated therewith with a nerve delivery molecule comprising a peptide sequence according to Formula (IIa):

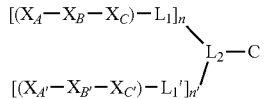

wherein $X_A$ and $X_{A'}$ are each independently selected from: D-Asp, D-Arg, D-Glu, D-Thr, D-His, D-Lys, D-Phe, or D-Ser; $X_B$ and $X_{B'}$ are each independently selected from: D-His, D-Lys, D-Thr, D-Glu, D-Ser, D-Asp, D-Phe, or D-Arg; $X_C$ and $X_{C'}$ are each independently selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_{A'}$ is selected from: D-Arg, D-His, or D-Lys. In some embodiments, $X_{A'}$ is selected from: D-Asp, D-Glu, D-Thr or D-Ser. In some embodiments, $X_{A'}$ is selected from: D-Asp or D-Glu. In some embodiments, $X_{A'}$ is selected from: D-Thr or D-Ser. In some embodiments, $X_{A'}$ is selected from: D-Glu or D-Thr. In some embodiments, $X_{A'}$ is D-Glu. In some embodiments, $X_{A'}$ is D-Thr. In some embodiments, $X_{A'}$ is D-Asp. In some embodiments, $X_{A'}$ is D-Arg. In some embodiments, $X_{A'}$ is D-His. In some embodiments, $X_{A'}$ is D-Lys. In some embodiments, $X_{A'}$ is D-Ser. In some embodiments, $X_{A'}$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_{B'}$ is selected from: D-His, D-Lys, D-Glu or D-Arg. In some embodiments, $X_{B'}$ is selected from: D-Thr, D-Glu, D-Ser or D-Asp. In some embodiments, $X_{B'}$ is selected from: D-His, D-Thr, D-Ser or D-Asp. In some embodiments, $X_{B'}$ is D-His. In some embodiments, $X_{B'}$ is D-Lys. In some embodiments, $X_{B'}$ is D-Thr. In some embodiments, $X_{B'}$ is D-Glu. In some embodiments, $X_{B'}$ is D-Ser. In some embodiments, $X_{B'}$ is D-Asp. In some embodiments, $X_{B'}$ is D-Arg. In some embodiments, $X_{B'}$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_{C'}$ is selected from: D-Arg, D-His or D-Lys. In some embodiments, $X_{C'}$ is selected from: D-Asp, D-Glu, D-Thr or D-Ser. In some embodiments, $X_{C'}$ is selected from: D-Asp or D-Glu. In some embodiments, $X_{C'}$ is selected from: D-Thr or D-Ser. In some embodiments, $X_{C'}$ is selected from: D-Glu or D-Thr. In some embodiments, $X_{C'}$ is D-Glu. In some embodiments, $X_{C'}$ is D-Thr. In some embodiments, $X_{C'}$ is D-Asp. In some embodiments, $X_{C'}$ is D-Arg. In some embodiments, $X_{C'}$ is D-His. In some embodiments, $X_{C'}$ is D-Lys. In some embodiments, $X_{C'}$ is D-Ser. In some embodiments, $X_{C'}$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $X_{A'}$—$X_{B'}$—$X_{C'}$ is EHT or THE, in which the amino acid residues are D-amino acid residues. In some instances, $X_{A'}$—$X_{B'}$—$X_{C'}$ is EHT, in which the amino acid residues are D-amino acid residues. In other instances, $X_{A'}$—$X_{B'}$—$X_{C'}$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 1-10 amino acids. In some embodiments, $L_1$ comprises 2 amino acids. In some embodiments, $L_1$ comprises 3 amino acids. In some embodiments, $L_1$ and $L_{1'}$ each independently comprises a series of D-10 Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ and $L_{1'}$ each independently comprises a series of 3 D-Ala residues and $L_2$ comprises an amino acid selected from Lys or Cys. In some embodiments, $L_1$ and $L_{1'}$ each independently comprises a series of 2 D-Ala residues and $L_2$ comprises an amino acid selected from Lys or Cys. In some embodiments, $L_1$ and $L_{1'}$ each independently comprises a series of 3 D-Ala residues and $L_2$ comprises an amino acid selected from D-Lys or D-Cys. In some embodiments, $L_1$ and $L_{1'}$ each independently comprises a series of 2 D-Ala residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A''}$. In some embodiments, $L_{1'}$ is bound to $X_{B''}$. In some embodiments, $L_{1'}$ is bound to $X_{C''}$.

Disclosed herein, in certain embodiments, are methods of delivering an imaging cargo to a target neuron, nerve, or tissue or external structure associated therewith, comprising contacting the target neuron, nerve, or tissue or external structure associated therewith with a nerve delivery molecule comprising a peptide sequence according to Formula (III):

$$[(X_A-X_B-X_C)-L_1]_n \underset{L_{1'}-[L_{2'}-C']}{\overset{}{\top}} [L_2-C]$$

wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently an imaging cargo; and n is an integer between 1 and 5; and wherein $L_1$ is bound to at any position on $X_A-X_B-X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A-X_B-X_C$ is EHT or THE. In some instances, $X_A-X_B-X_C$ is EHT. In other instances, $X_A-X_B-X_C$ is THE.

In some embodiments, the nerve delivery molecule of Formula (III) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 1-10 amino acids. In some embodiments, $L_1$ comprises 2 amino acids. In some embodiments, $L_1$ comprises 3 amino acids. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_1$ and $L_{1'}$ each independently comprises a series of 3 Ala residues and $L_2$ and $L_{2'}$ each independently comprises an amino acid selected from Lys or Cys. In some embodiments, $L_1$ and $L_{1'}$ each independently comprises a series of 2 Ala residues and $L_2$ and $L_{2'}$ each independently comprises an amino acid selected from Lys or Cys. In some embodiments, $L_1$ and $L_{1'}$ each independently comprises a series of 3 Gly residues and $L_2$ and $L_{2'}$ each independently comprises an amino acid selected from Lys or Cys. In some embodiments, $L_1$ and $L_{1'}$ each independently comprises a series of 3 Ala residues and $L_2$ and $L_{2'}$ each independently comprises an amino acid selected from D-Lys or D-Cys. In some embodiments, $L_1$ and $L_{1'}$ each independently comprises a series of 2 Ala residues and $L_2$ and $L_{2'}$ each independently comprises an amino acid selected from D-Lys or D-Cys. In some embodiments, $L_1$ and $L_{1'}$ each independently comprises a series of 3 Gly residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_{1'}$ is bound to $L_2$. In some embodiments, $L_{1'}$ is bound to $L_1$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complex, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N''-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the nerve delivery molecule of Formula (III) comprises two or more imaging cargos. In some cases, the imaging cargos are fluorescent. In some cases, a first fluorescent imaging cargo undergoes energy transfer to second or multiple fluorescent cargos that functionally extends the fluorescence emission to longer wavelengths. In some of these cases the emission is separated from the excitation light which facilitates detection of the emitted light. In some of these cases the extended, longer wavelength emission will have reduced tissue attenuation and deeper tissue detection properties. In some cases, the first fluorescent cargo is a xanthene. In some cases, the first fluorescent cargo is a fluorescein. In some cases, the second or multiple fluorescent cargo is an indocarbocyanine dye. In some cases, the emission is extended into the near infra-red wavelengths.

In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in certain embodiments, are methods of delivering an imaging cargo to a target neuron, nerve, or tissue or external structure associated therewith, comprising contacting the target neuron, nerve, or tissue or external structure associated therewith with a nerve delivery molecule comprising a peptide sequence according to Formula (IIIa):

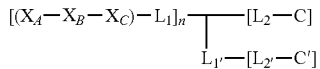

wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently an imaging cargo; and n is an integer between 1 and 5; and wherein $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 1-10 amino acids. In some embodiments, $L_1$ comprises 2 amino acids. In some embodiments, $L_1$ comprises 3 amino acids. In some embodiments, $L_1$ and $L_{1'}$ each independently comprises a series of 10 D-Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_1$ and $L_{1'}$ each independently comprises a series of 3 D-Ala residues and $L_2$ and $L_{2'}$ each independently comprises an amino acid selected from Lys or Cys. In some embodiments, $L_1$ and $L_{1'}$ each independently comprises a series of 2 D-Ala residues and $L_2$ and $L_{2'}$ each independently comprises an amino acid selected from Lys or Cys. In some embodiments, $L_1$ and $L_{1'}$ each independently comprises a series of 3 D-Ala residues and $L_2$ and $L_{2'}$ each independently comprises an amino acid selected from D-Lys or D-Cys. In some embodiments, $L_1$ and $L_{1'}$ each independently comprises a series of 2 D-Ala residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_{1'}$ is bound to $L_2$. In some embodiments, $L_{1'}$ is bound to $L_1$.

Methods of Visualizing a Target Neuron, Nerve, or Tissue or External Structure Associated Therewith Disclosed herein, in some embodiments, are methods of visualizing a target neuron, nerve, or tissue or external structure associated therewith in a subject in need thereof, comprising: (i) administering to the subject a nerve delivery molecule comprising a peptide sequence according to Formula (I) that localizes to the target neuron, nerve, or tissue or external structure associated therewith in the subject:

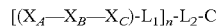

$$[(X_A—X_B—X_C)\text{-}L_1]_n\text{-}L_2\text{-}C$$

wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ is absent or is a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n is an integer between 1 and 5; and wherein $L_1$ is bound to at any position on $X_A—X_B—X_C$, $L_2$ is bound to $L_1$, and C is bound to $L_2$; and (ii) visualizing the imaging cargo.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A—X_B—X_C$ is EHT or THE. In some instances, $X_A—X_B—X_C$ is EHT. In other instances, $X_A—X_B—X_C$ is THE.

In some embodiments, the nerve delivery molecule of Formula (I) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ comprises an L-amino acid. In some embodiments, $L_1$ comprises a D-amino acid. In some embodiments, $L_1$ comprises 1-10 amino acids. In some embodiments, $L_1$ comprises 2 amino acids. In some embodiments, $L_1$ comprises 3 amino acids. In some embodiments, $L_1$ comprises a series of 10 Ala residues (SEQ ID NO: 3). In some embodiments, $L_1$ comprises a series of 9 Ala residues (SEQ ID NO: 4). In some embodiments, $L_1$ comprises a series of 8 Ala residues (SEQ ID NO: 5). In some embodiments, $L_1$ comprises a series of 7 Ala residues (SEQ ID NO: 6). In some embodiments, $L_1$ comprises a series of 6 Ala residues (SEQ ID NO: 7). In some embodiments, $L_1$ comprises a series of 5 Ala residues (SEQ ID NO: 8). In some embodiments, $L_1$ comprises a series of 4 Ala residues (SEQ ID NO: 9). In some embodiments, $L_1$ comprises a series of 3 Ala residues. In some embodiments, $L_1$ comprises a series of 2 Ala residues. In some embodiments, $L_1$ comprises a series of 1 Ala residue. In some embodiments, $L_1$ comprises a series of 10 Gly residues (SEQ ID NO: 10). In some embodiments, $L_1$ comprises a series of 9 Gly residues (SEQ ID NO: 21). In some embodiments, $L_1$ comprises a series of 8 Gly residues (SEQ ID NO: 22). In some embodiments, $L_1$ comprises a series of 7 Gly residues (SEQ ID NO: 23). In some embodiments, $L_1$ comprises a series of 6 Gly residues (SEQ ID NO: 24). In some embodiments, $L_1$ comprises a series of 5 Gly residues (SEQ ID NO: 11). In some embodiments, $L_1$ comprises a series of 4 Gly residues (SEQ ID NO: 12). In some embodiments, $L_1$ comprises a series of 3 Gly residues.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ comprises a series of 3 Ala residues and $L_2$ comprises an amino acid selected from Lys or Cys. In some embodiments, $L_1$ comprises a series of 2 Ala residues and $L_2$ comprises an amino acid selected from Lys or Cys. In some embodiments, $L_1$ comprises a series of 3 Gly residues and $L_2$ comprises an amino acid selected from Lys or Cys. In some embodiments, $L_1$ comprises a series of 3 Ala residues and $L_2$ comprises an amino acid selected from D-Lys or D-Cys. In some embodiments, $L_1$ comprises a series of 2 Ala residues and $L_2$ comprises an amino acid selected from D-Lys or D-Cys. In some embodiments, $L_1$ comprises a series of 3 Gly residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N''-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, 124, 111In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in some embodiments, are methods of visualizing a target neuron, nerve, or tissue or external structure associated therewith in a subject in need thereof, comprising: (i) administering to the subject a nerve delivery molecule comprising a peptide sequence according to Formula (Ia) that localizes to the target neuron, nerve, or tissue or external structure associated therewith in the subject:

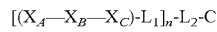

wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ is absent or is a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n is an integer between 1 and 5; and wherein $L_1$ is bound to at any position on $X_A$—$X_B$—$X_C$, $L_2$ is bound to $L_1$, and C is bound to $L_2$; and (ii) visualizing the imaging cargo.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $L_1$ comprises 1-10 amino acids. In some embodiments, $L_1$ comprises a series of 10 D-Ala residues. In some embodiments, $L_1$ comprises a series of 9 D-Ala residues. In some embodiments, $L_1$ comprises a series of 8 D-Ala residues. In some embodiments, $L_1$ comprises a series of 7 D-Ala residues. In some embodiments, $L_1$ comprises a series of 6 D-Ala residues. In some embodiments, $L_1$ comprises a series of 5 D-Ala residues. In some embodiments, $L_1$ comprises a series of 4 D-Ala residues. In some embodiments, $L_1$ comprises a series of 3 D-Ala residues. In some embodiments, $L_1$ comprises a series of 2 D-Ala residues. In some embodiments, $L_1$ comprises a series of 1 D-Ala residue.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ comprises a series of 3 D-Ala residues and $L_2$ comprises an amino acid selected from Lys or Cys. In some embodiments, $L_1$ comprises a series of 2 D-Ala residues and $L_2$ comprises an amino acid selected from Lys or Cys. In some embodiments, $L_1$ comprises a series of 3 D-Ala residues and $L_2$ comprises an amino acid selected from D-Lys or D-Cys. In some embodiments, $L_1$ comprises a series of 2 D-Ala residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

Disclosed herein, in some embodiments, are methods of visualizing a target neuron, nerve, or tissue or external structure associated therewith in a subject in need thereof, comprising: (i) administering to the subject a nerve delivery molecule comprising a peptide sequence according to Formula (II) that localizes to the target neuron, nerve, or tissue or external structure associated therewith in the subject:

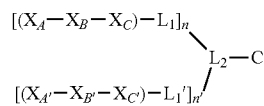

wherein $X_A$ and $X_{A'}$ are each independently selected from: Asp, Arg, Glu, Thr, His, Lys, Phe, or Ser; $X_B$ and $X_{B'}$ are each independently selected from: His, Lys, Thr, Glu, Ser, Asp, Phe, or Arg; $X_C$ and $X_{C'}$ are each independently selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$; and (ii) visualizing the imaging cargo.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_{A'}$ is selected from: Arg, His, or Lys. In some embodiments, $X_{A'}$ is selected from: Asp, Glu, Thr or Ser. In some embodiments, $X_{A'}$ is selected from: Asp or Glu. In some embodiments, $X_{A'}$ is selected from: Thr or Ser. In some embodiments, $X_{A'}$ is selected from: Glu or Thr. In some embodiments, $X_{A'}$ is Glu. In some embodiments, $X_{A'}$ is Thr. In some embodiments, $X_{A'}$ is Asp. In some embodiments, $X_{A'}$ is Arg. In some embodiments, $X_{A'}$ is His. In some embodiments, $X_{A'}$ is Lys. In some embodiments, $X_{A'}$ is Ser. In some embodiments, $X_{A'}$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_{B'}$ is selected from: His, Lys, Glu or Arg. In some embodiments, $X_{B'}$ is selected from: Thr, Glu, Ser or Asp. In some embodiments, $X_{B'}$ is selected from: His, Thr, Ser or Asp. In some embodiments, $X_{B'}$ is His. In some embodiments, $X_{B'}$ is Lys. In some embodiments, $X_{B'}$ is Thr. In some embodiments, $X_{B'}$ is Glu. In some embodiments, $X_{B'}$ is Ser. In some embodiments, $X_{B'}$ is Asp. In some embodiments, $X_{B'}$ is Arg. In some embodiments, $X_{B'}$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_{C'}$ is selected from: Arg, His or Lys. In some embodiments, $X_{C'}$ is selected from: Asp, Glu, Thr or Ser. In some embodiments, $X_{C'}$ is selected from: Asp or Glu. In some embodiments, $X_{C'}$ is selected from: Thr or Ser. In some embodiments, $X_{C'}$ is selected from: Glu or Thr. In some embodiments, $X_{C'}$ is Glu. In some embodiments, $X_{C'}$ is Thr. In some embodiments, $X_{C'}$ is Asp. In some embodiments, $X_{C'}$ is Arg. In some embodiments, $X_{C'}$ is His. In some embodiments, $X_{C'}$ is Lys. In some embodiments, $X_{C'}$ is Ser. In some embodiments, $X_{C'}$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, $X_{A'}$—$X_{B'}$—$X_{C'}$ is EHT or THE. In some instances, $X_{A'}$—$X_{B'}$—$X_{C'}$ is EHT. In other instances, $X_{A'}$—$X_{B'}$—$X_{C'}$ is THE.

In some embodiments, the nerve delivery molecule of Formula (II) comprises a naturally occurring amino acid or a non-naturally occurring amino acid. In some embodiments, $X_A$, $X_B$, $X_C$, $X_{A'}$, $X_{B'}$, and $X_{C'}$ each independently comprises a D-amino acid. In some embodiments, the amino acid residues of $X_A$, $X_B$ and $X_C$ are D-amino acids. In some embodiments, the amino acid residues of $X_{A'}$, $X_{B'}$ and $X_{C'}$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 1-10 amino acids. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ and $L_{1'}$ each independently comprises a series of 3 Ala residues and $L_2$ comprises an amino acid selected from Lys or Cys. In some embodiments, $L_1$ and $L_{1'}$ each independently comprises a series of 2 Ala residues and $L_2$ comprises an amino acid selected from Lys or Cys. In some embodiments, $L_1$ and $L_{1'}$ each independently comprises a series of 3 Gly residues and $L_2$ comprises an amino acid selected from Lys or Cys. In some embodiments, $L_1$ and $L_{1'}$ each independently comprises a series of 3 Ala residues and $L_2$ comprises an amino acid selected from D-Lys or D-Cys. In some embodiments, $L_1$ and $L_{1'}$ each independently comprises a series of 2 Ala residues and $L_2$ comprises an amino acid selected from D-Lys or D-Cys. In some embodiments, $L_1$ and $L_{1'}$ each independently comprises a series of 3 Gly residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A'}$. In some embodiments, $L_{1'}$ is bound to $X_{B'}$. In some embodiments, $L_{1'}$ is bound to $X_{C'}$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N''-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in some embodiments, are methods of visualizing a target neuron, nerve, or tissue or external structure associated therewith in a subject in need thereof, comprising: (i) administering to the subject a nerve delivery molecule comprising a peptide sequence according to Formula (IIa) that localizes to the target neuron, nerve, or tissue or external structure associated therewith in the subject:

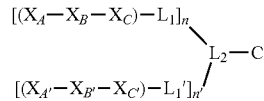

wherein $X_A$ and $X_{A'}$ are each independently selected from: D-Asp, D-Arg, D-Glu, D-Thr, D-His, D-Lys, D-Phe, or D-Ser; $X_B$ and $X_{B'}$ are each independently selected from: D-His, D-Lys, D-Thr, D-Glu, D-Ser, D-Asp, D-Phe, or D-Arg; $X_C$ and $X_{C'}$ are each independently selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$; and (ii) visualizing the imaging cargo.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_{A'}$ is selected from: D-Arg, D-His, or D-Lys. In some embodiments, $X_{A'}$ is selected from: D-Asp, D-Glu, D-Thr or D-Ser. In some embodiments, $X_{A'}$ is selected from: D-Asp or D-Glu. In some embodiments, $X_{A'}$ is selected from: D-Thr or D-Ser. In some embodiments, $X_{A'}$ is selected from: D-Glu or D-Thr. In some embodiments, $X_{A'}$ is D-Glu. In some embodiments, $X_{A'}$ is D-Thr. In some embodiments, $X_{A'}$ is D-Asp. In some embodiments, $X_{A'}$ is D-Arg. In some embodiments, $X_{A'}$ is D-His. In some embodiments, $X_{A'}$ is D-Lys. In some embodiments, $X_{A'}$ is D-Ser. In some embodiments, $X_{A'}$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_{B'}$ is selected from: D-His, D-Lys, D-Glu or D-Arg. In some embodiments, $X_{B'}$ is selected from: D-Thr, D-Glu, D-Ser or D-Asp. In some embodiments, $X_{B'}$ is selected from: D-His, D-Thr, D-Ser or D-Asp. In some embodiments, $X_{B'}$ is D-His. In some embodiments, $X_{B'}$ is D-Lys. In some embodiments, $X_{B'}$ is D-Thr. In some embodiments, $X_{B'}$ is D-Glu. In some embodiments, $X_{B'}$ is D-Ser. In some embodiments, $X_{B'}$ is D-Asp. In some embodiments, $X_{B'}$ is D-Arg. In some embodiments, $X_{B'}$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_{C'}$ is selected from: D-Arg, D-His or D-Lys. In some embodiments, $X_{C'}$ is selected from: D-Asp, D-Glu, D-Thr or D-Ser. In some embodiments, $X_{C'}$ is selected from: D-Asp or D-Glu. In some embodiments, $X_{C'}$ is selected from: D-Thr or D-Ser. In some embodiments, $X_{C'}$ is selected from: D-Glu or D-Thr. In some embodiments, $X_{C'}$ is D-Glu. In some embodiments, $X_{C'}$ is D-Thr. In some embodiments, $X_{C'}$ is D-Asp. In some embodiments, $X_{C'}$ is D-Arg. In some embodiments, $X_{C'}$ is D-His. In some embodiments, $X_{C'}$ is D-Lys. In some embodiments, $X_{C'}$ is D-Ser. In some embodiments, $X_{C'}$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $X_{A'}$—$X_{B'}$—$X_{C'}$ is EHT or THE, in which the amino acid residues are D-amino acid residues. In some instances, $X_{A'}$—$X_{B'}$—$X_{C'}$ is EHT, in which the amino acid residues are D-amino acid residues. In other instances, $X_{A'}$—$X_{B'}$—$X_{C'}$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 1-10 amino acids. In some embodiments, $L_1$ and $L_{1'}$ each independently comprises a series of D-10 Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ and $L_{1'}$ each independently comprises a series of 3 D-Ala residues and $L_2$ comprises an amino acid selected from Lys or Cys. In some embodiments, $L_1$ and $L_{1'}$ each independently comprises a series of 2 D-Ala residues and $L_2$ comprises an amino acid selected from Lys or Cys. In some embodiments, $L_1$ and $L_{1'}$ each independently comprises a series of 3 D-Ala residues and $L_2$ comprises an amino acid selected from D-Lys or D-Cys. In some embodiments, $L_1$ and $L_{1'}$ each independently comprises a series of 2 D-Ala residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A'}$. In some embodiments, $L_{1'}$ is bound to $X_{B'}$. In some embodiments, $L_{1'}$ is bound to $X_{C'}$.

Disclosed herein, in some embodiments, are methods of visualizing a target neuron, nerve, or tissue or external structure associated therewith in a subject in need thereof, comprising: (i) administering to the subject a nerve delivery molecule comprising a peptide sequence according to Formula (III) that localizes to the target neuron, nerve, or tissue or external structure associated therewith in the subject:

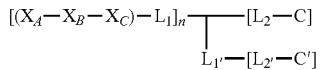

wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently an imaging cargo; and n is an integer between 1 and 5; and wherein, $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$; and (ii) visualizing the imaging cargo.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, the nerve delivery molecule of Formula (III) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 1-10 amino acids. In some embodiments, $L_1$ and $L_{1'}$ each independently comprises a series of 10 Ala residues. (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_1$ and $L_{1'}$ each independently comprises a series of 3 Ala residues and $L_2$ and $L_{2'}$ each independently comprises an amino acid selected from Lys or Cys. In some embodiments, $L_1$ and $L_{1'}$ each independently comprises a series of 2 Ala residues and $L_2$ and $L_{2'}$ each independently comprises an amino acid selected from Lys or Cys. In some embodiments, $L_1$ and $L_{1'}$ each independently comprises a series of 3 Gly residues and $L_2$ and $L_{2'}$ each independently comprises an amino acid selected from Lys or Cys. In some embodiments, $L_1$ and $L_{1'}$ each independently comprises a series of 3 Ala residues and $L_2$ and $L_{2'}$ each independently comprises an amino acid selected from D-Lys or D-Cys. In some embodiments, $L_1$ and $L_{1'}$ each independently comprises a series of 2 Ala residues and $L_2$ and $L_{2'}$ each independently comprises an amino acid selected from D-Lys or D-Cys. In some embodiments, $L_1$ and $L_{1'}$ each independently comprises a series of 3 Gly residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_{1'}$ is bound to $L_2$. In some embodiments, $L_{1'}$ is bound to $L_1$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complex, a rare-earth metal chelate complex, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the nerve delivery molecule of Formula (III) comprises two or more imaging cargos. In some cases, the imaging cargos are fluorescent. In some cases, a first fluorescent imaging cargo undergoes energy transfer to second or multiple fluorescent cargos that functionally extends the fluorescence emission to longer wavelengths. In some of these cases the emission is separated from the excitation light which facilitates detection of the emitted light. In some of these cases the extended, longer wavelength emission will have reduced tissue attenuation and deeper tissue detection properties. In some cases, the first fluorescent cargo is a xanthene. In some cases, the first fluorescent cargo is a fluorescein. In some cases, the second or multiple fluorescent cargo is an indocarbocyanine dye. In some cases, the emission is extended into the near infra-red wavelengths.

In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in some embodiments, are methods of visualizing a target neuron, nerve, or tissue or external structure associated therewith in a subject in need thereof, comprising: (i) administering to the subject a nerve delivery molecule comprising a peptide sequence according to Formula (IIIa) that localizes to the target neuron, nerve, or tissue or external structure associated therewith in the subject:

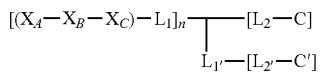

wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently an imaging cargo; and n is an integer between 1 and 5; and wherein, $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$; and (ii) visualizing the imaging cargo.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 1-10 amino acids. In some embodiments, $L_1$ and $L_{1'}$ each independently comprises a series of 10 D-Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_1$ and $L_{1'}$ each independently comprises a series of 3 D-Ala residues and $L_2$ and $L_{2'}$ each independently comprises an amino acid selected from Lys or Cys. In some embodiments, $L_1$ and $L_{1'}$ each independently comprises a series of 2 D-Ala residues and $L_2$ and $L_{2'}$ each independently comprises an amino acid selected from Lys or Cys. In some embodiments, $L_1$ and $L_{1'}$ each independently comprises a series of 3 D-Ala residues and $L_2$ and $L_{2'}$ each independently comprises an amino acid selected from D-Lys or D-Cys. In some embodiments, $L_1$ and $L_{1'}$ each independently comprises a series of 2 D-Ala residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_{1'}$ is bound to $L_2$. In some embodiments, $L_{1'}$ is bound to $L_1$.

Methods of Imaging a Target Neuron, Nerve, or Tissue or External Structure Associated Therewith Disclosed herein, in some embodiments, are methods of imaging a target neuron, nerve, or tissue or external structure associated therewith, comprising imaging a target neuron, nerve, or tissue or external structure associated therewith contacted with a nerve delivery molecule comprising a peptide sequence according to Formula (I):

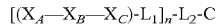

wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ is absent or is a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n is an integer between 1 and 5; and wherein $L_1$ is bound to at any position on $X_A$—$X_B$—$X_C$, $L_2$ is bound to $L_1$, and C is bound to $L_2$; and (ii) visualizing the imaging cargo.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, the nerve delivery molecule of Formula (I) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ comprises an L-amino acid. In some embodiments, $L_1$ comprises a D-amino acid. In some embodiments, $L_1$ comprises 1-10 amino acids. In some embodiments, $L_1$ comprises a series of 10 Ala residues (SEQ ID NO: 3). In some embodiments, $L_1$ comprises a series of 9 Ala residues (SEQ ID NO: 4). In some embodiments, $L_1$ comprises a series of 8 Ala residues (SEQ ID NO: 5). In some embodiments, $L_1$ comprises a series of 7 Ala residues (SEQ ID NO: 6). In some embodiments, $L_1$ comprises a series of 6 Ala residues (SEQ ID NO: 7). In some embodiments, $L_1$ comprises a series of 5 Ala residues (SEQ ID NO: 8). In some embodiments, $L_1$ comprises a series of 4 Ala residues (SEQ ID NO: 9). In some embodiments, $L_1$ comprises a series of 3 Ala residues. In some embodiments, $L_1$ comprises a series of 2 Ala residues. In some embodiments, $L_1$ comprises a series of 1 Ala residue. In some embodiments, $L_1$ comprises a series of 10 Gly residues (SEQ ID NO: 10). In some embodiments, $L_1$ comprises a series of 9 Gly residues (SEQ ID NO: 21). In some embodiments, $L_1$ comprises a series of 8 Gly residues (SEQ ID NO: 22). In some embodiments, $L_1$ comprises a series of 7 Gly residues (SEQ ID NO: 23). In some embodiments, $L_1$ comprises a series of 6 Gly residues (SEQ ID NO: 24). In some embodiments, $L_1$ comprises a series of 5 Gly residues (SEQ ID NO: 11). In some embodiments, $L_1$ comprises a series of 4 Gly residues (SEQ ID NO: 12). In some embodiments, $L_1$ comprises a series of 3 Gly residues.

In some embodiments, $L_1$ comprises an L-amino acid. In some embodiments, $L_1$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ comprises a series of 3 Ala residues and $L_2$ comprises an amino acid selected from Lys or Cys. In some embodiments, $L_1$ comprises a series of 2 Ala residues and $L_2$ comprises an amino acid selected from Lys or Cys. In some embodiments, $L_1$ comprises a series of 3 Gly residues and $L_2$ comprises an amino acid selected from Lys or Cys. In some embodiments, $L_1$ comprises a series of 3 Ala residues and $L_2$ comprises an amino acid selected from D-Lys or D-Cys. In some embodiments, $L_1$ comprises a series of 2 Ala residues and $L_2$ comprises an amino acid selected from D-Lys or D-Cys. In some embodiments, $L_1$ comprises a series of 3 Gly residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complex, a rare-earth metal chelate complex, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N''-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in some embodiments, are methods of imaging a target neuron, nerve, or tissue or external structure associated therewith, comprising imaging a target neuron, nerve, or tissue or external structure associated therewith contacted with a nerve delivery molecule comprising a peptide sequence according to Formula (Ia):

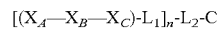

$$[(X_A-X_B-X_C)-L_1]_n-L_2-C$$

wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ is absent or is a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n is an integer between 1 and 5; and wherein $L_1$ is bound to at any position on $X_A$—$X_B$—$X_C$, $L_2$ is bound to $L_1$, and C is bound to $L_2$; and (ii) visualizing the imaging cargo.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $L_1$ comprises 1-10 amino acids. In some embodiments, $L_1$ comprises a series of 10 D-Ala residues. In some embodiments, $L_1$ comprises a series of 9 D-Ala residues. In some embodiments, $L_1$ comprises a series of 8 D-Ala residues. In some embodiments, $L_1$ comprises a series of 7 D-Ala residues. In some embodiments, $L_1$ comprises a series of 6 D-Ala residues. In some embodiments, $L_1$ comprises a series of 5 D-Ala residues. In some embodiments, $L_1$ comprises a series of 4 D-Ala residues. In some embodiments, $L_1$ comprises a series of 3 D-Ala residues. In some embodiments, $L_1$ comprises a series of 2 D-Ala residues. In some embodiments, $L_1$ comprises a series of 1 D-Ala residue.

In some embodiments, $L_1$ comprises an L-amino acid. In some embodiments, $L_1$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ comprises a series of 3 D-Ala residues and $L_2$ comprises an amino acid selected from Lys or Cys. In some embodiments, $L_1$ comprises a series of 2 D-Ala residues and $L_2$ comprises an amino acid selected from Lys or Cys. In some embodiments, $L_1$ comprises a series of 3 D-Ala residues and $L_2$ comprises an amino acid selected from D-Lys or D-Cys. In some embodiments, $L_1$ comprises a series of 2 D-Ala residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

Disclosed herein, in some embodiments, are methods of imaging a target neuron, nerve, or tissue or external structure associated therewith, comprising imaging a target neuron, nerve, or tissue or external structure associated therewith contacted with a nerve delivery molecule comprising a peptide sequence according to Formula (II):

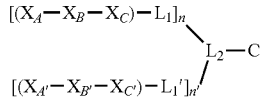

wherein $X_A$ and $X_{A'}$ are each independently selected from: Asp, Arg, Glu, Thr, His, Lys, Phe, or Ser; $X_B$ and $X_{B'}$ are each independently selected from: His, Lys, Thr, Glu, Ser, Asp, Phe, or Arg; $X_C$ and $X_{C'}$ are each independently selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$; and (ii) visualizing the imaging cargo.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_{A'}$ is selected from: Arg, His, or Lys. In some embodiments, $X_{A'}$ is selected from: Asp, Glu, Thr or Ser. In some embodiments, $X_{A'}$ is selected from: Asp or Glu. In some embodiments, $X_{A'}$ is selected from: Thr or Ser. In some embodiments, $X_{A'}$ is selected from: Glu or Thr. In some embodiments, $X_{A'}$ is Glu. In some embodiments, $X_{A'}$ is Thr. In some embodiments, $X_{A'}$ is Asp. In some embodiments, $X_{A'}$ is Arg. In some embodiments, $X_{A'}$ is His. In some embodiments, $X_{A'}$ is Lys. In some embodiments, $X_{A'}$ is Ser. In some embodiments, $X_{A'}$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_{B'}$ is selected from: His, Lys, Glu or Arg. In some embodiments, $X_{B'}$ is selected from: Thr, Glu, Ser or Asp. In some embodiments, $X_{B'}$ is selected from: His, Thr, Ser or Asp. In some embodiments, $X_{B'}$ is His. In some embodiments, $X_{B'}$ is Lys. In some embodiments, $X_{B'}$ is Thr. In some embodiments, $X_{B'}$ is Glu. In some embodiments, $X_{B'}$ is Ser. In some embodiments, $X_{B'}$ is Asp. In some embodiments, $X_{B'}$ is Arg. In some embodiments, $X_{B'}$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_{C'}$ is selected from: Arg, His or Lys. In some embodiments, $X_{C'}$ is selected from: Asp, Glu, Thr or Ser. In some embodiments, $X_{C'}$ is selected from: Asp or Glu. In some embodiments, $X_{C'}$ is selected from: Thr or Ser. In some embodiments, $X_{C'}$ is selected from: Glu or Thr.

In some embodiments, $X_{C'}$ is Glu. In some embodiments, $X_{C'}$ is Thr. In some embodiments, $X_{C'}$ is Asp. In some embodiments, $X_{C'}$ is Arg. In some embodiments, $X_{C'}$ is His. In some embodiments, $X_{C'}$ is Lys. In some embodiments, $X_{C'}$ is Ser. In some embodiments, $X_{C'}$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, $X_{A'}$—$X_{B'}$—$X_{C'}$ is EHT or THE. In some instances, $X_{A'}$—$X_{B'}$—$X_{C'}$ is EHT. In other instances, $X_{A'}$—$X_{B'}$—$X_{C'}$ is THE.

In some embodiments, the nerve delivery molecule of Formula (II) comprises a naturally occurring amino acid or a non-naturally occurring amino acid. In some embodiments, $X_A$, $X_B$, $X_C$, $X_{A'}$, $X_{B'}$, and $X_{C'}$ each independently comprises a D-amino acid. In some embodiments, the amino acid residues of $X_A$, $X_B$ and $X_C$ are D-amino acids. In some embodiments, the amino acid residues of $X_{A'}$, $X_{B'}$, and $X_{C'}$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 1-10 amino acids. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ and $L_{1'}$ each independently comprises a series of 3 Ala residues and $L_2$ comprises an amino acid selected from Lys or Cys. In some embodiments, $L_1$ and $L_{1'}$ each independently comprises a series of 2 Ala residues and $L_2$ comprises an amino acid selected from Lys or Cys. In some embodiments, $L_1$ and $L_{1'}$ each independently comprises a series of 3 Gly residues and $L_2$ comprises an amino acid selected from Lys or Cys. In some embodiments, $L_1$ and $L_{1'}$ each independently comprises a series of 3 Ala residues and $L_2$ comprises an amino acid selected from D-Lys or D-Cys. In some embodiments, $L_1$ and $L_{1'}$ each independently comprises a series of 2 Ala residues and $L_2$ comprises an amino acid selected from D-Lys or D-Cys. In some embodiments, $L_1$ and $L_{1'}$ each independently comprises a series of 3 Gly residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A'}$. In some embodiments, $L_{1'}$ is bound to $X_{B'}$. In some embodiments, $L_{1'}$ is bound to $X_{C'}$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complexe, a rare-earth metal chelate complexe, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6-isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in some embodiments, are methods of imaging a target neuron, nerve, or tissue or external structure associated therewith, comprising imaging a target neuron, nerve, or tissue or external structure associated therewith contacted with a nerve delivery molecule comprising a peptide sequence according to Formula (IIa):

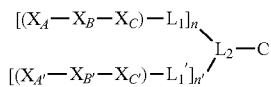

wherein $X_A$ and $X_{A'}$ are each independently selected from: D-Asp, D-Arg, D-Glu, D-Thr, D-His, D-Lys, D-Phe, or D-Ser; $X_B$ and $X_{B'}$ are each independently selected from: D-His, D-Lys, D-Thr, D-Glu, D-Ser, D-Asp, D-Phe, or D-Arg; $X_C$ and $X_{C'}$ are each independently selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is an imaging cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$; and (ii) visualizing the imaging cargo.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_{A'}$ is selected from: D-Arg, D-His, or D-Lys. In some embodiments, $X_{A'}$ is selected from: D-Asp, D-Glu, D-Thr or D-Ser. In some embodiments, $X_{A'}$ is selected from: D-Asp or D-Glu. In some embodiments, $X_{A'}$ is selected from: D-Thr or D-Ser. In some embodiments, $X_{A'}$ is selected from: D-Glu or D-Thr. In some embodiments, $X_{A'}$ is D-Glu. In some embodiments, $X_{A'}$ is D-Thr. In some embodiments, $X_{A'}$ is D-Asp. In some embodiments, $X_{A'}$ is D-Arg. In some embodiments, $X_{A'}$ is D-His. In some embodiments, $X_{A'}$ is D-Lys. In some embodiments, $X_{A'}$ is D-Ser. In some embodiments, $X_{A'}$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_{B'}$ is selected from: D-His, D-Lys, D-Glu or D-Arg. In some embodiments, $X_{B'}$ is selected from: D-Thr, D-Glu, D-Ser or D-Asp. In some embodiments, $X_{B'}$ is selected from: D-His, D-Thr, D-Ser or D-Asp. In some embodiments, $X_{B'}$ is D-His. In some embodiments, $X_{B'}$ is D-Lys. In some embodiments, $X_{B'}$ is D-Thr. In some embodiments, $X_{B'}$ is D-Glu. In some embodiments, $X_{B'}$ is D-Ser. In some embodiments, $X_{B'}$ is D-Asp. In some embodiments, $X_{B'}$ is D-Arg. In some embodiments, $X_{B'}$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_{C'}$ is selected from: D-Arg, D-His or D-Lys. In some embodiments, $X_{C'}$ is selected from: D-Asp, D-Glu, D-Thr or D-Ser. In some embodiments, $X_{C'}$ is selected from: D-Asp or D-Glu. In some embodiments, $X_{C'}$ is selected from: D-Thr or D-Ser. In some embodiments, $X_{C'}$ is selected from: D-Glu or D-Thr. In some embodiments, $X_{C'}$ is D-Glu. In some embodiments, $X_{C'}$ is D-Thr. In some embodiments, $X_{C'}$ is D-Asp. In some embodiments, $X_{C'}$ is D-Arg. In some embodiments, $X_{C'}$ is D-His. In some embodiments, $X_{C'}$ is D-Lys. In some embodiments, $X_{C'}$ is D-Ser. In some embodiments, $X_{C'}$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $X_{A'}$—$X_{B'}$—$X_{C'}$ is EHT or THE, in which the amino acid residues are D-amino acid residues. In some instances, $X_{A'}$—$X_{B'}$—$X_{C'}$ is EHT, in which the amino acid residues are D-amino acid residues. In other instances, $X_{A'}$—$X_{B'}$—$X_{C'}$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 1-10 amino acids. In some embodiments, $L_1$ and $L_{1'}$ each independently comprises a series of D-10 Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ and $L_{1'}$ each independently comprises a series of 3 D-Ala residues and $L_2$ comprises an amino acid selected from Lys or Cys. In some embodiments, $L_1$ and $L_{1'}$ each independently comprises a series of 2 D-Ala residues and $L_2$ comprises an amino acid selected from Lys or Cys. In some embodiments, $L_1$ and $L_{1'}$ each independently comprises a series of 3 D-Ala residues and $L_2$ comprises an amino acid selected from D-Lys or D-Cys. In some embodiments, $L_1$ and $L_{1'}$ each independently comprises a series of 2 D-Ala residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A'}$. In some embodiments, $L_{1'}$ is bound to $X_{B'}$. In some embodiments, $L_{1'}$ is bound to $X_{C'}$.

Disclosed herein, in some embodiments, are methods of imaging a target neuron, nerve, or tissue or external structure associated therewith, comprising imaging a target neuron, nerve, or tissue or external structure associated therewith contacted with a nerve delivery molecule comprising a peptide sequence according to Formula (III):

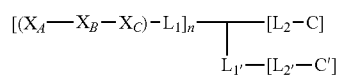

wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently an imaging cargo; and n is an integer between 1 and 5; and wherein, $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$; and (ii) visualizing the imaging cargo.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, the nerve delivery molecule of Formula (III) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 1-10 amino acids. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_1$ and $L_{1'}$ each independently comprises a series of 3 Ala residues and $L_2$ and $L_{2'}$ each independently comprises an amino acid selected from Lys or Cys. In some embodiments, $L_1$ and $L_{1'}$ each independently comprises a series of 2 Ala residues and $L_2$ and $L_{2'}$ each independently comprises an amino acid selected from Lys or Cys. In some embodiments, $L_1$ and $L_{1'}$ each independently comprises a series of 3 Gly residues and $L_2$ and $L_{2'}$ each independently comprises an amino acid selected from Lys or Cys. In some embodiments, $L_1$ and $L_{1'}$ each independently comprises a series of 3 Ala residues and $L_2$ and $L_{2'}$ each independently comprises an amino acid selected from D-Lys or D-Cys. In some embodiments, $L_1$ and $L_{1'}$ each independently comprises a series of 2 Ala residues and $L_2$ and $L_{2'}$ each independently comprises an amino acid selected from D-Lys or D-Cys. In some embodiments, $L_1$ and $L_{1'}$ each independently comprises a series of 3 Gly residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_1$ is bound to $L_2$. In some embodiments, $L_{1'}$ is bound to $L_1$.

In some embodiments, the imaging cargo comprises a dye, a fluorescent moiety, a positron-emitting isotope, a gamma-emitting isotope, or a paramagnetic molecule or nanoparticle. In some embodiments, the imaging cargo comprises a fluorescent protein, a fluorescent peptide, a fluorescent dye, a fluorescent material or a combination thereof. In some embodiments, the imaging cargo comprises a xanthene, a bimane, a coumarin, an aromatic amine, a benzofuran, a fluorescent cyanine, an indocarbocyanine, a carbazole, a dicyanomethylene pyrane, a polymethine, an oxabenzanthrane, a pyrylium, a carbostyl, a perylene, an acridone, a quinacridone, a rubrene, an anthracene, a coronene, a phenanthrecene, a pyrene, a butadiene, a stilbene, a porphyrin, a pthalocyanine, a lanthanide metal chelate complex, a rare-earth metal chelate complex, derivatives thereof, or a combination thereof. In some embodiments, the imaging cargo comprises halogenated xanthene, fluorinated xanthene, fluorinated fluorescein, fluorinated 5-carboxyfluorescein, fluorinated 6-carboxyfluorescein, 5-carboxyfluorescein, fluorescein-5-isothiocyanate, fluorescein-6-isothiocyanate, 6-carboxyfluorescein, tetramethylrhodamine-6- isothiocyanate, 5-carboxytetramethylrhodamine, 5-carboxy rhodol derivatives, tetramethyl and tetraethyl rhodamine, diphenyldimethyl and diphenyldiethyl rhodamine, dinaphthyl rhodamine, rhodamine 101 sulfonyl chloride, Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, Green Fluorescent Protein, EBFP, EBFP2, Azurite, mKalama1, ECFP, Cerulean, CyPet, YFP, Citrine, Venus, YPet, or a combination thereof. In some embodiments, the imaging cargo comprises a gadolinium chelate, an iron oxide particle, a super paramagnetic iron oxide particle, an ultra small paramagnetic particle, a manganese chelate, gallium containing agent, or a combination thereof. In some embodiments, the imaging cargo is a radionucleotide chelate selected from: diethylene triamine pentaacetic acid (DTPA), 1,4,7,10-tetraazacyclododecane-1,4,7,10-tetraacetic acid (DOTA), 1,4,7-triazacyclononane-N,N',N"-triacetic acid (NOTA), 6-Hydrazinopyridine-3-carboxylic acid (HYNIC), or a combination thereof. In some embodiments, the imaging cargo is a radionucleotide selected from: $^{99m}$Tc, $^{64}$Cu, $^{18}$F, $^{124}$I, $^{111}$In, or a combination thereof. In some embodiments, the imaging cargo is $^{211}$At, $^{131}$I, $^{125}$I, $^{90}$Y, $^{186}$Re, $^{188}$Re, $^{153}$Sm, $^{212}$Bi, $^{32}$P, $^{11}$C, $^{201}$Tl, $^{57}$Ga, a radioactive isotope of Lu, or a combination thereof. In some embodiments, the imaging cargo is an indocarbocyanine dye. In some embodiments, the imaging cargo is Cy3, Cy3B, Cy3.5, Cy5, Cy5.5, Cy7, DyLight650, IRDye650, IRDye680, DyLight750, Alexa Fluor 647, Alexa Fluor 750, IR800CW, ICG, or a combination thereof. In some embodiments, the imaging cargo is Cy5 indocarbocyanine dye. In some embodiments, the imaging cargo is 6-carboxyfluorescein.

In some embodiments, the nerve delivery molecule of Formula (III) comprises two or more imaging cargos. In some cases, the imaging cargos are fluorescent. In some cases, a first fluorescent imaging cargo undergoes energy transfer to second or multiple fluorescent cargos that functionally extends the fluorescence emission to longer wavelengths. In some of these cases the emission is separated from the excitation light which facilitates detection of the emitted light. In some of these cases the extended, longer wavelength emission will have reduced tissue attenuation and deeper tissue detection properties. In some cases, the first fluorescent cargo is a xanthene. In some cases, the first fluorescent cargo is a fluorescein. In some cases the second or multiple fluorescent cargo is an indocarbocyanine dye. In some cases, the emission is extended into the near infra-red wavelengths.

In some embodiments, the target is neurons, nerves, or tissues (e.g., the sinoatrial node and the atrioventricular node) or structures associated therewith (e.g., neuromuscular junctions). The nerve is any nerve (e.g., motor nerves, sensory nerves, sympathetic and parasympathetic nerves, periprostatic neurovascular bundle, sciatic nerves, cranial nerves including olfactory nerve, optic nerve, oculomotor nerve, trochlear nerve, trigeminal nerve, abducens nerve, facial nerve, vestibulocochlear nerve, glossopharyngeal nerve, vagus nerve, accessory nerve, hypoglossal nerve, spinal nerves, brachial plexus, lumbrosacral plexus, splenic nerves, thoracic nerves, abdominal nerves, perineal nerves, sural nerves, intercostal nerves, sacral plexus, or cutaneous nerves). The neuron is any neuron (e.g., sensory neurons (afferent neurons), motor neurons (efferent neurons), interneurons, unipolar neurons, bipolar neurons, multipolar neurons, basket cells, Betz cells, medium spiny neurons, Purkinje cells, pyramidal cells, Renshaw cells, Granule cells, anterior horn cells). In some embodiments, the neuron or nerve is myelinated. In some embodiments, the neuron or nerve is unmyelinated. In some embodiments, the neuron or nerve is demyelinated. In some embodiments, the neuron or nerve is undergoing demyelination. In some embodiments, the target is a component of a neuron or nerve. The component of a neuron or nerve is any component of a neuron or nerve. In some embodiments, the target is tissue within or surrounding a neuron or nerve (e.g., epineurium, perineurium, or endoneurium). In some embodiments, the target is an external structure associated with a nerve or neuron (e.g., a neuromuscular junction). In some embodiments, the target is a neuromuscular junction. In some embodiments, the target is a component of myelin, (e.g., myelin basic protein (MBP), myelin oligodendrocyte glycoprotein, or proteolipid protein). In some embodiments, the target is expressed by Schwann cells, (e.g., MBP, glial fibrillary acidic protein, S-100, or myelin protein zero). In some embodiments, the target is a component of neuron or nerve tissue, (e.g., elastin, fibrillin, e-cadherin, cytokeratin, vimentin, collagen I, collagen, III, collagen IV, or collagen V). In some embodiments, the target is a neurotrophic factor receptor expressed in neuron or nerves, (e.g., tyrosine kinase receptors TrkA, TrkB, and TrkC, low affinity neuron or nerve growth receptor or p75 neurotrophin receptor, or GDNF family receptor alpha-1 or -2). In some embodiments, the target is a non-neurotrophic factor receptor expressed in a neuron or nerve tissue, (e.g., epithelial growth factor receptors, transforming growth factor beta receptors, vascular endothelial growth factor receptors, endothelin A receptors, endothelin B receptors, and integrin receptors). In some embodiments, the target is electrically excitable tissue including nerves and muscle. In some embodiments, the target is the conducting fibers of electrically excitable tissues. In some embodiments, the target is cardiac excitable tissue.

Disclosed herein, in some embodiments, are methods of imaging a target neuron, nerve, or tissue or external structure associated therewith, comprising imaging a target neuron, nerve, or tissue or external structure associated therewith contacted with a nerve delivery molecule comprising a peptide sequence according to Formula (IIIa):

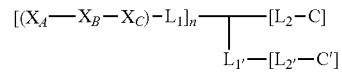

wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently an imaging cargo; and n is an integer between 1 and 5; and wherein, $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$; and (ii) visualizing the imaging cargo.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 1-10 amino acids. In some embodiments, $L_1$ and $L_{1'}$ each independently comprises a series of 10 D-Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_1$ and $L_{1'}$ each independently comprises a series of 3 D-Ala residues and $L_2$ and $L_{2'}$ each independently comprises an amino acid selected from Lys or Cys. In some embodiments, $L_1$ and $L_{1'}$ each independently comprises a series of 2 D-Ala residues and $L_2$ and $L_{2'}$ each independently comprises an amino acid selected from Lys or Cys. In some embodiments, $L_1$ and $L_{1'}$ each independently comprises a series of 3 D-Ala residues and $L_2$ and $L_{2'}$ each independently comprises an amino acid selected from D-Lys or D-Cys. In some embodiments, $L_1$ and $L_{1'}$ each independently comprises a series of 2 D-Ala residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_{1'}$ is bound to $L_2$. In some embodiments, $L_{1'}$ is bound to $L_1$.

Imaging Uses

Disclosed herein, in certain embodiments, are methods of labeling neurons, nerves, or tissues (e.g., the sinoatrial node and the atrioventricular node) or structures associated therewith (e.g., neuromuscular junctions) by contacting the neurons, nerves, or tissues (e.g., the sinoatrial node and the atrioventricular node) or structures associated therewith (e.g., neuromuscular junctions) with a nerve delivery molecule described herein.

In some embodiments, the contacting occurs in vivo. In some embodiments, the contacting occurs in vitro.

In some embodiments, the neurons, nerves, or tissues (e.g., the sinoatrial node and the atrioventricular node) or structures associated therewith (e.g., neuromuscular junctions) are labeled for identification during surgery. In some embodiments, the method comprises administering a nerve delivery molecule disclosed herein to a subject that will undergo surgery. In some embodiments, the method comprises administering a nerve delivery molecule disclosed herein to a subject that is undergoing surgery. In some embodiments, a nerve delivery molecule disclosed herein is administered to a patient systemically. In some embodiments, a nerve delivery molecule disclosed herein is administered to a patient locally.

Methods of Delivering Therapeutic Cargo

In some embodiments, disclosed herein is a method of delivering a therapeutic cargo to a target neuron, nerve, or tissue or external structure associated therewith of interest, which comprises a nerve delivery molecule of Formula (I):

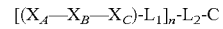

[$(X_A$—$X_B$—$X_C)$-$L_1]_n$-$L_2$-C wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ is absent or is a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is a therapeutic cargo; and n is an integer between 1 and 5; and wherein $L_1$ is bound to at any position on $X_A$—$X_B$—$X_C$, $L_2$ is bound to $L_1$, and C is bound to $L_2$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, the nerve delivery molecule of Formula (I) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ comprises an L-amino acid. In some embodiments, $L_1$ comprises a D-amino acid. In some embodiments, $L_1$ comprises 1-10 amino acids. In some embodiments, $L_1$ comprises 2 amino acids. In some embodiments, $L_1$ comprises 3 amino acids. In some embodiments, $L_1$ comprises a series of 10 Ala residues (SEQ ID NO: 3). In some embodiments, $L_1$ comprises a series of 9 Ala residues (SEQ ID NO: 4). In some embodiments, $L_1$ comprises a series of 8 Ala residues (SEQ ID NO: 5). In some embodiments, $L_1$ comprises a series of 7 Ala residues (SEQ ID NO: 6). In some embodiments, $L_1$ comprises a series of 6 Ala residues (SEQ ID NO: 7). In some embodiments, $L_1$ comprises a series of 5 Ala residues (SEQ ID NO: 8). In some embodiments, $L_1$ comprises a series of 4 Ala residues (SEQ ID NO: 9). In some embodiments, $L_1$ comprises a series of 3 Ala residues. In some embodiments, $L_1$ comprises a series of 2 Ala residues. In some embodiments, $L_1$ comprises a series of 1 Ala residue. In some embodiments, $L_1$ comprises a series of 10 Gly residues (SEQ ID NO: 10). In some embodiments, $L_1$ comprises a series of 9 Gly residues (SEQ ID NO: 21). In some embodiments, $L_1$ comprises a series of 8 Gly residues (SEQ ID NO: 22). In some embodiments, $L_1$ comprises a series of 7 Gly residues (SEQ ID NO: 23). In some embodiments, $L_1$ comprises a series of 6 Gly residues (SEQ ID NO: 24). In some embodiments, $L_1$ comprises a series of 5 Gly residues (SEQ ID NO: 11). In some embodiments, $L_1$ comprises a series of 4 Gly residues (SEQ ID NO: 12). In some embodiments, $L_1$ comprises a series of 3 Gly residues.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ comprises a series of 3 Ala residues and $L_2$ comprises an amino acid selected from Lys or Cys. In some embodiments, $L_1$ comprises a series of 2 Ala residues and $L_2$ comprises an amino acid selected from Lys or Cys. In some embodiments, $L_1$ comprises a series of 3 Gly residues and $L_2$ comprises an amino acid selected from Lys or Cys. In some embodiments, $L_1$ comprises a series of 3 Ala residues and $L_2$ comprises an amino acid selected from D-Lys or D-Cys. In some embodiments, $L_1$ comprises a series of 2 Ala residues and $L_2$ comprises an amino acid selected from D-Lys or D-Cys. In some embodiments, $L_1$ comprises a series of 3 Gly residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

In some embodiments, the therapeutic cargo comprises a chemotherapeutic agent, a cytotoxin, a steroid, an immunotherapeutic agent, a targeted therapy agent, or an anti-inflammatory agent. In some embodiments, the therapeutic cargo comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is a cargo that promotes regeneration of neuron or nerve tissue. In some embodiments, the therapeutic cargo is a growth factor.

In some embodiments, the therapeutic cargo is a local anesthetic.

In some embodiments, the therapeutic cargo is an antiepileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

In some embodiments, also described herein is a method of delivering a therapeutic cargo to a target neuron, nerve, or tissue or external structure associated therewith of interest, which comprises a nerve delivery molecule comprising a peptide sequence according to Formula (Ia):

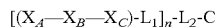

[($X_A$—$X_B$—$X_C$)-$L_1$]$_n$-$L_2$-C wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ is absent or is a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is a therapeutic cargo; and n is an integer between 1 and 5; and wherein $L_1$ is bound to at any position on $X_A$—$X_B$—$X_C$, $L_2$ is bound to $L_1$, and C is bound to $L_2$.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $L_1$ comprises 1-10 amino acids. In some embodiments, $L_1$ comprises 2 amino acids. In some embodiments, $L_1$ comprises 3 amino acids. In some embodiments, $L_1$ comprises a series of 10 D-Ala residues. In some embodiments, $L_1$ comprises a series of 9 D-Ala residues. In some embodiments, $L_1$ comprises a series of 8 D-Ala residues. In some embodiments, $L_1$ comprises a series of 7 D-Ala residues. In some embodiments, $L_1$ comprises a series of 6 D-Ala residues. In some embodiments, $L_1$ comprises a series of 5 D-Ala residues. In some embodiments, $L_1$ comprises a series of 4 D-Ala residues. In some embodiments, $L_1$ comprises a series of 3 D-Ala residues. In some embodiments, $L_1$ comprises a series of 2 D-Ala residues. In some embodiments, $L_1$ comprises a series of 1 D-Ala residue.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ comprises a series of 3 D-Ala residues and $L_2$ comprises an amino acid selected from D-Lys or D-Cys. In some embodiments, $L_1$ comprises a series of 2 D-Ala residues and $L_2$ comprises an amino acid selected from Lys or Cys. In some embodiments, $L_1$ comprises a series of 2 D-Ala residues and $L_2$ comprises an amino acid selected from Lys or Cys. In some embodiments, $L_1$ comprises a series of 3 D-Ala residues and $L_2$ comprises an amino acid selected from D-Lys or D-Cys. In some embodiments, $L_1$ comprises a series of 2 D-Ala residues and $L_2$ comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$.

In some embodiments, disclosed herein is a method of delivering a therapeutic cargo to a target neuron, nerve, or tissue or external structure associated therewith of interest, which comprises a nerve delivery molecule comprising a peptide sequence according to Formula (II):

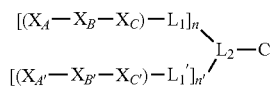

wherein $X_A$ and $X_{A'}$ are each independently selected from: Asp, Arg, Glu, Thr, His, Lys, Phe, or Ser; $X_B$ and $X_{B'}$ are each independently selected from: His, Lys, Thr, Glu, Ser, Asp, Phe, or Arg; $X_C$ and $X_{C'}$ are each independently selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is a therapeutic cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_{A'}$ is selected from: Arg, His, or Lys. In some embodiments, $X_{A'}$ is selected from: Asp, Glu, Thr or Ser. In some embodiments, $X_{A'}$ is selected from: Asp or Glu. In some embodiments, $X_{A'}$ is selected from: Thr or Ser. In some embodiments, $X_{A'}$ is selected from: Glu or Thr. In some embodiments, $X_{A'}$ is Glu. In some embodiments, $X_{A'}$ is Thr. In some embodiments, $X_{A'}$ is Asp. In some embodiments, $X_{A'}$ is Arg. In some embodiments, $X_{A'}$ is His. In some embodiments, $X_{A'}$ is Lys. In some embodiments, $X_{A'}$ is Ser. In some embodiments, $X_{A'}$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_{B'}$ is selected from: His, Lys, Glu or Arg. In some embodiments, $X_{B'}$ is selected from: Thr, Glu, Ser or Asp. In some embodiments, $X_{B'}$ is selected from: His, Thr, Ser or Asp. In some embodiments, $X_{B'}$ is His. In some embodiments, $X_{B'}$ is Lys. In some embodiments, $X_{B'}$ is Thr. In some embodiments, $X_{B'}$ is Glu. In some embodiments, $X_{B'}$ is Ser. In some embodiments, $X_{B'}$ is Asp. In some embodiments, $X_{B'}$ is Arg. In some embodiments, $X_{B'}$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_{C'}$ is selected from: Arg, His or Lys. In some embodiments, $X_{C'}$ is selected from: Asp, Glu, Thr or Ser. In some embodiments, $X_{C'}$ is selected from: Asp or Glu. In some embodiments, $X_{C'}$ is selected from: Thr or Ser. In some embodiments, $X_{C'}$ is selected from: Glu or Thr. In some embodiments, $X_{C'}$ is Glu. In some embodiments, $X_{C'}$ is Thr. In some embodiments, $X_{C'}$ is Asp. In some embodiments, $X_{C'}$ is Arg. In some embodiments, $X_{C'}$ is His. In some embodiments, $X_{C'}$ is Lys. In some embodiments, $X_{C'}$ is Ser. In some embodiments, $X_{C'}$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, $X_{A'}$—$X_{B'}$—$X_{C'}$ is EHT or THE. In some instances, $X_{A'}$—$X_{B'}$—$X_{C'}$ is EHT. In other instances, $X_{A'}$—$X_{B'}$—$X_{C'}$ is THE.

In some embodiments, the nerve delivery molecule of Formula (II) comprises a naturally occurring amino acid or a non-naturally occurring amino acid. In some embodiments, $X_A$, $X_B$, $X_C$, $X_{A'}$, $X_{B'}$, and $X_{C'}$ each independently comprises a D-amino acid. In some embodiments, the amino acid residues of $X_A$, $X_B$ and $X_C$ are D-amino acids. In some embodiments, the amino acid residues of $X_{A'}$, $X_{B'}$ and $X_{C'}$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 1-10 amino acids. In some embodiments, $L_1$ comprises 2 amino acids. In some embodiments, $L_1$ comprises 3 amino acids. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ and $L_{1'}$ each independently comprises a series of 3 Ala residues and $L_2$ comprises an amino acid selected from Lys or Cys. In some embodiments, $L_1$ and $L_{1'}$ each independently comprises a series of 2 Ala residues and $L_2$ comprises an amino acid selected from Lys or Cys. In some embodiments, $L_1$ and $L_{1'}$ each independently comprises a series of 3 Gly residues and $L_2$ comprises an amino acid selected from Lys or Cys. In some embodiments, $L_1$ and $L_{1'}$ each independently comprises a series of 3 Ala residues and $L_2$ comprises an amino acid selected from D-Lys or D-Cys. In some embodiments, $L_1$ and $L_{1'}$ each independently comprises a series of 2 Ala residues and $L_2$ comprises an amino acid selected from D-Lys or D-Cys. In some embodiments, $L_1$ and $L_{1'}$ each independently comprises a series of 3 Gly residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A'}$. In some embodiments, $L_{1'}$ is bound to $X_{B'}$. In some embodiments, $L_{1'}$ is bound to $X_{C'}$.

In some embodiments, the therapeutic cargo comprises a chemotherapeutic agent, a cytotoxin, a steroid, an immunotherapeutic agent, a targeted therapy agent, or an anti-inflammatory agent. In some embodiments, the therapeutic cargo comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is an agent that promotes regeneration of neuron or nerve tissue. In some embodiments, the therapeutic cargo is a growth factor.

In some embodiments, the therapeutic cargo is a drug that reduces pain (either the perception of pain or activity of a painful stimulant). In some embodiments, the therapeutic cargo is a local anesthetic.

In some embodiments, the therapeutic cargo is an anti-epileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

In some embodiments, disclosed herein is a method of delivering a therapeutic cargo to a target neuron, nerve, or tissue or external structure associated therewith of interest, which comprises a nerve delivery molecule comprising a peptide sequence according to Formula (IIa):

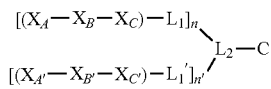

wherein $X_A$ and $X_{A'}$ are each independently selected from: D-Asp, D-Arg, D-Glu, D-Thr, D-His, D-Lys, D-Phe, or D-Ser; $X_B$ and $X_{B'}$ are each independently selected from: D-His, D-Lys, D-Thr, D-Glu, D-Ser, D-Asp, D-Phe, or D-Arg; $X_C$ and $X_{C'}$ are each independently selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ is a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C is a therapeutic cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_{A'}$ is selected from: D-Arg, D-His, or D-Lys. In some embodiments, $X_{A'}$ is selected from: D-Asp, D-Glu, D-Thr or D-Ser. In some embodiments, $X_{A'}$ is selected from: D-Asp or D-Glu. In some embodiments, $X_{A'}$ is selected from: D-Thr or D-Ser. In some embodiments, $X_{A'}$ is selected from: D-Glu or D-Thr. In some embodiments, $X_{A'}$ is D-Glu. In some embodiments, $X_{A'}$ is D-Thr. In some embodiments, $X_{A'}$ is D-Asp. In some embodiments, $X_{A'}$ is D-Arg. In some embodiments, $X_{A'}$ is D-His. In some embodiments, $X_{A'}$ is D-Lys. In some embodiments, $X_{A'}$ is D-Ser. In some embodiments, $X_{A'}$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_{B'}$ is selected from: D-His, D-Lys, D-Glu or D-Arg. In some embodiments, $X_{B'}$ is selected from: D-Thr, D-Glu, D-Ser or D-Asp. In some embodiments, $X_{B'}$ is selected from: D-His, D-Thr, D-Ser or D-Asp. In some embodiments, $X_{B'}$ is D-His. In some embodiments, $X_{B'}$ is D-Lys. In some embodiments, $X_{B'}$ is D-Thr. In some embodiments, $X_{B'}$ is D-Glu. In some embodiments, $X_{B'}$ is D-Ser. In some embodiments, $X_{B'}$ is D-Asp. In some embodiments, $X_{B'}$ is D-Arg. In some embodiments, $X_{B'}$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_{C'}$ is selected from: D-Arg, D-His or D-Lys. In some embodiments, $X_{C'}$ is selected from: D-Asp, D-Glu, D-Thr or D-Ser. In some embodiments, $X_{C'}$ is selected from: D-Asp or D-Glu. In some embodiments, $X_{C'}$ is selected from: D-Thr or D-Ser. In some embodiments, $X_{C'}$ is selected from: D-Glu or D-Thr. In some embodiments, $X_{C'}$ is D-Glu. In some embodiments, $X_{C'}$ is D-Thr. In some embodiments, $X_{C'}$ is D-Asp. In some embodiments, $X_{C'}$ is D-Arg. In some embodiments, $X_{C'}$ is D-His. In some embodiments, $X_{C'}$ is D-Lys. In some embodiments, $X_{C'}$ is D-Ser. In some embodiments, $X_{C'}$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $X_{A'}$—$X_{B'}$—$X_{C'}$ is EHT or THE, in which the amino acid residues are D-amino acid residues. In some instances, $X_{A'}$—$X_{B'}$—$X_{C'}$ is EHT, in which the amino acid residues are D-amino acid residues. In other instances, $X_{A'}$—$X_{B'}$—$X_{C'}$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 1-10 amino acids. In some embodiments, $L_1$ comprises 2 amino acids. In some embodiments, $L_1$ comprises 3 amino acids. In some embodiments, $L_1$ and $L_{1'}$ each independently comprises a series of D-10 Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_2$ comprises an L-amino acid. In some embodiments, $L_2$ comprises a D-amino acid. In some embodiments, $L_2$ comprises an amino acid selected from Lys or Cys. In some embodiments, $L_2$ is Lys. In some embodiments, $L_2$ is Cys. In some embodiments, $L_2$ is Glu. In some embodiments, $L_2$ is Asp. In some embodiments, $L_2$ comprises an amino acid selected from D-Lys or D-Cys. In some embodiments, $L_2$ is D-Lys. In some embodiments, $L_2$ is D-Cys. In some embodiments, $L_2$ is D-Glu. In some embodiments, $L_2$ is D-Asp.

In some embodiments, $L_1$ and $L_{1'}$ each independently comprises a series of 3 D-Ala residues and $L_2$ comprises an amino acid selected from Lys or Cys. In some embodiments, $L_1$ and $L_{1'}$ each independently comprises a series of 2 D-Ala residues and $L_2$ comprises an amino acid selected from Lys or Cys. In some embodiments, $L_1$ and $L_{1'}$ each independently comprises a series of 3 D-Ala residues and $L_2$ comprises an amino acid selected from D-Lys or D-Cys. In some embodiments, $L_1$ and $L_{1'}$ each independently comprises a series of 2 D-Ala residues and $L_2$ comprises an amino acid selected from D-Lys or D-Cys.

In some embodiments, n and n' each independently is 5. In some embodiments, n and n' each independently is 4. In some embodiments, n and n' each independently is 3. In some embodiments, n and n' each independently is 2. In some embodiments, n and n' each independently is 1.

In some embodiments, $L_1$ is bound to $X_A$. In some embodiments, $L_1$ is bound to $X_B$. In some embodiments, $L_1$ is bound to $X_C$.

In some embodiments, $L_{1'}$ is bound to $X_{A'}$. In some embodiments, $L_{1'}$ is bound to $X_{B'}$. In some embodiments, $L_{1'}$ is bound to $X_{C'}$.

In some embodiments, disclosed herein is a method of delivering a therapeutic cargo to a target neuron, nerve, or tissue or external structure associated therewith of interest, which comprises a nerve delivery molecule comprising a peptide sequence according to Formula (III):

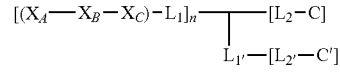

wherein $X_A$ is selected from: Asp, Arg, Glu, Thr, His, Lys, Phe, or Ser; $X_B$ is selected from: His, Lys, Thr, Glu, Ser, Asp, Phe, or Arg; $X_C$ is selected from: Asp, Arg, Glu, Thr, His, Lys, Phe, or Ser; $L_1$ and $L_{1'}$ are each independently absent or are each independently a linker comprising: (i) 1-10 Ala residues (SEQ ID NO: 1); (ii) 3-10 Gly residues (SEQ ID NO: 2); (iii) a polymer comprising 1-10 ethylene glycol units; or (iv) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently a therapeutic cargo; and n is an integer between 1 and 5; and wherein $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$.

In some embodiments, $X_A$ is selected from: Arg, His, or Lys. In some embodiments, $X_A$ is selected from: Asp, Glu, Thr or Ser. In some embodiments, $X_A$ is selected from: Asp or Glu. In some embodiments, $X_A$ is selected from: Thr or Ser. In some embodiments, $X_A$ is selected from: Glu or Thr. In some embodiments, $X_A$ is Glu. In some embodiments, $X_A$ is Thr. In some embodiments, $X_A$ is Asp. In some embodiments, $X_A$ is Arg. In some embodiments, $X_A$ is His. In some embodiments, $X_A$ is Lys. In some embodiments, $X_A$ is Ser. In some embodiments, $X_A$ is Phe.

In some embodiments, $X_B$ is selected from: His, Lys, Glu or Arg. In some embodiments, $X_B$ is selected from: Thr, Glu, Ser or Asp. In some embodiments, $X_B$ is selected from: His, Thr, Ser or Asp. In some embodiments, $X_B$ is His. In some embodiments, $X_B$ is Lys. In some embodiments, $X_B$ is Thr. In some embodiments, $X_B$ is Glu. In some embodiments, $X_B$ is Ser. In some embodiments, $X_B$ is Asp. In some embodiments, $X_B$ is Arg. In some embodiments, $X_B$ is Phe.

In some embodiments, $X_C$ is selected from: Arg, His or Lys. In some embodiments, $X_C$ is selected from: Asp, Glu, Thr or Ser. In some embodiments, $X_C$ is selected from: Asp or Glu. In some embodiments, $X_C$ is selected from: Thr or Ser. In some embodiments, $X_C$ is selected from: Glu or Thr. In some embodiments, $X_C$ is Glu. In some embodiments, $X_C$ is Thr. In some embodiments, $X_C$ is Asp. In some embodiments, $X_C$ is Arg. In some embodiments, $X_C$ is His. In some embodiments, $X_C$ is Lys. In some embodiments, $X_C$ is Ser. In some embodiments, $X_C$ is Phe.

In some embodiments, $X_A$—$X_B$—$X_C$ is EHT or THE. In some instances, $X_A$—$X_B$—$X_C$ is EHT. In other instances, $X_A$—$X_B$—$X_C$ is THE.

In some embodiments, the nerve delivery molecule of Formula (III) comprises a naturally occurring amino acid or a non-naturally occurring amino acid. In some embodiments, $X_A$, $X_B$ and $X_C$ each independently comprises a D-amino acid. In some embodiments, the amino acid residues of $X_A$, $X_B$ and $X_C$ are D-amino acids.

In some embodiments, $L_1$ and $L_{1'}$ are same. In some embodiments, $L_1$ and $L_{1'}$ are different. In some embodiments, $L_1$ and $L_{1'}$ each independently comprises an L-amino acid. In some embodiments, $L_1$ and $L_{1'}$ each independently comprises a D-amino acid. In some embodiments, $L_1$ and $L_{1'}$ each independently comprises 1-10 amino acids. In some embodiments, $L_1$ comprises 2 amino acids. In some embodiments, $L_1$ comprises 3 amino acids. In some embodiments, $L_1$ and $L_{1'}$ each independently comprises a series of 10 Ala residues (SEQ ID NO: 3). In some embodiments, $L_1$ and $L_{1'}$ each independently comprises a series of 9 Ala residues (SEQ ID NO: 4). In some embodiments, $L_1$ and $L_{1'}$ each independently comprises a series of 8 Ala residues (SEQ ID NO: 5). In some embodiments, $L_1$ and $L_{1'}$ each independently comprises a series of 7 Ala residues (SEQ ID NO: 6). In some embodiments, $L_1$ and $L_{1'}$ each independently comprises a series of 6 Ala residues (SEQ ID NO: 7). In some embodiments, $L_1$ and $L_{1'}$ each independently comprises a series of 5 Ala residues (SEQ ID NO: 8). In some embodiments, $L_1$ and $L_{1'}$ each independently comprises a series of 4 Ala residues (SEQ ID NO: 9). In some embodiments, $L_1$ and $L_{1'}$ each independently comprises a series of 3 Ala residues. In some embodiments, $L_1$ and $L_{1'}$ each independently comprises a series of 2 Ala residues. In some embodiments, $L_1$ and $L_{1'}$ each independently comprises a series of 1 Ala residue. In some embodiments, $L_1$ and $L_{1'}$ each independently comprises a series of 10 Gly residues (SEQ ID NO: 10). In some embodiments, $L_1$ and $L_{1'}$ each independently comprises a series of 9 Gly residues (SEQ ID NO: 21). In some embodiments, $L_1$ and $L_{1'}$ each independently comprises a series of 8 Gly residues (SEQ ID NO: 22). In some embodiments, $L_1$ and $L_{1'}$ each independently comprises a series of 7 Gly residues (SEQ ID NO: 23). In some embodiments, $L_1$ and $L_{1'}$ each independently comprises a series of 6 Gly residues (SEQ ID NO: 24). In some embodiments, $L_1$ and $L_{1'}$ each independently comprises a series of 5 Gly residues (SEQ ID NO: 11). In some embodiments, $L_1$ and $L_{1'}$ each independently comprises a series of 4 Gly residues (SEQ ID NO: 12). In some embodiments, $L_1$ and $L_{1'}$ each independently comprises a series of 3 Gly residues.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_1$ and $L_{1'}$ each independently comprises a series of 3 Ala residues and $L_2$ and $L_{2'}$ each independently comprises an amino acid selected from Lys or Cys. In some embodiments, $L_1$ and $L_{1'}$ each independently comprises a series of 2 Ala residues and $L_2$ and $L_{2'}$ each independently comprises an amino acid selected from Lys or Cys. In some embodiments, $L_1$ and $L_{1'}$ each independently comprises a series of 3 Gly residues and $L_2$ and $L_{2'}$ each independently comprises an amino acid selected from Lys or Cys. In some embodiments, $L_1$ and $L_{1'}$ each independently comprises a series of 3 Ala residues and $L_2$ and $L_{2'}$ each independently comprises an amino acid selected from D-Lys or D-Cys. In some embodiments, $L_1$ and $L_{1'}$ each independently comprises a series of 2 Ala residues and $L_2$ and $L_{2'}$ each independently comprises an amino acid selected from D-Lys or D-Cys. In some embodiments, $L_1$ and $L_{1'}$ each independently comprises a series of 3 Gly residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_{1'}$ is bound to $L_2$. In some embodiments, $L_{1'}$ is bound to $L_1$.

In some embodiments, the therapeutic cargo comprises a chemotherapeutic agent, a cytotoxin, a steroid, an immunotherapeutic agent, a targeted therapy agent, or an anti-inflammatory agent. In some embodiments, the therapeutic cargo comprises an antihistamine, a GABA receptor modulator, a neurotransmitter reuptake inhibitor, a local anesthetic, an anticholinergic, a sodium channel blocker, a calcium channel blocker, a thyrotropin-releasing hormone, a γ-secretase inhibitor, an AMPA receptor agonist or antagonist, an NMDA receptor agonist or antagonist, an mGlu receptor agonist or antagonist, a growth factor, an antiemetic agent, a corticosteroid, a cytotoxic agent, an antioxidant, an iron chelator, a mitochondrial modulator, a sirtuin modulator, a nitric oxide (NO) and/or nitric oxide synthase (NOS) modulator, a potassium channel agonist or antagonist, a purigenic receptor agonist or antagonist, or a combination thereof.

In some embodiments, the therapeutic cargo is a cargo that promotes regeneration of neuron or nerve tissue. In some embodiments, the therapeutic cargo is a growth factor.

In some embodiments, the therapeutic cargo is a drug that reduces pain (either the perception of pain or activity of a painful stimulant). In some embodiments, the therapeutic cargo is a local anesthetic.

In some embodiments, the therapeutic cargo is an anti-epileptic drug that targets ion channels.

In some embodiments, the therapeutic cargo is a sphingosine receptor modulator.

In some embodiments, the therapeutic cargo is conjugated to a nanoparticle. In some instances, the nanoparticle is an aptamer/hairpin DNA-gold nanoparticle which when illuminated with plasmon-resonant light (e.g., at 532 nm), the therapeutic cargo is released from the therapeutic cargo: nanoparticle conjugate. In some instances, the nanoparticle is a spherical fluorescent carbon-core nanoparticle (nanodot) that can be activated with ultraviolet radiation.

In some embodiments, the therapeutic cargo comprises a photosensitizer. In some instances, photosensitizers are generally inert in the absence of light treatment but irradiation by light of a specific wavelength activates the photosensitizer. In some cases, photosensitizers are photoexcited to a higher electronic state, and energy generated from this excited state lead to a production of reactive oxygen species.

In some embodiments, the therapeutic cargo comprises a radiosensitizer that enhances the cytotoxic effect of ionizing radiation on a cell.

In some embodiments, the therapeutic cargo comprises an alpha emitter, e.g., a radioactive isotope that emits alpha particles.

In some embodiments, disclosed herein is a method of delivering a therapeutic cargo to a target neuron, nerve, or tissue or external structure associated therewith of interest, which comprises a nerve delivery molecule comprising a peptide sequence according to Formula (IIIa):

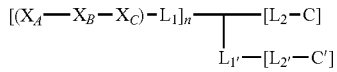

wherein $X_A$ is selected from: D-Asp, D-Arg, D-Glu, D-Thr, D-His, D-Lys, D-Phe, or D-Ser; $X_B$ is selected from: D-His, D-Lys, D-Thr, D-Glu, D-Ser, D-Asp, D-Phe, or D-Arg; $X_C$ is selected from: D-Asp, D-Arg, D-Glu, D-Thr, D-His, D-Lys, D-Phe, or D-Ser; $L_1$ and $L_{1'}$ are each independently absent or are each independently a linker comprising: (i) 1-10 D-Ala residues; (ii) a polymer comprising 1-10 ethylene glycol units; or (iii) an aliphatic chain comprising a chain length of 1-10 carbon atoms; $L_2$ and $L_{2'}$ are each independently a linker comprising: (i) an amino acid selected from: Lys, Glu, Cys, or Asp; (ii) a polymer comprising 1-10 ethylene glycol units; or (iii) an aliphatic chain comprising a chain length of 1-10 carbon atoms; C and C' are each independently a therapeutic cargo; and n is an integer between 1 and 5; and wherein $L_1$ is bound to at any position on $X_A$—$X_B$—$X_C$; $L_2$ is bound to $L_1$; C is bound to $L_2$; $L_{1'}$ is bound to $L_2$ or is bound to $L_1$; $L_{2'}$ is bound to $L_{1'}$; and C' is bound to $L_{2'}$.

In some embodiments, $X_A$ is selected from: D-Arg, D-His or D-Lys. In some embodiments, $X_A$ is selected from: D-Asp, D-Glu, D-Thr or D-Ser. In some embodiments, $X_A$ is selected from: D-Asp or D-Glu. In some embodiments, $X_A$ is selected from: D-Thr or D-Ser. In some embodiments, $X_A$ is selected from: D-Glu or D-Thr. In some embodiments, $X_A$ is D-Glu. In some embodiments, $X_A$ is D-Thr. In some embodiments, $X_A$ is D-Asp. In some embodiments, $X_A$ is D-Arg. In some embodiments, $X_A$ is D-His. In some embodiments, $X_A$ is D-Lys. In some embodiments, $X_A$ is D-Ser. In some embodiments, $X_A$ is D-Phe.

In some embodiments, $X_B$ is selected from: D-His, D-Lys, D-Glu or D-Arg. In some embodiments, $X_B$ is selected from: D-Thr, D-Glu, D-Ser or D-Asp. In some embodiments, $X_B$ is selected from: D-His, D-Thr, D-Ser or D-Asp. In some embodiments, $X_B$ is D-His. In some embodiments, $X_B$ is D-Lys. In some embodiments, $X_B$ is D-Thr. In some embodiments, $X_B$ is D-Glu. In some embodiments, $X_B$ is D-Ser. In some embodiments, $X_B$ is D-Asp. In some embodiments, $X_B$ is D-Arg. In some embodiments, $X_B$ is D-Phe.

In some embodiments, $X_C$ is selected from: D-Arg, D-His or D-Lys. In some embodiments, $X_C$ is selected from: D-Asp, D-Glu, D-Thr or D-Ser. In some embodiments, $X_C$ is selected from: D-Asp or D-Glu. In some embodiments, $X_C$ is selected from: D-Thr or D-Ser. In some embodiments, $X_C$ is selected from: D-Glu or D-Thr. In some embodiments, $X_C$ is D-Glu. In some embodiments, $X_C$ is D-Thr. In some embodiments, $X_C$ is D-Asp. In some embodiments, $X_C$ is D-Arg. In some embodiments, $X_C$ is D-His. In some embodiments, $X_C$ is D-Lys. In some embodiments, $X_C$ is D-Ser. In some embodiments, $X_C$ is D-Phe.

In some embodiments, $X_A$—$X_B$—$X_C$ is EHT or THE, in which the amino acid residues are D-amino acid residues. In some instances, $X_A$—$X_B$—$X_C$ is EHT, in which the amino acid residues are D-amino acid residues. In other instances, $X_A$—$X_B$—$X_C$ is THE, in which the amino acid residues are D-amino acid residues.

In some embodiments, $L_1$ and $L_{1'}$ are same. In some embodiments, $L_1$ and $L_{1'}$ are different. In some embodiments, $L_1$ and $L_{1'}$ each independently comprises 1-10 amino acids. In some embodiments, $L_1$ comprises 2 amino acids. In some embodiments, $L_1$ comprises 3 amino acids. In some embodiments, $L_1$ and $L_{1'}$ each independently comprises a series of 10 D-Ala residues. In some embodiments, $L_1$ and $L_{1'}$ each independently comprises a series of 9 D-Ala residues. In some embodiments, $L_1$ and $L_{1'}$ each independently comprises a series of 8 D-Ala residues. In some embodiments, $L_1$ and $L_{1'}$ each independently comprises a series of 7 D-Ala residues. In some embodiments, $L_1$ and $L_{1'}$ each independently comprises a series of 6 D-Ala residues. In some embodiments, $L_1$ and $L_{1'}$ each independently comprises a series of 5 D-Ala residues. In some embodiments, $L_1$ and $L_{1'}$ each independently comprises a series of 4 D-Ala residues. In some embodiments, $L_1$ and $L_{1'}$ each independently comprises a series of 3 D-Ala residues. In some embodiments, $L_1$ and $L_{1'}$ each independently comprises a series of 2 D-Ala residues. In some embodiments, $L_1$ and $L_{1'}$ each independently comprises a series of 1 D-Ala residue.

In some embodiments, $L_2$ and $L_{2'}$ are same. In some embodiments, $L_2$ and $L_{2'}$ are different. In some embodiments, $L_2$ and $L_{2'}$ each independently comprises an L-amino acid. In some embodiments, $L_2$ and $L_{2'}$ each independently comprises a D-amino acid. In some embodiments, $L_2$ and $L_{2'}$ each independently comprises an amino acid selected from Lys or Cys. In some embodiments, $L_2$ and $L_{2'}$ each independently is Lys. In some embodiments, $L_2$ and $L_{2'}$ each independently is Cys. In some embodiments, $L_2$ and $L_{2'}$ each independently is Glu. In some embodiments, $L_2$ and $L_{2'}$ each independently is Asp. In some embodiments, $L_2$ and $L_{2'}$ each independently comprises an amino acid selected from D-Lys or D-Cys. In some embodiments, $L_2$ and $L_{2'}$ each independently is D-Lys. In some embodiments, $L_2$ and $L_{2'}$ each independently is D-Cys. In some embodiments, $L_2$ and $L_{2'}$ each independently is D-Glu. In some embodiments, $L_2$ and $L_{2'}$ each independently is D-Asp.

In some embodiments, $L_1$ and $L_{1'}$ each independently comprises a series of 3 D-Ala residues and $L_2$ and $L_{2'}$ each independently comprises an amino acid selected from Lys or Cys. In some embodiments, $L_1$ and $L_{1'}$ each independently comprises a series of 2 D-Ala residues and $L_2$ and $L_{2'}$ each independently comprises an amino acid selected from Lys or Cys. In some embodiments, $L_1$ and $L_{1'}$ each independently comprises a series of 3 D-Ala residues and $L_2$ and $L_{2'}$ each independently comprises an amino acid selected from D-Lys or D-Cys. In some embodiments, $L_1$ and $L_{1'}$ each independently comprises a series of 2 D-Ala residues and $L_2$ and $L_{2'}$ each independently comprises an amino acid selected from D-Lys or D-Cys.

In some embodiments, n is 5. In some embodiments, n is 4. In some embodiments, n is 3. In some embodiments, n is 2. In some embodiments, n is 1.

In some embodiments, $L_1$ is bound to $X_A$. In some embodiments, $L_1$ is bound to $X_B$. In some embodiments, $L_1$ is bound to $X_C$. In some embodiments, $L_{1'}$ is bound to $L_2$. In some embodiments, $L_{1'}$ is bound to $L_1$.

Pharmaceutical Compositions

Disclosed herein, in certain embodiments, are pharmaceutical compositions comprising a nerve delivery molecule disclosed herein, and a pharmaceutically acceptable carrier or excipient. In some embodiments, a pharmaceutical composition described herein comprises a nerve delivery molecule comprising a peptide sequence according to Formula (I):

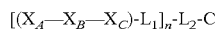

wherein, $X_A$ is selected from: Asp, Arg, Glu, Thr, His, Lys, Phe, or Ser;

$X_B$ is selected from: His, Lys, Thr, Glu, Ser, Asp, Phe, or Arg;

$X_C$ is selected from: Asp, Arg, Glu, Thr, His, Lys, Phe, or Ser;

$L_1$ is absent or is a linker comprising:
i) 1-10 Ala residues (SEQ ID NO: 1);
ii) 3-10 Gly residues (SEQ ID NO: 2);
iii) a polymer comprising 1-10 ethylene glycol units; or
iv) an aliphatic chain comprising a chain length of 1-10 carbon atoms;

$L_2$ is a linker comprising:
i) an amino acid selected from: Lys, Glu, Cys, or Asp;
ii) a polymer comprising 1-10 ethylene glycol units; or
iii) an aliphatic chain comprising a chain length of 1-10 carbon atoms;

C is a cargo; and n is an integer between 1 and 5; and wherein $L_1$ is bound to at any position on $X_A$—$X_B$—$X_C$, $L_2$ is bound to $L_1$, and C is bound to $L_2$, and a pharmaceutically acceptable carrier or excipient.

In some embodiments, a pharmaceutical composition described herein comprises a nerve delivery molecule comprising a peptide sequence according to Formula (Ia):

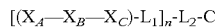

wherein, $X_A$ is selected from: D-Asp, D-Arg, D-Glu, D-Thr, D-His, D-Lys, D-Phe, or D-Ser;

$X_B$ is selected from: D-His, D-Lys, D-Thr, D-Glu, D-Ser, D-Asp, D-Phe, or D-Arg;

$X_C$ is selected from: D-Asp, D-Arg, D-Glu, D-Thr, D-His, D-Lys, D-Phe, or D-Ser;

$L_1$ is absent or is a linker comprising:
i) 1-10 D-Ala residues;
ii) a polymer comprising 1-10 ethylene glycol units; or
iii) an aliphatic chain comprising a chain length of 1-10 carbon atoms;

$L_2$ is a linker comprising:
i) an amino acid selected from: Lys, Glu, Cys, or Asp;
ii) a polymer comprising 1-10 ethylene glycol units; or
iii) an aliphatic chain comprising a chain length of 1-10 carbon atoms;

C is a cargo; and n is an integer between 1 and 5; and wherein $L_1$ is bound to at any position on $X_A$—$X_B$—$X_C$, $L_2$ is bound to $L_1$, and C is bound to $L_2$, and a pharmaceutically acceptable carrier or excipient.

In some embodiments, a pharmaceutical composition described herein comprises a nerve delivery molecule comprising a peptide sequence according to Formula (II):

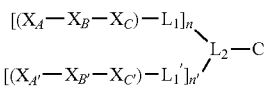

wherein, $X_A$ and $X_{A'}$ are each independently selected from: Asp, Arg, Glu, Thr, His, Lys, Phe, or Ser;

$X_B$ and $X_{B'}$ are each independently selected from: His, Lys, Thr, Glu, Ser, Asp, Phe, or Arg;

$X_C$ and $X_{C'}$ are each independently selected from: Asp, Arg, Glu, Thr, His, Lys, Phe, or Ser;

$L_1$ and $L_{1'}$ are each independently absent or are each independently a linker comprising:
i) 1-10 Ala residues (SEQ ID NO: 1);
ii) 3-10 Gly residues (SEQ ID NO: 2);
iii) a polymer comprising 1-10 ethylene glycol units; or
iv) an aliphatic chain comprising a chain length of 1-10 carbon atoms;

$L_2$ is a linker comprising:
i) an amino acid selected from: Lys, Glu, Cys, or Asp;
ii) a polymer comprising 1-10 ethylene glycol units; or
iii) an aliphatic chain comprising a chain length of 1-10 carbon atoms;

C is a cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$, and a pharmaceutically acceptable carrier or excipient.

In some embodiments, a pharmaceutical composition described herein comprises a nerve delivery molecule comprising a peptide sequence according to Formula (IIa):

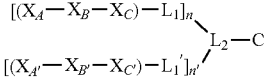

wherein, $X_A$ and $X_{A'}$ are each independently selected from: D-Asp, D-Arg, D-Glu, D-Thr, D-His, D-Lys, D-Phe, or D-Ser;

$X_B$ and $X_{B'}$ are each independently selected from: D-His, D-Lys, D-Thr, D-Glu, D-Ser, D-Asp, D-Phe, or D-Arg;

$X_C$ and $X_{C'}$ are each independently selected from: D-Asp, D-Arg, D-Glu, D-Thr, D-His, D-Lys, D-Phe, or D-Ser;

$L_1$ and $L_{1'}$ are each independently absent or are each independently a linker comprising:

i) 1-10 D-Ala residues;

ii) a polymer comprising 1-10 ethylene glycol units; or iii) an aliphatic chain comprising a chain length of 1-10 carbon atoms;

$L_2$ is a linker comprising:

i) an amino acid selected from: Lys, Glu, Cys, or Asp;

ii) a polymer comprising 1-10 ethylene glycol units; or iii) an aliphatic chain comprising a chain length of 1-10 carbon atoms;

C is a cargo; and n and n' are each independently an integer between 1 and 5; and wherein $L_1$ is bound to at any position on $X_A$—$X_B$—$X_C$, $L_{1'}$ is bound to at any position on $X_{A'}$—$X_{B'}$—$X_{C'}$, $L_2$ is bound to $L_1$ and $L_{1'}$, and C is bound to $L_2$, and a pharmaceutically acceptable carrier or excipient.

In some embodiments, a pharmaceutical composition described herein comprises a nerve delivery molecule comprising a peptide sequence according to Formula (III):

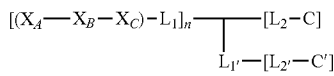

$$[(X_A—X_B—X_C)—L_1]_n—[L_2—C]$$
$$L_{1'}—[L_{2'}—C']$$

wherein, $X_A$ is selected from: Asp, Arg, Glu, Thr, His, Lys, Phe, or Ser;

$X_B$ is selected from: His, Lys, Thr, Glu, Ser, Asp, Phe, or Arg;
$X_C$ is selected from: Asp, Arg, Glu, Thr, His, Lys, Phe, or Ser;

$L_1$ and $L_1$ are each independently absent or are each independently a linker comprising:

i) 1-10 Ala residues (SEQ ID NO: 1);

ii) 3-10 Gly residues (SEQ ID NO: 2);

iii) a polymer comprising 1-10 ethylene glycol units; or iv) an aliphatic chain comprising a chain length of 1-10 carbon atoms;

$L_2$ and $L_{2'}$ are each independently a linker comprising:

i) an amino acid selected from: Lys, Glu, Cys, or Asp;

ii) a polymer comprising 1-10 ethylene glycol units; or iii) an aliphatic chain comprising a chain length of 1-10 carbon atoms;

C and C' are each independently a cargo; and n is an integer between 1 and 5; and wherein, $L_1$ is bound to at any position on $X_A$—$X_B$—$X_C$;

$L_2$ is bound to $L_1$;
C is bound to $L_2$;
$L_{1'}$ is bound to $L_2$ or is bound to $L_1$;
$L_{2'}$ is bound to $L_{1'}$; and

C' is bound to $L_{2'}$, and a pharmaceutically acceptable carrier or excipient.

In some embodiments, a pharmaceutical composition described herein comprises a nerve delivery molecule comprising a peptide sequence according to Formula (IIIa):

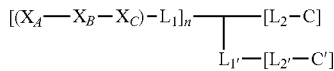

$$[(X_A—X_B—X_C)—L_1]_n—[L_2—C]$$
$$L_{1'}—[L_{2'}—C']$$

wherein, $X_A$ is selected from: D-Asp, D-Arg, D-Glu, D-Thr, D-His, D-Lys, D-Phe, or D-Ser;

$X_B$ is selected from: D-His, D-Lys, D-Thr, D-Glu, D-Ser, D-Asp, D-Phe, or D-Arg;
$X_C$ is selected from: D-Asp, D-Arg, D-Glu, D-Thr, D-His, D-Lys, D-Phe, or D-Ser;
$L_1$ and $L_{1'}$ are each independently absent or are each independently a linker comprising:

i) 1-10 D-Ala residues;

ii) a polymer comprising 1-10 ethylene glycol units; or iii) an aliphatic chain comprising a chain length of 1-10 carbon atoms;

$L_2$ and $L_{2'}$ are each independently a linker comprising:

i) an amino acid selected from: Lys, Glu, Cys, or Asp;

ii) a polymer comprising 1-10 ethylene glycol units; or iii) an aliphatic chain comprising a chain length of 1-10 carbon atoms;

C and C' are each independently a cargo; and n is an integer between 1 and 5; and wherein, $L_1$ is bound to at any position on $X_A$—$X_B$—$X_C$;

$L_2$ is bound to $L_1$;
C is bound to $L_2$;
$L_{1'}$ is bound to $L_2$ or is bound to $L_1$;
$L_{2'}$ is bound to $L_{1'}$; and

C' is bound to $L_{2'}$, and a pharmaceutically acceptable carrier or excipient.

Disclosed herein, in certain embodiments, is a pharmaceutical composition comprising a nerve delivery molecule according to NDM-36 and a pharmaceutically acceptable carrier or excipient.

Disclosed herein, in certain embodiments, is a pharmaceutical composition comprising a nerve delivery molecule according to NDM-37 and a pharmaceutically acceptable carrier or excipient.

Disclosed herein, in certain embodiments, is a pharmaceutical composition comprising a nerve delivery molecule according to NDM-38 and a pharmaceutically acceptable carrier or excipient.

Disclosed herein, in certain embodiments, is a pharmaceutical composition comprising a nerve delivery molecule according to NDM-39 and a pharmaceutically acceptable carrier or excipient.

Disclosed herein, in certain embodiments, is a pharmaceutical composition comprising a nerve delivery molecule according to NDM-40 and a pharmaceutically acceptable carrier or excipient.

Disclosed herein, in certain embodiments, is a pharmaceutical composition comprising a nerve delivery molecule according to NDM-41 and a pharmaceutically acceptable carrier or excipient.

Disclosed herein, in certain embodiments, is a pharmaceutical composition comprising a nerve delivery molecule according to NDM-42 and a pharmaceutically acceptable carrier or excipient.

Disclosed herein, in certain embodiments, is a pharmaceutical composition comprising a nerve delivery molecule according to NDM-43 and a pharmaceutically acceptable carrier or excipient.

Disclosed herein, in certain embodiments, is a pharmaceutical composition comprising a nerve delivery molecule according to NDM-44 and a pharmaceutically acceptable carrier or excipient.

Disclosed herein, in certain embodiments, is a pharmaceutical composition comprising a nerve delivery molecule according to NDM-45 and a pharmaceutically acceptable carrier or excipient.

Disclosed herein, in certain embodiments, is a pharmaceutical composition comprising a nerve delivery molecule according to NDM-46 and a pharmaceutically acceptable carrier or excipient.

Disclosed herein, in certain embodiments, is a pharmaceutical composition comprising a nerve delivery molecule according to NDM-47 and a pharmaceutically acceptable carrier or excipient.

Disclosed herein, in certain embodiments, is a pharmaceutical composition comprising a nerve delivery molecule according to NDM-48 and a pharmaceutically acceptable carrier or excipient.

Disclosed herein, in certain embodiments, is a pharmaceutical composition comprising a nerve delivery molecule according to NDM-49 and a pharmaceutically acceptable carrier or excipient.

Disclosed herein, in certain embodiments, is a pharmaceutical composition comprising a nerve delivery molecule according to NDM-50 and a pharmaceutically acceptable carrier or excipient.

Disclosed herein, in certain embodiments, is a pharmaceutical composition comprising a nerve delivery molecule according to NDM-51 and a pharmaceutically acceptable carrier or excipient.

Disclosed herein, in certain embodiments, is a pharmaceutical composition comprising a nerve delivery molecule according to NDM-52 and a pharmaceutically acceptable carrier or excipient.

Disclosed herein, in certain embodiments, is a pharmaceutical composition comprising a nerve delivery molecule according to NDM-53 and a pharmaceutically acceptable carrier or excipient.

Disclosed herein, in certain embodiments, is a pharmaceutical composition comprising a nerve delivery molecule according to NDM-54 and a pharmaceutically acceptable carrier or excipient.

Disclosed herein, in certain embodiments, is a pharmaceutical composition comprising a nerve delivery molecule according to NDM-55 and a pharmaceutically acceptable carrier or excipient.

Disclosed herein, in certain embodiments, is a pharmaceutical composition comprising a nerve delivery molecule according to NDM-56 and a pharmaceutically acceptable carrier or excipient.

Disclosed herein, in certain embodiments, is a pharmaceutical composition comprising a nerve delivery molecule according to NDM-57 and a pharmaceutically acceptable carrier or excipient.

Disclosed herein, in certain embodiments, is a pharmaceutical composition comprising a nerve delivery molecule according to NDM-58 and a pharmaceutically acceptable carrier or excipient.

Disclosed herein, in certain embodiments, is a pharmaceutical composition comprising a nerve delivery molecule according to NDM-59 and a pharmaceutically acceptable carrier or excipient.

Disclosed herein, in certain embodiments, is a pharmaceutical composition comprising a nerve delivery molecule according to NDM-60 and a pharmaceutically acceptable carrier or excipient.

Disclosed herein, in certain embodiments, is a pharmaceutical composition comprising a nerve delivery molecule according to NDM-61 and a pharmaceutically acceptable carrier or excipient.

Disclosed herein, in certain embodiments, is a pharmaceutical composition comprising a nerve delivery molecule according to NDM-62 and a pharmaceutically acceptable carrier or excipient.

Disclosed herein, in certain embodiments, is a pharmaceutical composition comprising a nerve delivery molecule according to NDM-63 and a pharmaceutically acceptable carrier or excipient.

Disclosed herein, in certain embodiments, is a pharmaceutical composition comprising a nerve delivery molecule according to NDM-64 and a pharmaceutically acceptable carrier or excipient.

Disclosed herein, in certain embodiments, is a pharmaceutical composition comprising a nerve delivery molecule according to NDM-65 and a pharmaceutically acceptable carrier or excipient.

Disclosed herein, in certain embodiments, is a pharmaceutical composition comprising a nerve delivery molecule according to NDM-66 and a pharmaceutically acceptable carrier or excipient.

Disclosed herein, in certain embodiments, is a pharmaceutical composition comprising a nerve delivery molecule according to NDM-67 and a pharmaceutically acceptable carrier or excipient.

Disclosed herein, in certain embodiments, is a pharmaceutical composition comprising a nerve delivery molecule according to NDM-68 and a pharmaceutically acceptable carrier or excipient.

Disclosed herein, in certain embodiments, is a pharmaceutical composition comprising a nerve delivery molecule according to NDM-69 and a pharmaceutically acceptable carrier or excipient.

Disclosed herein, in certain embodiments, is a pharmaceutical composition comprising a nerve delivery molecule according to NDM-70 and a pharmaceutically acceptable carrier or excipient.

Disclosed herein, in certain embodiments, is a pharmaceutical composition comprising a nerve delivery molecule according to NDM-71 and a pharmaceutically acceptable carrier or excipient.

Disclosed herein, in certain embodiments, is a pharmaceutical composition comprising a nerve delivery molecule according to NDM-72 and a pharmaceutically acceptable carrier or excipient.

Disclosed herein, in certain embodiments, is a pharmaceutical composition comprising a nerve delivery molecule according to NDM-73 and a pharmaceutically acceptable carrier or excipient.

Disclosed herein, in certain embodiments, is a pharmaceutical composition comprising a nerve delivery molecule according to NDM-74 and a pharmaceutically acceptable carrier or excipient.

Disclosed herein, in certain embodiments, is a pharmaceutical composition comprising a nerve delivery molecule according to NDM-75 and a pharmaceutically acceptable carrier or excipient.

Disclosed herein, in certain embodiments, is a pharmaceutical composition comprising a nerve delivery molecule according to NDM-76 and a pharmaceutically acceptable carrier or excipient.

Disclosed herein, in certain embodiments, is a pharmaceutical composition comprising a nerve delivery molecule according to NDM-77 and a pharmaceutically acceptable carrier or excipient.

Disclosed herein, in certain embodiments, is a pharmaceutical composition comprising a nerve delivery molecule according to NDM-78 and a pharmaceutically acceptable carrier or excipient.

Disclosed herein, in certain embodiments, is a pharmaceutical composition comprising a nerve delivery molecule according to NDM-79 and a pharmaceutically acceptable carrier or excipient.

Disclosed herein, in certain embodiments, is a pharmaceutical composition comprising a nerve delivery molecule according to NDM-80 and a pharmaceutically acceptable carrier or excipient.

Disclosed herein, in certain embodiments, is a pharmaceutical composition comprising a nerve delivery molecule according to NDM-81 and a pharmaceutically acceptable carrier or excipient.

Disclosed herein, in certain embodiments, is a pharmaceutical composition comprising a nerve delivery molecule according to NDM-82 and a pharmaceutically acceptable carrier or excipient.

Disclosed herein, in certain embodiments, is a pharmaceutical composition comprising a nerve delivery molecule according to NDM-83 and a pharmaceutically acceptable carrier or excipient.

Disclosed herein, in certain embodiments, is a pharmaceutical composition comprising a nerve delivery molecule according to NDM-84 and a pharmaceutically acceptable carrier or excipient.

Disclosed herein, in certain embodiments, is a pharmaceutical composition comprising a nerve delivery molecule according to NDM-85 and a pharmaceutically acceptable carrier or excipient.

Disclosed herein, in certain embodiments, is a pharmaceutical composition comprising a nerve delivery molecule according to NDM-86 and a pharmaceutically acceptable carrier or excipient.

Disclosed herein, in certain embodiments, is a pharmaceutical composition comprising a nerve delivery molecule according to NDM-87 and a pharmaceutically acceptable carrier or excipient.

Disclosed herein, in certain embodiments, is a pharmaceutical composition comprising a nerve delivery molecule according to NDM-88 and a pharmaceutically acceptable carrier or excipient.

Disclosed herein, in certain embodiments, is a pharmaceutical composition comprising a nerve delivery molecule according to NDM-89 and a pharmaceutically acceptable carrier or excipient.

Disclosed herein, in certain embodiments, is a pharmaceutical composition comprising a nerve delivery molecule according to NDM-90 and a pharmaceutically acceptable carrier or excipient.

Disclosed herein, in certain embodiments, is a pharmaceutical composition comprising a nerve delivery molecule according to NDM-91 and a pharmaceutically acceptable carrier or excipient.

Disclosed herein, in certain embodiments, is a pharmaceutical composition comprising a nerve delivery molecule according to NDM-92 and a pharmaceutically acceptable carrier or excipient.

Disclosed herein, in certain embodiments, is a pharmaceutical composition comprising a nerve delivery molecule according to NDM-93 and a pharmaceutically acceptable carrier or excipient.

Disclosed herein, in certain embodiments, is a pharmaceutical composition comprising a nerve delivery molecule according to NDM-94 and a pharmaceutically acceptable carrier or excipient.

Disclosed herein, in certain embodiments, is a pharmaceutical composition comprising a nerve delivery molecule according to NDM-95 and a pharmaceutically acceptable carrier or excipient.

Disclosed herein, in certain embodiments, is a pharmaceutical composition comprising a nerve delivery molecule according to NDM-96 and a pharmaceutically acceptable carrier or excipient.

Disclosed herein, in certain embodiments, is a pharmaceutical composition comprising a nerve delivery molecule according to NDM-97 and a pharmaceutically acceptable carrier or excipient.

Disclosed herein, in certain embodiments, is a pharmaceutical composition comprising a nerve delivery molecule according to NDM-98 and a pharmaceutically acceptable carrier or excipient.

Disclosed herein, in certain embodiments, is a pharmaceutical composition comprising a nerve delivery molecule according to NDM-99 and a pharmaceutically acceptable carrier or excipient.

In some embodiments, a pharmaceutical composition described herein comprises a T-NDM illustrated in Table 1 and a pharmaceutically acceptable carrier or excipient.

In some embodiments, a pharmaceutical composition described herein comprises T-NDM-1 and a pharmaceutically acceptable carrier or excipient.

In some embodiments, a pharmaceutical composition described herein comprises T-NDM-2 and a pharmaceutically acceptable carrier or excipient.

In some embodiments, a pharmaceutical composition described herein comprises T-NDM-3 and a pharmaceutically acceptable carrier or excipient.

In some embodiments, a pharmaceutical composition described herein comprises T-NDM-4 and a pharmaceutically acceptable carrier or excipient.

In some embodiments, a pharmaceutical composition described herein comprises T-NDM-5 and a pharmaceutically acceptable carrier or excipient.

In some embodiments, a pharmaceutical composition described herein comprises T-NDM-6 and a pharmaceutically acceptable carrier or excipient.

In some embodiments, a pharmaceutical composition described herein comprises T-NDM-7 and a pharmaceutically acceptable carrier or excipient.

In some embodiments, a pharmaceutical composition described herein comprises T-NDM-8 and a pharmaceutically acceptable carrier or excipient.

In some embodiments, a pharmaceutical composition described herein comprises T-NDM-9 and a pharmaceutically acceptable carrier or excipient.

In some embodiments, a pharmaceutical composition described herein comprises T-NDM-10 and a pharmaceutically acceptable carrier or excipient.

In some embodiments, a pharmaceutical composition described herein comprises T-NDM-11 and a pharmaceutically acceptable carrier or excipient.

In some embodiments, a pharmaceutical composition described herein comprises T-NDM-12 and a pharmaceutically acceptable carrier or excipient.

In some embodiments, a pharmaceutical composition described herein comprises T-NDM-13 and a pharmaceutically acceptable carrier or excipient.

In some embodiments, a pharmaceutical composition described herein comprises T-NDM-14 and a pharmaceutically acceptable carrier or excipient.

In some embodiments, a pharmaceutical composition described herein comprises T-NDM-15 and a pharmaceutically acceptable carrier or excipient.

In some embodiments, a pharmaceutical composition described herein comprises T-NDM-16 and a pharmaceutically acceptable carrier or excipient.

In some embodiments, a pharmaceutical composition described herein comprises T-NDM-17 and a pharmaceutically acceptable carrier or excipient.

In some embodiments, a pharmaceutical composition described herein comprises T-NDM-18 and a pharmaceutically acceptable carrier or excipient.

In some embodiments, a pharmaceutical composition described herein comprises T-NDM-19 and a pharmaceutically acceptable carrier or excipient.

In some embodiments, a pharmaceutical composition described herein comprises T-NDM-20 and a pharmaceutically acceptable carrier or excipient.

In some embodiments, a pharmaceutical composition described herein comprises T-NDM-21 and a pharmaceutically acceptable carrier or excipient.

In some embodiments, a pharmaceutical composition described herein comprises T-NDM-22 and a pharmaceutically acceptable carrier or excipient.

In some embodiments, a pharmaceutical composition described herein comprises T-NDM-23 and a pharmaceutically acceptable carrier or excipient.

In some embodiments, a pharmaceutical composition described herein comprises T-NDM-24 and a pharmaceutically acceptable carrier or excipient.

In some embodiments, a pharmaceutical composition described herein comprises T-NDM-25 and a pharmaceutically acceptable carrier or excipient.

In some embodiments, a pharmaceutical composition described herein comprises T-NDM-26 and a pharmaceutically acceptable carrier or excipient.

In some embodiments, a pharmaceutical composition described herein comprises T-NDM-27 and a pharmaceutically acceptable carrier or excipient.

In some embodiments, a pharmaceutical composition described herein comprises T-NDM-28 and a pharmaceutically acceptable carrier or excipient.

In some embodiments, a pharmaceutical composition described herein comprises T-NDM-29 and a pharmaceutically acceptable carrier or excipient.

In some embodiments, a pharmaceutical composition described herein comprises T-NDM-30 and a pharmaceutically acceptable carrier or excipient.

In some embodiments, a pharmaceutical composition described herein comprises T-NDM-31 and a pharmaceutically acceptable carrier or excipient.

In some embodiments, a pharmaceutical composition described herein comprises T-NDM-32 and a pharmaceutically acceptable carrier or excipient.

In some embodiments, a pharmaceutical composition described herein comprises T-NDM-33 and a pharmaceutically acceptable carrier or excipient.

In some embodiments, a pharmaceutical composition described herein comprises T-NDM-34 and a pharmaceutically acceptable carrier or excipient.

In some embodiments, a pharmaceutical composition described herein comprises T-NDM-35 and a pharmaceutically acceptable carrier or excipient.

In some embodiments, a pharmaceutical composition described herein comprises T-NDM-36 and a pharmaceutically acceptable carrier or excipient.

In some embodiments, a pharmaceutical composition described herein comprises T-NDM-37 and a pharmaceutically acceptable carrier or excipient.

In some embodiments, a pharmaceutical composition described herein comprises T-NDM-38 and a pharmaceutically acceptable carrier or excipient.

In some embodiments, a pharmaceutical composition described herein comprises T-NDM-39 and a pharmaceutically acceptable carrier or excipient.

In some embodiments, a pharmaceutical composition described herein comprises T-NDM-40 and a pharmaceutically acceptable carrier or excipient.

In some embodiments, a pharmaceutical composition described herein comprises T-NDM-41 and a pharmaceutically acceptable carrier or excipient.

In some embodiments, a pharmaceutical composition described herein comprises T-NDM-42 and a pharmaceutically acceptable carrier or excipient.

In some embodiments, a pharmaceutical composition described herein comprises T-NDM-43 and a pharmaceutically acceptable carrier or excipient.

In some embodiments, a pharmaceutical composition described herein comprises T-NDM-44 and a pharmaceutically acceptable carrier or excipient.

In some embodiments, a pharmaceutical composition described herein comprises T-NDM-45 and a pharmaceutically acceptable carrier or excipient.

In some embodiments, a pharmaceutical composition described herein comprises T-NDM-46 and a pharmaceutically acceptable carrier or excipient.

In some embodiments, a pharmaceutical composition described herein comprises T-NDM-47 and a pharmaceutically acceptable carrier or excipient.

In some embodiments, a pharmaceutical composition described herein comprises T-NDM-48 and a pharmaceutically acceptable carrier or excipient.

In some embodiments, a pharmaceutical composition described herein comprises T-NDM-49 and a pharmaceutically acceptable carrier or excipient.

In some embodiments, a pharmaceutical composition described herein comprises T-NDM-50 and a pharmaceutically acceptable carrier or excipient.

In some embodiments, a pharmaceutical composition described herein comprises T-NDM-51 and a pharmaceutically acceptable carrier or excipient.

In some embodiments, a pharmaceutical composition described herein comprises T-NDM-52 and a pharmaceutically acceptable carrier or excipient.

In some embodiments, a pharmaceutical composition described herein comprises T-NDM-53 and a pharmaceutically acceptable carrier or excipient.

In some embodiments, a pharmaceutical composition described herein comprises T-NDM-54 and a pharmaceutically acceptable carrier or excipient.

The term "pharmaceutical compositions" encompasses both compositions for therapeutic use and compositions for non-therapeutic use (e.g., for diagnostic uses). Pharmaceutical compositions herein are formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

In certain embodiments, a pharmaceutical composition disclosed herein further comprises a pharmaceutically acceptable diluent(s), excipient(s), or carrier(s). In some embodiments, the pharmaceutical compositions includes other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

In certain embodiments, a pharmaceutical composition disclosed herein is administered to a subject by any suitable administration route, including but not limited to, parenteral (intravenous, subcutaneous, intraperitoneal, intramuscular, intravascular, intrathecal, intravitreal, infusion, intracerebral, intracerebroventricular or intracranial) administration. In some instances, the administration is systemic administration. In other instances, the administration is local administration. In some cases, a NDM described herein is formulated for injection. In other cases, a NDM described herein is formulated for infusion.

Formulations suitable for parenteral (e.g., intravenous, subcutaneous, intraperitoneal, intramuscular, intravascular, intrathecal, intravitreal, infusion, intracerebral, intracerebroventricular or intracranial) injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent is optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. In some embodiments, the pharmaceutical composition described herein are in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

In some embodiments, the pharmaceutical composition described herein is in unit dosage forms suitable for single administration of precise dosages. In unit dosage form, the formulation is divided into unit doses containing appropriate quantities of an active agent disclosed herein. In some embodiments, the unit dosage is in the form of a package containing discrete quantities of the formulation. Non-limiting examples are packaged tablets or capsules, and powders in vials or ampoules. In some embodiments, aqueous suspension compositions are packaged in single-dose non-reclosable containers. Alternatively, multiple-dose reclosable containers are used, in which case it is typical to include a preservative in the composition. By way of example only, formulations for parenteral injection are presented in unit dosage form, which include, but are not limited to ampoules, or in multi dose containers, with an added preservative.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

For example, the container(s) include one or more NDMs described herein, and optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

HPLC-grade acetonitrile was purchased from Fisher Scientific (Phillipsburg, Pa.). Purified water was collected through Milli-Q water purification system (Millipore, Bedford, Mass.). Trifluoroacetic acid (TFA), dimethylformamide (DMF) and N-methylmorpholine (NMM) were supplied by Sigma-Aldrich (Milwaukee, Wis.). Lyophilized peptides, unless noted, were supplied by Bachem, Torrance, Calif., CPC Scientific Inc. (Sunnyvale, Calif.), or WuXi AppeTec (Tianjin, China).

LC-MS analysis was carried out on a Waters 2695 separation module equipped with a Waters 2487 dual λ absorbance detector in combination with a Finnigan LCQ Deca XP mass spectrometer. The equipment is associated with Xcalibur analytical software and a Peeke Scientific column (Titan 200 5 μm, C18-MC, 50×2.1 mm) or a Phenomenex column (Kinetex 5 μm, EVO C18 100 Å, 50×4.6 mm). HPLC analysis was carried out on a Phenomenex column (Gemini, 5μ, C18-100 Å, 50×2.00 mm ID) with an Agilent 1100 system equipped with a diode array detector and a fluorescence detector. The mobile phase consisted of a water (0.05% TFA)(mobile phase A)/acetonitrile (0.05% TFA) (mobile phase B) gradient.

Preparative HPLC were carried out on a Waters PrepLC System equipped with a Waters 2487 dual λ absorbance detector, Fraction Collector III, Masslynx software and a Phenomenex column (luna, C18(2), 5μ, 100A AX 150×30 mm). The mobile phase consisted of a water (0.05% TFA) (mobile phase A)/acetonitrile (0.05% TFA)(mobile phase B) gradient.

Centrifugation was carried out at 4° C. on an Eppendorf centrifuge 5417R. Lyophilization was carried out on a Labconco FreeZone 4.5.

Example 1—Synthesis Method 1

General procedure for preparation of Cy5 or 6-FAM labeled peptides through sulfyhydryl maleimide chemistry. The mixture of Cy5 mono maleimide (or 6-FAM maleimide) and the peptide with a free cysteine residue (1.2 equivalents) in DMF and NMM was stirred at room temperature in the dark for 30 min. The reaction mixture was purified to afford the product by HPLC.

Example 2—Synthesis Method 2

General procedure for preparation of Cy5 or 6-FAM labeled peptides through standard Fmoc solid-phase synthesis. Fmoc protected amino acids containing dyes conjugated via lysine side chain modification were directly used in the solid-phase synthesis of some peptide dye containing molecules.

Example 3—Mass Spectra of Fluorescently Labeled Peptides Generated Using Methods 1 and 2

NDM-36
Ac-[D-Cys(Cy5)]-(D-Ala)-(D-Ala)-(D-Ala)-(D-Thr)-(D-His)-(D-Glu)-NH$_2$
Calculated: [M+H]$^+$ (C$_{68}$H$_{93}$N$_{14}$O$_{20}$S$_3$) m/z=1522; Found ESI: [M+H]$^+$ (C$_{68}$H$_{93}$N$_{14}$O$_{20}$S$_3$) m/z=1522.

NDM-37
Ac-Glu-His-Thr-Ala-Ala-Ala-Cys(Cy5)-NH$_2$ (SEQ ID NO: 13)
Calculated: [M+H]$^+$ (C$_{68}$H$_{93}$N$_{14}$O$_{20}$S$_3$) m/z=1522; Found ESI: [M+H]$^+$ (C$_{68}$H$_{93}$N$_{14}$O$_{20}$S$_3$) m/z=1522.

NDM-38
Ac-[D-Lys(6-FAM)]-(D-Ala)-(D-Ala)-(D-Ala)-(D-Thr)-(D-His)-(D-Glu)-NH$_2$
Calculated: [M+H]$^+$ (C$_{53}$H$_{64}$N$_{11}$O$_{17}$) m/z=1126; Found ESI: [M+H]$^+$ (C$_{53}$H$_{64}$N$_{11}$O$_{17}$) m/z=1126.

NDM-39
Ac-Glu-His-Thr-Ala-Ala-Ala-Lys(6-FAM)-NH$_2$ (SEQ ID NO: 14)
Calculated: [M+H]$^+$ (C$_{53}$H$_{64}$N$_{11}$O$_{17}$) m/z=1126; Found ESI: [M+H]$^+$ (C$_{53}$H$_{64}$N$_{11}$O$_{17}$) m/z=1126.

NDM-40
Ac-[D-Cys(6-FAM)]-(D-Ala)-(D-Ala)-(D-Ala)-(D-Thr)-(D-His)-(D-Glu)-NH$_2$
Calculated: [M+H]$^+$ (C$_{56}$H$_{65}$N$_{12}$O$_{19}$S) m/z=1241; Found ESI: [M+H]$^+$ (C$_{56}$H$_{65}$N$_{12}$O$_{19}$S) m/z=1241.

NDM-41
Ac-Glu-His-Thr-Ala-Ala-Ala-Cys(6-FAM)-NH$_2$ (SEQ ID NO: 15)
Calculated: [M+H]$^+$ (C$_{56}$H$_{65}$N$_{12}$O$_{19}$S) m/z=1241; Found ESI: [M+H]$^+$ (C$_{56}$H$_{65}$N$_{12}$O$_{19}$S) m/z=1241.

NDM-42
Ac-Glu-His-Thr-Cys(Cy5)-NH$_2$ (SEQ ID NO: 16)
Calculated: [M+H]$^+$ (C$_{59}$H$_{78}$N$_{11}$O$_{17}$S$_3$) m/z=1308; Found ESI: [M+H]$^+$ (C$_{59}$H$_{78}$N$_{11}$O$_{17}$S$_3$) m/z=1308.

NDM-43
Ac-Glu-His-Thr-o-Cys(Cy5)-NH$_2$
Calculated: [M+H]$^+$ (C$_{63}$H$_{85}$N$_{12}$O$_{19}$S$_3$) m/z=1409; Found ESI: [M+H]$^+$ (C$_{63}$H$_{85}$N$_{12}$O$_{19}$S$_3$) m/z=1409.

NDM-44
Ac-[D-Lys(6FAM)]-Gly-Gly-Gly-(D-Thr)-(D-His)-(D-Glu)-NH$_2$
Calculated: [M+H]$^+$ (C$_{50}$H$_{58}$N$_{11}$O$_{17}$) m/z=1085; Found ESI: (C$_{50}$H$_{58}$N$_{11}$O$_{17}$) m/z=1085.

NDM-50
Ac-(D-Thr)-(D-His)-(D-Glu)-(D-Ala)-(D-la)-(D-Ala)-[D-Lys(6FAM)]-(D-Ala)-(D-Ala)-(D-Ala)-(D-Thr)-(D-His)-(D-Glu)-NH$_2$
Calculated: [M+2H]$^{2+}$ (C$_{77}$H$_{101}$N$_{19}$O$_{26}$) m/z=854; Found ESI: (C$_{77}$H$_{101}$N$_{19}$O$_{26}$) m/z=854.

NDM-52
Ac-(D-Thr)-(D-His)-(D-Glu)-(D-Ala)-(D-Ala)-(D-Ala)-[D-Cys(Cy5)]-(D-Ala)-(D-Ala)-(D-Ala)-(D-Thr)-(D-His)-(D-Glu)-NH$_2$
Calculated: [M+2H]$^{2+}$ (C$_{91}$H$_{128}$N$_{22}$O$_{29}$S$_3$) m/z=1045; Found ESI: (C$_{91}$H$_{128}$N$_{22}$O$_{29}$S$_3$) m/z=1045.

NDM-69
Ac-[D-Lys(6FAM)]-(D-Ala)-(D-Ala)-(D-Ala)-(D-Thr)-(D-His)-(D-Arg)-NH$_2$
Calculated: [M+H]$^+$ (C$_{54}$H$_{69}$N$_{14}$O$_{15}$) m/z=1153; Found ESI: (C$_{54}$H$_{69}$N$_{14}$O$_{15}$) m/z=1153.

NDM-70
Ac-[D-Cys(Cy5)]-(D-Ala)-(D-Ala)-(D-Ala)-[D-Lys(6FAM)]-(D-Ala)-(D-Ala)-(D-Ala)-(D-Thr)-(D-His)-(D-Glu)-NH$_2$
Calculated: [M+2H]$^{2+}$ (C$_{104}$H$_{130}$N$_{18}$O$_{31}$S$_3$) m/z=1111; Found ESI: (C$_{104}$H$_{130}$N$_{18}$O$_{31}$S$_3$) m/z=1111

NDM-71
Ac-[D-Lys(6FAM)]-(D-Ala)-(D-Ala)-(D-Ala)-(D-Thr)-(D-Lys)-(D-Glu)-NH$_2$
Calculated: [M+H]$^+$ (C$_{53}$H$_{69}$N$_{10}$O$_{17}$) m/z=1117; Found ESI: (C$_{53}$H$_{69}$N$_{10}$O$_{17}$) m/z=1117.

NDM-81
Ac-[D-Lys(6FAM)]-PEG2-(D-Thr)-(D-His)-(D-Glu)-NH$_2$
Calculated: [M+H]$^+$ (C$_{51}$H$_{62}$N$_9$O$_{17}$) m/z=1072; Found ESI: (C$_{51}$H$_{62}$N$_9$O$_{17}$) m/z=1072.

NDM-82
Ac-[D-Lys(6FAM)]-(D-Ala)-(D-Ala)-(D-Ala)-(D-Thr)-(D-His)-(D-Glu)-(D-Ala)-(D-Ala)-(D-Ala)-(D-Thr)-(D-His)-(D-Glu)-NH$_2$
Calculated: [M+2H]$^{2+}$ (C$_{77}$H$_{111}$N$_{19}$O$_{26}$) m/z=854; Found ESI: (C$_{77}$H$_{101}$N$_{19}$O$_{26}$) m/z=854.

NDM-90
Ac-[D-Lys(6FAM)]-(D-Ala)-(D-Ala)-(D-Ala)-(D-Ala)-(D-His)-(D-Glu)-NH$_2$
Calculated: [M+H]$^+$ (C$_{52}$H$_{62}$N$_{11}$O$_{16}$) m/z=1096; Found ESI: (C$_{52}$H$_{62}$N$_{11}$O$_{16}$) m/z=1096.

NDM-91
Ac-[D-Lys(6FAM)]-(D-Ala)-(D-Ala)-(D-Ala)-(D-Glu)-(D-His)-(D-Thr)-NH$_2$

Calculated: [M+H]$^+$ ($C_{53}H_{64}N_{11}O_{17}$) m/z=1126; Found ESI: ($C_{53}H_{64}N_{11}O_{17}$) m/z=1126.

NDM-92

Ac-[D-Lys(6FAM)]-(D-Ala)-(D-Ala)-(D-Ala)-(D-Thr)-(D-His)-(D-Phe)-NH$_2$

Calculated: [M+H]$^+$ ($C_{57}H_{66}N_{11}O_{15}$) m/z=1145; Found ESI: ($C_{57}H_{66}N_{11}O_{15}$) m/z=1145.

Example 4—Assay Method for Determining Fluorescence Contrast in Murine Nerves

The visualization contrast activity of fluorescent peptides for nerve imaging was assessed using male immunocompetent hairless SKH1-E mice purchased from Charles River (Charles River, Wilmington, Mass. 01887, USA). SKH1-E mice weighing 25-30 grams were housed in group of 4 in individually ventilated IVC disposable cages (Innovive, Inc., San Diego, Calif. 92121, USA) and maintained under controlled environmental conditions (12-h/12-h light/dark cycle; temperature of 64-79F and relative humidity of 30-70%) for at least 5 days before experimental use. Animals had free access to standard laboratory rodent diet (Cat. #2018, Teklad Global 18% Protein Rodent Diet; Harlan Laboratories, Inc. Indianapolis, Ind. 46250, USA) and acidified drinking water throughout the course of study. All experiments were carried out under Institutional Animal Care and Use Committee (IACUC) approved protocol.

On the day of study, each involved mouse was weighed, examined for general condition and restrained using a rotating tail injector (Cat. #RTI, Braintree Scientific, Braintree, Mass. 021585, USA) for intravenous (tail vein) injection of test compound in conscious animal. The test compounds were tested (25-150 nmol in 0.1 mL/mouse) was then injected intravenously in mouse using a 28G1/2 Insulin syringe (Cat. #14-826-79, Becton Dickinson and Company, Franklin Lakes, N.J. 07417, USA). After the intravenous injection, each involved mouse was housed back in its assigned cage and kept under controlled environmental conditions before being examined for fluorescence labeling of the sciatic nerve.

Two hours after the intravenous injection, each involved mouse was terminally anesthetized with a mixture of ketamine HCl (Zetamine™, 100 mg/mL, ANADA 200-055 approved by FDA, NDC-13985-702-10; VETone®, Boise, Id. 83705, USA) and xylazine (Rompun™, 100 mg/mL, NADA-047-956 approved by FDA, Bayer HealthCare, LLC, Animal Health Divison, KS 66201, USA) which consisted of a combination of 100 mg/kg of ketamine with 10 mg/kg of xylazine administered intraperitoneally. The terminally anesthetized mouse was transferred on the piece of cork (4×4 inches, Quartet®, ACCO Brands, Lincolnshire, Ill. 60069, USA) for blunt dissection of sciatic nerve after checking the toe pinch reflex. The sciatic nerve was exposed by removing skin from the dorsal surface of the thigh and blunt dissecting the muscles parallel and posterior to the femur after checking righting reflex (no reflex to toe pinch) in terminally anesthetized mouse. Full body imaging of the terminally anesthetized mouse with both sciatic nerves exposed was then performed using a computerized UVP BioSpectrum® 500 Imaging System fitted with appropriate excitation/emission filters for fluorescein, Cy5, or other dye detection and a VisionWorks® LS Software (UVP-BioSpectrum Imaging System, Upland, Calif., USA) for image acquisition and analysis. After the mouse full body imaging, the exposed and saline moisturized sciatic nerves were subsequently imaged using computerized fluorescence stereomicroscope (SZX 10, Olympus Optical, CO, LTD, Japan) interfaced with PictureFrame™, an image processing application suitable for image acquisition and analysis (Optronics, Goleta, Calif. 93117) or an in-house built Microscope Imaging System interfaced with Spot Software 5.0 (SPOT Imaging Solutions, Sterling Heights, Mich. 48314) for image acquisition and analysis. All above-mentioned Imaging Systems were equipped with appropriate excitation/emission filters for fluorescein, Cy5, or other dye detection.

Following the imaging session, all captured images of fluorescently labeled sciatic nerves were examined and analyzed using the image processing program Image J to generate quantitative fluorescence data. For each involved mouse, fluorescence intensity of each examined sciatic nerve was acquired by drawing an area on the surface of the exposed sciatic nerve using Image J features and capabilities. In order to calculate the nerve sciatic fluorescence contrast, the background defined as fluorescence intensities on the upper and lower muscle apart from the sciatic nerve were also acquired as above and averaged to generate a Mean±SEM background value. For each screened nerve peptide, nerve to background (N/B) contrast ratio defined and calculated as N/B=IN/IB, (where IN is the nerve fluorescence intensity and IB the average background intensity proximal to sciatic nerve). Nerve to skin (N/S) contrast was calculated as N/S=IN/IS (where IS is the measured skin fluorescence).

An example of fluorescence contrast (nerve/background) of mouse sciatic nerve using nerve delivery molecule is shown in FIG. 1.

Table 2 exemplifies the difference in the nerve intensity to adjacent background intensity (N/B) contrast for various new fluorescent peptide conjugates. Unexpectedly, some NDMs have substantially higher N/B and N/S contrast (e.g. NDM-38, NDM-40) due to the structure comprising retro-inverso peptide sequences (D-amino acids) when compared to the equivalent NDMs (e.g. NDM-39, NDM-41) instead comprising L-amino acids. Furthermore, NDMs (e.g., NDM-38) comprising alanine linkers have higher N/B and N/S contrast (e.g. NDM-38) relative to NDMs (e.g., NDM-44) with glycine linkers.

TABLE 2

In vivo imaging result summary of nerve peptides. The nerve intensity to adjacent background intensity (N/B) contrast and nerve intensity to skin (N/S) contrast for various new fluorescent peptide conjugates.

| NDM- | N/B Contrast | N/S Contrast |
| --- | --- | --- |
| 36 | Medium | Medium |
| 37 | High | Medium |
| 38 | Very High | Very High |
| 39 | High | Medium |
| 40 | Very High | Very High |
| 41 | High | Medium |
| 42 | High | High |
| 43 | Medium | Medium |
| 44 | Very High | High |
| 50 | High | Low |
| 69 | High | Medium |
| 71 | Very High | Medium |
| 81 | Very High | High |
| 82 | Very High | Medium |
| 90 | Very High | High |
| 91 | Very High | High |
| 92 | Very High | High |

N/B is nerve intensity to background contrast.
Low = values ≤ 2
Medium = values 2.01 to 2.6
High = values 2.61 to 4.99
Very High = values ≥ 5
N/S is nerve intensity to skin contrast.
Low = values ≤ 0.5
Medium = values 0.51 to 0.99
High = values 1.0 to 1.99
Very High = values ≥ 2

Example 5—Delivery of a Therapeutic Agent to Murine Nerves

Male immunocompetent hairless SKH1-E mice purchased from Charles River (Charles River, Wilmington, Mass. 01887, USA) are used. SKH1-E mice weighing 25-30 grams are housed in group of 4 in individually ventilated IVC disposable cages (Innovive, Inc., San Diego, Calif. 92121, USA) and are maintained under controlled environmental conditions (12-h/12-h light/dark cycle; temperature of 64-79 F and relative humidity of 30-70%) for at least 5 days before experimental use. Animals have free access to standard laboratory rodent diet (Cat. #2018, Teklad Global 18% Protein Rodent Diet; Harlan Laboratories, Inc. Indianapolis, Ind. 46250, USA) and acidified drinking water throughout the course of study. All experiments are carried out under Institutional Animal Care and Use Committee (IACUC) approved protocol.

On the day of study, each involved mouse is weighed, examined for general condition and restrained using a rotating tail injector (Cat. #RTI, Braintree Scientific, Braintree, Mass. 021585, USA) for intravenous (tail vein) injection of test compound in conscious animal. A selected test compound (25-150 nmol in 0.1 mL/mouse) is injected intravenously in the mouse using a 28G1/2 Insulin syringe (Cat. #14-826-79, Becton Dickinson and Company, Franklin Lakes, N.J. 07417, USA). After the intravenous injection, each mouse is then kept under controlled environmental conditions before being examined for delivery of the test compound to the sciatic nerve.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:
1. A nerve delivery molecule according to NDM-38:
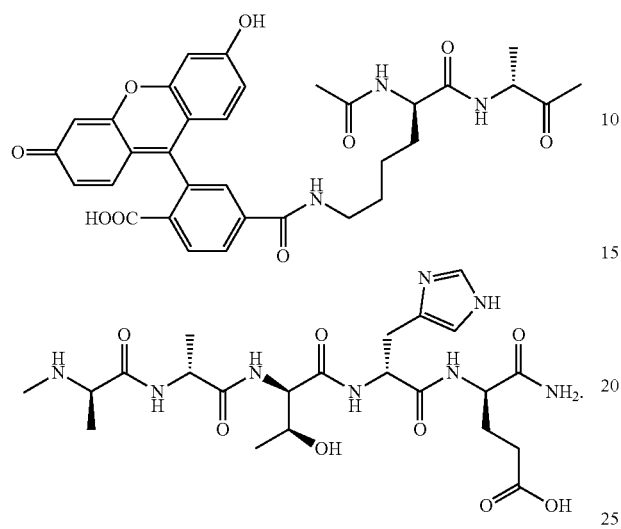
2. A nerve delivery molecule according to NDM-37:
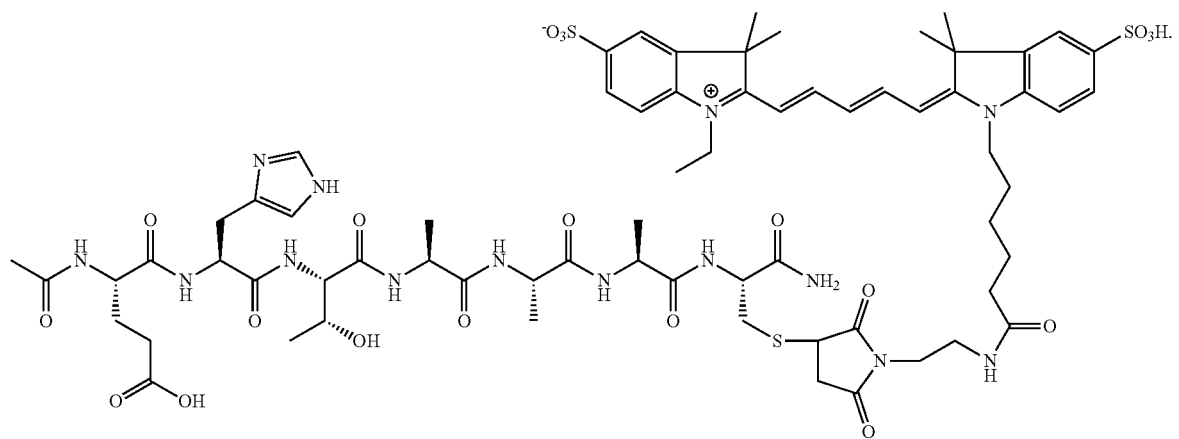
* * * * *

SEQUENCE LISTING

```
<160> NUMBER OF SEQ ID NOS: 24

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 1-10 residues

<400> SEQUENCE: 1

Ala Ala Ala Ala Ala Ala Ala Ala Ala Ala
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(10)
<223> OTHER INFORMATION: This sequence may encompass 3-10 residues

<400> SEQUENCE: 2

Gly Gly Gly Gly Gly Gly Gly Gly Gly Gly
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ala Ala Ala Ala Ala Ala Ala Ala Ala
1               5                   10
```

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ala Ala Ala Ala Ala Ala Ala Ala
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ala Ala Ala Ala Ala Ala Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Ala Ala Ala Ala Ala Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Ala Ala Ala Ala
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Ala Ala Ala
1               5

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 9

Ala Ala Ala Ala
1

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Gly Gly Gly Gly Gly Gly Gly Gly
1               5                   10

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Gly
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Gly Gly
1

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Glu His Thr Ala Ala Ala Cys
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu His Thr Ala Ala Ala Lys
1               5

<210> SEQ ID NO 15
<211> LENGTH: 7
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 15

Glu His Thr Ala Ala Ala Cys
1               5

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Glu His Thr Cys
1

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu His Thr Ala Ala Ala Cys
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Glu His Thr Ala Ala Ala Lys
1               5

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Glu His Thr Cys
1

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu His Thr Ala Ala Ala Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Gly Gly Gly Gly Gly
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly Gly Gly Gly Gly Gly Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Gly Gly Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Gly Gly Gly Gly
1               5